US012797360B2

(12) United States Patent
Obidin et al.

(10) Patent No.: US 12,797,360 B2
(45) Date of Patent: Nov. 17, 2026

(54) SAFER PSYCHOACTIVE COMPOSITIONS

(71) Applicant: Arcadia Medicine, Inc., San Francisco, CA (US)

(72) Inventors: Nikita Obidin, Seattle, WA (US); James Heywood, Newton, MA (US)

(73) Assignee: Arcadia Medicine, Inc., San Francisco, CA (US)

( * ) Notice: Subject to any disclaimer, the term of this patent is extended or adjusted under 35 U.S.C. 154(b) by 352 days.

(21) Appl. No.: 18/577,183

(22) PCT Filed: Jul. 7, 2022

(86) PCT No.: PCT/US2022/036427

§ 371 (c)(1),
(2) Date: Jan. 5, 2024

(87) PCT Pub. No.: WO2023/283386

PCT Pub. Date: Jan. 12, 2023

(65) Prior Publication Data

US 2024/0335418 A1 Oct. 10, 2024

Related U.S. Application Data

(60) Provisional application No. 63/219,302, filed on Jul. 7, 2021.

(51) Int. Cl.

| | |
|---|---|
| ***A61K 31/357*** | (2006.01) |
| ***A61K 31/137*** | (2006.01) |
| ***A61K 31/4045*** | (2006.01) |
| ***A61P 25/22*** | (2006.01) |
| ***A61P 25/30*** | (2006.01) |

(52) U.S. Cl.

CPC .......... *A61K 31/357* (2013.01); *A61K 31/137* (2013.01); *A61K 31/4045* (2013.01); *A61P 25/22* (2018.01); *A61P 25/30* (2018.01)

(58) Field of Classification Search

CPC .................................................... A61K 31/357

See application file for complete search history.

(56) References Cited

U.S. PATENT DOCUMENTS

| | | | | |
|---|---|---|---|---|
| 4,327,725 | A | 5/1982 | Cortese et al. | |
| 4,624,848 | A | 11/1986 | Lee | |
| 4,871,549 | A | 10/1989 | Ueda et al. | |
| 4,968,509 | A | 11/1990 | Radebaugh et al. | |
| 5,011,692 | A | 4/1991 | Fujioka et al. | |
| 5,017,381 | A | 5/1991 | Maruyama et al. | |
| 5,229,135 | A | 7/1993 | Philippon et al. | |
| 5,260,068 | A | 11/1993 | Chen | |
| 5,260,069 | A | 11/1993 | Chen | |
| 5,456,923 | A | 10/1995 | Nakamichi et al. | |
| 5,461,140 | A | 10/1995 | Heller et al. | |
| 5,508,040 | A | 4/1996 | Chen | |
| 5,516,527 | A | 5/1996 | Curatolo | |
| 5,567,441 | A | 10/1996 | Chen | |
| 5,622,721 | A | 4/1997 | Dansereau et al. | |
| 5,686,105 | A | 11/1997 | Kelm et al. | |
| 5,700,410 | A | 12/1997 | Nakamichi et al. | |
| 5,837,284 | A | 11/1998 | Mehta et al. | |
| 5,840,329 | A | 11/1998 | Bai | |
| 5,977,175 | A | 11/1999 | Lin | |
| 6,465,014 | B1 | 10/2002 | Moroni et al. | |
| 6,932,983 | B1 | 8/2005 | Straub et al. | |
| 7,638,651 | B2 | 12/2009 | Gant et al. | |
| 8,277,840 | B2 | 10/2012 | Joshi et al. | |
| 10,034,832 | B2 | 7/2018 | Salce, Jr. et al. | |
| 10,981,859 | B2 | 4/2021 | Nivorozhkin et al. | |
| 11,939,312 | B2 * | 3/2024 | Obidin ................. | A61K 9/0053 |
| 12,053,452 | B2 * | 8/2024 | Kadysh ................ | A61K 31/357 |
| 2019/0388430 | A1 | 12/2019 | Bosse et al. | |
| 2020/0384188 | A1 | 12/2020 | Becker et al. | |

(Continued)

FOREIGN PATENT DOCUMENTS

| | | | |
|---|---|---|---|
| WO | 2005000334 | A1 | 1/2005 |
| WO | 2017180589 | A1 | 10/2017 |

(Continued)

OTHER PUBLICATIONS

European Search Report and Search Opinion dated May 28, 2025 in Applicant's copending EP 22816978.5 (regional phase entry of PCT/US2022/032275).

Mithoefer. A Manual for MDMA-Assisted Psychotherapy in the Treatment of Posttraumatic Stress Disorder. Maps. Aug. 19, 2015.

Mohamed et al. MDMA: interactions with other psychoactive drugs. Pharmacol Biochem Behav. 2011;99(4):759-774.

Monks et al. Serotonergic neurotoxicity of methylenedioxyamphetamine and methylenedioxymetamphetamine. Adv Exp Med Biol. 2001;500:397-406.

Mwesiga. Hallucinogen rating scale. Mendeley Data. Aug. 27, 2020.

Nardou et al. Oxytocin-dependent reopening of a social reward learning critical period with MDMA. Nature. 2019;569(7754):116-120.

Nichols DE, et al., 2,3-Dihydrobenzofuran Analogues of Hallucinogenic Phenethylamines. J Med Chem, 1991; 34(1):276-81.

(Continued)

*Primary Examiner* — Golam M Shameem

(74) *Attorney, Agent, or Firm* — CALYX LAW; Graham Pechenik

(57) ABSTRACT

Provided are therapeutic combinations comprising hallucinogenic agents and entactogenic agents. Also provided are compositions, such as pharmaceutical compositions, comprising such combinations and methods of using the same. In some embodiments, the entactogenic agent is a non-racemic entactogen. In some embodiments, a provided therapeutic combination or composition thereof is administered to a subject to treat a mental health condition, a substance abuse disorder, or a condition that features impaired social reward or social cognition, such as social anxiety and autism. In some aspects, the features of the combinations, e.g., neuromodulatory activity, improve physiological and psychological effects by, for example, reducing potential for abuse, neurotoxic effects, and improving subjective experience and therapeutic efficacy.

13 Claims, 9 Drawing Sheets

(56) References Cited

U.S. PATENT DOCUMENTS

2021/0069170 A1 † 3/2021 Stamets
2021/0315840 A1 10/2021 Robbins et al.

FOREIGN PATENT DOCUMENTS

WO 2018104729 A1 6/2018
WO 2019220139 A1 11/2019
WO 2021255737 A1 12/2021
WO 2022047256 A1 3/2022
WO 2022053696 A1 3/2022
WO 2022106947 A1 5/2022
WO 2023019369 A1 2/2023

OTHER PUBLICATIONS

Nichols DE, Psychedelics, Pharmacological Reviews, 2016; 68(2):264-355.
Nichols DE, Hallucinogens. Pharmacol Ther. 2004;101(2):131-181.
Nichols et al. Asymmetric synthesis of psychotomimetic phenylisopropylamines. J Med Chem. 1973;16(5):480-483.
Nichols et al. Derivatives of 1-(1,3-benzodioxol-5-yl)-2-butanamine: representatives of a novel therapeutic class. J Med Chem. 1986;29(10):2009-2015.
Nichols et al. N-Benzyl-5-methoxytryptamines as Potent Serotonin 5-HT2 Receptor Family Agonists and Comparison with a Series of Phenethylamine Analogues. ACS Chem Neurosci. 2015;6(7):1165-1175.
Nisell et al. Systemic nicotine-induced dopamine release in the rat nucleus accumbens is regulated by nicotinic receptors in the ventral tegmental area. Synapse. 1994;16(1):36-44.
O'Dell & Khroyan. Rodent models of nicotine reward: What do they tell US about tobacco abuse in humans?. Pharmacology Biochemistry and Behavior, 2009; 91(4): 481-488.
Oeri HE. Beyond ecstasy: Alternative entactogens to 3,4-methylenedioxymethamphetamine with potential applications in psychotherapy. J Psychopharmacol. 2021;35(5):512-536.
Oumeziane et al. "Why don't they 'like' me more?": Comparing the time courses of social and monetary reward processing. Neuropsychologia. 2017;107:48-59.
Payakachat et al. Autism spectrum disorders: a review of measures for clinical, health services and cost-effectiveness applications. Expert Rev Pharmacoecon Outcomes Res. 2012;12(4):485-503.
PCT/US/2022/036427. International Preliminary Report on Patentability. Dec. 14, 2023.
PCT/US/2022/036427. International Search Report. Jan. 11, 2023.
PCT/US/2022/036427. Search History. Oct. 26, 2022.
PCT/US/2022/036427.Written Opinion of the International Searching Authority. Jan. 11, 2023.
Perez Silanes S, et al., J Heterocyclic Chem, 2001; 38(5):1025-30.
Pierce & Kumaseran. The mesolimbic dopamine system: The final common pathway for the reinforcing effect of drugs of abuse?. Neurosci. Biobehav. Rev., 2006; 30(2):215-38.
Pilecki et al. Ethical and legal issues in psychedelic harm reduction and integration therapy. Harm Reduct J. 2021;18(1):40.
Pitts et al. (±)-MDMA and its enantiomers: potential therapeutic advantages of R(−)-MDMA. Psychopharmacology (Berl). 2018;235(2):377-392.
Pizarro et al. Determination of MDMA and its metabolites in blood and urine by gas chromatography-mass spectrometry and analysis of enantiomers by capillary electrophoresis. J Anal Toxicol. 2002;26(3):157-165.
Pizzaro et al. Synthesis and Capillary Electrophoretic Analysis of Enantiomerically Enriched Reference Standards of MDMA and its Main Metabolites. Bioorganic & Medicinal Chemistry. 2002;10:1085-1092.
Preller & Vollenweider. Modulation of Social Cognition via Hallucinogens and "Entactogens". Front Psychiatry. 2019;10:881.
Proudfit GH. The reward positivity: from basic research on reward to a biomarker for depression. Psychophysiology. 2015;52(4):449-459.
PsychonautWiki. Experience: 150mg MDMA + 20mg 2C-B—I designed it this way myself. Feb. 15, 2020.
Ranta et al. Social Anxiety Scale for Adolescents (SAS-A): measuring social anxiety among Finnish adolescents. Child Psychiatry Hum Dev. 2012;43(4):574-591.
Rasmussen et al. Chiral separation and quantification of R/S-amphetamine, R/S-methamphetamine, R/S-MDA, R/S-MDMA, and R/S-MDEA in whole blood by GC-EI-MS. J Chromatogr B Analyt Technol Biomed Life Sci. 2006;842(2):136-141.
Reaven et al. Use of the ADOS and ADI-R in children with psychosis: importance of clinical judgment. Clin Child Psychol Psychiatry. 2008;13(1):81-94.
Riba et al. Psychometric assessment of the Hallucinogen Rating Scale. Drug Alcohol Depend. 2001;62(3):215-223.
Ricaurte et al. Lasting effects of (+−)-3,4-methylenedioxymethamphetamine (MDMA) on central serotonergic neurons in nonhuman primates: neurochemical observations. J Pharmacol Exp Ther. 1992;261(2):616-622.
Robb-Dover. The Dangers of Combining Xanax and Molly. FHEHealth. Jun. 17, 2021.
Robinson et al. Reliability of the Timeline Followback for cocaine, cannabis, and cigarette use. Psychol Addict Behav. 2014;28(1):154-162.
Ronsley et al. Treatment of stimulant use disorder: A systematic review of reviews. PLoS One, 2020; 15(6):e0234809.
Roseman et al. Quality of Acute Psychedelic Experience Predicts Therapeutic Efficacy of Psilocybin for Treatment-Resistant Depression, Front Pharmacol. 2018;8:974.
Roth. NIMH Psychoactive Drug Screening Program (PDSP) Assay Protocol Book Ver. III, 2018.
Rudin et al. Molecular and clinical aspects of potential neurotoxicity induced by new psychoactive stimulants and psychedelics. Exp Neurol. 2021;343:113778.
Schechter MD. 'Candyflipping': synergistic discriminative effect of LSD and MDMA. Eur J Pharmacol. 1998;341(2-3):131-134.
Schenberg EE, Psychedelic-Assisted Psychotherapy: A Paradigm Shift in Psychiatric Research and Development. Neuropharmacology, 2018;9:733.
Seifritz et al. No Abuse Potential of Silexan in Healthy Recreational Drug Users: A Randomized Controlled Trial. Int J Neuropsychopharmacol. 2021;24(3):171-180.
Setola et al. 3,4-methylenedioxymethamphetamine (MDMA, "Ecstasy") induces fenfluramine-like proliferative actions on human cardiac valvular interstitial cells in vitro. Mol Pharmacol. 2003;63(6):1223-1229.
Shulgin & Shulgin. Pihkal: A Chemical Love Story, 1992 Transform Press, Berkeley CA.
Shulgin & Shulgin. TiHKAL: The Continuation, 1997 Transform Press.
Sobell et al. The reliability of the Alcohol Timeline Followback when administered by telephone and by computer. Drug Alcohol Depend. 1996;42(1):49-5.
Sofuoglu & Sewell. Norepinephrine and stimulant addiction. Addict Biol., 2009; 14(2): 119-129.
Spreckelmeyer et al. Anticipation of monetary and social reward differently activates mesolimbic brain structures in men and women. Soc Cogn Affect Neurosci. 2009;4(2):158-165.
Steenkamp et al. First-line Psychotherapies for Military-Related PTSD. JAMA. 2020;323(7):656-657.
"The Use of MDMA for Disorders Listed in the DSM-5", Research Disclosure, Kenneth Mason Publications, Hampshire, UK, GB Publications, Hampshire, UK, GB , vol. 685, No. 43 1 vol. May 685, 2021 no. (May 1, 2021), 43 XP007149374, ISSN: 0374-4353 Retrieved from the Internet.
European Search Report and Search Opinion dated May 13, 2025 in Applicant's copending EP 22838440.0 (regional phase entry of PCT/US2022/036427).
Reiff Collin M. M. et et al: al: ""Psychedelics and and Psychedelic-AssistedPsychedelic-Assisted Psychotherapy"Psychotherapy", American Journal of Psychiatry, vol. 177, No. 5, May 1, 2020 (May 1,

(56) References Cited

OTHER PUBLICATIONS

2020), pp. 391-410, XP093243740, ISSN: 0002-953X, 0002-953X, DOI: 10.1176/appi.ajp.2019.19010035.

Siegel Ashley NN etet al:al: ""Registered clinical studies investigating psychedelic drugs for psychiatric disorders", disorders", Journal of Psychiatric Research, Elsevier Journal of Psychiatric Research, Elsevier Ltd, GB, vol. 139, May 18, 2021 2021(May 18, 2021), (May 18, 2021), pp. 71-81, XP086613721, ISSN: 0022-3956, DOI: 10.1016/J.JPSYCHIRES.2021.05.019.

Steidl et al. Opioid-induced Rewards, Locomotion, and DopamineActivation: A Proposed Model for Control by Mesopontine andRostromedial Tegmental Neurons. Neurosci. Biobehav. Rev., 2017; 83:72-82.

Steinkellner et al. The ugly side of amphetamines: short- and long-term toxicity of 3,4-methylenedioxymethamphetamine (MDMA, 'Ecstasy'), methamphetamine and D-amphetamine. Biol Chem. 2011;392(0):103-115.

Stove et al. Mice in ecstasy: advanced animal models in the study of MDMA. Curr Pharm Biotechnol. 2010;11(5):421-433.

Studerus et al. Psychometric Evaluation of the Altered States of Consciousness Rating Scale (OAV). PloS one, 2010; 5(8), e12412.

Taghizadeh G, et al., Protective effects of physical exercise on MDMA-induced cognitive and mitochondrial impairment. Free Radic. Biol. Med. 2016;99:11-9.

Takano H, Cognitive Function and Monoamine Neurotransmission in Schizophrenia: Evidence From Positron Emission Tomography Studies. Front Psychiatry, 2018;9:228.

Tarawneh R, et al., Cerebrospinal Fluid Markers of Neurodegeneration and Rates of Brain Atrophy in Early Alzheimer Disease, Neurol. 2015; 72(6): 656-65.

Toh EA, et al., Comparison of cognitive and UHDRS measures in monitoring disease progression in Huntington's disease: a 12-month longitudinal study, Transl Neurodegener. 2014;3:15.

Tucker et al. The Demethylenation of Methylenedioxymethamphetamine ("Ecstasy") by Debrisoquine Hydroxylase (CYP2D6). Biochemical Pharmacology, 1994;47(7):1151-1156.

Verbitsky et al. Rodent models of post-traumatic stress disorder: behavioral assessment. Transl Psychiatry. 2020;10(1):132.

White et al. Functional MRI approach to developmental methylmercury and polychlorinated biphenyl neurotoxicity. Neurotoxicology. 2011;32(6):975-980.

Wise RA. Catecholamine Theories of Reward: A Critical Review. Brain Res., 1978; 152(2):215-47.

Wong & Gjedde. Monoamines: Human Brain Imaging. Encyclopedia of Neuroscience. 2009;14:939-952.

Wong DF & Gjedde A, Monoamines: Human brain imaging, Encyclopedia of Neuroscience, 2009; 939-52.

Yamamoto et al. Detection of Nausea-Like Response in Rats by Monitoring Facial Expression. Front. Pharmacol. 2017;7:534.

Yamamoto et al. Metabolism of methamphetamine, amphetamine and p-hydroxymethamphetamine by rat-liver microsomal preparations in vitro. Xenobiotica, 1984;14(11)867-75.

Zanos et al. (R)-Ketamine exerts antidepressant actions partly via conversion to (2R,6R)-hydroxynorketamine, while causing adverse effects at sub-anaesthetic doses. Br J Pharmacol. 2019;176(14):2573-2592.

Zhou et al. 3,4-Methylenedioxymethamphetamine (MDMA) abuse may cause oxidative stress and potential free radical damage. Free Radic Res. 2003;37(5):491-497.

Zimmer & Roberts. Cocaine Self-Administration in Rats: Hold-Down Procedures. Psychiatric Disorders, 2011;279-290.

Glennon R, et al., 5-HT1 and 5-HT2 binding characteristics of 1-(2,5-dimethoxy-4-bromophenyl)-2-aminopropane analogs. J Med Chem 1986;29(2):194-9.

Gotham et al. Standardizing ADOS scores for a measure of severity in autism spectrum disorders. J Autism Dev Disord. 2009;39(5):693-705.

Gouzoulis-Mayfrank. Differential actions of an entactogen compared to a stimulant and a hallucinogen in healthy humans. Heffter Rev. Psychedelic Res. 2001;2:64-72.

Greene TA & Wuts PGM, "Protective Groups in Organic Chemistry," (Wiley, 2nd ed. 1991).

Griffiths et al. Psilocybin produces substantial and sustained decreases in depression and anxiety in patients with life-threatening cancer: A randomized double-blind trial. J Psychopharmacol. 2016;30(12):1181-1197.

Grob CS & Grigsby J, Handbook of Medical Hallucinogens, 2021.

Halberstadt & Geyer. Characterization of the head-twitch response induced by hallucinogens in mice: detection of the behavior based on the dynamics of head movement. Psychopharmacology (Berl). 2013;227(4):727-739.

Halberstadt & Geyer. Effects of the hallucinogen 2,5-dimethoxy-4-iodophenethylamine (2C—I) and superpotent N-benzyl derivatives on the head twitch response. Neuropharmacology. 2014;77:200-207.

Halberstadt et al. Differential contributions of serotonin receptors to the behavioral effects of indoleamine hallucinogens in mice. J Psychopharmacol. 2011;25(11):1548-1561.

Han et al. The self-disproportionation of enantiomers (SDE): a menace or an opportunity?. Chem Sci. 2018;9(7):1718-1739.

Hanssen et al. Neural, behavioural and real-life correlates of social context sensitivity and social reward learning during interpersonal interactions in the schizophrenia spectrum. Aust N Z J Psychiatry. 2022;56(1):59-70.

Harris DS, et al. "Subjective and hormonal effects of 3, 4-methylenedioxymethamphetamine (MDMA) in humans." Psychopharmacology 2002;162:396-405.

Harrison IT & Harrison S, et al., "Compendium of Synthetic Organic Methods," 1971-1996 vols. 1-8 John Wiley and Sons.

Harvey et al. Development of Rapidly Metabolized and Ultra-Short-Acting Ketamine Analogs. Anesth Analg. 2015;121(4):925-933.

Helmlin et al. Analysis of 3,4-methylenedioxymethamphetamine (MDMA) and its metabolites in plasma and urine by HPLC-DAD and GC-MS. J Anal Toxicol. 1996;20(6):432-440.

Herndon JM, et al., Glial Cell Response to 3,4-(±)-Methylenedioxymethamphetamine and Its Metabolites, Toxicological Sciences, 2014;138(1):130-8.

Hiramatsu & Cho. Enantiomeric differences in the effects of 3,4-methylenedioxymethamphetamine on extracellular monoamines and metabolites in the striatum of freely-moving rats: an in vivo microdialysis study. Neuropharmacology. 1990;29(3):269-275.

Holford & Sheiner. Understanding the dose-effect relationship: clinical application of pharmacokinetic-pharmacodynamic models. Clin Pharmacokinet. 1981;6(6):429-453.

Holroyd et al. The feedback correct-related positivity: sensitivity of the event-related brain potential to unexpected positive feedback. Psychophysiology. 2008;45(5):688-697.

Holze et al. Distinct acute effects of LSD, MDMA, and D-amphetamine in healthy subjects. Neuropsychopharmacology. 2020;45:462-471.

Huang et al. Isobologram Analysis: A Comprehensive Review of Methodology and Current Research. Front Pharmacol. 2019;10:1222.

Hysek et al. The norepinephrine transporter inhibitor reboxetine reduces stimulant effects of MDMA ("ecstasy") in humans. Clin Pharmacol Ther. 2011;90(2):246-255.

Indave et al. Antipsychotic medications for cocaine dependence. Cochrane Database Syst Rev. 2016;3(3):CD006306.

Isik & Uzbe. Personality traits and positive/negative affects: An analysis of meaning in life among adults. Kuram ve Uygulamada Eğitim Bilimleri/Educational Sciences: Theory & Practice. 2015;15(3):587-595.

Izuma et al. Processing of social and monetary rewards in the human striatum. Neuron. 2008;58(2):284-294.

Jahan & Burgess. "Substance Use Disorder," Treasure Island (FL): StatPearls Publishing; 2022.

Janikian. Described as intense and transcendent, here's everything you should know when you candy flip, from dosage to harm reduction, and more. Double Blind. Updated Jul. 22, 2021. Accessed Jul. 3, 2022.

Johnson et al. Effects of the enantiomers of MDA, MDMA and related analogues on [3H]serotonin and [3H] dopamine release from superfused rat brain slices. Eur J Pharmacol. 1986; 132(2-3):269-276.

(56) References Cited

OTHER PUBLICATIONS

Johnson et al. The abuse potential of medical psilocybin according to the 8 factors of the Controlled Substances Act. Neuropharmacology. 2018;142:143-166.
Johnson M, Richards W & Griffiths R, Human hallucinogen research: guidelines for safety. J Psychopharmacology, 2008;22: 603-20.
Kampman & Jarvis. American Society of Addiction Medicine (ASAM) National Practice Guideline for the Use of Medications in the Treatment of Addiction Involving Opioid Use. J Addict Med. 2015;9(5):358-367.
Kasteel & Westerink. Refining in vitro and in silico neurotoxicity approaches by accounting for interspecies and interindividual differences in toxicodynamics. Expert Opin Drug Metab Toxicol. 2021;17(8):1007-1017.
Kedrowski SMA, et al., 1-Oxo-5-hydroxytryptamine: A Surprisingly Potent Agonist of the 5-HT3 (Serotonin) Receptor. Organic Letters, 2007; 9(17):3205-7.
Keri RP, et al., An overview of benzo[b]thiophene-based medicinal chemistry. European J Med Chem, 2017;138:1002-33.
Kirkpatrick et al. Plasma oxytocin concentrations following MDMA or intranasal oxytocin in humans. Psychoneuroendocrinology. 2014;46:23-31.
Klein et al. Receptor binding profiles and behavioral pharmacology of ring-substituted N,N-diallyltryptamine analogs. Neuropharmacology. 2018; 142:231-239.
Knights et al. In Vitro Drug Metabolism Using Liver Microsomes. Curr Protoc Pharmacol. 2016;74:7.8.1-7.8.24.
Kosten & George. The neurobiology of opioid dependence: implications for treatment. Sci Pract Perspect. 2002;1(1):13-20.
Laviolette & Van De Kooy. The neurobiology of nicotine addiction: bridging the gap from molecules to behaviour. Nat Rev Neurosci. 2004;5(1):55-65.
Lezak et al. Behavioral methods to study anxiety in rodents. Dialogues Clin Neurosci. 2017;19(2):181-191.
Llabres et al. Molecular basis of the selective binding of MDMA enantiomers to the alpha4beta2 nicotinic receptor subtype: synthesis, pharmacological evaluation and mechanistic studies. Eur J Med Chem. 2014;81:35-46.
Lourenco et al. Chiral separation of 3,4-methylenedioxymethamphetamine (MDMA) enantiomers using batch chromatography with peak shaving recycling and its effects on oxidative stress status in rat liver. J Pharm Biomed Anal. 2013;73:13-17.
Luethi D & Liechti ME, Designer drugs: mechanism of action and adverse effects, Arch. Toxicol., 2020; 94, 1085-133.
Maclean et al. Factor Analysis of the Mystical Experience Questionnaire: A Study of Experiences Occasioned by the Hallucinogen Psilocybin. J Sci Study Relig. 2012;51(4):721-737.
Mas M, et al. Cardiovascular and neuroendocrine effects and pharmacokinetics of 3,4-methylenedioxymethamphetamine in humans. J Pharmacol Exp. Ther 1999;290(1):136-45.
Matyjek et al. Multidimensional View on Social and Non-Social Rewards. Front Psychiatry. 2020;11:818.
Meyer et al. The role of human hepatic cytochrome P450 isozymes in the metabolism of racemic 3,4-methylenedioxy-methamphetamine and its enantiomers. Drug Metab Dispos. 2008;36(11):2345-2354.
Mind Foundation. Beyond the Therapeutic Alliance How MDMA and Classic Psychedelics Modify Social Learning—An Interview With Gül Dölen. Jan. 26, 2021.
Minozzi et al. Dopamine agonists for the treatment of cocaine dependence. Cochrane Database Syst Rev. 2015;2015(5):CD003352.
Mithoefer et al. Durability of improvement in post-traumatic stress disorder symptoms and absence of harmful effects or drug dependency after 3,4-methylenedioxymethamphetamine-assisted psychotherapy: a prospective long-term follow-up study. J Psychopharmacol. 2013;27(1):28-39.
Al-Hasani & Bruchas. Molecular mechanisms of opioid receptor-dependent signaling and behavior. Anesthesiology. 2011;115(6):1363-1381.
Apfel et al. How to study postoperative nausea and vomiting. Acta Anaesthesiol. Scand. 2002:46:921-928.
Araujo et al. The hallucinogenic world of tryptamines: an updated review. Arch Toxicol. 2015;89(8):1151-1173.
Armstrong et al. Potentiation of (DL)-3,4-methylenedioxymethamphetamine (MDMA)-induced toxicity by the serotonin 2A receptior partial agonist d-lysergic acid diethylamide (LSD), and the protection of same by the serotonin 2A/2C receptor antagonist MDL 11,939. Neuroscience Research Communications. 2004;35: 83-95.
Baker et al. Anxiety Symptoms Questionnaire (ASQ): development and validation. Gen Psychiatr. 2019;32(6):e100144.
Baker et al. DSM criteria for tobacco use disorder and tobacco withdrawal: a critique and proposed revisions for DSM-5. Addiction. 2012;107(2):263-275.
Baker et al. Investigating Changes in Reward-Related Neural Correlates After Peers Intervention in Adolescents With ASD: Preliminary Evidence of a "Precision Medicine" Approach. Front Psychiatry. 2021; 12:742280.
Barrett et al. Validation of the revised Mystical Experience Questionnaire in experimental sessions with psilocybin. J Psychopharmacol. 2015;29(11):1182-1190.
Baumann et al. 3,4-Methylenedioxymethamphetamine (MDMA) neurotoxicity in rats: a reappraisal of past and present findings. Psychopharmacology (Berl). 2007;189(4):407-424.
Baumann et al. Potentially Mistaking Enantiomers for Different Compounds Due to the Self-Induced Diastereomeric Anisochronism (SIDA) Phenomenon. Symmetry. 2020;12(7):1106.
Berge et al., Pharmaceutical Salts. J.Pharm. Sci., 1977;66:1-19.
Bhanji & Delgado. The social brain and reward: social information processing in the human striatum. Wiley Interdiscip Rev Cogn Sci. 2014;5(1):61-73.
Bogenschutz & Forcehimes. Development of a psychotherapeutic model for psilocybin-assisted treatment of alcoholism. J Humanist Psychol. 2017;57:389-414.
Brambilla et al. GABAergic dysfunction in mood disorders. Mol Psychiatry. 2003;8(8):721-715.
Carhart-Harris & Nutt. Experienced drug users assess the relative harms and benefits of drugs: a web-based survey. J Psychoactive Drugs. 2013;45(4):322-328.
Carhart-Harris et al. Neural correlates of the psychedelic state as determined by fMRI studies with psilocybin. Proc Natl Acad Sci U S A. 2012;109(6):2138-2143.
Carter et al. The Vineland Adaptive Behavior Scales: supplementary norms for individuals with autism. J Autism Dev Disord. 1998;28(4):287-302.
Carvalho et al. Mechanisms Underlying the Hepatotoxic Effects of Ecstasy. Curr. Pharm. Biotechnol., 2010;11(5):476-95.
Carvalho et al. Metabolism is required for the expression of ecstasy-induced cardiotoxicity in vitro. Chem Res Toxicol. 2004;17(5):623-632.
Chaliha et al. A Systematic Review of the MDMA Model to Address Social Impairment in Autism. Curr Neuropharmacol. 2021;19(7):1101-1154.
Chan FK, et al., Programmed Necrosis in the Cross Talk of Cell Death and Inflammation, Annu Rev Immunol. 2015;33:79-10.
Chefer VI, et al., Curr Protoc Neurosci. 2009; Chapter: Unit 7.1.
Chi et al. Neuronal cell death mechanisms in major neurodegenerative diseases, Int J Mol Sci. 2018;19(10):3082.
Chou & Talalay. Quantitative analysis of dose-effect relationships: the combined effects of multiple drugs or enzyme inhibitors. Adv Enzyme Regul. 1984;22:27-55.
Cordero-Erausquin et al. Nicotinic receptor function: new perspectives from knockout mice. Trends Pharmacol Sci. 2000;21(6):211-217.
Costa & Golembiowska. Neurotoxicity of MDMA: Main effects and mechanisms. Exp Neurol. 2022;347:113894.
Costa G, et al., Activation of Antioxidant and Proteolytic Pathways in the Nigrostriatal Dopaminergic System After 3,4-Methylenedioxymethamphetamine Administration: Sex-Related Differences, Front Pharmacol. 2021;12:713486.

(56) References Cited

OTHER PUBLICATIONS

Curry et al. Separating the agony from ecstasy: R(−)-3,4-methylenedioxymethamphetamine has prosocial and therapeutic-like effects without signs of neurotoxicity in mice. Neuropharmacology. 2018;128:196-206.

Danforth et al. Reduction in social anxiety after MDMA-assisted psychotherapy with autistic adults: a randomized, double-blind, placebo-controlled pilot study. Psychopharmacology (Berl). 2018;235(11):3137-3148.

Darvesh AS, et al., In vivo brain microdialysis: advances in neuropsychopharmacology and drug discovery. Expert Opin Drug Discov. 2011; 6(2): 109-27.

Davis et al. The Economic Burden of Posttraumatic Stress Disorder in the United States From a Societal Perspective. J Clin Psychiatry. 2022;83(3):21m14116.

De La Torre et al. MDMA, methamphetamine, and CYP2D6 pharmacogenetics: what is clinically relevant?. Front Genet. 2012;3:235.

De La Torre et al. Non-linear pharmacokinetics of MDMA ('ecstasy') in humans. Br J Clin Pharmacol. 2000;49(2):104-109.

Deci. Effects of Externally Mediated Rewards on Intrinsic Motivation. Journal of Personality and Social Psychology. 1971;18:105-115.

Diana M. The dopamine hypothesis of drug addiction and its potential therapeutic value. Front Psychiatry. 2011;2:64. Published Nov. 29, 2011.

Dittrich A. The standardized psychometric assessment of altered states of consciousness (ASCs) in humans. Pharmacopsychiatry. 1998;31 Suppl 2:80-84.

Dugger BN & Dickson DW, Pathology of Neurodegenerative Diseases. Cold Spring Harb Perspect Biol. 2017;9(7):a028035.

Elyse. "Hippie Flipping: What to Know About Mixing MDMA and Mushrooms," Double Blind. Updated Oct. 27, 2021. Accessed Jul. 3, 2022.

Fallon et al. Stereospecific analysis and enantiomeric disposition of 3, 4-methylenedioxymethamphetamine (Ecstasy) in humans. Clin Chem. 1999;45(7):1058-1069.

Fantegrossi et al. Pharmacological characterization of the effects of 3,4-methylenedioxymethamphetamine ("ecstasy") and its enantiomers on lethality, core temperature, and locomotor activity in singly housed and crowded mice. Psychopharmacology (Berl). 2003;166(3):202-211.

Fattore et al. Analysis of Opioid-Seeking Behavior Through the Intravenous Self-Administration Reinstatement Model in Rats. Methods Mol Biol. 2021;2201:231-245.

Fields & Margolis. Understanding opioid reward. Trends Neurosci. 2015;38(4):217-225.

Fitzgerald et al. Stereoselective pharmacokinetics of 3,4-methylenedioxymethamphetamine in the rat. Chirality. 1990;2(4):241-248.

Foster & Weinshenker. Neural Mechanisms of Addiction. 2019; 221-236.

Frau L, et al., Effect of crowding, temperature and age on glia activation and dopaminergic neurotoxicity induced by MDMA in the mouse brain, Neurotoxicology. 2016;56:127-38.

Frau L, et al., Microglial and astroglial activation by 3,4-methylenedioxymethamphetamine (MDMA) in mice depends on S(+) enantiomer and is associated with an increase in body temperature and motility. J. Neurochem., 2013;124(1):69-78.

Fredrickson BL. The role of positive emotions in positive psychology. The broaden-and-build theory of positive emotions. Am Psychol. 2001;56(3):218-226.

Galaj et al. Dopamine D3 receptor-based medication development for the treatment of opioid use disorder: Rationale, progress, and challenges. Neurosci Biobehav Rev. 2020;114:38-52.

Gift AG. Visual analogue scales: measurement of subjective phenomena. Nurs Res. 1989;38(5):286-288.

Glennon R, Arylalkylamine Drugs of Abuse: An Overview of Drug Discrimination Studies, Pharmacology Biochemistry and Behavior, 1999; 64, 251-56.

* cited by examiner
† cited by third party

R-MDMA

S-MDMA

SAFER PSYCHOACTIVE COMPOSITIONS

CROSS-REFERENCE

This application is a national stage entry under 35 U.S.C. § 371 of International Application No. PCT/US22/36427, filed Jul. 7, 2022, which claims priority under PCT Article 8(1) and Rule 4.10 to U.S. Provisional Application No. 63/219,302, filed Jul. 7, 2021, both of which are incorporated by reference for all purposes as if fully set forth herein.

FIELD OF THE INVENTION

The present disclosure relates in some aspects to therapeutic combinations comprising hallucinogenic agents and entactogenic agents, and compositions comprising such combinations. In some aspects, the disclosure further relates to methods of using the disclosed therapeutic combinations and compositions thereof, for example, to treat a condition in a subject. In some embodiments, the condition is a disease or a disorder, such as a mental health condition, a substance abuse disorder, or a condition that features impaired social reward or social cognition, such as social anxiety and autism. In some aspects, features of the combinations, for example, comprising a hallucinogen and a non-racemic entactogen, and compositions thereof include neuromodulation that facilitates an absence of neurotoxicity or a reduction in neurotoxic effects, and reduced potential for abuse, such as reduced affinity for transporters of dopamine (DAT) and norepinephrine (NET). In some aspects, features of the combinations, for example, comprising a hallucinogen and a non-racemic entactogen, and compositions thereof include improvements in subjective experience upon administration to a subject, as determined using various measures of mystical experiences, positive affect, and negative affect. In some embodiments, such enhanced subjective experiences improve treatment efficacy and/or extend therapeutic window.

BACKGROUND OF THE INVENTION

Various strategies are available for using certain hallucinogens and entactogens in the treatment of different conditions, such as mental health conditions. For example, strategies are available for administering a hallucinogen and an entactogen to a subject. Improved strategies are necessary, for example, to improve the subjective experience, safety, e.g., to reduce neurotoxic effects and abuse potential, and therapeutic efficacy of such compounds, including when used as part of drug-assisted therapy. Provided are therapeutic combinations, pharmaceutical compositions, kits, and methods that meet these and other needs.

INCORPORATION BY REFERENCE

Each cited patent, publication, and non-patent literature is hereby incorporated by reference in its entirety as if each was incorporated by reference individually. Unless specifically stated otherwise, reference to any document herein is not to be construed as an admission that the document referred to or any underlying information in the document is prior art in any jurisdiction, or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments in a simplified form as a prelude to the detailed description that follows.

In some aspects are provided therapeutic combinations comprising a hallucinogenic agent and an entactogenic agent. In some embodiments, the hallucinogenic agent is selected from a substituted phenethylamine hallucinogen, substituted tryptamine hallucinogen, semi-synthetic alkaloid, and lysergamide; and the entactogenic agent is selected from a substituted amphetamine, substituted benzofuran, substituted phenethylamine entactogen, and substituted tryptamine entactogen.

In some embodiments, the hallucinogenic agent is selected from a 2C-X compound, psilocybin, psilocin, DMT, 5-MeO-DMT, mescaline, salvinorin A, THC, 4-Aco-DMT, 5-Br-DMT, 5-C-DMT, 5-F-DMT, 4,5-MDO-DMT, 4,5-MDO-DiPT, PRO-LAD, ETH-LAD, AL-LAD, 1P-LSD, LSD, DiPT, and salts and derivatives thereof; and the entactogenic agent is selected from R-MDMA, S-MDMA, racemic MDMA, non-racemic MDMA, 4-MTA, MDAI, 5-methyl-MDA, 5-APB, 6-APB, DiFMDA, MBDB, BDB, MDA, MDEA, R-MDEA, S-MDEA, and salts and derivatives thereof.

In some embodiments, the 2C-X compound is selected from the group consisting essentially of 2C-B, 2C-B-AN, 2C-B-FLY, 2C-B-BUTTERFLY, 2C-B-FLY-NBOMe, 2C-B-FLY-NB2EtO5Cl, 2C-Bn, 2C-Bu, 2C-B-5-HEMIFLY, 2C-C, 2C-C-3, 2C-CN, 2C-CP, 2C-D, 2C-E, 2C-EF, 2C-F, 2C-G, 2C-G-1, 2C-G-2, 2C-G-3, 2C-G-4, 2C-G-5, 2C-G-6, 2C-G-N, 2C-H, 2C-I, 2CB-Ind, 2C-iP, 2C-N, 2C-NH2, 2C-PYR, 2C-PIP, 2C-O, 2C-O-4, 2C-MOM, 2C-P, 2C-Ph, 2C-Se, 2C-T, 2C-T-2, 2C-T-3, 2C-T-4, 2C-T-5, 2C-T-6, 2C-T-7, 2C-T-8, 2C-T-9, 2C-T-10, 2C-T-11, 2C-T-12, 2C-T-13, 2C-T-14, 2C-T-15, 2C-T-16, 2C-T-17, 2C-T-18, 2C-T-19, 2C-T-21, 2C-T-21.5, 2C-T-22, 2C-T-23, 2C-T-24, 2C-T-25, 2C-T-27, 2C-T-28, 2C-T-30, 2C-T-31, 2C-T-32, 2C-T-33, 2C-DFM, 2C-TFM, 2C-TFE, 2C-YN, 2C-V, and 2C-AL. In some embodiments, the 2C-X compound is 2C-B.

In some embodiments, the entactogenic agent is non-racemic MDMA or a salt thereof comprising: an enantiomeric excess of R-MDMA; or an enantiomeric excess of S-MDMA.

In some embodiments, the enantiomeric excess of R-MDMA is 90% or less. In some embodiments, the enantiomeric excess of R-MDMA is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the enantiomeric excess of R-MDMA is about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the enantiomeric excess of R-MDMA is about 10%, 15%, 20%, 25%, 30%, 35%, 40%, 45%, 50%, 55%, 60%, 65%, 70%, 75%, 80%, 85%, 90%, or 95%. In some embodiments, the enantiomeric excess of R-MDMA is about 75%, 76%, 77%, 78%, 79%, 80%, 81%, 82%, 83%, 84%, or 85%. In some embodiments, the enantiomeric excess of R-MDMA is about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, the enantiomeric excess of R-MDMA is about 79.5%, 79.6%, 79.7%, 79.8%, 79.9%, 80%, 80.1%, 80.2%, 80.3%, 80.4%, or 80.5%. In some embodiments, the R-MDMA in enantiomeric excess comprises R-MDMA to S-MDMA in a ratio of about 6:1 to 12:1, 7:1 to 11:1, or 8:1 to 10:1. In some embodiments, the R-MDMA in enantiomeric excess comprises R-MDMA to S-MDMA in a ratio of about 6:1, 7:1, 8:1, 9:1, 10:1, 11:1, or 12:1. In some embodiments, the R-MDMA in enantiomeric excess comprises R-MDMA to S-MDMA in a ratio of 9:1. In some embodiments, the enantiomeric excess of R-MDMA is within 0.05% of 90%, or within 0.1% of 90%.

In some embodiments, the salt is a hydrochloride, sulfate, tartrate, sodium, acetate, phosphate, chloride, or potassium salt. In some embodiments, the salt of R-MDMA and the salt of S-MDMA are the same. In some embodiments, the salt of R-MDMA and the salt of S-MDMA are different.

In some aspects are provided combinations comprising R-MDMA HCl and S-MDMA HCl in a ratio of about 6:1, 7:1, 8:1, 9:1, 10:1, 11:1, or 12:1. In some embodiments, the R-MDMA HCl and S-MDMA HCl are in a ratio of 9:1. In some embodiments, the R-MDMA HCl is in enantiomeric excess of within 0.05% of 90%, or within 0.1% of 90%.

In some embodiments, the hallucinogenic agent is selected from psilocybin, psilocin, DMT, 5-MeO-DMT, mescaline, salvinorin A, THC, 4-Aco-DMT, 5-Br-DMT, 5-Cl-DMT, 5-F-DMT, 4,5-MDO-DMT, 4,5-MDO-DiPT, PRO-LAD, ETH-LAD, AL-LAI), 1P-LSD, LSD, DiPT, 2C-B, 2C-C, 2C-D, 2C-E, 2C-F, 2C-G, 2C-H, 2C-I, 2C-N, 2C-O, 2C-P, 2C-Se, 2C-T, 2C-V and salts and derivatives thereof; and the entactogenic agent is non-racemic MDMA or a salt thereof comprising R-MDMA and S-MDMA in a ratio of about 6:1, 7:1, 8:1, 9:1, 10:1, 11:1, or 12:1.

In some embodiments, the combination is selected from psilocybin and 9:1 R:S-MDMA, psilocin and 9:1 R:S-MDMA, DMT and 9:1 R:S-MDMA, 5-MeO-DMT and 9:1 R: S-MDMA, mescaline and 9:1 R: S-MDMA, salvinorin A and 9:1 R:S-MDMA, THC and 9:1 R: S-MDMA, 4-Aco-DMT and 9:1 R:S-MDMA, 5-Br-DMT and 9:1 R:S-MDMA, 5-Cl-DMT and 9:1 R:S-MDMA, 5-F-DMT and 9:1 R:S-MDMA, 4,5-MDO-DMT and 9:1 R:S-MDMA, 4,5-MDO-DiPT and 9:1 R:S-MDMA, PRO-LAD and 9:1 R:S-MDMA, ETH-LAD and 9:1 R:S-MDMA, AL-LAD and 9:1 R:S-MDMA, 1P-LSD and 9:1 R:S-MDMA, LSD and 9:1 R:S-MDMA, DiPT and 9:1 R: S-MDMA, 2C-B or an analog thereof and 9:1 R: S-MDMA, 2C-C or an analog thereof and 9:1 R: S-MDMA, 2C-D or an analog thereof and 9:1 R: S-MDMA, 2C-E or an analog thereof and 9:1 R: S-MDMA, 2C-F or an analog thereof and 9:1 R:S-MDMA, 2C-G or an analog thereof and 9:1 R:S-MDMA, 2C-H or an analog thereof and 9:1 R:S-MDMA, 2C-I or an analog thereof and 9:1 R:S-MDMA, 2C-N or an analog thereof and 9:1 R:S-MDMA, 2C-O or an analog thereof and 9:1 R: S-MDMA, 2C-P or an analog thereof and 9:1 R: S-MDMA, 2C-Se or an analog thereof and 9:1 R: S-MDMA, 2C-T or an analog thereof and 9:1 R: S-MDMA, and 2C-V or an analog thereof and 9:1 R:S-MDMA.

In some embodiments, the hallucinogenic agent is selected from psilocybin, psilocin, DMT, 5-MeO-DMT, mescaline, LSD, 2C-B, 2C-B-FLY, 2C-B-dragonFLY, 3C-B-FLY, 2C-B-hemiFLY-2, 2C-B-hemiFLY-5, 2C-B-hemidragonFLY-2, and Bromo-dragonFLY; and the entactogenic agent is 9:1 R:S-MDMA or a salt thereof.

In some embodiments, the salt of 9:1 R:S-MDMA is a hydrochloride, sulfate, tartrate, sodium, acetate, phosphate, chloride, or potassium salt. In some embodiments, the combination is selected from psilocybin and 9:1 R:S MDMA HCl, psilocin and 9:1 R:S MDMA HCl, DMT and 9:1 R:S MDMA HCl, 5-MeO-DMT and 9:1 R:S MDMA HCl, mescaline and 9:1 R:S MDMA HCl, LSD and 9:1 R:S MDMA HCl, 2C-B and 9:1 R:S MDMA HCl, 2C-B-FLY and 9:1 R:S MDMA HCl, 2C-B-dragonFLY and 9:1 R: S MDMA HCl, 3C-B-FLY and 9:1 R:S MDMA HCl, 2C-B-hemiFLY-2 and 9:1 R: S MDMA HCl, 2C-B-hemiFLY-5 and 9:1 R:S MDMA HCl, 2C-B-hemidragonFLY-2 and 9:1 R:S MDMA HCl, and Bromo-dragonFLY and 9:1 R:S MDMA HCl. In some embodiments, the combination is selected from psilocybin and 9:1 R:S MDMA sulfate, psilocin and 9:1 R:S MDMA sulfate, DMT and 9:1 R:S MDMA sulfate, 5-MeO-DMT and 9:1 R:S MDMA sulfate, mescaline and 9:1 R:S MDMA HCl, LSD and 9:1 R:S MDMA sulfate, 2C-B and 9:1 R:S MDMA sulfate, 2C-B-FLY and 9:1 R: S MDMA sulfate, 2C-B-dragonFLY and 9:1 R: S MDMA sulfate, 3C-B-FLY and 9:1 R: S MDMA sulfate, 2C-B-hemiFLY-2 and 9:1 R:S MDMA sulfate, 2C-B-hemiFLY-5 and 9:1 R:S MDMA sulfate, 2C-B-hemidragonFLY-2 and 9:1 R:S MDMA sulfate, and Bromo-dragonFLY and 9:1 R: S MDMA sulfate.

In some aspects are provided pharmaceutical compositions for administration to a subject, comprising a hallucinogenic agent and an entactogenic agent, such as a non-racemic entactogen, wherein administration of the composition produces at least one improved physiological or psychological effect relative to a comparator, wherein the comparator is either the hallucinogenic agent or the entactogenic agent alone.

In some embodiments, the improved physiological or psychological effect is selected from: a reduction in nausea and vomiting, an improved pharmacokinetic profile, a reduction in subjective body load during the therapeutic window, an improvement in the subjective valence of the experience, an improvement in feelings of positive affect, an increase in the therapeutic window, an improvement in behavioral integration, a reduction of anxiety, a reduction in addictive liability or abuse potential, a reduction in neurotoxicity, a reduction in hyperthermia or hypothermia, and a reduction in stimulation.

In some embodiments, the therapeutic combination or pharmaceutical composition further comprises an anti-nausea agent. In some embodiments, the anti-nausea agent is ondansetron, promethazine, promethazine, metoclopramide, prochlorperazine, or lorazepam.

In some embodiments, the therapeutic combination or pharmaceutical composition further comprises an agent for the treatment of serotonin syndrome. In some embodiments, the agent for the treatment of serotonin syndrome is clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, midazolam, clobazam, or cyproheptadine.

In some embodiments, the therapeutic combination or pharmaceutical composition further comprises an oxytocin-releasing agent. In some embodiments, the oxytocin-releasing agent is selected from a MC receptor agonist, a MSH, α-melanocortin, α-melanotropin, MT-11, bremelanotide, a 5-$HT_{1A}$ agonist, a 5-$HT_{2A}$ agonist, a 5-$HT_{2C}$ agonist, 6-APDB, 6-APB, flesinoxan, osemozotan, buspirone, gepirone, befiradol, eptapirone, 8-OH-DPAT, tandospirone, serotonin, ergine, ergotamine, lysergic acid, LSD, psilocybin, psilocin, DMT, 5-MeO-DMT, mescaline, an entactogen, 2C-B, MDA, MDEA, MMDA, MDMA, tenamfetamine, or lorcaserin, or a salt or derivative thereof.

In some embodiments, the therapeutic combination or pharmaceutical composition further comprises one or more additional active compounds selected from the group consisting of: amino acids, antioxidants, anti-inflammatory agents, analgesics, antineuropathic and antinociceptive agents, antimigraine agents, anxiolytics, antidepressants, antipsychotics, anti-PTSD agents, immunostimulants, anticancer agents, antiemetics, orexigenics, antiulcer agents, antihistamines, antihypertensives, anticonvulsants, antiepileptics, bronchodilators, neuroprotectants, nootropics, entactogens and empathogens, entheogens, psychedelics, monoamine oxidase inhibitors, sedatives, sleep aids, ADHD drugs, supplements, stimulants, and vitamins.

In some embodiments, the composition is suitable for oral, mucosal, rectal, subcutaneous, intravenous, intramuscular, intranasal, inhaled, or transdermal administration. In some embodiments, the composition is in a unit dosage form. In some embodiments, the composition is an immediate release, controlled release, sustained release, extended release, delayed release, or modified release formulation.

In some aspects are provided methods of administering a hallucinogenic agent and an entactogenic agent to a subject, comprising administering a first dosage form comprising the hallucinogenic agent to the subject and a second dosage form comprising the entactogenic agent to the subject. In some embodiments, the first dosage form and the second dosage form are selected from any of an oral dosage form for oral administration, a mucosal dosage form for sublingual, buccal, intranasal, or rectal administration, a vaporizable dosage form for inhalation, and a parenteral dosage form for injection. In some embodiments, the first dosage form and the second dosage form are formulated for different routes of administration. In some embodiments, the mucosal dosage form for sublingual, buccal, intranasal, or rectal administration is selected from a solution, a film or strip, a tablet, a lozenge, and a suppository. In some embodiments, the oral dosage form for oral administration is selected from a solution, a tablet, a capsule, a lozenge, and a film or strip.

In some embodiments, the first dosage form comprising the hallucinogenic agent is a mucosal dosage form for sublingual, buccal, intranasal, or rectal administration; and the second dosage form comprising the entactogenic agent is an oral dosage form for oral administration. In some embodiments, the first dosage form comprising the hallucinogenic agent is an oral dosage form for oral administration; and the second dosage form comprising the entactogenic agent is a mucosal dosage form for sublingual, buccal, intranasal, or rectal administration. In some embodiments, the first dosage form comprising hallucinogenic agent and the second dosage form comprising the entactogenic agent are administered simultaneously. In some embodiments, the first dosage form comprising hallucinogenic agent and the second dosage form comprising the entactogenic agent are administered sequentially. In some embodiments, the hallucinogenic agent is administered prior to administering non-racemic MDMA. In some embodiments, the hallucinogenic agent is administered after administering non-racemic MDMA. In some embodiments, administering the first dosage form comprising hallucinogenic agent and administering the second dosage form comprising the entactogenic agent is separated by about 0.25 to 6 hours, 0.5 to 5.5 hours, 1 to 5 hours, 1.5 to 4.5 hours, 2 to 4 hours, or 2.5 to 3.5 hours.

In some embodiments, administering the first and the second dosage form produces at least one improved physiological or psychological effect relative to administration of any one of i) the hallucinogenic agent alone; ii) non-racemic MDMA alone; and iii) the hallucinogenic agent and racemic MDMA.

In some aspects are provided methods of administering a therapeutic combination comprising a hallucinogenic agent and non-racemic MDMA to a subject, wherein the combination produces at least one improved physiological or psychological effect relative to administration of any one of i) the hallucinogenic agent alone; ii) non-racemic MDMA alone; and iii) the hallucinogenic agent and racemic MDMA. In some embodiments, the combination produces at least one improved physiological or psychological effect relative to administration of the hallucinogenic agent and racemic MDMA.

In some embodiments, the hallucinogenic agent and non-racemic MDMA are administered simultaneously. In some embodiments, the hallucinogenic agent and non-racemic MDMA are administered sequentially. In some embodiments, administering the dose of the hallucinogenic agent and administering the dose of non-racemic MDMA is separated by about 0.25 to 6 hours, 0.5 to 5.5 hours, 1 to 5 hours, 1.5 to 4.5 hours, 2 to 4 hours, or 2.5 to 3.5 hours. In some embodiments, the hallucinogenic agent is administered prior to administering non-racemic MDMA. In some embodiments, the hallucinogenic agent is administered after administering non-racemic MDMA.

In some aspects are provided methods of administering a therapeutic combination comprising a hallucinogenic agent and non-racemic MDMA, wherein R-MDMA or a salt thereof is present in enantiomeric excess, to a subject, wherein the administering produces an enhanced subjective experience in said subject relative to administering a comparator combination comprising the same hallucinogen and racemic MDMA. In some embodiments, the enhanced subjective experience comprises greater scores on one or more of the Hallucinogenic Rating Scale, the Mystical Experiences Questionnaire, or the 5 Dimensions of Altered States of Consciousness' (5D-ASC) Oceanic Boundlessness scale compared to the scores observed following administration of the hallucinogen alone, the entactogen alone, or the comparator combination comprising the same hallucinogen and racemic MDMA. In some embodiments, the enhanced subjective experience comprises lower scores on 5 Dimensions of Altered States of Consciousness' (5D-ASC) Anxious Ego Dissolution scale relative to the score reported following administration of a hallucinogen alone, the entactogen alone, or the comparator combination comprising the same hallucinogen and racemic MDMA. In some embodiments, the enhanced subjective experience comprises: a) a greater score one or more of the Hallucinogen Rating Scale, the Mystical Experiences Questionnaire, and the 5 Dimensions of Altered States of Consciousness' (5D-ASC) Oceanic Boundlessness scale; and b) a lower score on the 5 Dimensions of Altered States of Consciousness' (5D-ASC) Anxious Ego Dissolution scale; compared to the scores reported following administration of the hallucinogen alone, the entactogen alone, or the comparator combination comprising the same hallucinogen and racemic MDMA. In some embodiments, administering a reduced dose of a hallucinogenic agent in combination with non-racemic MDMA, wherein R-MDMA or a salt thereof is present in enantiomeric excess, produces an enhanced subjective experience. In some embodiments, the enhanced subjective experience improves treatment efficacy.

In some embodiments, the dose of the hallucinogen is reduced by at least 10%, at least 15%, at least 20%, at least 25%, at least 30%, at least 35%, at least 40%, at least 45%, or at least 50%, relative to an effective dose of the hallucinogen alone or in the comparator combination comprising the same hallucinogen and racemic MDMA. In some embodiments, the dose of the hallucinogen is reduced by about 10% to 75%, 15% to 50%, or 20 to 45% relative to an effective dose of the hallucinogen alone or in the comparator combination comprising the same hallucinogen and racemic MDMA. In some embodiments, the dose of the hallucinogen is reduced by about 10%, 20%, 30%, 40%, or 50% relative to an effective dose of the hallucinogen alone or in the comparator combination comprising the same hallucinogen and racemic MDMA.

In some embodiments, administering the combination does not cause neurotoxic effects or results in reduced neurotoxic effects relative to administration of a comparator combination comprising the same hallucinogen and racemic MDMA. In some embodiments, an absence or reduction of neurotoxic effects is determined by tests and procedures that are conducted in silico, in vitro, or in vivo. In some embodiments, the absence or reduction of neurotoxic effects is determined by computer analysis or simulation; by biochemical assays or tissue culture; or by behavioral assessment, functional observational batteries, tests of motor activity, tests of schedule-controlled operant behavior, tests of neurological function, tests of neurophysiological function, tests of nerve-conduction, tests of evoked-potential, neurochemical measures, neuroendocrine measures, neuropathological measures, EEG, or imaging. In some embodiments, the absence or the reduction of neurotoxic effects is evidenced by determining any one or more of: a) the level of at least one toxic metabolite of MDMA; b) oxidative stress and dopamine-based quinones; c) mitochondrial dysfunction; and d) activation of glial cells. In some embodiments, the reduction of a neurotoxic effect is at least a 5% reduction, at least a 10% reduction, at least a 15% reduction, at least a 25% reduction, at least a 50% reduction, at least a 75% reduction, at least a 90% reduction, at least a 95% reduction, at least a 99% reduction, or a 100% reduction relative to administration of a comparator combination comprising the same hallucinogen and racemic MDMA.

In some embodiments, the administering modulates neurotransmission in the subject. In some embodiments, the neurotransmission is one or more of serotonergic neurotransmission, dopaminergic neurotransmission, and noradrenergic neurotransmission. In some embodiments, the serotonergic neurotransmission comprises agonizing 5-$HT_{2A}$ and/or binding to SERT, thereby increasing levels of serotonin in the CNS, and wherein serotonergic neurotransmission is increased relative to that of R-MDMA.

In some embodiments, the therapeutic combination comprising the hallucinogen and non-racemic MDMA, wherein R-MDMA or a salt thereof is present in enantiomeric excess, has reduced affinity for DAT and/or NET, as compared to the comparator combination comprising the same hallucinogen and racemic MDMA. In some embodiments, the reduced affinity for DAT and/or NET reduces abuse potential relative to racemic MDMA.

In some embodiments, the modulating neurotransmission comprises agonizing an alpha-4 beta-2 nicotinic receptor ($\alpha4\beta2$ nAChR). In some embodiments, the therapeutic combination comprising a hallucinogenic agent and non-racemic MDMA, wherein R-MDMA or a salt thereof is present in enantiomeric excess, has comparable or greater potency at $\alpha4\beta2$ nAChR relative to the comparator combination comprising the same hallucinogen and racemic MDMA.

In some embodiments, the administering does not change the subject's body temperature or does not change the subject's body temperature by more than 0.1° C., 0.2° C., or 0.3° C. In some embodiments, the administering does not increase the subject's body temperature or does not increase the subject's body temperature by more than 0.1° C., 0.2° C., or 0.3° C. In embodiments, the administering does not cause hyperthermia in the subject. In some embodiments, the administering does not reduce the subject's body temperature or does not increase the subject's body temperature by more than 0.1° C., 0.2° C., or 0.3° C. In embodiments, the administering does not cause hypothermia in the subject.

In some embodiments, the administering treats a disorder in the subject. In some embodiments, the disorder is a mental health disorder. In some embodiments, the mental health disorder is selected from depression, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, anxiety and phobia disorders, generalized anxiety disorder (GAD), agoraphobia, panic disorder, separation anxiety disorder, social anxiety disorder, post-traumatic stress disorder, adjustment disorders, feeding and eating disorders, including binge eating, bulimia, and anorexia nervosa, other binge behaviors, body dysmorphic syndromes, drug abuse or dependence disorders, disruptive behavior disorders, impulse control disorders, gaming disorders, gambling disorders, memory loss, dementia of aging, attention deficit hyperactivity disorder, personality disorders, including antisocial, avoidant, borderline, histrionic, narcissistic, obsessive compulsive, paranoid, schizoid and schizotypal personality disorders, attachment disorders, autism, social anxiety in autistic subject, and dissociative disorders. In some embodiments, the mental health disorder is any one or more of PTSD, generalized anxiety disorder (GAD), social anxiety disorder, depression, major depressive disorder (MDD), and treatment-resistant depression (TRD). In some embodiments, the mental health disorder is PTSD.

In some embodiments, the disorder is a neurodegenerative disorder. In some embodiments, the neurodegenerative disorder is selected from dementia, Alzheimer's disease, Huntington's disease, multiple sclerosis, and Parkinson's disease. In some embodiments, the disorder is a substance abuse disorder. In some embodiments, the substance abuse disorder is selected from the group consisting of alcohol use disorder, opioid use disorder, nicotine dependence and tobacco use disorder, a sedative, hypnotic, and anxiolytic use disorder, and a stimulant use disorder. In some embodiments, the disorder is mediated by impaired reward learning and/or social cognition. In some embodiments, the disorder is social anxiety disorder and/or an autism spectrum disorder.

In some aspects are provided methods of treating a subject in need thereof, comprising administering to the subject a pharmaceutical composition comprising a hallucinogenic agent and non-racemic MDMA, wherein R-MDMA or a salt thereof is present in enantiomeric excess. In some embodiments, the pharmaceutical composition is administered in combination with one or more psychotherapy sessions. In some embodiments, the subject has a mental health disorder. In some embodiments, the subject has a neurodegenerative disorder. In some embodiments, the subject has a substance abuse disorder. In some embodiments, the subject has a disorder that is mediated by impaired reward learning and/or social cognition.

In some aspects are provided methods of reducing the symptoms of a mental health disorder in a human, comprising administering to the human a pharmaceutical composition comprising a hallucinogenic agent and non-racemic MDMA, wherein R-MDMA of a salt thereof is present in enantiomeric excess. In some embodiments, the mental health disorder is PTSD. In some embodiments, the symptoms of PTSD are reduced and/or a PTSD diagnosis is reversed, as determined by the Clinician-Administered PTSD Scale for DSM-5 (CAPS-5). In some embodiments, the symptoms of PTSD include flashbacks, nightmares, distressing and intense memories, distress or physical reactions after being exposed to triggers, blaming self or others for the trauma, decreased interest in things that were once enjoyable, negative feelings about self and the world, inability to remember the trauma clearly, difficulty feeling positive, feelings of isolation, negative affect, difficulty feeling positive, avoidance, aggression or irritability, hypervigilance and hyper-awareness, difficulty concentrating, difficulty sleeping, heightened startle response, engaging in self-destructive, or risky behavior, difficulty sleeping or staying asleep, or suicidal ideation.

In some aspects are provided methods of managing emotional regulation in a subject in need thereof, comprising administering to the subject a pharmaceutical composition comprising a hallucinogenic agent and non-racemic MDMA, wherein R-MDMA or a salt thereof is present in enantiomeric excess. In some embodiments, the subject has at least one of a stress disorder, acute stress disorder, brief psychotic disorder with marked stressor(s), delirium, mild cognitive impairment (MCI), dementia, psychosis, psychotic major depression, autism, and psychological distress related to life-threatening illness or death. In some embodiments, the subject is in long-term or institutional care.

In some embodiments, the subject has a genetic variation associated with a mental health disorder, trauma or stressor related disorder, depression, or anxiety, and including a genetic variation in mGluR5 or FKBP5.

The foregoing has outlined broadly some pertinent features of certain exemplary embodiments of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be also realized that such equivalent structures do not depart from the spirit and scope of the invention as set forth in the appended claims. Hence, this summary has been made with the understanding that it is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled.

BRIEF SUMMARY OF THE DRAWINGS

To further clarify various aspects of the invention, a more particular description of the invention will be rendered by reference to certain exemplary embodiments thereof which are illustrated in the included figures. It should be understood and appreciated that the figures depict only illustrated embodiments of the invention and are therefore not to be considered limiting of its scope. They are simply provided as exemplary illustrations of certain concepts of some embodiments of the invention. Certain aspects of the invention are therefore further described and explained with additional specificity and detail, but still by way of example only, with reference to the accompanying figures in which.

DETAILED DESCRIPTION

Figure 1:
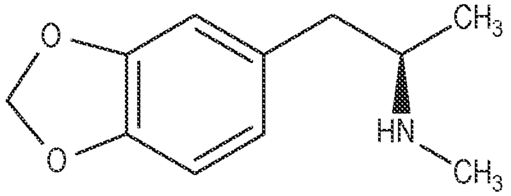
FIG. 1: structures of the R-(−) enantiomer of 3,4-methylenedioxymethamphetamine (R-MDMA) and the S-(+) enantiomer of 3,4-methylenedioxymethamphetamine (S-MDMA).
Figure 1:
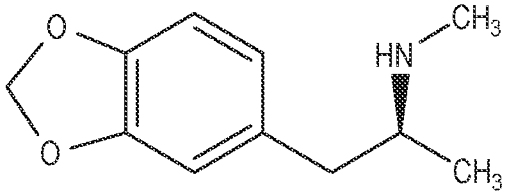
Figure 2:
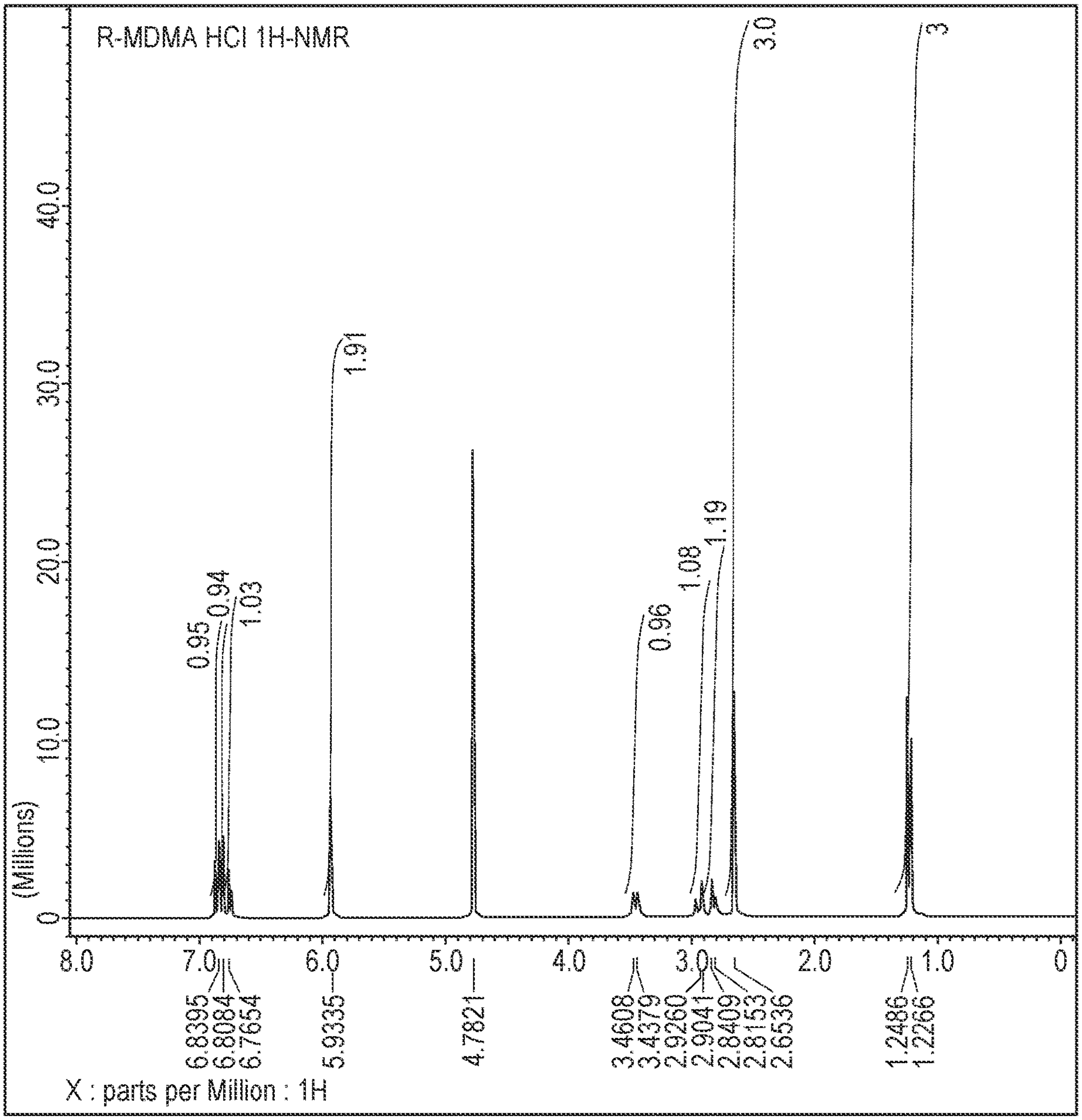
FIG. 2: 1H-NMR characterization of R-MDMA HCl.
Figure 3:
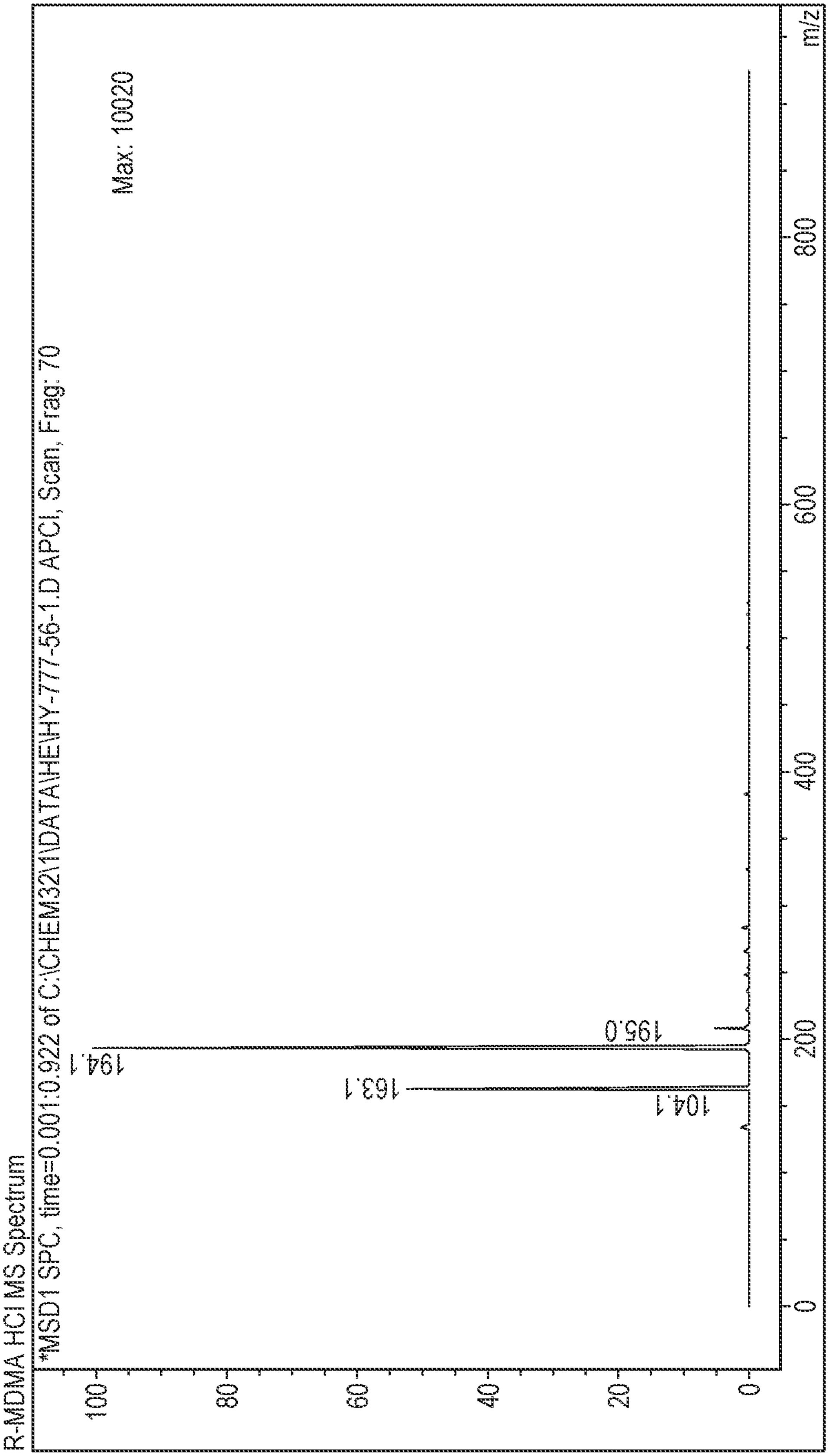
FIG. 3: atmospheric pressure chemical ionization mass spectrometry (MS) characterization of R-MDMA HCl.
Figure 4:
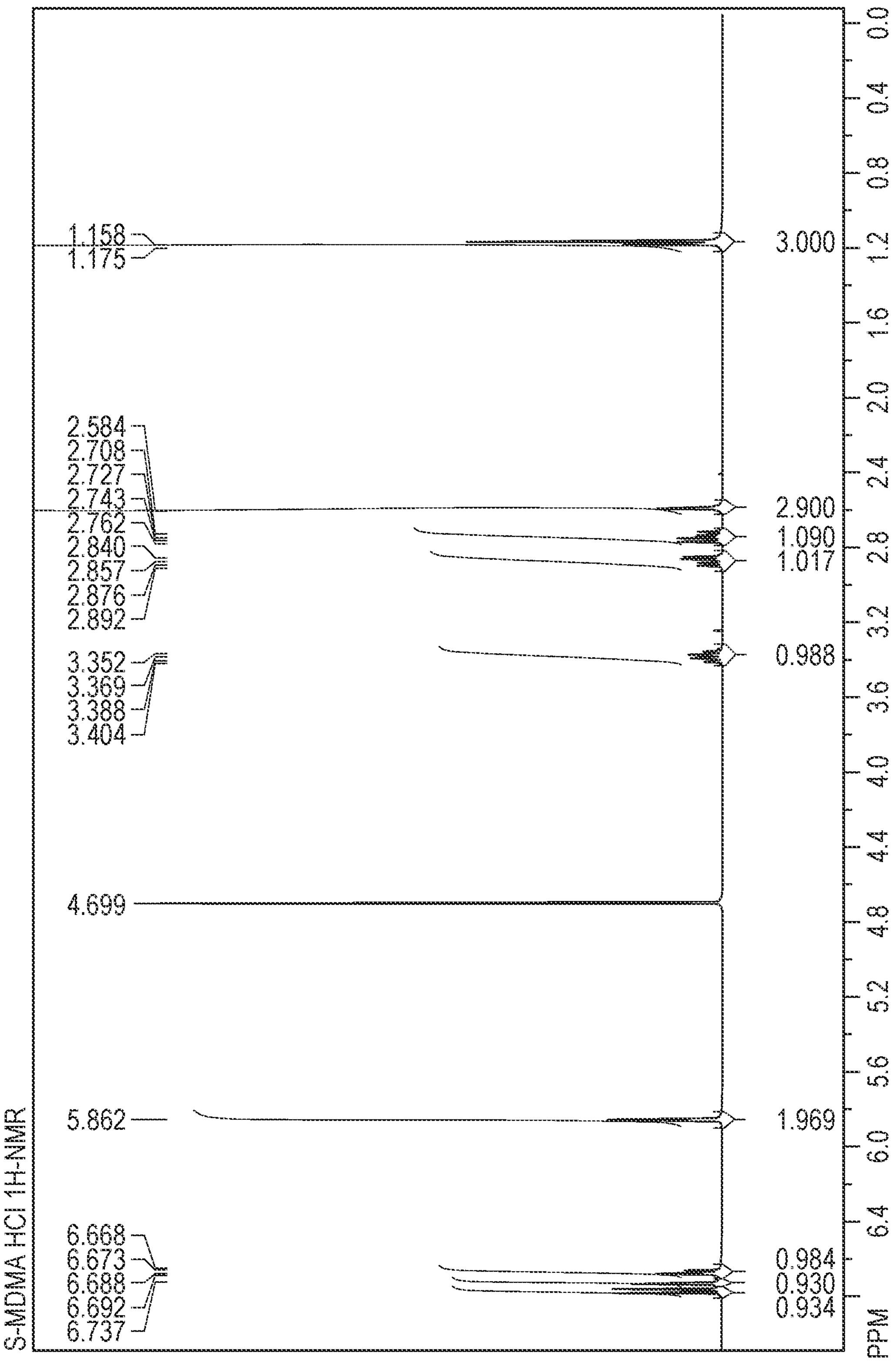
FIG. 4: 1H-NMR characterization of S-MDMA HCl.
Figure 5:
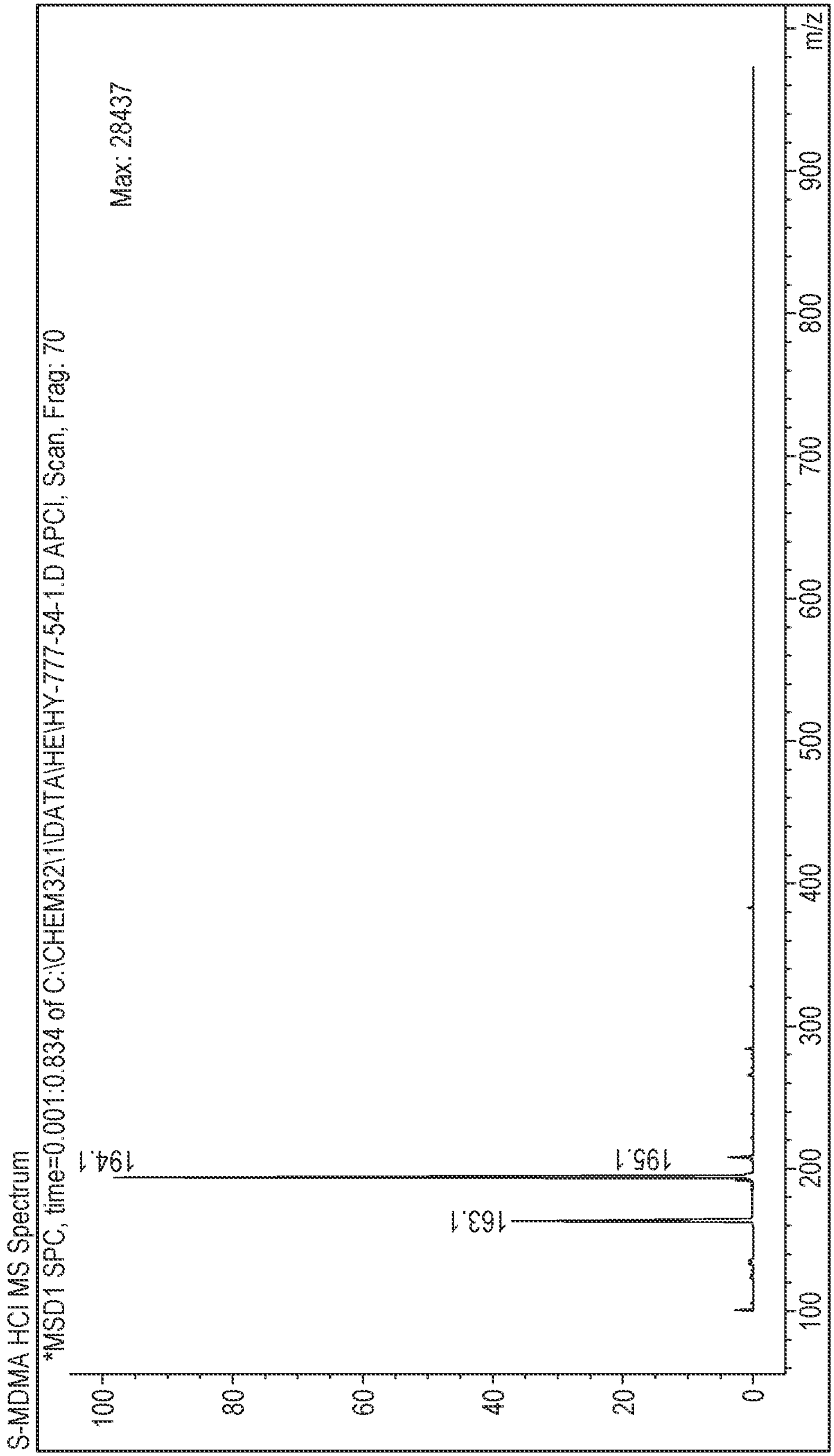
FIG. 5: atmospheric pressure chemical ionization MS of S-MDMA HCl.

While various aspects and features of certain embodiments have been summarized above, the following detailed description illustrates several exemplary embodiments in further detail to enable one of skill in the art to practice such embodiments, and to make and use the full scope of the invention claimed. The described examples are provided for illustrative purposes and are not intended to limit the scope of the invention or its applications. It will be understood that many modifications, substitutions, changes, and variations in the described examples, embodiments, applications, and details of the invention illustrated herein can be made by those skilled in the art without departing from the spirit of the invention, or the scope of the invention as described in the appended claims, and the general principles defined herein may be applied to a wide range of aspects. Thus, the invention is not intended to be limited to the aspects presented, but is to be accorded the widest scope consistent with the principles and novel features disclosed. The description below is designed to make such embodiments apparent to a person of ordinary skill, in that the embodiments shall be both readily cognizable and readily creatable without undue experimentation, solely using the teachings herein together with general knowledge of the art.

Among the various aspects of the present invention are therapeutic combinations and pharmaceutical compositions (sometimes, as shorthand, "combinations" and "compositions") of psychoactive substances comprising hallucinogenic agents and entactogenic agents.

In some embodiments, the entactogenic agent in a combination or composition comprises non-racemic MDMA, wherein R-MDMA is present in enantiomeric excess. Exemplary features of combinations and compositions comprising non-racemic MDMA, wherein the non-racemic MDMA comprises R-MDMA in enantiomeric excess, include reduced neurotoxic effects and low abuse potential, for example as mediated by reduced activity at dopamine and norepinephrine transporters relative to racemic MDMA. In addition to such advantages over racemic MDMA, non-racemic MDMA comprising R-MDMA in enantiomeric excess, modulates activity alpha-4 beta-2 nicotinic receptor ($\alpha4\beta2$ nAChR) with similar potency to MDMA, thereby for example facilitating enhanced reinforcement, behavioral integration, and reward learning. In a further advantage, combinations and compositions comprising non-racemic MDMA, wherein the non-racemic MDMA comprises R-MDMA in enantiomeric excess, facilitate mystical experiences with comparable potency to combinations and compositions comprising racemic MDMA. Moreover, in some embodiments, adverse effects such as feelings of anxiety and/or stimulation will be reduced, substantially reduced, or absent from the effects of disclosed combinations and compositions, when administered in therapeutic amounts, such as according to the disclosed methods.

When an entactogen is combined with a hallucinogen according to this disclosure, various advantages are realized, including flexibility in dosing, improved subjective effects, which may translate to enhanced therapeutic efficacy and an extended therapeutic window, physically safer therapeutic effects, e.g., a reduced potential for neurotoxicity of the entactogen, and the improvement of reward learning, such as social reward learning, and cognitive functioning. Such advantages are, for example, evident in comparison to a hallucinogen alone, an entactogen such as racemic MDMA alone, or a comparable combination comprising the hallucinogen and the entactogen, such as racemic MDMA.

The scope of the disclosed invention includes all embodiments and formulations thereof and it will be understood that many modifications, substitutions, changes, and variations in the described embodiments, applications, and details of the invention illustrated herein can be made by those skilled in the art without departing from the spirit of the invention, or the scope of the invention as described in the appended claims.

A. Compounds, Combinations, and Uses

In some aspects, provided herein are therapeutic combinations comprising a hallucinogenic agent and an entactogenic agent, where the combination results in certain desired physiological or psychological effects. In some embodiments, disclosed therapeutic combinations further comprise a dissociative agent in addition to a hallucinogenic agent and an entactogenic agent. In some embodiments, disclosed therapeutic combinations comprise a dissociative agent, in place of a hallucinogenic agent, and an entactogenic agent. In some embodiments, the entactogenic agent of a disclosed combination is a non-racemic entactogen. In some embodiments, the non-racemic entactogen is MDMA, where R-MDMA is present in enantiomeric excess. In some embodiments, the non-racemic entactogen is 9:1 R:S MDMA. Herein, the terms "having" or "is present," as they relate to enantiomeric excess, will be understood to mean that the non-racemic mixture comprises the specified degree of enantiomeric excess. For example, "a therapeutic combination comprising a hallucinogenic agent and non-racemic MDMA, wherein R-MDMA or a salt thereof is present in enantiomeric excess of 90% or less," refers to non-racemic MDMA comprising R-MDMA in enantiomeric excess of 90% or less.

"Compounds" include hallucinogenic agents, dissociative agents, and entactogenic agents. Hallucinogenic agents, dissociative agents, and entactogenic agents (alternately, as shorthand, hallucinogens, dissociatives, and entactogens), include those specifically disclosed herein, those generally known as such by one of skill in accordance with the teachings herein and the general knowledge in the art, and those encompassed by the disclosed structural formulae, including specific compounds within such formulae whose structure is disclosed herein. The compounds of the invention may be identified either by their chemical structure and/or chemical name. When the chemical structure and chemical name conflict, the chemical structure is determinative of the identity of the compound.

Methods for synthesizing disclosed compounds, and any necessary starting materials, will be readily apparent to the skilled artisan in view of this disclosure along with general references well known in the art. See, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes I-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). In general, approaches used for similar compounds may be applied or adapted, as would be known and understood to those of skill (see, e.g., Shulgin & Shulgin, PiHKAL: A Chemical Love Story, Transform Press, 1992 ("PiHKAL"); Shulgin and Shulgin, TiHKAL: The Continuation, Transform Press, 1997 ("TiHKAL"); Glennon et al., J Med Chem, 1986; 29(2), 194-199; Nichols et al., J Med Chem, 1991; 34(1), 276-281; Kedrowski et al., Organic Letters, 2007; 9(17), 3205-3207; Heravi & Zadsirjan, Current Organic Synthesis, 2016; 13(6), 780-833; Keri et al., European J Med Chem, 2017; 138, 1002-1033; PerezSilanes et al., J Heterocyclic Chem, 2001; 38(5), 1025-1030; and references therein). Compounds may contain one or more chiral centers and/or double bonds and therefore may exist as stereoisomers, such as double-bond isomers (i.e., geometric isomers), enantiomers, or diastereomers. Accordingly, the chemical structures depicted herein encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. See, e.g., Lourengo et al., J Pharm Biomed Anal., 2013; 73:13-7 and Rasmussen et al., J Chromatogr B Analyt Technol Biomed Life Sci., 2006; 842(2):136-41.

In some embodiments, a combination or composition comprises a compound that is pure or substantially pure. A "pure" or "substantially pure" compound is defined as a preparation of the compound having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of a high performance liquid chromatography (HPLC) profile or other similar detection method. Preferably the pure or substantially pure compound used in the invention is substantially free of any other active compounds which are not intended to be administered to a subject. In this context, “substantially free” refers to the fact that no active compound(s), other than the active compound intended to be administered to a subject, are detectable by HPLC or another similar detection method, or are below a desired threshold of detection such as defined above.

In embodiments, production of a disclosed compound, combination, or composition complies with current Good Manufacturing Practice (“GMP” or “cGMP”) requirements.

In some embodiments, a disclosed therapeutic combination comprises a single enantiomer or a non-racemic mixture of a compound, such as the hallucinogenic agent and/or the entactogenic agent. An enantiomer that is isolated is one that is substantially free of the corresponding enantiomer. Thus, an isolated enantiomer refers to a compound that is separated via separation techniques or prepared free of the corresponding enantiomer. The term “substantially free” as used herein (or “substantially pure,” when referring to a single enantiomer), means that the compound is made up of a significantly greater proportion of one enantiomer. In preferred embodiments, the compound includes at least about 90% by weight of a preferred enantiomer. In other embodiments, the compound includes at least about 95%, at least about 96%, at least about 97%, at least about 98%, at least about 99%, at least about 99.5%, at least about 99.9%, or up to and including 100% by weight of a preferred enantiomer. Preferred enantiomers can be isolated from racemic mixtures by any method known to those skilled in the art, including HPLC and the formation and crystallization of chiral salts, or preferred enantiomers can be prepared by methods described herein.

The present disclosure also includes stereoisomers of the compounds described herein, where applicable, either individually or admixed in any proportions. Stereoisomers may include enantiomers, diastereomers, racemic mixtures, and combinations thereof. Such stereoisomers can be prepared and separated using conventional techniques, either by reacting enantiomeric starting materials, or by separating isomers of compounds disclosed herein. Isomers may include geometric isomers. Examples of geometric isomers include cis isomers or trans isomers across a double bond. Other isomers are contemplated among the compounds of the present disclosure. The isomers may be used either in pure form or in admixture with other isomers of the compounds described herein.

Various methods are known in the art to obtain optical isomers of compounds. Examples of such methods include the following: I. Physical separation of crystals whereby macroscopic crystals of the individual enantiomers are manually separated. This technique may particularly be used if crystals of the separate enantiomers exist (i.e., the material is a conglomerate), and the crystals are visually distinct; II. Simultaneous crystallization whereby the individual enantiomers are separately crystallized from a solution of the racemate, possible only if the latter is a conglomerate in the solid state; III. Enzymatic resolutions whereby partial or complete separation of a racemate by virtue of differing rates of reaction for the enantiomers with an enzyme; IV. Enzymatic asymmetric synthesis, a synthetic technique whereby at least one step of the synthesis uses an enzymatic reaction to obtain an enantiomerically pure or enriched synthetic precursor of the desired enantiomer; V. Chemical asymmetric synthesis whereby the desired enantiomer is synthesized from an achiral precursor under conditions that produce asymmetry (i.e., chirality) in the product, which may be achieved using chiral catalysts or chiral auxiliaries; VI. Diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; VII. First- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; VIII. Kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; IX. Enantiospecific synthesis from non-racemic precursors whereby the desired enantiomer is obtained from non-chiral starting materials and where the stereochemical integrity is not or is only minimally compromised over the course of the synthesis; X. Chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; XI. Chiral gas chromatography whereby the racemate is volatilized and enantiomers are separated by virtue of their differing interactions in the gaseous mobile phase with a column containing a fixed non-racemic chiral adsorbent phase; XII. Extraction with chiral solvents whereby the enantiomers are separated by virtue of preferential dissolution of one enantiomer into a particular chiral solvent; and XIII. Transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane, which allows only one enantiomer of the racemate to pass through.

Reference herein to hallucinogens, dissociatives, and entactogens also include prodrugs thereof. Prodrugs are compounds that are metabolized or otherwise transformed inside the body to the active pharmacologic agent(s) of interest. Thus, prodrug will contain an “active” component, e.g., a compound of the invention, and a prodrug moiety. Examples include addition of amino acids to the amine, which can be removed within the body by esterases or similar enzymes, and reactions at the keto-group to form enol ethers, enol esters, and imines, but other prodrugs and precursors should be understood to be within the scope of the invention. Prodrugs are frequently (though not necessarily) pharmacologically less active or inactive until converted to the parent drug. This is done in the body by a chemical or biological reaction. In some cases, the moiety or chemicals formed from it may also have beneficial effects, including increasing therapeutic effects, decreasing undesirable side effects, or otherwise altering the pharmacokinetics or pharmacodynamics of the active drug. When the chemical formed from the prodrug moiety has beneficial effects that contribute to the overall beneficial effects of administering the prodrug, then the formed chemical is considered a "codrug." In embodiments, compounds of the invention also include codrugs.

Types of prodrugs contemplated to be within the scope and spirit of the invention include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes; CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive; alternatively, they may be conjugated to alkylglucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or conjugated with a linear polysaccharide such as pectin that will delay activation until the combination reaches the bacteria in the colon. Besides these exemplary prodrug forms, many others will be known to those of skill, and MDMA prodrugs have been disclosed, e.g., in PCT Pub. Nos. WO2005/000334, WO2022/05396, and WO2022/106947.

a. Hallucinogenic Agents

In some embodiments, "hallucinogenic agents" of a provided therapeutic combination comprise any of substituted phenethylamines, substituted tryptamines, semi-synthetic alkaloids, and lysergamides. For reference, and as non-limiting examples, 2C-B is an example of a substituted phenethylamine, psilocin and psilocybin are examples of substituted tryptamines, and LSD is an exemplary semi-seynthetic alkaloid of the lysergamide class. In some embodiments, the hallucinogenic agents of a provided therapeutic combination comprises any of psilocybin (3-(2-Dimethylaminoethyl)-1H-indol-4-yl] dihydrogen phosphate); psilocin (4-hydroxy-N,N-dimethyltryptamine); DMT (2-(1H-Indol-3-yl)-N,N-dimethylethanamine); 5-MeO-DMT (2-(5-Methoxy-1H-indol-3-yl)-N,N-dimethylethanamine); mescaline, salvinorin A, THC ((6aR,10aR)-6,6,9-Trimethyl-3-pentyl-6a,7,8,10a-tetrahydro-6H-benzo[c]chromen-1-ol) (which may be considered hallucinogenic at certain doses, see Barrett et al., *Cannabis* & Cannabinoid Res., 2018; 85-93); 4-Aco-DMT (4-acetoxy-N,N-dimethyltryptamine), 5-Br-DMT (5-bromo-N,N-dimethyltryptamine), 5-Cl-DMT (5-Chloro-N,N-dimethyltryptamine), 5-F-DMT (5-Fluoro-N,N-dimethyltryptamine), 4,5-methylenedioxy-N,N-dimethyltryptamine (4,5-MDO-DMT), 4,5-methylenedioxy-N,N-diisopropyltryptamine (4,5-MDO-DiPT), PRO-LAD (6-propyl-6-nor-lysergic acid diethylamide), ETH-LAD (6-ethyl-6-nor-lysergic acid diethylamide), AL-LAD (6-allyl-6-nor-lysergic acid diethylamide), 1P-LSD (1-propionyl-lysergic acid diethylamide), LSD (lysergic acid diethylamide), DiPT (N,N-diisopropyltryptamine), a 2C-X compound, and others described herein. Hallucinogenic agents also may be referred to herein as "hallucinogens" or "psychedelics." Herein, a "derivative" and "derivatives" of a hallucinogenic agent may be used to generally refer to prodrugs, metabolites, and analogs of the hallucinogenic agent.

In some embodiments, a disclosed therapeutic combination comprises a 2C-X compound, psychedelic phenethylamines containing methoxy groups on the 2 and 5 positions of the benzene ring. Generally known as the "2C" or "2C-X" series, such compounds will be known to those in the art as hallucinogenic agent(s). In some embodiments, the 2C-X compound has the structure of Formula(I) below:

Formula (I)

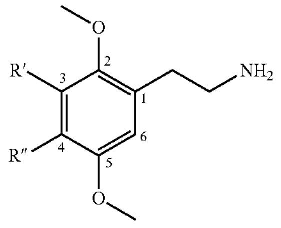

wherein, R' and R" are selected independently from hydrogen, N, $NO_2$, Cl, Br, F, I, $CH_3$, $CH_3O$—, $CH_3CH_2O$—, $CH_3CH_2CH_2O$—, $CF_3O$—, $CF_3CH_2O$—, $CF_3CH_2CH_2O$—, $CH_3CH_2$—, $CH_3CH_2CH_2$—, $CH_3S$—, $CH_3CH_2S$—, $(CH_3)_2CHS$—, $CH_3CH_2CH_2S$—, $CH_3CH_2CH_2CH_2S$—, $(CH_3)_3CS$—, $CF_3CH_2$—, $CF_3CH_2CH_2$, $CF_3S$—, $CF_3CH_2S$—, $CF_3CH_2CH_2S$, $FCH_2CH_2S$—; or R' and R" are joined to form a fused or unfused 3-, 4-, 5-, or 6-membered ring system, which may include a bridged or aromatic ring system; or one or both of the methoxy groups at positions 2 and 5 are joined with an alkyl group at positions 3 (i.e., R') and/or 6, respectively, to form one or two fused rings, each independently of five or six members.

In some embodiments, R' is hydrogen and R" is as defined above. In some embodiments, both R' and R" are hydrogen.

In some embodiments, R' is hydrogen and R" is a lipophilic substituent.

In some embodiments, the methoxy group at position 5 is instead at position 6.

In some embodiments, the 2C-X compound is a 2C-X compound taught in PiHKAL.

In some embodiments, the 2C-X compound is any of 2C-B, 2C-B-AN, 2C-B-Butterfly, 2C-B-Fly-NBOMe, 2C-B-Fly-NB2EtO5Cl, 2C-Bn, 2C-Bu, 2C-1-5-Hemifly, 2C-C, 2C-C-3, 2C-CN, 2C-CP, 2C-D, 2C-E, 2C-EF, 2C-F, 2C-G, 2C-G-1, 2C-G-2, 2C-G-3, 2C-G-4, 2C-G-5, 2C-G-6, 2C-G-N, 2C-H, 2C-I, 2CB-Ind, 2C-iP, 2C-N, 2C-NH12, 2C-PYR, 2C-PTP, 2C-, 2C-O-4, 2C-MOM, 2C-P, 2C-Ph, 2C-Se, 2C-T, 2C-T-2, 2C-T-3, 2C-T-4, 2C-T-5, 2C-T-6, 2C-T-7, 2C-T-8, 2C-T-9, 2C-T-10, 2C-T-11, 2C-T-12, 2C-T-13, 2C-T-14, 2C-T-15, 2C-T-16, 2C-T-17, 2C-T-18, 2C-T-19, 2C-T-21, 2C-T-21.5, 2C-T-22, 2C-T-23, 2C-T-24, 2C-T-25, 2C-T-27, 2C-T-28, 2C-T-30, 2C-T-31, 2C-T-32, 2C-T-33, 2C-DFM, 2C-TFM, 2C-TFE, 2C-YN, 2C-V, and 2C-AL. Herein, 2C-X compounds may be referred to as "a 2C-X compound or an analog thereof." In a non-limiting example, analogs of 2C-B3 include, for example, 2C-B-FLY, 2C-B-dragonFLY, 3C-1B-FLY, 2C-B-hemiFLY-2, 2C-B-hemiFLY-5, 2C-B-hemidragonFLY-2, and Bromo-dragonFLY In some embodiments, the 2C-X compound is a compound of Table 1 below.

TABLE 1

| Exemplary 2C-X Compounds | | |
|---|---|---|
| 2C-X Compound | Chemical Name | 2C-X Structure |
| 2C-B | 4-Bromo-2,5-dimethoxyphen-ethylamine | 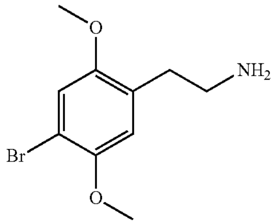 |
| 2C-B-AN | 2-phenyl-2-[2-(2,5-dimethoxy-4-bromophenyl)ethylamino] acetonitrile | 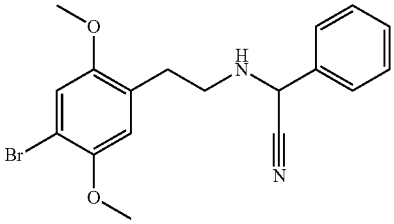 [SMILES: COc1cc(CCNC(C#N)c2ccccc2)c(OC)cc1Br] |
| 2C-B-FLY-NBOMe | 2-(8-Bromo-2,3,6,7-tetrahydrobenzo[1,2-b:4,5-b'] difuran-4-yl)-N-[(2-methoxyphenyl)methyl] ethan-1-amine | 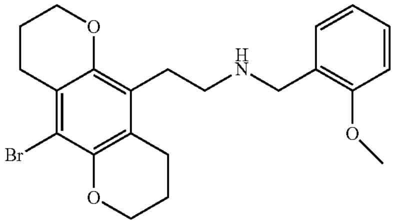 [SMILES: COc1ccccc1CNCCc1c2c(c(Br)c3c1OCCC3)OCCC2] |
| 2C-B-FLY | 8-Bromo-2,3,6,7-benzo-dihydro-difuran-ethylamine | 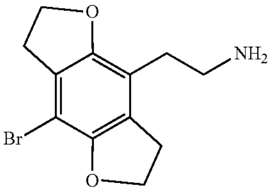 [SMILES: NCCc1c2c(c(Br)c3c1OCC3)OCC2] |
| 2C-Bu | 2-(4-Butyl-2,5-dimethoxyphenyl) ethan-1-amine | 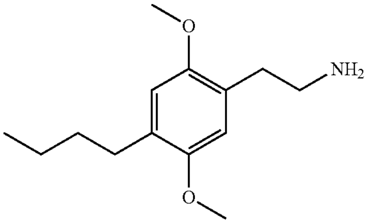 |
| 2C-B-5-hemiFLY | 2-(7-Bromo-5-methoxy-2,3-dihydro-1-benzofuran-4-yl) ethan-1-amine | 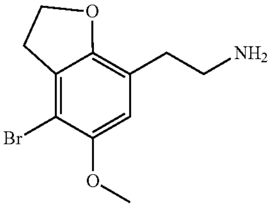 |

TABLE 1-continued
| Exemplary 2C-X Compounds | | |
|---|---|---|
| 2C-X Compound | Chemical Name | 2C-X Structure |
| 2C-C | 4-Chloro-2,5-dimethoxyphen-ethylamine | 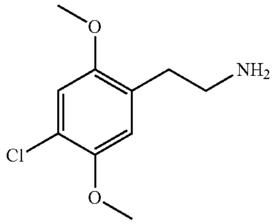 |
| 2C-CN | 4-(2-Aminoethyl)-2,5-dimethoxy benzonitrile | 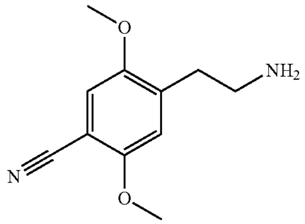 |
| 2C-CP | 2-(4-cyclopropyl-2,5-dimethoxyphenyl)ethanamine | 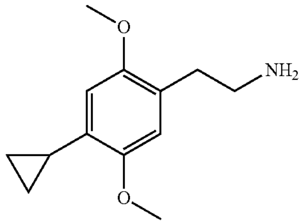 [SMILES: COc1cc(C2CC2)c(OC)cc1CCN] |
| 2C-D | 4-Methyl-2,5-dimethoxyphen-ethylamine | 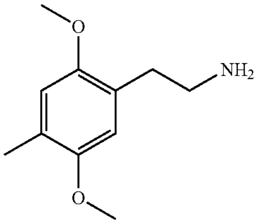 |
| 2C-E | 4-Ethyl-2,5-dimethoxyphen-ethylamine | 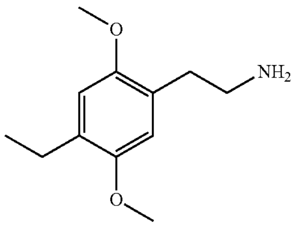 |
| 2C-F | 4-Fluoro-2,5-dimethoxyphen-ethylamine | 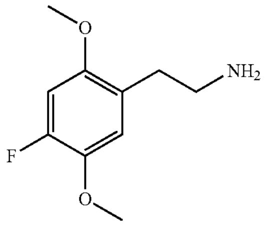 |

TABLE 1-continued
| Exemplary 2C-X Compounds | | |
|---|---|---|
| 2C-X Compound | Chemical Name | 2C-X Structure |
| 2C-G | 3,4-Dimethyl-2,5-dimethoxy-phenethylamine | 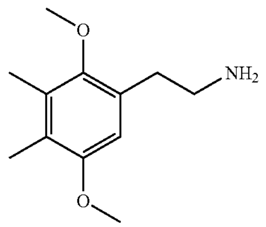 |
| 2C-I | 4-Iodo-2,5-dimethoxyphen-ethylamine | 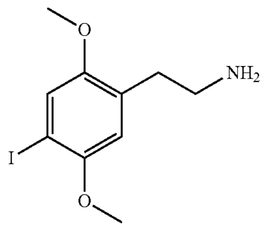 |
| 2C-I-Fly | 8-Iodo-2,3,6,7-benzo-dihydro-difuran-ethylamine | 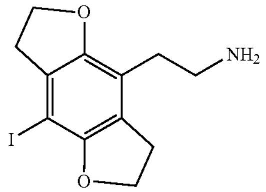 [SMILES: NCCc1c2c(c(I)c3c1OCC3)OCC2] |
| 2C-N | 4-Nitro-2,5-dimethoxyphen-ethylamine | 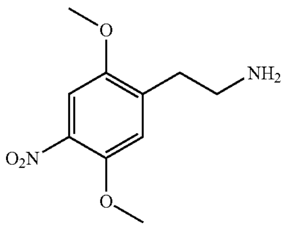 [SMILES: COc1cc([N+](=O)[O-])c(OC)cc1CCN] |
| 2C-P | 4-Propyl-2,5-dimethoxyphen-ethylamine | 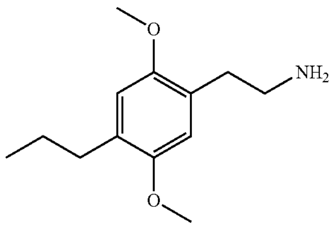 [SMILES: CCCc1cc(OC)c(CCN)cc1OC] |
| 2C-SE | 4-Methylseleno-2,5-di-methoxyphenethylamine | 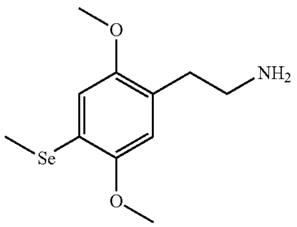 |

TABLE 1-continued
Exemplary 2C-X Compounds
| 2C-X Compound | Chemical Name | 2C-X Structure |
|---|---|---|
| 2C-T | 4-Methylthio-2,5-di-methoxyphenethylamine | 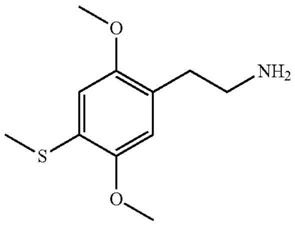 |
| 2C-T-2 | 4-Ethylthio-2,5-di-methoxy-b-phenethylamine | 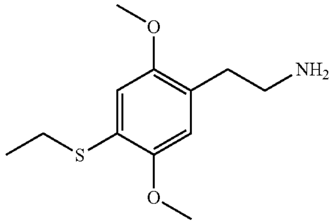 [SMILES: CCSc1cc(OC)c(CCN)cc1OC] |
| 2C-T-4 | 2,5-dimethoxy-4-isopropyl-thiophenethylamine | 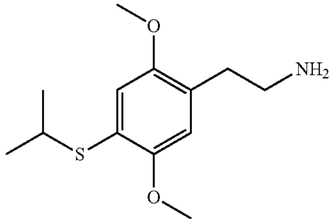 [SMILES: COc1cc(SC(C)C)c(OC)cc1CCN] |
| psi-2C-T-4 | 2,6-dimethoxy-4-isopropyl-thiophenethylamine | 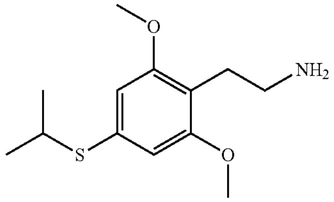 [SMILES: COc1cc(SC(C)C)cc(OC)c1CCN] |
| 2C-T-7 | 2,5-dimethoxy-4-propyl-thiophenethylamine | 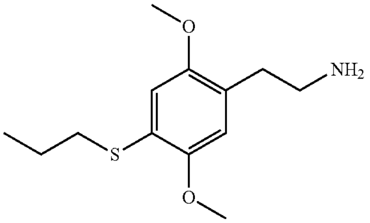 |
| 2C-T-8 | 4-cyclopropylmethylthio-2,5-dimethoxyphenethylamine | 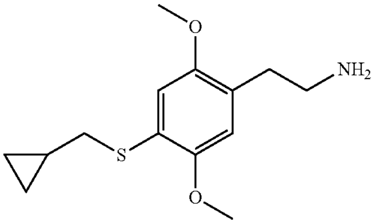 [SMILES: COc1cc(SCC2CC2)c(OC)cc1CCN] |

TABLE 1-continued

| Exemplary 2C-X Compounds | | |
|---|---|---|
| 2C-X Compound | Chemical Name | 2C-X Structure |
| 2C-T-9 | 4-(t)-butylthio-2,5-dimethoxy-phenethylamine | 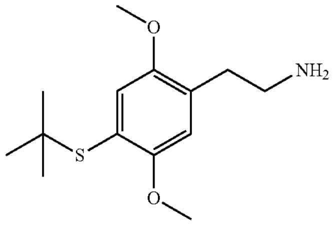 [SMILES: COc1cc(SC(C)(C)C)c(OC)cc1CCN] |
| 2C-T-13 | 2,5-dimethoxy-4-(2-methoxy-ethylthio)phenethylamine | 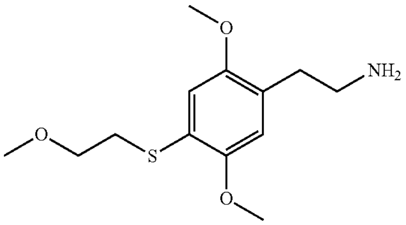 [SMILES: COCCSc1cc(OC)c(CCN)cc1OC] |
| 2C-T-15 | 4-cyclopropylthio-2,5-di-methoxyphenethylamine | 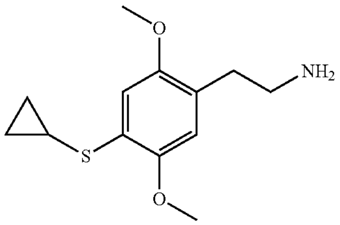 [SMILES: COc1cc(SC2CC2)c(OC)cc1CCN] |
| 2C-T-17 | 4-(s)-butylthio-2,5-di-methoxyphenethylamine | 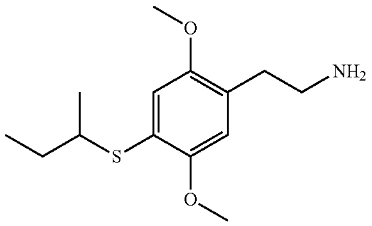 [SMILES: CCC(C)Sc1cc(OC)c(CCN)cc1OC] |
| 2C-T-21 | 2,5-dimethoxy-4-(2-fluoro-ethylthio)phenethylamine | 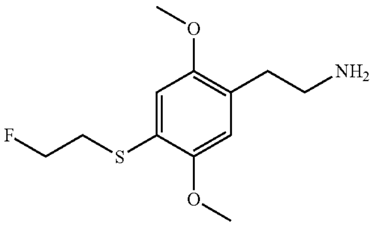 [SMILES: COc1cc(SCCF)c(OC)cc1CCN] |

Other hallucinogenic agents useful for purposes of the invention and therefore contemplated for inclusion therein will be as generally known in the art (see, e.g., Grob & Grigsby, Handbook of Medical Hallucinogens, 2021; Luethi & Liechti, Arch. Toxicol., 2020; 94, 1085-1133; Nichols, Pharmacological Reviews, 2016; 68(2), 264-355; Glennon, Pharmacology Biochemistry and Behavior, 1999; 64, 251-256). In some embodiments, the hallucinogenic agent is a short-acting hallucinogen. In some embodiments, the hallucinogenic agent is present in a disclosed combination in the form of a non-racemic mixture.

Hallucinogens, such as LSD or psilocybin, are psychoactive substances that alter perception, mood, and cognitive processes. They are characterized by producing mystical-type experiences that alter waking consciousness (Preller et al., Front Psychiatry. 2019; 10:881). Additionally, feelings of spiritual significance are common (Nichols. Hallucinogens. Pharmacol Ther. 2004; 101(2):131-81). One widely used questionnaire used to assess subjective effects of hallucinogens is the Mystical Experience Questionnaire (MEQ). Results from the MEQ show increases in several categories, including spiritual experience, personal well-being, and openness (Maclean et al., J Sci Study Relig. 2012; 51(4):721-737). Experiences with hallucinogens may result in reduced depressive symptoms or improved anxiety symptoms (Griffiths et al., J Psychopharmacol. 2016; 30(12): 1181-1197). Physically, certain hallucinogens may elicit a minor increase in blood pressure and body temperature (Gouzoulis-Mayfrank, Heffter Rev Psychedelic Res 2001; 2: 64-72).

b. Dissociative Agents

In some embodiments, a disclosed therapeutic combination comprising a hallucinogenic agent and an entactogenic agent further comprises a dissociative agent, e.g., a dissociative anesthetic. In some embodiments, a disclosed therapeutic combination comprises a dissociative agent in place of the hallucinogenic agent, together with the entactogenic agent. In some embodiments, a disclosed therapeutic combination comprises a dissociative agent and an entactogenic agent.

Non-limiting examples of dissociative anesthetics and dissociative agents include arylcyclohexylamine compounds, e.g., racemic ketamine, esketamine, arketamine, ketamine metabolites, synthetic ketamine, ketamine derivatives, and/or analogs of any of the foregoing. "Ketamine" as used herein may refer to as shorthand and encompass both racemic and non-racemic ketamine, including a pure or substantially pure ketamine enantiomer (i.e., pure or substantially pure S(+) or R(−) enantiomer), and an enantiomerically enriched mixture of ketamine, including salts thereof, and combinations of any of the foregoing. Other dissociative agents also may be present in a disclosed combination as a non-racemic mixture. Herein, a "derivative" and "derivatives" of a dissociative agent may be used to generally refer to prodrugs, metabolites, and analogs of the dissociative agent.

Ketamine metabolites that may be included in a disclosed therapeutic combination include any of the 12 HNK metabolites formed from the metabolism of ketamine in vivo, including any of the stereoselective metabolites of R- or S-ketamine, such as norketamines (NKs), dehydronorketamines (DHNKs), hydroxyketamines, and hydroxynorketamines (HNKs), as both R- and S-enantiomers, non-racemic mixtures, and racemates, and including (2S,6S;2R,6R)-HNK, (2R,4R;2S,4S-2S,6R;2R,6S)-HNK, and (2R,4S;2S,4R-2S,5S;2R,5R)-HNK (Farmer, 2020), as well as such derivatives as, e.g., (2S,6S)-hydroxynorketamine (—HNK), (2R,6R)-HNK, (25,6R)-HNK, (2R,6S)-HNK, (R,S)-dehydronorketamine (-DHNK), R-5,6-DHNK, and S-5,6-DHNK. Additional ketamine metabolites and derivatives useful in the practice of the invention are described in, e.g., US2021/0315840A1, WO2018/104729A1, and WO2019/220139. In embodiments, ketamine derivatives include such arylcyclohexylamine derivatives as are disclosed in, e.g., WO2022/047256A1, US2022/0041540A1, and WO2021/255737A1. Ketamine derivatives and analogs also include such "designer drug" or "research chemical" ketamine analogs such as methoxetamine (2-MeO-2-deschloroketamine, MXE), 3-MeO-PCE, KEA-1010, N-ethyl-deschloroketamine (2'-Oxo-PCE, O-PCE), 2-fluoro-deschloroketamine [2-(2-fluorophenyl)-2-methylamino-cyclohexanone] (2-FDCK), deschloro-ketamine (2-phenyl-2-methylamino-cyclohexanone), DXE (2'-Oxo-PCM, aka DCK), alkyne-norketamine (A-NK), and the like.

Additional exemplary dissociative agents include 1-(1-phencyclohexyl)piperidine (phencyclidine or PCP) and analogs thereof, and (RS)2-(3-methoxyphenyl)-2-(ethylamino) cyclohexanone (3-MeO-2'-Oxo-PCE or methoxetamine), and analogs thereof, such as 3-MeO-2'-Oxo-PCiPr (MXiPr).

Use of a deuterated compound, such as a deuterated dissociative agent, such as deuterated ketamine, may improve pharmacokinetics and metabolism, for example because of the kinetic isotope effect (KIE). In one example, deuteration of (R)-ketamine, (6,6-dideutero-(R)-ketamine, (R)-d2-ketamine), hindered its metabolism to (2R,6R)-HNK without modifying NMDA receptor binding or functional inhibition of the same (Zanos et al., Br J Pharmacol. 2019; 176(14):2573-2592). Deuterated ketamine and derivatives thereof are described in, e.g., WO2017/180589A1, U.S. Ser. No. 10/981,859B2, and U.S. Pat. No. 7,638,651B2.

Use of a short-acting dissociative agent in a disclosed therapeutic combination provides the advantages of reduced treatment time, which may facilitate greater ease of treatment and broader adoption. Short-acting and ultra-rapidly metabolized dissociatives include, e.g., ketamine esters and other compounds that would be recognized by one of skill in the art as having a relatively reduced half-life and increased clearance. See, e.g., Harvey et al., Anesth Analg. 2015; 121(4):925-933.

In some embodiments, a disclosed therapeutic combination comprises a dissociative agent and an entactogenic agent. In some embodiments, a disclosed therapeutic combination comprising a hallucinogenic agent and an entactogenic agent further comprises a dissociative agent. In some embodiments, a disclosed therapeutic combination comprises ketamine or a metabolite thereof and an entactogenic agent. In some embodiments, a disclosed therapeutic combination comprising a hallucinogenic agent and an entactogenic agent further comprises ketamine or a derivative thereof. In some embodiments, a disclosed therapeutic combination comprises deuterated ketamine or a deuterated ketamine derivative. In some embodiments, a disclosed therapeutic combination comprises a short-acting dissociative agent. In some embodiments, a disclosed therapeutic combination comprises a short-acting ketamine derivative, such as a ketamine ester analog.

c. Entactogenic Agents

In some embodiments, "entactogenic agents" of a provided therapeutic combination comprise any of a substituted amphetamine, a substituted benzofuran, a substituted phenethylamine, or a substituted tryptamine. For reference, and as non-limiting examples, MDMA is a substituted amphetamine, 6-APB is a substituted phenethylamine and a substituted benzofuran (demonstrating that a compound may fall into multiple classes, as will be appreciated by those of skill), and 5-MeO-MiPT is one example of a substituted tryptamine with entactogen properties. In some embodiments, the entactogenic agent of a provided therapeutic combination comprises any of MDMA and enantiomers thereof, such as R-MDMA (i.e., the R(−) levo-enantiomer of 3,4-methylenedioxymethamphetamine, bearing the IUPAC name: (R)-1-(1,3-benzodioxol-5-yl)-N-methylpropan-2-amine (R-MDMA)) and S-MDMA (i.e., the S(+) levo-enantiomer of 3,4-methylenedioxy-methamphetamine, bearing the IUPAC name: (S)-1-(1,3-benzodioxol-5-yl)-N-methylpropan-2-amine (S-MDMA)), and non-racemic mixtures of the same; 4-MTA (4-methylthioamphetamine); MDAI (5,6-methylenedioxy-2-aminoindane); 5-methyl-MDA (5-methyl-3,4-methylenedioxy-amphetamine); 5-APB (5-(2-aminopropyl)benzofuran); 6-APB (6-(2-aminopropyl) benzofuran); DiFMDA (difluoromethylenedioxyamphetamine), MBDB (1,3-benzodioxolyl-N-methylbutanamine), BDB (1,3-benzodioxolylbutanamine), MDA (3,4-methylenedioxy-amphetamine), MDEA (3,4-methylenedioxy-N-ethylamphetamine), and such others as will be known, e.g., by reference to Oeri 2020, Luethi & Liechti 2020, and the general knowledge in the art. Entactogenic agents may be referred to herein as "entactogen," "entactogens," "empathogen," or "empathogens." In some embodiments, the entactogenic agent is present in a disclosed combination in the form of a non-racemic mixture. Herein, a "derivative" and "derivatives" of an entactogenic agent may be used to generally refer to prodrugs, metabolites, and analogs of the entactogenic agent.

"MDMA" refers to 3,4-methylenedioxymethamphetamine, i.e., 3,4-MDMA, 1-(1,3-benzodioxol-5-yl)N-methylpropan-2-amine (IUPAC), formula $C_{11}H_{15}NO_2$, m.w. 193.25 g/mol, whether in ion, freebase, or salt form, including polymorphs, as well as its isomers. "MDMA" as used herein will be understood to encompass the salt forms of MDMA, such as MDMA hydrochloride salt. 3,4-MDMA HCl is commercially available from, e.g., Cayman Chemical Co., Ann Arbor, MI, with purity 98%, Item No. 13971, NSC 168383, CAS No. 64057-70-1; and Lipomed AG, Arlesheim, CH, as Prod. Ref No. MDM-94-HC, DEA No. 7405 CI, and available as MDM-94-HC-lLM (1.0 mg base/1 ml solution in methanol), and MDM-94-HC-10, -50, and -100 (10, 50, and 100 mg powder racemic MDMA HCl).

MDMA will be appreciated as including the drug substance MDMA as a racemic mixture, i.e., S,R(+/−)-3,4-methylenedioxymethamphetamine (S,R-MDMA), as an enantiomerically enriched mixture (of whatever proportions), or as individual enantiomers (i.e., pure or substantially pure R-MDMA or S-MDMA). Both enantiomers function as monoamine releasers (Hiramatsu and Cho, Neuropharmacol., 1990; 29:269-75; Johnson et al., Eur. J Pharmacol., 1986; 132:269-276; Setola et al., Mol. Pharmacol., 2003; 63:1223-1229), with S-MDMA being the more potent of the two and generally considered the "active isomer" (Anderson et al., NIDA Res. Monogr., 1978; 8-15) (both cited in Curry et al., Neuropharmacology, 2018; 128: 196-206). Herein, when referring generically to "MDMA" it will be understood to mean racemic MDMA, unless context demands otherwise.

Although entactogens such as MDMA share some effects with hallucinogens, they can be distinguished in several ways. Like hallucinogens, entactogens produce increases on all scales of the MEQ. A standard result is experiences of oneness and emotional openness. Additionally, entactogens significantly modulate social processing and have acute prosocial effects like increased empathy and communication (Preller et al., Front Psychiatry. 2019; 10:881). A unique part of the spectrum of psychological actions of entactogens is the drop in defenses and anxiety and increased self-acceptance, empathy, and peacefulness following administration. Such effects are reflected in scores of greater magnitude on measurements of mystical type experiences, e.g., the Oceanic Boundlessness scale of the 5-Dimensional Altered States of Consciousness (5D-ASC) questionnaire and the MEQ. In some cases, these pleasant emotional experiences may be contrasted with a strong endocrine and autonomic effect, including significantly increased blood pressure and heart rate, as compared to the effects of hallucinogens (Gouzoulis-Mayfrank, Heffter Rev Psychedelic Res 2001; 2: 64-72). See also distinctions between LSD and MDMA using the 5D-ASC, MEQ43, MEQ30, autonomic responses, including blood pressure and body temperature, as described by Holze et al., Neuropsychopharmacology, 2020; 45:462-471. However, some entactogens, such as non-racemic MDMA having R-MDMA in enantiomeric excess, may facilitate increases in entactogen-specific effects, such as positive affect, prosocial behavior, empathy, and feelings of authenticity, among others, without physical activation.

i. MDMA Enantiomers and Non-Racemic Mixtures Thereof

In some aspects, provided herein are therapeutic combinations comprising single enantiomers of MDMA, i.e., R-MDMA or S-MDMA. FIG. 1 shows the structures of R-MDMA and S-MDMA. In some embodiments, R-MDMA or S-MDMA is present as a pure or substantially pure single enantiomer.

In other aspects, provided herein are non-racemic mixtures of MDMA enantiomers. In some embodiments, non-racemic mixtures of MDMA comprise enantiomerically enriched mixtures of MDMA enantiomers. A "non-racemic mixture" refers to a non-racemic enantiomeric mixture wherein the amount of each chiral molecule is not equal. Such mixtures may be referred to herein simply as an "enantiomeric mixture." In some embodiments, the non-racemic mixtures of MDMA comprise R-MDMA in enantiomeric excess. In some embodiments, the non-racemic mixtures of MDMA comprise S-MDMA in enantiomeric excess. In some embodiments, the non-racemic mixtures of MDMA comprise R-MDMA and S-MDMA in proportions of 9:1 (i.e., 9:1 R:S, R-MDMA:S-MDMA).

Different naming conventions can be used to describe enantiomers. According to the R/S system, R and S refer to the absolute configuration possessed by the chiral center. Enantiomers can also be described according to the direction that a solution of the molecule rotates plane-polarized light, anticlockwise or clockwise. Levorotary, or "L," "1," or refers to an enantiomer that rotates plane polarized light in a left-handed, anticlockwise direction, also described contraclockwise or counterclockwise. Dextrorotatory, or "D, "d," or "(+)," refers to an enantiomer that rotates plane polarized light in a right-handed, clockwise direction. "R-MDMA" refers to the levorotatory R(−) enantiomer of 3,4-MDMA, bearing the IUPAC name (R)-1-(1,3-Benzodioxol-5-yl)-N-methylpropan-2-amine. R-MDMA may be referred to herein as "(−)-MDMA" or "(R)-(−)-3,4-MDMA." An "R-MDMA salt" refers to any pharmaceutically acceptable salt form of R-MDMA, and will be understood to include at least its hydrochloride, sulfate, tartrate, sodium, acetate, phosphate, chloride, and potassium salts. "S-MDMA" refers to the dextrorotary S(+) enantiomer of 3,4-MDMA, bearing the IUPAC name (S)-1-(1,3-Benzodioxol-5-yl)-N-methylpropan-2-amine. S-MDMA may be referred to herein as "(+)-MDMA" or "(S)-(+)-3,4-MDMA." An "S-MDMA salt" refers to any pharmaceutically acceptable salt form of S-MDMA, understood to include at least its hydrochloride, sulfate, tartrate, sodium, acetate, phosphate, chloride, and potassium salts.

In some embodiments, a disclosed compound may be provided in an enantiomerically enriched composition, such as a mixture of enantiomers. In some embodiments, the enantiomerically enriched composition comprises an enantiomer present in enantiomeric excess of at least 75%, at least 80%, at least 85%, at least 90%, at least 95%, at least 98%, at least 99%, at least 99.5%, or at least 99.9%, up to and including 100%. In some embodiments, the compound is MDMA. In some embodiments, the enantiomer is R-MDMA. In some embodiments, the enantiomer is S-MDMA.

In some aspects, provided herein are non-racemic enantiomeric mixtures comprising the (R)-enantiomer and (S)-enantiomer of MDMA, such as R-MDMA and S-MDMA. In some embodiments, the provided compositions comprise R-MDMA in enantiomeric excess (ee). In some embodiments, a provided non-racemic mixture comprises 90% or less of R-MDMA and 10% or more of S-MDMA. In some embodiments, the mixture comprises R-MDMA and S-MDMA in a ratio of 6:1 to 12:1, 7:1 to 11:1, or 8:1 to 10:1. In some embodiments, the mixture comprises R-MDMA and S-MDMA in a ratio of about 4:1, 5:1, 6:1, 7:1, 8:1, 9:1, 10:1, 11:1, or 12:1. In some embodiments, the mixture comprises R-MDMA and S-MDMA in a ratio of greater than 10:1, 11:1, 12:1, 13:1, 14:1, or 15:1 and including ranges in between. In some embodiments, the mixture comprises R-MDMA and S-MDMA in a ratio of about 7:1, 8:1, 9:1, or 10:1. In some embodiments, the mixture comprises R-MDMA and S-MDMA in a ratio of 9:1. It will be understood that the content of the provided ratios may also be represented as percentages, e.g., a 7:1 R:S ratio represents a mixture comprising 88% R-MDMA and 12% S-MDMA, a 8:1 R:S ratio represents a mixture comprising 89% R-MDMA and 11% S-MDMA, a 9:1 R:S ratio represents a mixture comprising 90% R-MDMA and 10% S-MDMA, a 10:1 R:S ratio represents a mixture comprising 91% R-MDMA and 9% S-MDMA.

In certain embodiments, a mixture of R-MDMA to S-MDMA of 9:1 (R:S) and 10:1 (R:S) are preferred. In some embodiments, a provided mixture or combination or composition thereof comprises R-MDMA to S-MDMA in a ratio of 9:1. In some embodiments, a provided mixture or combination or composition thereof comprises R-MDMA to S-MDMA in a ratio of 10:1. The provided ratios will be understood to refer either to weight by weight ratios or molar ratios, except in the case where a provided mixture comprises MDMA salts with different molecular weights. In all such embodiments, R-MDMA and S-MDMA will be understood to include the salts, polymorphs, prodrugs, and derivatives thereof.

In some embodiments, a provided non-racemic enantiomeric mixture of R-MDMA and S-MDMA comprises R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a provided non-racemic enantiomeric mixture of R-MDMA and S-MDMA comprises R-MDMA in enantiomeric excess of 10%-95%, 20%-95%, 30%-95%, 40%-95%, 50%-95%, 55%-95%, 60%-90%, 65%-90%, 70%-85%, or 75%-85%, wherein each range is inclusive. In some embodiments, a non-racemic mixture of R-MDMA and S-MDMA comprises R-MDMA in enantiomeric excess of 10%, 15%, 20%, 25%, 30%, 35%, 40%, 45%, 50%, 55%, 60%, 65%, 70%, 75%, 80%, 85%, 90%, or 95%. In some embodiments, a non-racemic mixture of R-MDMA and S-MDMA comprises R-MDMA in enantiomeric excess of 75%, 76%, 77%, 78%, 79%, 80%, 81%, 82%, 83%, 84%, or 85%. In some embodiments, a non-racemic mixture of R-MDMA and S-MDMA comprises R-MDMA in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a non-racemic mixture of R-MDMA and S-MDMA comprises R-MDMA in an enantiomeric excess of 79.5%, 79.6%, 79.7%, 79.8%, 79.9%, 80%, 80.1%, 80.2%, 80.3%, 80.4%, or 80.5%. In some embodiments, a non-racemic mixture of R-MDMA and S-MDMA comprises R-MDMA in an enantiomeric excess of 80%.

Enantiomeric excess (ee) refers to the excess of one enantiomer over another in a given mixture. EE can be determined from enantiomer concentration, such as in mol/Litre (M), and can range from 0%-100%. As an example, a racemic mixture has an ee of 0%, while a single completely pure enantiomer has an ee of 100%. A mixture comprising 70% of one enantiomer and 30% of the other has an ee of 40% (70%-30%). The following formulas may be used to calculate ee. See, e.g., Polavarapu, Org Biomol Chem., 2020; 18(35):6801-6806.

Enantiomeric Excess (% ee)=[(moles of enantiomer−moles of other enantiomer)/total moles of both enantiomers]×100 Formula I:

Enantiomeric Excess (% ee)=([$R$]−[$S$])/([$R$]+[$S$])=% $R$−% $S$ Formula II:

In one example, R-MDMA and S-MDMA in a ratio of 9:1 was found to provide several advantages over racemic MDMA and either enantiomer alone (R-MDMA or S-MDMA). Exemplary features of 9:1 R:S-MDMA include i) improved neuromodulation, including reduced activity at dopamine and norepinephrine transporters (DAT and NET) relative to racemic MDMA and S-MDMA, which mediate neurotoxicity, hyperthermia, and abuse potential, ii) promotion of reinforcement and reward learning, as exemplified by comparable potency at the $\alpha4\beta2$ nicotinic acetylcholine receptor (nAChR) relative to MDMA, iii) improved pharmacokinetics, such as a reduced half-life relative to R-MDMA. Such advantages are compounded, in some instances synergistically, when 9:1 R:S-MDMA is combined with a hallucinogen, a dissociative, or a hallucinogen and a dissociative, facilitating flexible dosing regimens and subjective effects that mediate enhanced therapeutic efficacy and an extended therapeutic window, as described herein.

ii. Synthesis of MDMA Enantiomers

Although numerous methods in the art can be used to obtain optical isomers of the compounds of the invention (e.g., by resolution of the racemate), enantiomeric R-MDMA also may be produced directly by chemical synthesis. Methods of synthesizing MDMA enantiomers are available to one of skill in the art. For example, enantiomerically enriched MDMA can be synthesized based on the reductive amination of 3,4-(methyl-enedioxy)phenylacetone and enantiomerically enriched alphaphenethylamine (Nichols et al., J Med. Chem., 1973; 16(5), 480-83). Pizarro et al., Bioorg. Med. Chem. Lett., 2002; 10, 1085-92 discloses a method of synthesis of enantiomerically enriched MDMA based on the resolution of a chiral intermediate. See also, Nichols et al., J Med. Chem., 1986; 29, 2009-15.

In one exemplary reaction scheme, the R-MDMA of the invention is synthesized by reacting Methylenedioxyphenylpropan-2-one with (R)-alpha-methylbenzamine, followed by hydrogenation for the production of R-MDA ((R-)-3,4-methylenedioxyamphetamine), which is then converted into R-MDMA through the reduction of the formamide. This synthetic scheme is shown in Scheme 1.

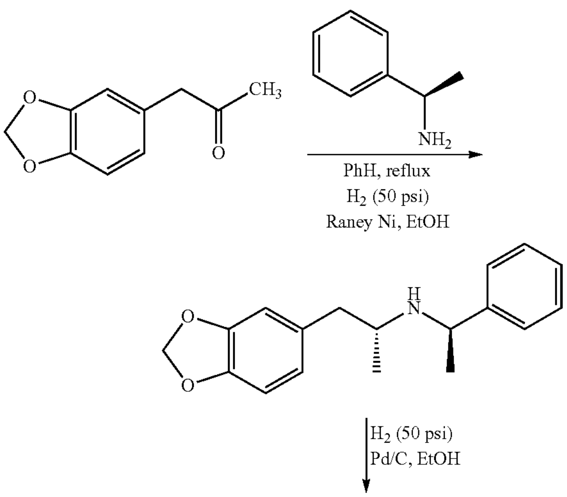

-continued
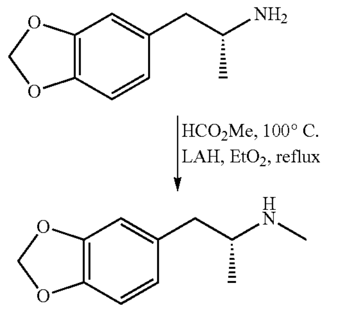
Scheme 1 shows an exemplary synthesis scheme for producing R-MDMA, using 3,4-methylenedioxyphenylpropan-2-one as a precursor.
Additionally, R-MDMA and S-MDMA may be synthesized using 3,4-dihydroxybenzoic acid as a precursor, as shown in Scheme 2 and Scheme 3.
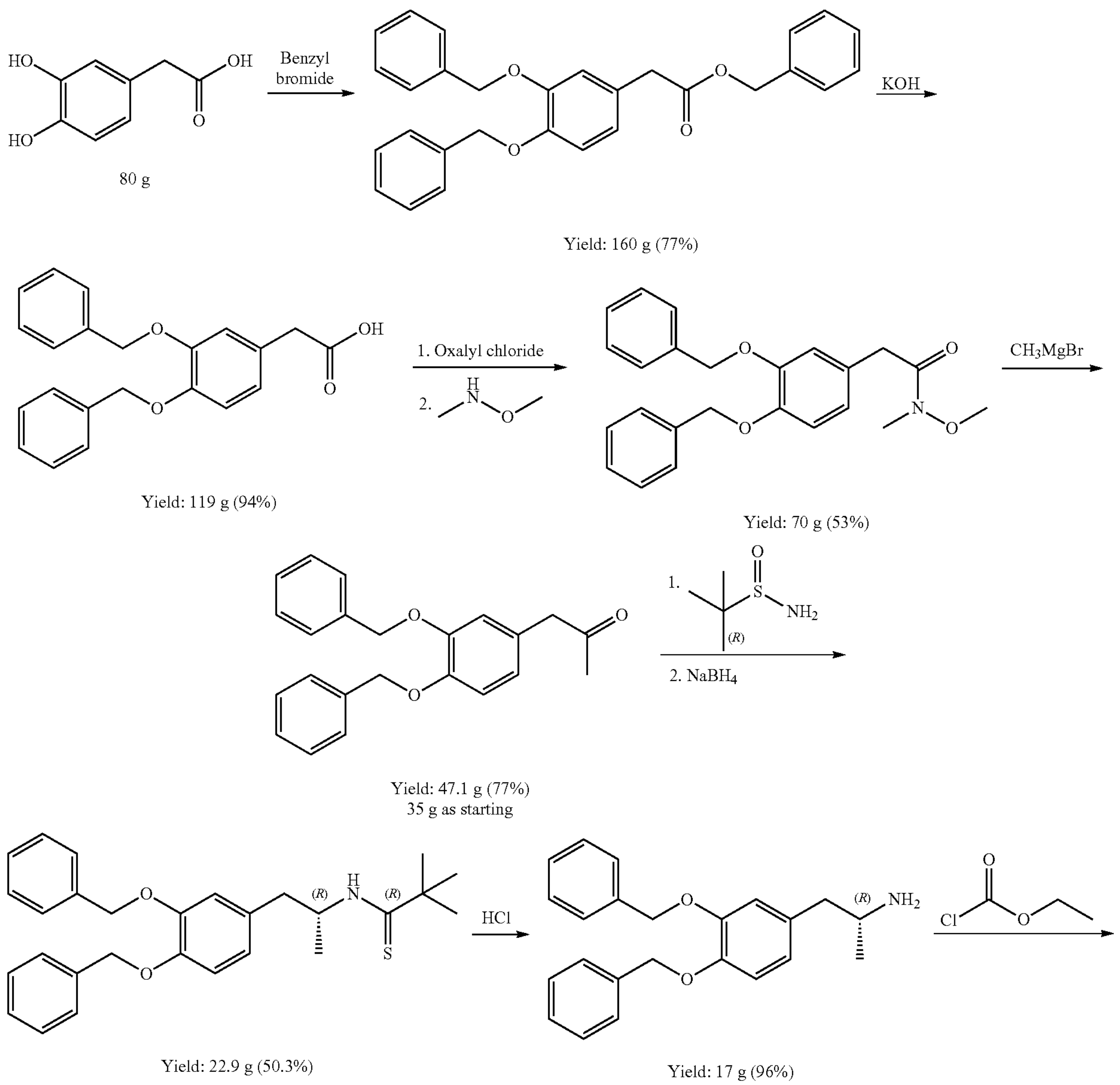

-continued
(continued on next page)
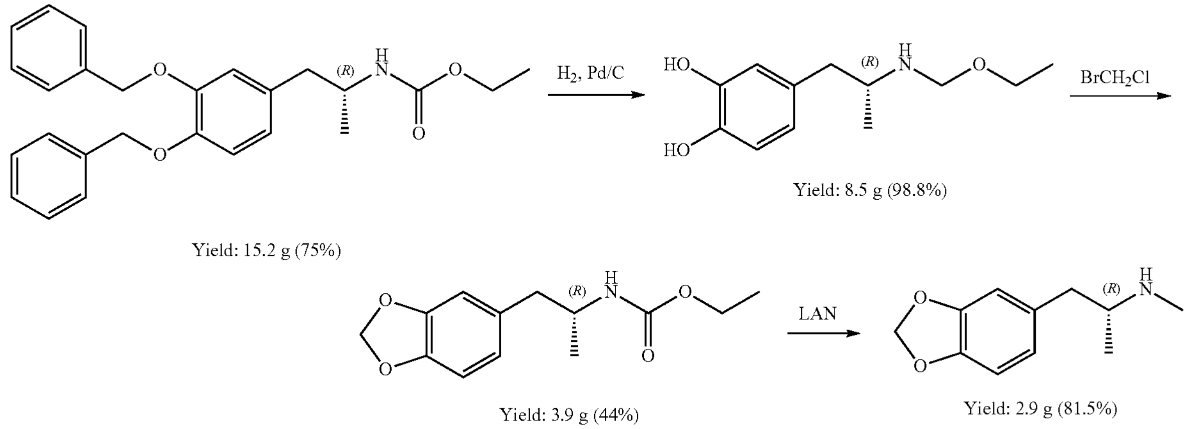
Scheme 2 shows synthesis of R-MDMA using 3,4-dihydroxybenzoic acid as a precursor (81.5% Yield: 2.9 g).
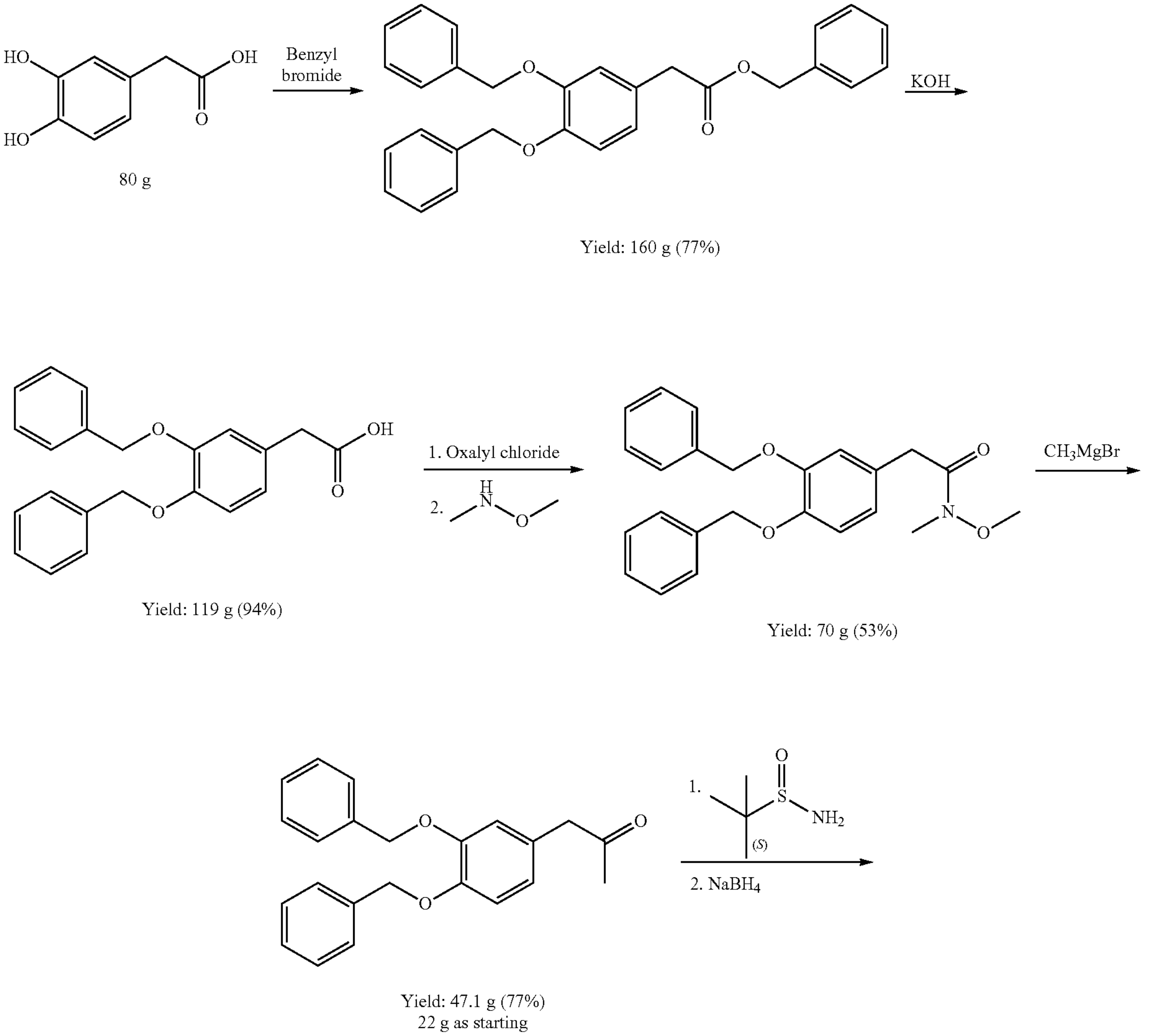

-continued

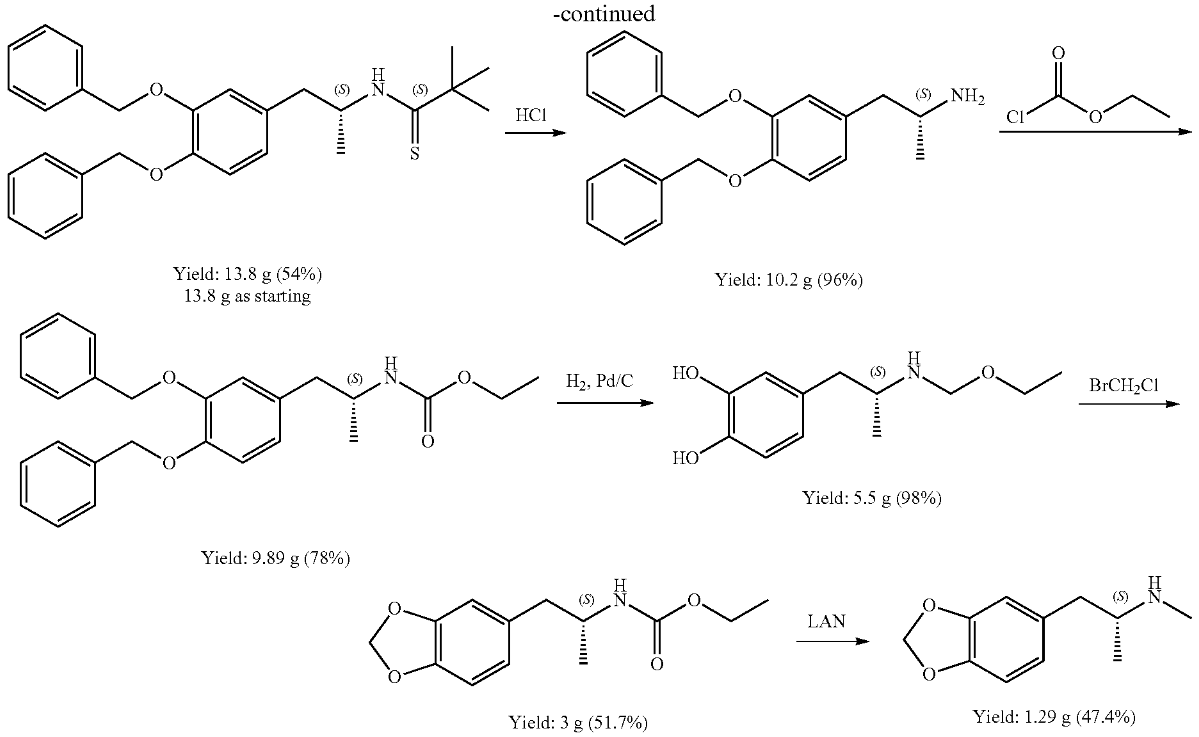

Scheme 3 shows synthesis of S-MDMA using 3,4-dihydroxybenzoic acid as a precursor (47.4% Yield: 1.29 g).

Additionally, MDMA enantiomers may be synthesized in accordance with the methods described in Example 10 with modifications. FIG. 2-5 show NMR spectroscopy and mass spectrometry on R-MDMA and S-MDMA produced in accordance with such methods. Other methods for synthesizing disclosed compounds and/or their starting materials are described in the art or will be readily apparent in view of the teachings and disclosure herein.

Methods of analyzing enantiomers, e.g., the enantiomeric content in a non-racemic enantiomeric mixture, are available to one of skill. For example, enantiomeric content of a provided non-racemic mixture may be determined using chiral HPLC or vibrational circular dichroism (VCD) spectroscopy. Alternatively, a derivatizing agent may be used to prepare a diastereomer, which can then be quantified according to analytical methods, e.g., NMR, HPLC, and others. See, e.g., Nichols et al., J Med Chem, 1973; 16(5), 480-83; Fallon et al., Clinical Chem, 1999; 45(7):1058-1069. Regarding the range of experimental error associated with determining the enantiomeric content, a person of ordinary skill in the art would understand that each analytical technique has its own degree of precision.

For the provided enantiomeric mixtures, it will be understood that the deviation from the nominal amount of a mixture, e.g., R:S in a ratio of 9:1 (90% R-MDMA and 10% S-MDMA), to the actual amount, such as determined by an analytical method, is 0.05% or less, within 0.05% to 0.99%, within 0.05% to 0.9%, within 0.05% to 0.8%, within 0.05% to 0.7%, within 0.05% to 0.6%, within 0.05% to 0.5%, within 0.05% to 0.4%, within 0.05% to 0.3%, within 0.05% to 0.2%, or within 0.05% to 0.1%, wherein the range is inclusive, or does not exceed 1%. In one example, the enantiomeric content of a non-racemic mixture in a nominal amount of 9:1 R:S MDMA may be determined to have 90%±0.05% R-MDMA, such as 89.95% or 90.05%, and 10%±0.05% S-MDMA, such as 9.95% or 10.05% S-MDMA. In another example, the enantiomeric content of a non-racemic mixture in a nominal amount of 9:1 R:S MDMA may be determined to have 90%±0.1% R-MDMA, such as 89.9% or 90.1%, and 10%±0.1% S-MDMA, such as 9.9% or 10.1% S-MDMA. As such, a nominal amount of 9:1 R:S MDMA may be determined to have from 89.9% to 90.1% R-MDMA, where the range is inclusive and including values in between, where the remainder is S-MDMA.

Challenges to characterizing enantiomers include self-disproportionation of enantiomers (SDE) and self-induced diastereomeric anisochronism (SIDA). SDE refers to the spontaneous fractionation of scalemic material into enantio-enriched and -depleted fractions in response to a physicochemical process. Such process may include (a) precipitation, (b) centrifugation, (c) evaporation, (d) distillation, (e) crystallization, (f) sublimation, and (g) achiral chromatography (e.g. column, flash, MPLC, HPLC, SEC, GC, etc) (Han et al., Chem. Sci., 2018; 9, 1718-1739). SIDA has been described in the context of NMR (Baumann et al., Symmetry, 2020; 12(7), 1106).

iii. MDMA Salts

In some aspects, provided herein are salts of MDMA, including salts of enantiomeric MDMA, such as salts of R-MDMA and salts of S-MDMA, and including salts of non-racemic mixtures of MDMA, such as 9:1 R:S-MDMA. In some embodiments, the salt is a pharmaceutically acceptable salt. In some embodiments, the salt of a provided MDMA enantiomer or non-racemic mixture thereof is a hydrochloride salt. In some embodiments, the salt is a phosphate salt. In some embodiments, the salt is a sulfate salt. In some embodiments, the salt of R-MDMA in a provided enantiomeric mixture is the same as the salt of S-MDMA in said mixture, for example, R-MDMA HCL and S-MDMA HCL. In some embodiments, the salt of R-MDMA in a provided enantiomeric mixture is different from the salt of S-MDMA in said mixture, for example R-MDMA HCL and R-MDMA sulfate. In some embodiments, R-MDMA or S-MDMA in the mixture is a hydrochloride salt and the other is a sulfate salt, such as R-MDMA HCL and S-MDMA sulfate or R-MDMA sulfate and S-MDMA HCL. In some embodiments, reference to "a salt" such as "R-MDMA, S-MDMA, or a salt thereof" therefore may mean more than a single salt.

In some embodiments, a provided non-racemic mixture comprises a salt of R-MDMA and a salt of S-MDMA, wherein R-MDMA is present in an enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a provided non-racemic mixture comprises a salt of R-MDMA and a salt of S-MDMA, wherein R-MDMA is present in an enantiomeric excess of 10%-95%, 20%-95%, 30%-95%, 40%-95%, 50%-95%, 55%-95%, 60%-90%, 65%-90%, or 75%-85%. In some embodiments, a non-racemic mixture comprises a salt of R-MDMA and a salt of S-MDMA, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95%. In some embodiments, a non-racemic mixture comprises a salt of R-MDMA and a salt of S-MDMA, wherein R-MDMA is present in enantiomeric excess of in enantiomeric excess of about 75%, 76%, 77%, 78%, 79%, 80%, 81%, 82%, 83%, 84%, or 85%. In some embodiments, a non-racemic mixture comprises a salt of R-MDMA and a salt of S-MDMA, wherein R-MDMA is present in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a non-racemic mixture comprises a salt of R-MDMA and a salt of S-MDMA, wherein R-MDMA is present in an enantiomeric excess of about about 79.5%, 79.6%, 79.7%, 79.8%, 79.9%, 80%, 80.1%, 80.2%, 80.3%, 80.4%, or 80.5%. In some embodiments, a provided non-racemic mixture for administration to a subject comprises 90% or less of R-MDMA and 10% or more of S-MDMA. In some embodiments, the non-racemic mixture comprises a salt of R-MDMA and a salt of S-MDMA in a ratio of about 6:1 to 12:1, 7:1 to 11:1, or 8:1 to 10:1. In some embodiments, the non-racemic mixture comprises a salt of R-MDMA and a salt of S-MDMA in a ratio of 6:1, 7:1, 8:1, 9:1, 10:1, 11:1, or 12:1. In some embodiments, the non-racemic mixture comprises a salt of R-MDMA and a salt of S-MDMA in a ratio of 6:1, 7:1, 8:1, 9:1, or 10:1. In some embodiments, the salt of an enantiomerically enriched mixture comprises a mixture of R-MDMA HCl and S-MDMA HCl in a ratio of about 8:1, 9:1, or 10:1. In some embodiments, the salt of an enantiomerically enriched mixture comprises a mixture of R-MDMA HCl and S-MDMA HCl in a ratio of 9:1. In some embodiments, a provided ratio describes a molar ratio of R-MDMA to S-MDMA. In embodiments where the salts of R-MDMA and S-MDMA are the same, a provided ratio may refer to a weight by weight ratio.

Where disclosed compounds are amines, they generally will be basic in nature and will react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like.

Exemplary salts of a provided MDMA enantiomer, for example, in a non-racemic mixture of MDMA enantiomers, or of a non-racemic mixture of MDMA, such as a 9:1 mixture of R:S-MDMA, include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. See, e.g., Berge et al., "Pharmaceutical Salts," J. Pharm. Sci., 1977; 66:1-19. In some embodiments, pharmaceutically acceptable salts are those employing a hydrochloride anion, e.g., R-MDMA HCl, S-MDMA HCl, and 9:1 R:S-MDMA HCl. In other embodiments, pharmaceutically acceptable salts include sulfate, tartrate, sodium, acetate, phosphate, chloride, and potassium salts.

iv. Methods of Making an Enantiomeric Mixture

In some aspects, provided herein are methods of making enantiomeric mixtures comprising R-MDMA and S-MDMA, such as non-racemic mixtures thereof. In some embodiments, a method of making a provided non-racemic mixture comprises synthesizing R-MDMA, S-MDMA, or a salt thereof, such as by enantiospecific synthesis. In some embodiments, the method comprises recrystallizing R-MDMA, S-MDMA, or a salt thereof in a weight ratio. In some embodiments, the weight ratio is 6:1, 7:1, 8:1, 9:1, 10:1, 11:1, or 12:1.

In some embodiments, the non-racemic enantiomeric mixture comprises the hydrochloride salt of R-MDMA and/or S-MDMA. In some embodiments, the non-racemic enantiomeric mixture comprises the phosphate salt of R-MDMA and/or S-MDMA. In some embodiments, the non-racemic enantiomeric mixture comprises the sulfate salt of R-MDMA and/or S-MDMA.

In some embodiments, the entactogenic agents of the invention are present as a pharmaceutically acceptable salt, hydrate, solvate, prodrug, metabolite, derivative, stereoisomer, and/or tautomer thereof, including in such salt forms as hydrochloride (HCl), sulfate, tartrate, sodium, acetate, phosphate, chloride, and potassium salts. In some embodiments, the entactogenic agent is in the form of a non-racemic mixture.

d. Additional Agents

In some embodiments, hallucinogenic agents or entactogenic agents useful in the practice of the invention will include those from the class of compounds known as "phenethylamines." Phenethylamines are readily understood by those in the art. Non-limiting examples of phenethylamines useful in the practice of the invention include a-ethyl-3,4,5-trimethoxyphenethylamine (AEM), 4-allyloxy-3,5-dimethoxyphenethylamine (AL), 2,5-dimethoxy-4-methylthioamphetamine (ALEPH), 2,5-dimethoxy-4-ethylthioamphetamine (ALEPH-2), 2,5-dimethoxy-4-isopropylthioamphetamine (ALEPH-4), 2,5-dimethoxy-4-phenylthioamphetamine (ALEPH-6), 2,5-dimethoxy-4-propylthioamphetamine (ALEPH-7), 2,5-dimethoxy-a-ethyl-4-methylphenethylamine (ARIADNE), 3,4-diethoxy-5-methoxyphenethylamine (ASB), 4-butoxy-3,5-dimethoxyphenethylamine (B), 2,5-dimethoxy-4,N-dimethylamphetamine (BEATRICE), 2,5-bismethylthio-4-methylamphetamine (BIS-TOM), 4-bromo-2,5,β-trimethoxyphenethylamine (BOB), 2,5, β-trimethoxy-4-methylphenethylamine (BOD), β-methoxy-3,4-methylenedioxyphenethylamine (BOH), 2,5-dimethoxy-β-hydroxy-4-methylphenethylamine (BOHD), 3,4,5,β-tetramethoxyphenethylamine (BOM), 4-bromo-3,5-dimethoxyamphetamine (4-Br-3,5-DMA), 2-bromo-4,5-methylenedioxyamphetamine (2-Br-4,5-MDA), 4-benzyloxy-3,5-dimethoxyamphetamine (3C-BZ), 3,5-dimethoxy-4-ethoxyamphetamine (3C-E), 4-cyclopropylmethoxy-3,5-dimethoxyphenethylamine (CPM), 3,5-dimethoxy-4-trideuteromethylphenethylamine (4-D), β,β-dideutero-3,4,5-trimethoxyphenethylamine (β-D), 3,5-dimethoxy-4-methyl-phenethylamine (DESOXY), 2,4-dimethoxyamphetamine (2,4-DMA), 2,5-dimethoxyamphetamine (2,5-DMA), 3,4-dimethoxyamphetamine (3,4-DMA), 2-(2,5-dimethoxy-4-methylphenyl)cyclopropylamine (DMCPA), 3,4-dimethoxy-B-hydroxyphenethylamine (DME), 2,5-dimethoxy-3,4-methylenedioxyamphetamine (DMMDA), 2,3-dimethoxy-4,5-methylenedioxyamphetamine (DMMDA-2), 3,4-dimethoxyphenethylamine (DMPEA), 4-amyl-2,5-dimethoxyamphetamine (DOAM), 4-bromo-2,5-dimethoxyamphetamine (DOB), 4-butyl-2,5-dimethoxyamphetamine (DOBU), 4-chloro-2,5-dimethoxyamphetamine (DOC), 2,5-dimethoxy-4-(2-fluoroethyl) amphetamine (DOEF), 2,5-dimethoxy-4-ethylamphetamine (DOET), 4-iodo-2,5-dimethoxyamphetamine (DOI), 2,5-dimethoxy-4-methylamphetamine (DOM (STP)), 2,6-dimethoxy-4-methylamphetamine (psi-DOM), 2,5-dimethoxy-4-nitroamphetamine (DON),2,5-dimethoxy-4-propylamphetamine (DOPR), 3,5-dimethoxy-4-ethoxyphenethylamine (E), 2,4,5-triethoxyamphetamine (EEE), 2,4-diethoxy-5-methoxyamphetamine (EEM), 2,5-diethoxy-4-methoxyamphetamine (EME), 4,5-dimethoxy-2-ethoxyamphetamine (EMM), 2-ethylamino-1-(3,4-methylenedioxyphenyl)butane (ETHYL-J), 2-ethylamino-1-(3,4-methylenedioxyphenyl)pentane (ETHYL-K), 6-(2-aminopropyl)-5-methoxy-2-methyl-2,3-dihydrobenzofuran (F-2), 6-(2-aminopropyl)-2,2-dimethyl-5-methoxy-2,3-dihydrobenzofuran (F-22), N-hydroxy-N-methyl-3,4-methylenedioxyamphetamine (FLEA), 2,5-dimethoxy-3,4-(trimethylene)amphetamine (G-3), 2,5-dimethoxy-3,4-(tetramethylene)amphetamine (G-4), 3,6-dimethoxy-4-(2-aminopropyl)benzonorbornane (G-5), 2,5-dimethoxy-3,4-dimethylamphetamine (GANESHA), 1,4-dimethoxynaphthyl-2-isopropylamine (G-N), 2,5-dimethoxy-4-ethylthio-N-hydroxyphenethylamine (HOT-2), 2,5-dimethoxy-N-hydroxy-4-(n)-propylthiophenethylamine (HOT-7), 4-(s)-butylthio-2,5-dimethoxy-N-hydroxyphenethylamine (HOT-17), 2,5-dimethoxy-N,N-dimethyl-4-iodoamphetamine (IDNNA), 2,3,4-trimethoxyphenethylamine (IM), 3,5-dimethoxy-4-isopropoxyphenethylamine (IP), 5-ethoxy-2-methoxy-4-methylamphetamine (IRIS), 2-amino-1-(3,4-methylenedioxyphenyl)butane(J, BDB), 3-methoxy-4,5-methylenedioxyphenethylamine (LOPHOPHINE), 3,4,5-trimethoxyphenethylamine (M), 4-methoxyamphetamine (4-MA, PMA), 2,N-dimethyl-4,5-methylenedioxyamphetamine (MADAM-6), 3,5-dimethoxy-4-methallyloxyphenethylamine (MAL), 3,4-methylenedioxyamphetamine (MDA), N-allyl-3,4-methylenedioxyamphetamine (MDAL), N-butyl-3,4-methylenedioxyamphetamine (MDBU), N-benzyl-3,4-methylenedioxyamphetamine (MDBZ), N-cyclopropylmethyl-3,4-methylenedioxyamphetamine (MDCPM), N,N-dimethyl-3,4-methylenedioxyamphetamine (MDDM), N-ethyl-3,4-methylenedioxyamphetamine (MDE), N-(2-hydroxyethyl)-3,4-methylenedioxyamphetamine (MDHOET), N-isopropyl-3,4-methylenedioxyamphetamine (MDIP), N-methyl-3,4-methylenedioxyamphetamine (MDMA), 3,4-ethylenedioxy-N-methylamphetamine (MDMC), N-methoxy-3,4-methylenedioxyamphetamine (MDMEO), N-(2-methoxyethyl)-3,4-methylenedioxyamphetamine (MDMEOET), 3,4-methylenedioxy-α,α,N-trimethylphenethylamine (MDMP), N-hydroxy-3,4-methylenedioxyamphetamine (MDOH), 3,4-methylenedioxyphenethylamine (MDPEA), α,α-dimethyl-3,4-methylenedioxyphenethylamine (MDPH), 3,4-methylenedioxy-N-propargylamphetamine (MDPL), 3,4-methylenedioxy-N-propyl-amphetamine (MDPR), 3,4-dimethoxy-5-ethoxyphenethylamine (ME), 4,5-ethylenedioxy-3-methoxyamphetamine (MEDA), 4,5-diethoxy-2-methoxyamphetamine (MEE), 2,5-dimethoxy-4-ethoxyamphetamine (MEM), 4-ethoxy-3-methoxyphenethylamine (MEPEA), 5-bromo-2,4-dimethoxyamphetamine (META-DOB), 2,4-dimethoxy-5-methylthioamphetamine (META-DOT), 2,5-dimethoxy-N-methylamphetamine (METHYL-DMA), 4-bromo-2,5-dimethoxy-N-methylamphetamine (METHYL-DOB), 2-methylamino-1-(3,4-methylenedioxyphenyl)butane (METHYL-J, MBDB), 2-methylamino-1-(3,4-methylenedioxyphenyl)pentane (METHYL-K), 4-methoxy-N-methylamphetamine (METHYL-MA, PMMA), 2-methoxy-N-methyl-4,5-methylenedioxyamphetamine (METHYL-MMDA-2), 3-methoxy-4,5-methylenedioxyamphetamine (MMDA), 2-methoxy-4,5-methylenedioxyamphetamine (MMDA-2), 2-methoxy-3,4-methylenedioxyamphetamine (MMDA-3a), 4-methoxy-2,3-methylenedioxyamphetamine (MMDA-3b), 2,4-dimethoxy-5-ethoxyamphetamine (MME), 3,4-dimethoxy-5-(n)-propoxyphenethylamine (MP), 2,5-dimethoxy-4-(n)-propoxyamphetamine (MPM), 4,5-dimethoxy-2-methylthioamphetamine (ORTHO-DOT), 3,5-dimethoxy-4-propoxyphenethylamine (P), 3,5-dimethoxy-4-phenethyloxyphenethylamine (PE), phenethylamine (PEA), 3,5-dimethoxy-4-(2-propynyloxy)phenethylamine (PROPYNYL), 3,5-diethoxy-4-methoxyphenethylamine (SB), 2,3,4,5-Tetramethoxyamphetamine (TA), 4-ethoxy-3-ethylthio-5-methoxyphenethylamine (3-TASB), 3-ethoxy-4-ethylthio-5-methoxyphenethylamine (4-TASB), 3,4-diethoxy-5-methylthiophenethylamine (5-TASB), 4-(n)-butylthio-3,5-dimethoxyphenethylamine (TB), 4-ethoxy-5-methoxy-3-methylthiophenethylamine (3-TE), 3,5-dimethoxy-4-ethylthiophenethylamine (TE or 4-TE), 3,4-dimethoxy-2-methylthiophenethylamine (2-TIM), 2,4-dimethoxy-3-methylthiophenethylamine (3-TIM), 2,3-dimethoxy-4-methylthiophenethylamine (4-TIM), 3,4-dimethoxy-5-methylthiophenethylamine (3-TM), 3,5-dimethoxy-4-methylthiophenethylamine (4-TM), 3,4,5-trimethoxyamphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), 4,5-dimethoxy-3-ethylthiophenethylamine (3-TME), 3-ethoxy-5-methoxy-4-methylthiophenethylamine (4-TME), 3-ethoxy-4-methoxy-5-methylthiophenethylamine (5-TME), 3,4-methylenedioxy-2-methylthioamphetamine (2T-MMDA-3a), 2-methoxy-4,5-methylenethiooxyamphetamine (4T-MMDA-2), 2,4,5-trimethoxyphenethylamine (TMPEA), 4-ethyl-5-methoxy-2-methylthioamphetamine (2-TOET), 4-ethyl-2-methoxy-5-methylthioamphetamine (5-TOET), 5-methoxy-4-methyl-2-methylthioamphetamine (2-TOM), 2-methoxy-4-methyl-5-methylthioamphetamine (5-TOM), 2-methoxy-4-methyl-5-methylsulfinylamphetamine (TOMSO), 3,5-dimethoxy-4-propylthiophenethylamine (TP), 3,4,5-triethoxyphenethylamine (TRIS), 3-ethoxy-5-ethylthio-4-methoxyphenethylamine (3-TSB), 3,5-diethoxy-4-methylthiophenethylamine (4-TSB), 3,4-diethoxy-5-ethylthiophenethylamine (3-T-TRIS), 3,5-diethoxy-4-ethylthiophenethylamine (4-T-TRIS), (R)-2,5-dimethoxy-4-iodoamphetamine (R-DOI), or a pharmaceutically acceptable salt, hydrate, solvate, prodrug, stereoisomer, or tautomer thereof, or a combination thereof. See also PiHKAL, which is incorporated by reference in its entirety herein.

In some embodiments, hallucinogenic agents or entactogenic agents useful in the practice of the invention will include those from the class of compounds known as "tryptamines." Non-limiting examples of tryptamines useful in the practice of the invention include those disclosed in TiHKAL, which is incorporated by reference in its entirety herein.

Non-limiting examples of tryptamines include but are not limited to: 6-allyl-N,N-diethyl-norlysergamide (AL-LAD), N,N-dibutyltryptamine (DBT), α,N-dimethyltryptamine (α,N-DMT), 6,N,N-triethylnorlysergamide (ETH-LAD), 3,4-dihydro-7-methoxy-1-methylcarboline (Harmaline), 7-methoxy-1-methylcarboline (Harmine), N,N-dibutyl-4-hydroxytryptamine (4-HO-DBT), N,N-diethyl-4-hydroxytryptamine (4-HO-DET), N,N-diisopropyl-4-hydroxytryptamine (4-HO-DiPT), N,N-dimethyl-4-hydroxytryptamine (4-HO-DMT), N,N-dimethyl-5-hydroxytryptamine (5-HO-DMT, bufotenine), N,N-dipropyl-4-hydroxytryptamine (4-HO-DPT), N-ethyl-4-hydroxy-N-methyltryptamine (4-HO-MET), 4-hydroxy-N-isopropyl-N-methyltryptamine (4-HO-MiPT), 4-hydroxy-N,N-tetramethylene-tryptamine (4-HO-pyr-T), 12-methoxyibogamine (Ibogaine), N-butyl-N-methyltryptamine (MBT), N,N-diisopropyl-5,6-methylenedioxytryptamine (5,6-MDO-DiPT), N,N-dimethyl-5,6-methylenedioxytryptamine (5,6-MDO-DMT), N-isopropyl-N-methyl-5,6-methylenedioxytryptamine (5,6-MDO-MiPT), N,N-diethyl-2-methyltryptamine (2-Me-DET), 2,N,N-trimethyltryptamine (2-Me-DMT), N-acetyl-5-methoxytryptamine (melatonin), N,N-diethyl-5-methoxytryptamine (5-MeO-DET), N,N-diisopropyl-5-methoxytryptamine (5-MeO-DiPT), N-isopropyl-4-methoxy-N-methyltryptamine (4-MeO-MiPT), N-isopropyl-5-methoxy-N-methyltryptamine (5-MeO-MiPT), 5,6-dimethoxy-N-isopropyl-N-methyltryptamine (5,6-MeO-MiPT), 5-methoxy-N,N-tetramethylenetryptamine (5-MeO-pyr-T), 6-methoxy-1-methyl-1,2,3,4-tetrahydrocarboline (6-MeO-THH), 5-methoxy-2,N,N-trimethyltryptamine (5-MeO-TMT), N,N-dimethyl-5-methylthiotryptamine (5-MeS-DMT), N-isopropyl-N-methyl-tryptamine (MiPT), 6-propylnorlysergamide (PRO-LAD), N,N-tetramethylenetryptamine (pyr-T), Tryptamine (T), 7-methoxy-1-methyl-1,2,3,4-tetrahydrocarboline (Tetrahydroharmine), or α,N-dimethyl-5-methoxytryptamine (α,N,O-TMS), baeocystin, norbaeocystin, 4-hydroxytryptamine, tryptamine, N-methyltryptamine, N-ethyltryptamine, N-propyltryptamine, N-isopropyltryptamine, N-allyltryptamine, N,N-dimethyltryptamine, N,N-diethyltryptamine, N,N-dipropyltryptamine, N,N-diisopropyltryptamine, N,N-diallyltryptamine, N-methyl-N-ethyltryptamine, N-methyl-N-propyltryptamine, N-methyl-N-isopropyltryptamine, N-methyl-N-allyltryptamine, N-ethyl-N-propyltryptamine, N-ethyl-N-isopropyltryptamine, N-ethyl-N-allyltryptamine, N-propyl-N-isopropyltryptamine, N-propyl-N-allyltryptamine, N-isopropyl-N-allyltryptamine, 4-hydroxy-tryptamine, 4-hydroxy-N-methyltryptamine, 4-hydroxy-N-ethyltryptamine, 4-hydroxy-N-propyltryptamine, 4-hydroxy-N-isopropyltryptamine, 4-hydroxy-N-allyltryptamine, 4-hydroxy-N,N-dimethyltryptamine, 4-hydroxy-N,N-diethyltryptamine, 4-hydroxy-N,N-dipropyltryptamine, 4-hydroxy-N,N-diisopropyltryptamine, 4-hydroxy-N,N-diallyltryptamine, 4-hydroxy-N-methyl-N-ethyltryptamine, 4-hydroxy-N-methyl-N-propyltryptamine, 4-hydroxy-N-methyl-N-isopropyl-tryptamine, 4-hydroxy-N-methyl-N-allyltryptamine, 4-hydroxy-N-ethyl-N-propyltryptamine, 4-hydroxy-N-ethyl-N-isopropyltryptamine, 4-hydroxy-N-ethyl-N-allyltryptamine, 4-hydroxy-N-propyl-N-isopropyltryptamine, 4-hydroxy-N-propyl-N-allyltryptamine, 4-hydroxy-N-isopropyl-N-allyltryptamine, 5-hydroxytryptamine, 5-hydroxy-N-methyltryptamine, 5-hydroxy-N-ethyltryptamine, 5-hydroxy-N-propyltryptamine, 5-hydroxy-N-isopropyltryptamine, 5-hydroxy-N-allyltryptamine, 5-hydroxy-N,N-dimethyltryptamine, 5-hydroxy-N,N-diethyltryptamine, 5-hydroxy-N,N-dipropyltryptamine, 5-hydroxy-N,N-diisopropyltryptamine, 5-hydroxy-N,N-diallyltryptamine, 5-hydroxy-N-methyl-N-ethyltryptamine, 5-hydroxy-N-methyl-N-propyl-tryptamine, 5-hydroxy-N-methyl-N-isopropyltryptamine, 5-hydroxy-N-methyl-N-allyltryptamine, 5-hydroxy-N-ethyl-N-propyltryptamine, 5-hydroxy-N-ethyl-N-isopropyl-tryptamine, 5-hydroxy-N-ethyl-N-allyltryptamine, 5-hydroxy-N-propyl-N-isopropyltryptamine, 5-hydroxy-N-propyl-N-allyltryptamine, 5-hydroxy-N-isopropyl-N-allyltryptamine, 4-methoxytryptamine, 4-methoxy-N-methyltryptamine, 4-methoxy-N-ethyltryptamine, 4-methoxy-N-propyltryptamine, 4-methoxy-N-isopropyltryptamine, 4-methoxy-N-allyltryptamine, 4-methoxy-N,N-dimethyltryptamine, 4-methoxy-N,N-diethyltryptamine, 4-methoxy-N,N-dipropyl-tryptamine, 4-methoxy-N,N-diisopropyltryptamine, 4-methoxy-N,N-diallyltryptamine, 4-methoxy-N-methyl-N-ethyltryptamine, 4-methoxy-N-methyl-N-propyltryptamine, 4-methoxy-N-methyl-N-isopropyltryptamine, 4-methoxy-N-methyl-N-allyltryptamine, 4-methoxy-N-ethyl-N-propyltryptamine, 4-methoxy-N-ethyl-N-isopropyltryptamine, 4-methoxy-N-ethyl-N-allyltryptamine, 4-methoxy-N-propyl-N-isopropyl-tryptamine, 4-methoxy-N-propyl-N-allyltryptamine, 4-methoxy-N-isopropyl-N-allyltryptamine, 5-methoxy-tryptamine, 5-methoxy-N-methyltryptamine, 5-methoxy-N-ethyltryptamine, 5-methoxy-N-propyltryptamine, 5-methoxy-N-isopropyltryptamine, 5-methoxy-N-allyltryptamine, 5-methoxy-N,N-dimethyltryptamine, 5-methoxy-N,N-diethyltryptamine, 5-methoxy-N,N-dipropyltryptamine, 5-methoxy-N,N-diisopropyltryptamine, 5-methoxy-N,N-diallyltryptamine, 5-methoxy-N-methyl-N-ethyltryptamine, 5-methoxy-N-methyl-N-propyltryptamine, 5-methoxy-N-methyl-N-isopropyl-tryptamine, 5-methoxy-N-methyl-N-allyltryptamine, 5-methoxy-N-ethyl-N-propyltryptamine, 5-methoxy-N-ethyl-N-isopropyltryptamine, 5-methoxy-N-ethyl-N-allyltryptamine, 5-methoxy-N-propyl-N-isopropyl-tryptamine, 5-methoxy-N-propyl-N-allyltryptamine, 5-methoxy-N-isopropyl-N-allyltryptamine, 4-acetoxy-tryptamine, 4-acetoxy-N-methyltryptamine, 4-acetoxy-N-ethyl-tryptamine, 4-acetoxy-N-propyltryptamine, 4-acetoxy-N-isopropyltryptamine, 4-acetoxy-N-allyltryptamine, 4-acetoxy-N,N-dimethyltryptamine, 4-acetoxy-N,N-diethyltryptamine, 4-acetoxy-N,N-dipropyltryptamine, 4-acetoxy-N,N-diisopropyltryptamine, 4-acetoxy-N,N-diallyl-tryptamine, 4-acetoxy-N-methyl-N-ethyltryptamine, 4-acetoxy-N-methyl-N-propyltryptamine, 4-acetoxy-N-methyl-N-isopropyl-tryptamine, 4-acetoxy-N-methyl-N-allyl-tryptamine, 4-acetoxy-N-ethyl-N-propyltryptamine, 4-acetoxy-N-ethyl-N-isopropyl-tryptamine, 4-acetoxy-N-ethyl-N-allyltryptamine, 4-acetoxy-N-propyl-N-isopropyl-tryptamine, 4-acetoxy-N-propyl-N-allyltryptamine, 4-acetoxy-N-isopropyl-N-allyltryptamine, 5-acetoxy-tryptamine, 5-acetoxy-N-methyltryptamine, 5-acetoxy-N-ethyltryptamine, 5-acetoxy-N-propyltryptamine, 5-acetoxy-N-isopropyltryptamine, 5-acetoxy-N-allyltryptamine, 5-acetoxy-N,N-dimethyltryptamine, 5-acetoxy-N,N-diethyltryptamine, 5-acetoxy-N,N-dipropyltryptamine, 5-acetoxy-N,N-diisopropyltryptamine, 5-acetoxy-N,N-diallyl-tryptamine, 5-acetoxy-N-methyl-N-ethyltryptamine, 5-acetoxy-N-methyl-N-propyltryptamine, 5-acetoxy-N-methyl-N-isopropyl-tryptamine, 5-acetoxy-N-methyl-N-allyltryptamine, 5-acetoxy-N-ethyl-N-propyltryptamine, 5-acetoxy-N-ethyl-N-isopropyltryptamine, 5-acetoxy-N-ethyl-N-allyltryptamine, 5-acetoxy-N-propyl-N-isopropyltryptamine, 5-acetoxy-N-propyl-N-allyltryptamine, 5-acetoxy-N-isopropyl-N-allyltryptamine, α-methyltryptamine, N-ethyl-N-isopropyltryptamine, N-methyl-N-butyl-tryptamine, 2,α-dimethyltryptamine, α-N-dimethyltryptamine, α-methyl-N,N-dimethyl-tryptamine, α-ethyltryptamine, 2-methyl-N,N-dimethyltryptamine, 2-methyl-N,N-diethyl-tryptamine, 1-methylpsilocin, 5-methoxy-α-methyltryptamine, ibogaine, 7-methoxy-1-methyl-1,2,3,4-tetrahydro-b-carboline (tetrahydroharmine), 9,10-didehydro-N,N,6-triethylergoline-8b-carboxamide (6,N,N-triethyl-norlysergic acid), 9,10-didehydro-6-propyl-N,N-diethylergoline-8b-carboxamide (6-propyl-norlysergic acid), or a pharmaceutically acceptable salt, ester, hydrate, solvate, precursor, prodrug, metabolite, derivative, analog, variant, tautomer, isomer, or stereoisomer (including pure or substantially pure individual enantiomers and enantiomerically enriched mixtures having any enantiomeric excess greater than 0%) thereof, or a combination thereof (and including all amorphous and polymorphic forms). Further examples of hallucinogenic tryptamines are found in numerous references known to those of skill (e.g., Aranjo, Arch. Toxicol., 2015; 89(8):1151-73).

In embodiments, where a compound is a tryptamine, its ring-substituted derivatives as known in the art also may be used in a disclosed combination. For example, ring-substituted derivatives (among others, and among other known derivatives) include 2-phenyl-, 4-acetoxy-, 4-hydroxy-, 5-methoxy-, 5-methoxy-2-methyl-, 5-fluoro-, 5-fluoro-2-methyl-, 5-bromo-, and 7-ethyl-derivatives (Klein et al., Neuropharmacol., 2018; 142:231-239).

Other hallucinogenic agents include, besides the phenethylamines and tryptamines (and including such complexly substituted tryptamines as ibogaine), ergolines such as LSD, and beta-carbolines, and other compounds that upon administration cause non-ordinary states of consciousness and psychedelic experiences, including via 5-$HT_{2A}$ receptor agonism.

Distinctive properties of a hallucinogen and an entactogen are available to one of skill in the art. In one example, the ability of a compound to activate the 5-$HT_{2A}$ receptor in vivo, and the potency thereof, can be determined in a head twitch response (HTR) rodent assay, the results of which are predictive of hallucinogenic effects in humans (Halberstadt et al., J Psychopharmacol. 2011; 25(11): 1548-1561). HTR methods are described in, e.g, Halberstadt & Geyer Psychopharmacol (Berl). 2013; 227(4):727-3, Halberstadt & Geyer, Neuropharmacol, 2014; 77:200-7; Nichols et al., ACS Chem Neurosci. 2015; 6(7): 1165-1175; Klein et al., Neuropharmacol, 2018; 142:231-239).

For distinction, a substituted phenethylamine with hallucinogenic properties is referred to herein as "a substituted phenethylamine hallucinogen," and a substituted tryptamine with hallucinogenic properties is referred to herein as "a substituted tryptamine hallucinogen." Accordingly, a substituted phenethylamine with entactogenic properties is referred to herein as "a substituted phenethylamine entactogen," and a substituted tryptamine with entactogenic properties is referred to herein as "a substituted tryptamine entactogen." In embodiments, a hallucinogen also may produce properties characteristic of an entactogen, or an entactogen also may produce properties that are characteristic of a hallucinogen. In either case, such compound may be included in a disclosed combination comprising an entactogen and a hallucinogen or a disclosed combination comprising an entactogen and a dissociative.

Hallucinogens and entactogens may be distinguished according to the effects thereof. For example, studies have shown that effects of hallucinogens vary widely, though alterations of optic, acoustic, and tactile perception have all been recorded. Additionally, formal thought is more or less impaired in all subjects. Contrastingly, entactogens have more uniform results, with an important characteristic being that the subjects still felt in control of the situation, whereas subjects that had taken hallucinogens (at least, at sufficient doses) did not. This mental state, combined with the previously-described subjective relaxation and physical activation divergence, make the effects of entactogens differentiable from the effects of hallucinogens (Gouzoulis-Mayfrank, Heffter Rev Psychedelic Res 2001; 2: 64-72.)

In some embodiments, a combination or composition of the invention will further comprise an additional active compound. In some embodiments, a combination or composition of the invention will further comprise one or more additional active compounds.

In some embodiments, the additional active compound is an anti-nausea agent such as ondansetron, promethazine, promethazine, metoclopramide, prochlorperazine, or lorazepam.

In some embodiments, the additional active compound is an agent for the treatment of serotonin syndrome. Agents for the treatment of serotonin syndrome include clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, midazolam, clobazam, cyproheptadine.

In some embodiments, the additional active compound is any one or more of amino acids, antioxidants, anti-inflammatory agents, analgesics, antineuropathic and antinociceptive agents, antimigraine agents, anxiolytics, antidepressants, antipsychotics, anti-PTSD agents, immunostimulants, anti-cancer agents, antiemetics, orexigenics, antiulcer agents, antihistamines, antihypertensives, anticonvulsants, antiepileptics, bronchodilators, neuroprotectants, nootropics, entactogens and empathogens, entheogens, psychedelics, monoamine oxidase inhibitors, sedatives, sleep aids, ADHD drugs, supplements, stimulants, and vitamins.

In some embodiments, the supplement is selected from the group consisting of alpha lipoic acid (ALA), magnesium, vitamin C, ascorbate, grape seed extract, grapefruit juice, acetyl-L-carnitine (ALCAR), green tea extract, 5-HTP, melatonin, and CoQ10.

Additional active compounds may be in ion, freebase, or salt form, and may be isomers, prodrugs, derivatives (including physiologically functional derivatives), or analogs.

In some embodiments, the additional active compound is an oxytocin agent. In some embodiments, the oxytocin agent is an oxytocin agonist and/or an oxytocin releasing agent (ORA). In some embodiments the ORA is any of a melanocortin (MC) receptor agonist, a melanocyte stimulating hormone, α-melanocortin, α-melanotropin, melanotan II (MT-II), bremelanotide, or an analog or derivative thereof. Other non-limiting examples of ORAs include serotonin receptor agonists such as 5-$HT_{1A}$, 5-$HT_{2A}$, or 5-$HT_{2C}$ receptor agonists, and including (4-fluoro-N-(2-{4-[(2S)-2-(hydroxymethyl)-2,3-dihydro-1,4-benzodioxin-5-yl]piperazin-1-yl}ethyl)benzamide (flesinoxan), 5-(3-[((2S)-1,4-benzodioxan-2-ylmethyl) amino]propoxy)-1,3-benzodioxole, (osemozotan), buspirone, gepirone, befiradol, eptapirone, 8-OH-DPAT, tandospirone, serotonin, ergine, ergotamine, lysergic acid, lysergic acid diethylamide (LSD), psilocybin, 4-hydroxy-dimethyltryptamine, N,N-dimethyltryptamine (DMT), 5-methoxy-dimethyltryptamine (5-MeO-DMT), mescaline, 4-bromo-2,5-dimethoxy phenethylamine, 3,4-methylenedioxyamphetamine (MDA), methylenedioxyethyl-amphetamine (MDEA), R-MDEA, S-MDEA, tenamfetamine, lorcaserin, their analogs, derivatives, and enantiomers, where applicable, and the prodrugs and salts thereof.

e. Combinations of Hallucinogenic Agents and Entactogenic Agents

In some embodiments, a therapeutic combination comprises a hallucinogenic agent and an entactogenic agent. In some embodiments, a therapeutic combination comprises a hallucinogenic agent that is any of a substituted phenethylamine, a substituted tryptamine, a semi-synthetic alkaloid, and a lysergamide, and an entactogenic agent that is any of a substituted amphetamine, a substituted benzofuran, a substituted phenethylamine, and a substituted tryptamine.

In some embodiments, a therapeutic combination comprises a hallucinogenic agent and a non-racemic entactogen. In some embodiments, a therapeutic combination comprises a substituted phenethylamine and a non-racemic entactogen. In some embodiments, a therapeutic combination comprises a substituted tryptamine and a non-racemic entactogen. In some embodiments, a therapeutic combination comprises a semi-synthetic alkaloid and a non-racemic entactogen. In some embodiments, a therapeutic combination comprises a lysergamide and a non-racemic entactogen.

In some embodiments, the non-racemic entactogen comprises 90% or less of one enantiomer, such as the (R)-enantiomer, and 10% or more of another enantiomer, such as the (S)-enantiomer. In some embodiments, the non-racemic entactogen comprises one enantiomer in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the non-racemic entactogen comprises one enantiomer in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the non-racemic entactogen comprises one enantiomer in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the non-racemic entactogen comprises the (R)- and (S)-enantiomers in a ratio of about 6:1 to 12:1, 7:1 to 11:1, or 8:1 to 10:1. In some embodiments, the non-racemic entactogen comprises the (R)- and (S)-enantiomers in a ratio of about 6:1, 7:1, 8:1, 9:1, 10:1, 11:1, or 12:1. In some embodiments, the non-racemic entactogen comprises the (R)- and (S)-enantiomers in a ratio of 9:1.

In some embodiments, a therapeutic combination comprises a hallucinogenic agent, wherein the hallucinogenic agent comprises any one or more of psilocybin, psilocin, DMT, 5-MeO-DMT, mescaline, salvinorin A, THC, 4-Aco-DMT, 5-Br-DMT, 5-Cl-DMT, 5-F-DMT, 4,5-MDO-DMT, 4,5-MDO-DiPT, PRO-LAD, ETH-LAD, AL-LAD, 1P-LSD, LSD, a 2C-X compound, e.g., 2C-B and others described herein, and DiPT, and an entactogenic agent, wherein the entactogenic agent comprises any one or more of MDMA, R-MDMA, S-MDMA, non-racemic MDMA, 4-MTA, MDAI, 5-methyl-MDA, 5-APB, 6-APB, DiFMDA, MBDB, BDB, MDA, MDEA, R-MDEA, and S-MDEA. In some embodiments, the entactogenic agent in a provided therapeutic combination is non-racemic MDMA.

In some embodiments, a therapeutic combination comprises a hallucinogenic agent, wherein the hallucinogenic agent is psilocybin, psilocin, DMT, 5-MeO-DMT, mescaline, salvinorin A, THC, 4-Aco-DMT, 5-Br-DMT, 5-Cl-DMT, 5-F-DMT, 4,5-MDO-DMT, 4,5-MDO-DiPT, PRO-LAD, ETH-LAD, AL-LAD, 1P-LSD, LSD, a 2C-X compound, e.g., 2C-B and others described herein, or DiPT, and an entactogenic agent, wherein the entactogenic agent is MDMA, R-MDMA, S-MDMA, non-racemic MDMA, 4-MTA, MDAI, 5-methyl-MDA, 5-APB, 6-APB, DiFMDA, MBDB, BDB, MDA, MDEA, R-MDEA, and S-MDEA.

In some embodiments, a therapeutic combination comprises a hallucinogenic agent and non-racemic MDMA. In some embodiments, the combination comprises the hallucinogenic agent and non-racemic MDMA comprising 90% or less of R-MDMA and 10% or more of S-MDMA, or a pharmaceutically acceptable salt thereof. In some embodiments, the combination comprises the hallucinogenic agent and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the combination comprises the hallucinogenic agent and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the combination comprises the hallucinogenic agent and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the combination comprises the hallucinogenic agent and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the combination comprises the hallucinogenic agent and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the combination comprises the hallucinogenic agent and non-racemic MDMA, wherein R-MDMA and S-MDMA, or pharmaceutically acceptable salt(s) thereof, are present in a ratio of 9:1.

In some embodiments, a therapeutic combination comprises a hallucinogenic agent and a non-racemic entactogen. In some embodiments, a disclosed therapeutic combination comprises any of psilocybin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, psilocin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-MeO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, mescaline and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, salvinorin A and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, THC and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4-Aco-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Br-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Cl-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-F-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-MDO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-MDO-DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, PRO-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, ETH-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, AL-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 1P-LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, and DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1.

In some embodiments, a therapeutic combination comprises one or more 2C-X compounds and a non-racemic entactogen. In some embodiments, a therapeutic combination comprises a 2C-X compound and a non-racemic entactogen. In some embodiments, the 2C-X compound is any of 2C-B, 2C-B-AN, 2C-B-FLY, 2C-B-BUTTERFLY, 2C-B-FLY-NBOMe, 2C-B-FLY-NB2EtO5Cl, 2C-Bn, 2C-Bu, 2C-B-5-HEMIFLY, 2C-C, 2C-C-3, 2C-CN, 2C-CP, 2C-D, 2C-E, 2C-EF, 2C-F, 2C-G, 2C-G-1, 2C-G-2, 2C-G-3, 2C-G-4, 2C-G-5, 2C-G-6, 2C-G-N, 2C-H, 2C-I, 2CB-Ind, 2C-iP, 2C-N, 2C-NH2, 2C-PYR, 2C-PIP, 2C-O, 2C-O-4, 2C-MOM, 2C-P, 2C-Ph, 2C-Se, 2C-T, 2C-T-2, 2C-T-3, 2C-T-4, 2C-T-5, 2C-T-6, 2C-T-7, 2C-T-8, 2C-T-9, 2C-T-10, 2C-T-11, 2C-T-12, 2C-T-13, 2C-T-14, 2C-T-15, 2C-T-16, 2C-T-17, 2C-T-18, 2C-T-19, 2C-T-21, 2C-T-21.5, 2C-T-22, 2C-T-23, 2C-T-24, 2C-T-25, 2C-T-27, 2C-T-28, 2C-T-30, 2C-T-31, 2C-T-32, 2C-T-33, 2C-DFM, 2C-TFM, 2C-TFE, 2C-YN, 2C-V, and 2C-AL. In some embodiments, the non-racemic entactogen is MDMA.

In some embodiments, a therapeutic combination comprises a 2C-X compound and non-racemic MDMA. In some embodiments, the combination comprises the 2C-X compound and non-racemic MDMA comprising 90% or less of R-MDMA and 10% or more of S-MDMA, or pharmaceutically acceptable salt(s) thereof. In some embodiments, the combination comprises the 2C-X compound and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the combination comprises the 2C-X compound and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the combination comprises the 2C-X compound and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the combination comprises the 2C-X compound and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the combination comprises the 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the combination comprises the 2C-X compound and non-racemic MDMA, wherein R-MDMA and S-MDMA, or pharmaceutically acceptable salt(s) thereof, are present in a ratio of 9:1.

In some embodiments, the combination comprises the 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, a disclosed therapeutic combination comprises any of 2C-B and about 6:1, 7:1, 8:1, 9:1, 10:1, 11:1, or 12:1 R:S-MDMA, 2C-B-AN and about 6:1, 7:1, 8:1, 9:1, 10:1, 11:1, or 12:1 R: S-MDMA, 2C-B-FLY and about 6:1, 7:1, 8:1, 9:1, 10:1, 11:1, or 12:1 R: S-MDMA, 2C-B-Butterfly and about 6:1, 7:1, 8:1, 9:1, 10:1, 11:1, or 12:1 R: S-MDMA, 2C-B-Fly-NBOMe and about 6:1, 7:1, 8:1, 9:1, 10:1, 11:1, or 12:1 R:S-MDMA, 2C-B-Fly-NB2EtO5Cl and about 6:1, 7:1, 8:1, 9:1, 10:1, 11:1, or 12:1 R:S-MDMA, 2C-Bn and about 6:1, 7:1, 8:1, 9:1, 10:1, 11:1, or 12:1 R: S-MDMA, 2C-Bu and about 6:1, 7:1, 8:1, 9:1, 10:1, 11:1, or 12:1 R: S-MDMA, 2C-B-5-Hemifly and about 6:1, 7:1, 8:1, 9:1, 10:1, 11:1, or 12:1 R:S-MDMA, 2C-C and about 6:1, 7:1, 8:1, 9:1, 10:1, 11:1, or 12:1 R: S-MDMA, 2C-C-3 and about 6:1, 7:1, 8:1, 9:1, 10:1, 11:1, or 12:1 R:S-MDMA, 2C-CN and about 6:1, 7:1, 8:1, 9:1, 10:1, 11:1, or 12:1 R:S-MDMA, 2C-CP and about 6:1, 7:1, 8:1, 9:1, 10:1, 11:1, or 12:1 R:S-MDMA, 2C-D and about 6:1, 7:1, 8:1, 9:1, 10:1, 11:1, or 12:1 R:S-MDMA, 2C-E and about 6:1, 7:1, 8:1, 9:1, 10:1, 11:1, or 12:1 R:S-MDMA, 2C-EF and about 6:1, 7:1, 8:1, 9:1, 10:1, 11:1, or 12:1 R: S-MDMA, 2C-F and about 6:1, 7:1, 8:1, 9:1, 10:1, 11:1, or 12:1 R:S-MDMA, 2C-G and about 6:1, 7:1, 8:1, 9:1, 10:1, 11:1, or 12:1 R:S-MDMA, 2C-G-1 and about 6:1, 7:1, 8:1, 9:1, 10:1, 11:1, or 12:1 R:S-MDMA, 2C-G-2 and about 6:1, 7:1, 8:1, 9:1, 10:1, 11:1, or 12:1 R:S-MDMA, 2C-G-3 and about 6:1, 7:1, 8:1, 9:1, 10:1, 11:1, or 12:1 R: S-MDMA, 2C-G-4 and about 6:1, 7:1, 8:1, 9:1, 10:1, 11:1, or 12:1 R:S-MDMA, 2C-G-5 and about 6:1, 7:1, 8:1, 9:1, 10:1, 11:1, or 12:1 R: S-MDMA, 2C-G-6 and about 6:1, 7:1, 8:1, 9:1, 10:1, 11:1, or 12:1 R:S-MDMA, 2C-G-N and about 6:1, 7:1, 8:1, 9:1, 10:1, 11:1, or 12:1 R: S-MDMA, 2C-H and about 6:1, 7:1, 8:1, 9:1, 10:1, 11:1, or 12:1 R:S-MDMA, 2C-I and about 6:1, 7:1, 8:1, 9:1, 10:1, 11:1, or 12:1 R:S-MDMA, 2CB-Ind and about 6:1, 7:1, 8:1, 9:1, 10:1, 11:1, or 12:1 R:S-MDMA, 2C-iP and about 6:1, 7:1, 8:1, 9:1, 10:1, 11:1, or 12:1 R: S-MDMA, 2C-N and about 6:1, 7:1, 8:1, 9:1, 10:1, 11:1, or 12:1 R:S-MDMA, 2C-NH2 and about 6:1, 7:1, 8:1, 9:1, 10:1, 11:1, or 12:1 R:S-MDMA, 2C-PYR and about 6:1, 7:1, 8:1, 9:1, 10:1, 11:1, or 12:1 R:S-MDMA, 2C-PIP and about 6:1, 7:1, 8:1, 9:1, 10:1, 11:1, or 12:1 R:S-MDMA, 2C-O and about 6:1, 7:1, 8:1, 9:1, 10:1, 11:1, or 12:1 R: S-MDMA, 2C-O-4 and about 6:1, 7:1, 8:1, 9:1, 10:1, 11:1, or 12:1 R: S-MDMA, 2C-MOM and about 6:1, 7:1, 8:1, 9:1, 10:1, 11:1, or 12:1 R:S-MDMA, 2C-P and about 6:1, 7:1, 8:1, 9:1, 10:1, 11:1, or 12:1 R:S-MDMA, 2C-Ph and about 6:1, 7:1, 8:1, 9:1, 10:1, 11:1, or 12:1 R:S-MDMA, 2C-Se and about 6:1, 7:1, 8:1, 9:1, 10:1, 11:1, or 12:1 R:S-MDMA, 2C-T and about 6:1, 7:1, 8:1, 9:1, 10:1, 11:1, or 12:1 R: S-MDMA, 2C-T-2 and about 6:1, 7:1, 8:1, 9:1, 10:1, 11:1, or 12:1 R:S-MDMA, 2C-T-3 and about 6:1, 7:1, 8:1, 9:1, 10:1, 11:1, or 12:1 R:S-MDMA, 2C-T-4 and about 6:1, 7:1, 8:1, 9:1, 10:1, 11:1, or 12:1 R:S-MDMA, 2C-T-5 and about 6:1, 7:1, 8:1, 9:1, 10:1, 11:1, or 12:1 R:S-MDMA, 2C-T-6 and about 6:1, 7:1, 8:1, 9:1, 10:1, 11:1, or 12:1 R: S-MDMA, 2C-T-7 and about 6:1, 7:1, 8:1, 9:1, 10:1, 11:1, or 12:1 R:S-MDMA, 2C-T-8 and about 6:1, 7:1, 8:1, 9:1, 10:1, 11:1, or 12:1 R:S-MDMA, 2C-T-9 and about 6:1, 7:1, 8:1, 9:1, 10:1, 11:1, or 12:1 R:S-MDMA, 2C-T-10 and about 6:1, 7:1, 8:1, 9:1, 10:1, 11:1, or 12:1 R:S-MDMA, 2C-T-11 and about 6:1, 7:1, 8:1, 9:1, 10:1, 11:1, or 12:1 R:S-MDMA, 2C-T-12 and about 6:1, 7:1, 8:1, 9:1, 10:1, 11:1, or 12:1 R:S-MDMA, 2C-T-13 and about 6:1, 7:1, 8:1, 9:1, 10:1, 11:1, or 12:1 R:S-MDMA, 2C-T-14 and about 6:1, 7:1, 8:1, 9:1, 10:1, 11:1, or 12:1 R:S-MDMA, 2C-T-15 and about 6:1, 7:1, 8:1, 9:1, 10:1, 11:1, or 12:1 R:S-MDMA, 2C-T-16 and about 6:1, 7:1, 8:1, 9:1, 10:1, 11:1, or 12:1 R:S-MDMA, 2C-T-17 and about 6:1, 7:1, 8:1, 9:1, 10:1, 11:1, or 12:1 R:S-MDMA, 2C-T-18 and about 6:1, 7:1, 8:1, 9:1, 10:1, 11:1, or 12:1 R:S-MDMA, 2C-T-19 and about 6:1, 7:1, 8:1, 9:1, 10:1, 11:1, or 12:1 R:S-MDMA, 2C-T-21 and about 6:1, 7:1, 8:1, 9:1, 10:1, 11:1, or 12:1 R:S-MDMA, 2C-T-21.5 and about 6:1, 7:1, 8:1, 9:1, 10:1, 11:1, or 12:1 R:S-MDMA, 2C-T-22 and about 6:1, 7:1, 8:1, 9:1, 10:1, 11:1, or 12:1 R: S-MDMA, 2C-T-23 and about 6:1, 7:1, 8:1, 9:1, 10:1, 11:1, or 12:1 R:S-MDMA, 2C-T-24 and about 6:1, 7:1, 8:1, 9:1, 10:1, 11:1, or 12:1 R:S-MDMA, 2C-T-25 and about 6:1, 7:1, 8:1, 9:1, 10:1, 11:1, or 12:1 R:S-MDMA, 2C-T-27 and about 6:1, 7:1, 8:1, 9:1, 10:1, 11:1, or 12:1 R:S-MDMA, 2C-T-28 and about 6:1, 7:1, 8:1, 9:1, 10:1, 11:1, or 12:1 R: S-MDMA, 2C-T-30 and about 6:1, 7:1, 8:1, 9:1, 10:1, 11:1, or 12:1 R:S-MDMA, 2C-T-31 and about 6:1, 7:1, 8:1, 9:1, 10:1, 11:1, or 12:1 R: S-MDMA, 2C-T-32 and about 6:1, 7:1, 8:1, 9:1, 10:1, 11:1, or 12:1 R:S-MDMA, 2C-T-33 and about 6:1, 7:1, 8:1, 9:1, 10:1, 11:1, or 12:1 R:S-MDMA, 2C-DFM and about 6:1, 7:1, 8:1, 9:1, 10:1, 11:1, or 12:1 R:S-MDMA, 2C-TFM and about 6:1, 7:1, 8:1, 9:1, 10:1, 11:1, or 12:1 R:S-MDMA, 2C-TFE and about 6:1, 7:1, 8:1, 9:1, 10:1, 11:1, or 12:1 R:S-MDMA, 2C-YN and about 6:1, 7:1, 8:1, 9:1, 10:1, 11:1, or 12:1 R: S-MDMA, 2C-V and about 6:1, 7:1, 8:1, 9:1, 10:1, 11:1, or 12:1 R:S-MDMA, and 2C-AL and about 6:1, 7:1, 8:1, 9:1, 10:1, 11:1, or 12:1 R:S-MDMA.

In some embodiments, a disclosed therapeutic combination comprises psilocybin and and 9:1 R:S-MDMA. In some embodiments, a disclosed therapeutic combination comprises psilocin and 9:1 R:S-MDMA. In some embodiments, a disclosed therapeutic combination comprises DMT and 9:1 R:S-MDMA. In some embodiments, a disclosed therapeutic combination comprises 5-MeO-DMT and 9:1 R:S-MDMA. In some embodiments, a disclosed therapeutic combination comprises mescaline and 9:1 R:S-MDMA. In some embodiments, a disclosed therapeutic combination comprises salvinorin A and 9:1 R:S-MDMA. In some embodiments, a disclosed therapeutic combination comprises THC and 9:1 R:S-MDMA. In some embodiments, a disclosed therapeutic combination comprises 4-Aco-DMT and 9:1 R:S-MDMA. In some embodiments, a disclosed therapeutic combination comprises 5-Br-DMT and 9:1 R:S-MDMA. In some embodiments, a disclosed therapeutic combination comprises 5-Cl-DMT and 9:1 R:S-MDMA. In some embodiments, a disclosed therapeutic combination comprises 5-F-DMT and 9:1 R:S-MDMA. In some embodiments, a disclosed therapeutic combination comprises 4,5-MDO-DMT and 9:1 R:S-MDMA. In some embodiments, a disclosed therapeutic combination comprises 4,5-MDO-DiPT and 9:1 R:S-MDMA. In some embodiments, a disclosed therapeutic combination comprises PRO-LAD and 9:1 R:S-MDMA. In some embodiments, a disclosed therapeutic combination comprises ETH-LAD and 9:1 R:S-MDMA. In some embodiments, a disclosed therapeutic combination comprises AL-LAD and 9:1 R:S-MDMA. In some embodiments, a disclosed therapeutic combination comprises 1P-LSD and 9:1 R:S-MDMA. In some embodiments, a disclosed therapeutic combination comprises LSD and 9:1 R:S-MDMA. In some embodiments, a disclosed therapeutic combination comprises DiPT and 9:1 R: S-MDMA.

In some embodiments, a disclosed therapeutic combination comprises 2C-B or an analog thereof and 9:1 R:S-MDMA. In some embodiments, a disclosed therapeutic combination comprises 2C-C or an analog thereof and 9:1 R:S-MDMA. In some embodiments, a disclosed therapeutic combination comprises 2C-D or an analog thereof and 9:1 R:S-MDMA. In some embodiments, a disclosed therapeutic combination comprises 2C-E or an analog thereof and 9:1 R:S-MDMA. In some embodiments, a disclosed therapeutic combination comprises 2C-F or an analog thereof and 9:1 R:S-MDMA. In some embodiments, a disclosed therapeutic combination comprises 2C-G or an analog thereof and 9:1 R:S-MDMA. In some embodiments, a disclosed therapeutic combination comprises 2C-H or an analog thereof and 9:1 R:S-MDMA. In some embodiments, a disclosed therapeutic combination comprises 2C-I or an analog thereof and 9:1 R:S-MDMA. In some embodiments, a disclosed therapeutic combination comprises 2C-N or an analog thereof and 9:1 R:S-MDMA. In some embodiments, a disclosed therapeutic combination comprises 2C-O or an analog thereof and 9:1 R:S-MDMA. In some embodiments, a disclosed therapeutic combination comprises 2C-P or an analog thereof and 9:1 R:S-MDMA. In some embodiments, a disclosed therapeutic combination comprises 2C-Se or an analog thereof and 9:1 R:S-MDMA. In some embodiments, a disclosed therapeutic combination comprises 2C-T or an analog thereof and 9:1 R:S-MDMA. In some embodiments, a disclosed therapeutic combination comprises 2C-V or an analog thereof and 9:1 R:S-MDMA.

In some embodiments, a disclosed therapeutic combination comprises 2C-B or an analog thereof and 9:1 R:S-MDMA HCl. In some embodiments, a disclosed therapeutic combination comprises 2C-B or an analog thereof and 9:1 R:S-MDMA phosphate. In some embodiments, a disclosed therapeutic combination comprises 2C-B or an analog thereof and 9:1 R:S-MDMA sulfate.

In some of any embodiments, a disclosed therapeutic combination further comprises a dissociative agent. In some of any embodiments, a disclosed combination comprises a dissociative agent in place of a hallucinogenic agent, i.e., the combination comprises a dissociative agent and an entactogenic agent. In some of any embodiments, a disclosed combination further comprises a deuterated dissociative agent. In some of any embodiments, a disclosed combination further comprises a short-acting dissociative agent. In some embodiments, the dissociative agent is ketamine or a derivative thereof.

B. Compositions, Formulations, and Kits

In some aspects, provided herein are compositions, such as pharmaceutical compositions comprising a disclosed therapeutic combination of a hallucinogen and an entactogen. In some embodiments, the pharmaceutical composition is a unit dosage form.

a. Pharmaceutical Compositions

In some embodiments, a provided pharmaceutical composition (sometimes for shorthand, "composition") comprises a hallucinogenic agent and an entactogenic agent, wherein the hallucinogenic agent comprises psilocybin, psilocin, DMT, 5-MeO-DMT, mescaline, salvinorin A, THC, 4-Aco-DMT, 5-Br-DMT, 5-Cl-1DMT, 5-F-DMT, 4,5-MDO-DMT, 4,5-MDO-DiPT, PRO-LAD, ETH-LAD, AL-LAD, 1P-LSD, DiPT, 2C-B, 2C-C or another 2C-x compound, and wherein the entactogenic agent comprises MDMA, R-MDMA, S-MDMA, non-racemic MDMA, 4-MTA, MDAI, 5-methyl-MDA, 5-APB, or 6-APB, DiFMDA, MBDB, BDB, MDA, MDEA, R-MDEA, and S-MDEA. In some embodiments, the pharmaceutical composition comprises a pharmaceutically acceptable salt, hydrate, solvate, prodrug, metabolite, derivative, stereoisomer, and/or tautomer of the hallucinogenic agent and/or the entactogenic agent. In some embodiments, the pharmaceutical composition comprises a pharmaceutically acceptable excipient.

In some embodiments, the entactogenic agent of a provided composition is non-racemic MDMA, which comprises a non-racemic mixture of MDMA enantiomers R-MDMA and S-MDMA. In some embodiments, the non-racemic mixture comprises 90% or less of R-MDMA and 10% or more of S-MDMA, or a pharmaceutically acceptable salt thereof. In some embodiments, the non-racemic mixture comprises R-MDMA or a pharmaceutically acceptable salt thereof in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the non-racemic mixture comprises R-MDMA or a pharmaceutically acceptable salt thereof in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the non-racemic mixture comprises R-MDMA or a pharmaceutically acceptable salt thereof in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the non-racemic mixture comprises R-MDMA and S-MDMA, or pharmaceutically acceptable salt(s) thereof, in an ratio of about 6:1 to 12:1, 7:1 to 11:1, or 8:1 to 10:1. In some embodiments, the non-racemic mixture comprises R-MDMA and S-MDMA, or pharmaceutically acceptable salt(s) thereof, in a ratio of about 6:1, 7:1, 8:1, 9:1, 10:1, 11:1, or 12:1. In some embodiments, the non-racemic mixture comprises R-MDMA and S-MDMA, or pharmaceutically acceptable salt(s) thereof, in a ratio of 9:1.

In some embodiments, a provided composition comprises a non-racemic mixture of MDMA, wherein R-MDMA and/or S-MDMA are any of pharmaceutically acceptable hydrochloride, sulfate, tartrate, sodium, acetate, phosphate, chloride, or potassium salts. In some embodiments, the composition comprises the same salt form of R-MDMA and S-MDMA. In some embodiments, the composition comprises R-MDMA HCL and S-MDMA HCL in a ratio of about 6:1, 7:1, 8:1, 9:1, 10:1, 11:1, or 12:1. In some embodiments, the composition comprises R-MDMA phosphate and S-MDMA phosphate in a ratio of about 6:1, 7:1, 8:1, 9:1, 10:1, 11:1, or 12:1. In some embodiments, the composition comprises R-MDMA sulfate and S-MDMA sulfate in a ratio of about 6:1, 7:1, 8:1, 9:1, 10:1, 11:1, or 12:1. In some embodiments, the composition comprises R-MDMA tartrate and S-MDMA tartrate in a ratio of about 6:1, 7:1, 8:1, 9:1, 10:1, 11:1, or 12:1. In some embodiments, the composition comprises R-MDMA citrate and S-MDMA citrate in a ratio of about 6:1, 7:1, 8:1, 9:1, 10:1, 11:1, or 12:1.

In some embodiments, the composition comprises different salt forms of R-MDMA and S-MDMA. Non-limiting exemplary embodiments of distinct salt forms of R-MDMA and S-MDMA include R-MDMA HCl and S-MDMA phosphate, R-MDMA phosphate and S-MDMA HCL, R-MDMA HCl and S-MDMA sulfate, R-MDMA sulfate and S-MDMA HCL, R-MDMA sulfate and S-MDMA phosphate, R-MDMA phosphate and S-MDMA sulfate, and others that would be understood in view of the disclosure herein. In some embodiments, different salt forms of MDMA enantiomers are present in molar ratios of about 6:1, 7:1, 8:1, 9:1, 10:1, 11:1, or 12:1 R-MDMA to S-MDMA.

In some embodiments, a disclosed composition comprises a hallucinogenic agent and non-racemic MDMA. In some embodiments, the composition comprises the hallucinogenic agent and non-racemic MDMA comprising 90% or less of R-MDMA and 10% or more of S-MDMA, or a pharmaceutically acceptable salt thereof. In some embodiments, the composition comprises the hallucinogenic agent and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the composition comprises the hallucinogenic agent and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the composition comprises the hallucinogenic agent and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the composition comprises the hallucinogenic agent and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the composition comprises the hallucinogenic agent and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the composition comprises the hallucinogenic agent and non-racemic MDMA, wherein R-MDMA and S-MDMA, or pharmaceutically acceptable salt(s) thereof, are present in a ratio of 9:1.

In some embodiments, a disclosed composition comprises a hallucinogenic agent and a non-racemic entactogen. In some embodiments, a disclosed composition comprises any of psilocybin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, psilocin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-MeO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, mescaline and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, salvinorin A and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, THC and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4-Aco-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Br-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Cl-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-F-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-MDO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-MVDO-DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, PRO-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, ETH-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, AL-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 1P-LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, and DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1.

In some embodiments, a disclosed composition comprises a 2C-X compound and non-racemic MDMA. In some embodiments, the composition comprises the 2C-X compound and non-racemic MDMA comprising 90% or less of R-MDMA and 10% or more of S-MDMA, or pharmaceutically acceptable salt(s) thereof. In some embodiments, the composition comprises the 2C-X compound and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the composition comprises the 2C-X compound and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the composition comprises the 2C-X compound and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the composition comprises the 2C-X compound and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the composition comprises the 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the composition comprises the 2C-X compound and non-racemic MDMA, wherein R-MDMA and S-MDMA, or pharmaceutically acceptable salt(s) thereof, are present in a ratio of 9:1.

In some embodiments, a disclosed compositions comprises a 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, a disclosed composition comprises any of 2C-B and about 6:1, 7:1, 8:1, 9:1, 10:1, 11:1, or 12:1 R:S-MDMA, 2C-B-AN and about 6:1, 7:1, 8:1, 9:1, 10:1, 11:1, or 12:1 R:S-MDMA, 2C-B-FLY and about 6:1, 7:1, 8:1, 9:1, 10:1, 11:1, or 12:1 R:S-MDMA, 2C-B-Butterfly and about 6:1, 7:1, 8:1, 9:1, 10:1, 11:1, or 12:1 R: S-MDMA, 2C-B-Fly-NBOMe and about 6:1, 7:1, 8:1, 9:1, 10:1, 11:1, or 12:1 R:S-MDMA, 2C-B-Fly-NB2EtO5Cl and about 6:1, 7:1, 8:1, 9:1, 10:1, 11:1, or 12:1 R:S-MDMA, 2C-Bn and about 6:1, 7:1, 8:1, 9:1, 10:1, 11:1, or 12:1 R: S-MDMA, 2C-Bu and about 6:1, 7:1, 8:1, 9:1, 10:1, 11:1, or 12:1 R: S-MDMA, 2C-B-5-Hemifly and about 6:1, 7:1, 8:1, 9:1, 10:1, 11:1, or 12:1 R:S-MDMA, 2C-C and about 6:1, 7:1, 8:1, 9:1, 10:1, 11:1, or 12:1 R: S-MDMA, 2C-C-3 and about 6:1, 7:1, 8:1, 9:1, 10:1, 11:1, or 12:1 R:S-MDMA, 2C-CN and about 6:1, 7:1, 8:1, 9:1, 10:1, 11:1, or 12:1 R:S-MDMA, 2C-CP and about 6:1, 7:1, 8:1, 9:1, 10:1, 11:1, or 12:1 R:S-MDMA, 2C-D and about 6:1, 7:1, 8:1, 9:1, 10:1, 11:1, or 12:1 R:S-MDMA, 2C-E and about 6:1, 7:1, 8:1, 9:1, 10:1, 11:1, or 12:1 R:S-MDMA, 2C-EF and about 6:1, 7:1, 8:1, 9:1, 10:1, 11:1, or 12:1 R:S-MDMA, 2C-F and about 6:1, 7:1, 8:1, 9:1, 10:1, 11:1, or 12:1 R:S-MDMA, 2C-G and about 6:1, 7:1, 8:1, 9:1, 10:1, 11:1, or 12:1 R:S-MDMA, 2C-G-1 and about 6:1, 7:1, 8:1, 9:1, 10:1, 11:1, or 12:1 R:S-MDMA, 2C-G-2 and about 6:1, 7:1, 8:1, 9:1, 10:1, 11:1, or 12:1 R:S-MDMA, 2C-G-3 and about 6:1, 7:1, 8:1, 9:1, 10:1, 11:1, or 12:1 R:S-MDMA, 2C-G-4 and about 6:1, 7:1, 8:1, 9:1, 10:1, 11:1, or 12:1 R:S-MDMA, 2C-G-5 and about 6:1, 7:1, 8:1, 9:1, 10:1, 11:1, or 12:1 R:S-MDMA, 2C-G-6 and about 6:1, 7:1, 8:1, 9:1, 10:1, 11:1, or 12:1 R:S-MDMA, 2C-G-N and about 6:1, 7:1, 8:1, 9:1, 10:1, 11:1, or 12:1 R: S-MDMA, 2C-H and about 6:1, 7:1, 8:1, 9:1, 10:1, 11:1, or 12:1 R:S-MDMA, 2C-I and about 6:1, 7:1, 8:1, 9:1, 10:1, 11:1, or 12:1 R:S-MDMA, 2CB-Ind and about 6:1, 7:1, 8:1, 9:1, 10:1, 11:1, or 12:1 R:S-MDMA, 2C-iP and about 6:1, 7:1, 8:1, 9:1, 10:1, 11:1, or 12:1 R:S-MDMA, 2C-N and about 6:1, 7:1, 8:1, 9:1, 10:1, 11:1, or 12:1 R:S-MDMA, 2C-NH2 and about 6:1, 7:1, 8:1, 9:1, 10:1, 11:1, or 12:1 R:S-MDMA, 2C-PYR and about 6:1, 7:1, 8:1, 9:1, 10:1, 11:1, or 12:1 R:S-MDMA, 2C-PIP and about 6:1, 7:1, 8:1, 9:1, 10:1, 11:1, or 12:1 R:S-MDMA, 2C-O and about 6:1, 7:1, 8:1, 9:1, 10:1, 11:1, or 12:1 R:S-MDMA, 2C-O-4 and about 6:1, 7:1, 8:1, 9:1, 10:1, 11:1, or 12:1 R:S-MDMA, 2C-MOM and about 6:1, 7:1, 8:1, 9:1, 10:1, 11:1, or 12:1 R:S-MDMA, 2C-P and about 6:1, 7:1, 8:1, 9:1, 10:1, 11:1, or 12:1 R:S-MDMA, 2C-Ph and about 6:1, 7:1, 8:1, 9:1, 10:1, 11:1, or 12:1 R:S-MDMA, 2C-Se and about 6:1, 7:1, 8:1, 9:1, 10:1, 11:1, or 12:1 R: S-MDMA, 2C-T and about 6:1, 7:1, 8:1, 9:1, 10:1, 11:1, or 12:1 R:S-MDMA, 2C-T-2 and about 6:1, 7:1, 8:1, 9:1, 10:1, 11:1, or 12:1 R:S-MDMA, 2C-T-3 and about 6:1, 7:1, 8:1, 9:1, 10:1, 11:1, or 12:1 R:S-MDMA, 2C-T-4 and about 6:1, 7:1, 8:1, 9:1, 10:1, 11:1, or 12:1 R:S-MDMA, 2C-T-5 and about 6:1, 7:1, 8:1, 9:1, 10:1, 11:1, or 12:1 R:S-MDMA, 2C-T-6 and about 6:1, 7:1, 8:1, 9:1, 10:1, 11:1, or 12:1 R:S-MDMA, 2C-T-7 and about 6:1, 7:1, 8:1, 9:1, 10:1, 11:1, or 12:1 R:S-MDMA, 2C-T-8 and about 6:1, 7:1, 8:1, 9:1, 10:1, 11:1, or 12:1 R:S-MDMA, 2C-T-9 and about 6:1, 7:1, 8:1, 9:1, 10:1, 11:1, or 12:1 R:S-MDMA, 2C-T-10 and about 6:1, 7:1, 8:1, 9:1, 10:1, 11:1, or 12:1 R:S-MDMA, 2C-T-11 and about 6:1, 7:1, 8:1, 9:1, 10:1, 11:1, or 12:1 R:S-MDMA, 2C-T-12 and about 6:1, 7:1, 8:1, 9:1, 10:1, 11:1, or 12:1 R:S-MDMA, 2C-T-13 and about 6:1, 7:1, 8:1, 9:1, 10:1, 11:1, or 12:1 R:S-MDMA, 2C-T-14 and about 6:1, 7:1, 8:1, 9:1, 10:1, 11:1, or 12:1 R:S-MDMA, 2C-T-15 and about 6:1, 7:1, 8:1, 9:1, 10:1, 11:1, or 12:1 R:S-MDMA, 2C-T-16 and about 6:1, 7:1, 8:1, 9:1, 10:1, 11:1, or 12:1 R:S-MDMA, 2C-T-17 and about 6:1, 7:1, 8:1, 9:1, 10:1, 11:1, or 12:1 R:S-MDMA, 2C-T-18 and about 6:1, 7:1, 8:1, 9:1, 10:1, 11:1, or 12:1 R:S-MDMA, 2C-T-19 and about 6:1, 7:1, 8:1, 9:1, 10:1, 11:1, or 12:1 R:S-MDMA, 2C-T-21 and about 6:1, 7:1, 8:1, 9:1, 10:1, 11:1, or 12:1 R:S-MDMA, 2C-T-21.5 and about 6:1, 7:1, 8:1, 9:1, 10:1, 11:1, or 12:1 R: S-MDMA, 2C-T-22 and about 6:1, 7:1, 8:1, 9:1, 10:1, 11:1, or 12:1 R:S-MDMA, 2C-T-23 and about 6:1, 7:1, 8:1, 9:1, 10:1, 11:1, or 12:1 R:S-MDMA, 2C-T-24 and about 6:1, 7:1, 8:1, 9:1, 10:1, 11:1, or 12:1 R:S-MDMA, 2C-T-25 and about 6:1, 7:1, 8:1, 9:1, 10:1, 11:1, or 12:1 R:S-MDMA, 2C-T-27 and about 6:1, 7:1, 8:1, 9:1, 10:1, 11:1, or 12:1 R:S-MDMA, 2C-T-28 and about 6:1, 7:1, 8:1, 9:1, 10:1, 11:1, or 12:1 R:S-MDMA, 2C-T-30 and about 6:1, 7:1, 8:1, 9:1, 10:1, 11:1, or 12:1 R:S-MDMA, 2C-T-31 and about 6:1, 7:1, 8:1, 9:1, 10:1, 11:1, or 12:1 R:S-MDMA, 2C-T-32 and about 6:1, 7:1, 8:1, 9:1, 10:1, 11:1, or 12:1 R: S-MDMA, 2C-T-33 and about 6:1, 7:1, 8:1, 9:1, 10:1, 11:1, or 12:1 R: S-MDMA, 2C-DFM and about 6:1, 7:1, 8:1, 9:1, 10:1, 11:1, or 12:1 R:S-MDMA, 2C-TFM and about 6:1, 7:1, 8:1, 9:1, 10:1, 11:1, or 12:1 R:S-MDMA, 2C-TFE and about 6:1, 7:1, 8:1, 9:1, 10:1, 11:1, or 12:1 R:S-MDMA, 2C-YN and about 6:1, 7:1, 8:1, 9:1, 10:1, 11:1, or 12:1 R:S-MDMA, 2C-V and about 6:1, 7:1, 8:1, 9:1, 10:1, 11:1, or 12:1 R:S-MDMA, and 2C-AL and about 6:1, 7:1, 8:1, 9:1, 10:1, 11:1, or 12:1 R: S-MDMA.

While it is possible to administer a combination or composition employed in the methods of this invention directly without any formulation, the compounds are usually administered in the form of pharmaceutical compositions. "Pharmaceutical compositions" are compositions that include the disclosed compound(s) together in an amount (for example, in a unit dosage form) with a pharmaceutically acceptable carrier, diluent, or excipient, and may also be referred to herein as "pharmaceutical formulations" or "formulations." It should be understood that some embodiments will not have a single carrier, diluent, or excipient alone, but will include multiple carriers, diluents, and/or excipients. Compositions can be prepared by standard pharmaceutical formulation techniques such as disclosed in, e.g., Remington: The Science and Practice of Pharmacy (2020) 23th ed., Academic Press., Cambridge, Mass.; The Merck Index (1996) 12th ed., Merck Publishing Group, Whitehouse, N.J.; Pharm. Principles of Solid Dosage Forms (1993), Technomic Publishing Co., Inc., Lancaster, Pa.; and Ansel and Stoklosa, Pharm. Calculations (2001) 11th ed., Lippincott Williams & Wilkins, Baltimore, Md.; and Poznansky et al. Drug Delivery Systems (1980), R. L. Juliano, ed., Oxford, N.Y., pp. 253-315).

"Pharmaceutically acceptable" as used in connection with an excipient, carrier, diluent, or other ingredient means that the ingredient is generally safe and, within the scope of sound medical judgment, suitable for use in contact with the cells of humans and other animals without undue toxicity, irritation, allergic response, or complication, and commensurate with a reasonable risk/benefit ratio.

Pharmaceutical compositions can be administered by a variety of routes including oral, mucosal, e.g., buccal, sublingual, ocular, rectal, intravaginal, transdermal, parenteral, subcutaneous, intravenous, intramuscular, inhaled, and intranasal. The compounds employed in the methods of this invention are effective as oral, mucosal (e.g., buccal, sublingual), rectal, transdermal, subcutaneous, intravenous, intramuscular, inhaled, and intranasal compositions. Such compositions are prepared in a manner well known in the pharmaceutical art and comprise at least one active compound. (See, e.g., Remington: The Science and Practice of Pharmacy (2020) 23th ed., Academic Press., Cambridge, Mass.)

In making the compositions employed in the present invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, microemulsions, liposomal dispersions, aqueous and non-aqueous solutions, slurries, syrups, aerosols (as a solid or in a liquid medium), ointments containing for example up to 10% by weight of the active compound, soft and hard gelatin capsules, suppositories, dry powders for inhalation, liquid preparations for vaporization and inhalation, topical preparations, transdermal patches, sterile injectable solutions, and sterile packaged powders. Compositions may be formulated as immediate release, controlled release, sustained (extended) release or modified release formulations.

Different embodiments of the invention include the following examples: Pharmaceutically acceptable complex derivatives of each drug in each group, including solvates, salts, esters, enantiomers, isomers (stereoisomers and/or constitutional, including ones based on substituting deuterium for hydrogen), derivatives or prodrugs, such as derivatives or prodrugs of an entactogenic agent, for instance R-MDMA.

Among derivatives of a compound are included its "physiologically functional derivatives," which refers to physiologically tolerated chemical derivatives of the compound having the same physiological function thereof, for example, by being convertible in the body thereto, and which on administration to a mammal such as a human is able to form (directly or indirectly) the compound or an active metabolite thereof (acting therefore, like a prodrug), or by otherwise having the same physiological function, despite one or more structural differences. According to the present invention, examples of physiologically functional derivatives include esters, amides, carbamates, ureas, and heterocycles.

Another embodiment of the invention includes multiple variations in the pharmaceutical dosages of each drug in the combination as further outlined below. Another embodiment of the invention includes various forms of preparations including using solids, liquids, immediate or delayed or extended-release forms. Many types of variations are possible as known to those skilled in the art. In some embodiments, compositions comprising compounds of the disclosed therapeutic combinations are provided in the same dosage form, whether administered simultaneously or separately, such as sequentially. In some embodiments, compositions comprising compounds of the disclosed therapeutic combinations, such as a composition comprising a hallucinogen and a composition comprising an entactogen, are formulated for distinct routes of administration, e.g., sublingual administration and oral administration, buccal administration and oral administration, rectal administration and oral administration, intranasal administration and oral administration, respectively, etc.

In some embodiments, the compositions of the invention are formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. The pharmaceutical compositions of the present invention also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

Herein, reference to an oral dosage form will be understood as a dosage form provided for oral administration to a subject, reference to a mucosal dosage form will be understood as a dosage form provided for mucosal administration to a subject, which can include sublingual, buccal, intranasal, rectal, and intravaginal administration, reference to a topical dosage form will be understood as a dosage form provided for topical administration to a subject, and reference to parenteral dosage form will be understood as a dosage form provided for parenteral administration to a subject, which can include subcutaneous (administration beneath the skin; hypodermic; synonymous with subdermal or hypodermal), intramuscular (administration within a muscle), intradermal (administration within the dermis), intravenous (administration within or into a vein or veins), intra-arterial (administration within an artery or arteries), intrathecal (administration within the cerebrospinal fluid at any level of the cerebrospinal axis, including injection into the cerebral ventricles), intraperitoneal (administration within the peritoneal cavity), and intravitreal (administration within the vitreous body of the eye).

In some embodiments, a composition comprising a hallucinogenic agent is provided for administration to a subject in an oral dosage form for oral administration, e.g., a solution, such as a solution for drinking or a tincture, a tablet, a capsule, a lozenge, a film or strip, such as blotter paper, such as an orodispersible film or strip. In some embodiments, a composition comprising a hallucinogenic agent is provided for mucosal administration to a subject in a mucosal dosage form, e.g., a solution, such as drops, a tincture, or a spray, a film or strip, such as blotter paper, a tablet, such as a multi-purpose tablet, an effervescent tablet, or a lozenge, or a suppository, In some embodiments, the mucosal dosage form is provided to a subject for sublingual, buccal, intranasal or rectal administration, among others. In some embodiments, a composition comprising a hallucinogenic agent is provided for parenteral administration to a subject in a parenteral dosage form, such as a solution for injection, e.g., for intravenous administration.

In some embodiments, a composition comprising a dissociative agent is provided for oral administration to a subject in an oral dosage form, e.g., a solution, such as a solution for drinking or a tincture, a tablet, a capsule, a lozenge, a film or strip, such as an orodispersible film or strip. In some embodiments, a composition comprising a dissociative agent is provided for mucosal administration to a subject in an mucosal dosage form, e.g., a solution, such as drops, a tincture, or a spray, blotter paper, a film or strip, a tablet, such as a multi-purpose tablet, an effervescent tablet, or a lozenge, or a suppository. In some embodiments, the mucosal dosage form is provided to a subject for sublingual, buccal, intranasal, or rectal administration, among others. In some embodiments, a composition comprising a dissociative agent is provided for parenteral administration to a subject in a parenteral dosage form, such as a solution for injection, e.g., for intravenous administration.

In some embodiments, a composition comprising an entactogenic agent is provided for oral administration to a subject in an oral dosage form, e.g., a solution, such as a solution for drinking or a tincture, a tablet, a capsule, a lozenge, a film or strip, such as an orodispersible film or strip. In some embodiments, a composition comprising an entactogenic agent is provided for mucosal administration to a subject in an mucosal dosage form, e.g., a solution, such as drops, a tincture, or a spray, blotter paper, a film or strip, a tablet, such as a multi-purpose tablet, an effervescent tablet, or a lozenge, or a suppository. In some embodiments, the mucosal dosage form is provided to a subject for sublingual, buccal, intranasal, or rectal administration, among others. In some embodiments, a composition comprising an entactogenic agent is provided for parenteral administration to a subject in a parenteral dosage form, such as a solution for injection, e.g., for intravenous administration.

Another embodiment of the invention includes multiple routes of administration which may differ in different patients according to their preference, comorbidities, side effect profile, pharmacokinetic and pharmacodynamic considerations, and other factors (IV, PO, transdermal, slow release oral capsules, etc.). In some embodiments, compositions comprising compounds of a disclosed therapeutic dosage form are provided for administration to a subject in distinct dosage forms. Non-limiting examples of distinct dosage forms comprising hallucinogens and entactogens for administration to a subject, include, e.g., a mucosal dosage form comprising a hallucinogenic agent and an oral dosage form comprising an entactogenic agent, an oral dosage form comprising a hallucinogenic agent and a mucosal dosage form comprising an entactogenic agent, a mucosal dosage form comprising a hallucinogenic agent and a parenteral dosage form comprising an entactogenic agent, a parenteral dosage form comprising a hallucinogenic agent and a mucosal dosage form comprising an entactogenic agent, an oral dosage form comprising a hallucinogenic agent and a parenteral dosage form comprising an entactogenic agent, a parenteral dosage form comprising a hallucinogenic agent and an oral dosage form comprising an entactogenic agent. Additional combinations will be understood in view of this disclosure and the knowledge of one of skill. In some embodiments, a dissociative is further provided in a separate dosage form or in the same dosage form as the hallucinogenic agent and/or the entactogenic agent.

Another embodiment of the invention includes the presence of other substances with the active drugs, known to those skilled in the art, such as fillers, carriers, gels, skin patches, lozenges, or other modifications in the preparation to facilitate absorption through various routes (such as gastrointestinal, transdermal, etc.) and/or to extend the effect of the drugs, and/or to attain higher or more stable serum levels or to enhance the therapeutic effect of the active drugs in the combination, In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art. Various methods for the preparation of the immediate release, modified release, controlled release, and extended-release dosage forms (e.g., as matrix tablets having one or more modified, controlled, or extended-release layers) and the vehicles therein are well known in the art. For example, a tablet may be made by compression or molding.

Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein. Generally recognized compendia of methods include: Remington, Remington: The Science and Practice of Pharmacy (2020) 23th ed., Academic Press., Cambridge, Mass.; Sheth et al. (1980), Compressed tablets, in Pharm. dosage forms, Vol. 1, Lieberman & Lachtman, eds., Dekker, NY Enteric coatings may also be used to prepare other controlled release dosage forms including extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

Coatings for providing a controlled, delayed, or extended release may be applied to the disclosed pharmaceutical compositions or to a core containing the compositions. The coating may comprise a pharmaceutically acceptable ingredient in an amount sufficient, e.g., to provide an extended release from e.g., about 1 hours to about 7 hours following ingestion before release of the compositions. Suitable coatings include one or more differentially degradable coatings including pH-sensitive coatings (enteric coatings), or non-enteric coatings having variable thickness to provide differential release of the active agents.

Many other types of modified release systems are known to those of ordinary skill in the art and are suitable for the formulations described herein. Examples of such delivery systems include both polymer- and nonpolymer-based systems, silastic systems, peptide-based systems, wax coatings, bioerodible dosage forms, and compressed tablets using conventional binders. (See, e.g., Liberman et al. Pharmaceutical Dosage Forms, 2 Ed., Vol. 1, pp. 209-214 (1990); Singh et al. Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.)

The compositions are preferably formulated in a unit dosage form, each dosage containing from about 0.05 to about 350 mg, more preferably about 5.0 to about 180 mg, of the active ingredients. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose), of the pharmaceutical composition administered.

Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein.

In other embodiments, disclosed pharmaceutical compositions may be formulated into a topical dosage form. Topical dosage forms include transmucosal and transdermal formulations, such as aerosols, emulsions, sprays, ointments, salves, gels, pastes, lotions, liniments, oils, and creams. For such formulations, penetrants and carriers can be included in the pharmaceutical composition. Penetrants are known in the art, and include, for transmucosal administration, detergents, bile salts, and fusidic acid derivatives. For transdermal administration carriers which may be used include Vaseline®, lanolin, PEG, alcohols, transdermal enhancers, and combinations thereof.

An exemplary topical delivery system is a transdermal delivery device ("patch") containing the active agents. Such transdermal patches may be used to provide continuous or discontinuous infusion of the compounds of the present invention in controlled amounts. Such patches may be constructed for continuous, gradual, pulsatile, or on demand delivery of pharmaceutical agents. A "patch" within the meaning of the invention may be simply a medicated adhesive patch, i.e., a patch impregnated with a composition of the invention for application onto the skin. Thus, a patch may be a single-layer or multi-layer drug-in-adhesive patch, wherein the one or more adhesive layers also contain the active agents.

A patch may also be a "matrix" (or "monolithic") patch, wherein the adhesive layer surrounds and overlays the drug layer (wherein a solution or suspension of the active agents is in a semisolid matrix). A "reservoir" patch may also be used, comprising a drug layer, typically as a solution or suspension of the active agents in a liquid compartment (i.e., the reservoir), separate from an adhesive layer. For example, the reservoir may be totally encapsulated in a shallow compartment molded from a drug-impermeable metallic plastic laminate, with a rate-controlling membrane made of vinyl acetate or a like polymer on one surface. A patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized One such transdermal patch technology as herein contemplated comprises a self-contained module including a built-in battery that produces a low-level electric current to heat the skin and deliver a prescribed dose of a composition of the invention, wherein a therapeutically effective amount of the composition crosses the skin and enters the underlying tissue, so as to produce a therapeutic effect. Such a transdermal delivery device may, for example, comprise an adhesive layer, a protective film, a drug-containing reservoir (for the disclosed pharmaceutical compositions), a heating coil, a battery, a hardware board, optionally all within a device holder, and optionally, functionally coupled to a device which is able to control drug delivery (e.g., a mobile device such as a smartphone) using a downloadable application, Such devices may, for instance, additionally shut off drug delivery automatically when a prescribed dose has been administered, or may shut off automatically upon reaching a certain temperature or defined time. Such transdermal devices may be reusable or disposable.

In other embodiments, disclosed pharmaceutical compositions may be formulated for subcutaneous administration, for example using infusion pumps for direct delivery of the substance(s). "Infusion pumps" for example include drug delivery devices comprising a reservoir and a pump mechanism, configured for subcutaneous administration, which may optionally contain a user interface or be coupled to a device with a user interface such as a smartphone. Such devices will be readily understood by reference to the general knowledge in the art, as disclosed for instance in US2020/0384188A1.

It should be apparent that the compositions of the invention are not limited to combinations of a single compound (e.g., for an entactogenic agent, the single compound R-MDMA, together with a hallucinogenic agent such as psilocybin), and a single carrier, diluent, or excipient alone, but also include combinations of multiple compounds (including additional active compounds), and/or multiple carriers, diluents, and excipients. Pharmaceutical compositions of this invention thus may comprise, in the above example, R-MDMA and psilocybin together with one or more other active agents (or their derivatives and analogs) in combination, together with one or more pharmaceutically-acceptable carriers, diluents, and/or excipients, and further with one or more additional active compounds.

In some embodiments, a formulation of the invention will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that are contemplated as being increased or added in embodiments of the invention include antioxidant, anti-inflammatory, analgesic, antineuropathic, antinociceptive, antimigraine, anxiolytic, antidepressant, antipsychotic, anti-PTSD, immunostimulant, anti-cancer, antiemetic, orexigenic, antiulcer, antihistamine, antihypertensive, anticonvulsant, antiepileptic, bronchodilator, neuroprotective, entactogenic, empathogenic, entheogenic, psychedelic, sedative, and stimulant effects.

In some embodiments, the disclosed combinations and compositions comprising the same have synergistic effects. "Synergistic effects" will be understood to include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components applied alone, thereby producing "1+1>2." Suitable methods include isobologran (or contour) analysis (Huang, Front. Pharmacol., 2019; 10:1222), the equation of Loewe additivity (Loewe & Muischnek, 1926, Arch. Exp. Pathol Pharmacol. 114: 313-326), the Sigmoid-Emax equation or concentration-effect curve (Holford & Scheiner, 1981, Clin. Pharmacokinet. 6: 429-453), and the median-effect equation or combination index curve (Chou & Talalay, 1984, Adv. Enzyme Regul. 22:27-55). Each equation referred to above may be applied to experimental data to generate a corresponding graph to aid in assessing the synergistic effects of a combination.

The goal of increasing an existing therapeutic effect, providing an additional therapeutic effect, increasing a desired property such as stability or shelf-life, decreasing an unwanted effect or property, altering a property in a desirable way (such as pharmacokinetics or pharmacodynamics), modulating a desired system or pathway (e.g, a neurotransmitter system), or otherwise inducing synergy, in some embodiments is achieved by the inclusion of an additional active compound.

By way of non-limiting and merely suggestive example, the following formulations may be used in the methods of the present invention, wherein "therapeutic compound" refers to one or more of the compounds of the present invention.

Example 1: Formulation of Tablets

A tablet is prepared using the ingredients below:

Exemplary tablet: Psilocybin and Entactogen

| Ingredient | Quantity (mg) |
|---|---|
| 9:1 R:S-MDMA | 275 mg |
| Psilocybin | 30 mg |
| Cellulose, microcrystalline | 170.0 |
| Colloidal silicon dioxide | 10.0 |
| Stearic acid | 7.5 |

Exemplary tablet: 5-MeO-DMT and Entactogen

| Ingredient | Quantity (mg) |
|---|---|
| 9:1 R:S-MDMA | 270 mg |
| 2C-B | 5 mg |
| Cellulose, microcrystalline | 170.0 |
| Colloidal silicon dioxide | 10.0 |
| Stearic acid | 7.5 |

The ingredients are blended and compressed to form tablets.

Example 2: Alternate Formulation of Tablets

Scorable tablets are prepared as follows:

Exemplary alternative tablet: Psilocybin and Entactogen

| Ingredient | Quantity (mg) |
|---|---|
| 9:1 R:S-MDMA | 275 mg |
| Psilocybin | 30 mg |
| Starch | 45.0 |
| Microcrystalline cellulose | 35.0 |
| PVP (as 10% solution in water) | 4.0 |
| Sodium carboxymethyl starch | 4.5 |
| Magnesium stearate | 0.5 |
| Talc | 1.0 |

Exemplary alternative tablet: 5-MeO-DMT and Entactogen

| Ingredient | Quantity (mg) |
|---|---|
| 9:1 R:S-MDMA | 270 mg |
| 5-MeO-DMT | 5 mg |
| Starch | 45.0 |
| Microcrystalline cellulose | 35.0 |
| PVP (as 10% solution in water) | 4.0 |
| Sodium carboxymethyl starch | 4.5 |
| Magnesium stearate | 0.5 |
| Talc | 1.0 |

Active agents, starch, and cellulose are passed through a No. 20 mesh U.S. sieve and mixed thoroughly. The solution of polyvinylpyrrolidone (PVP) is mixed with the resultant powders, which are then passed through a 16 mesh U.S. sieve. The granules so produced are dried at 50-60' C and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets. Tablets are scored to provide the ability to create equal half doses.

Example 3: Formulation of Capsules

Capsules are made as follows:

Exemplary capsule: Psilocybin and Entactogen

| Ingredient | Quantity (mg) |
|---|---|
| 9:1 R:S-MDMA | 275 mg |
| Psilocybin | 30 mg |
| Starch | 275 mg |
| Magnesium stearate | 1.0 mg |

Exemplary capsule: 5-MeO-DMT and Entactogen

| Ingredient | Quantity (mg) |
|---|---|
| 9:1 R:S-MDMA | 270 mg |
| 5-MeO-DMT | 5 mg |
| Starch | 275 mg |
| Magnesium stearate | 1.0 mg |

The active agents, cellulose, starch, and magnesium stearate are blended, passed through a No. 20 mesh U.S. sieve, and filled into hard or soft gelatin capsules.

Example 4: Formulation of Suspension

Suspensions are made as follows:

| Ingredient | Amount |
|---|---|
| LSD or a derivative or analog thereof | 250 μg |
| Entactogenic agent | 150 mg |
| Xanthan gum | 4.0 mg |
| Sodium carboxymethyl cellulose (11%) | 50.0 mg |
| Microcrystalline cellulose (89%) | 50.0 mg |
| Sucrose | 1.75 g |
| Sodium benzoate | 10.0 mg |
| Flavor and color (optional) | q.v. |
| Purified water | To 5.0 ml |

The active agents, sucrose, and xanthan gum are blended, passed through a No. 10 mesh U.S. sieve, and then mixed with a previously made solution of the microcrystalline cellulose and sodium carboxymethyl cellulose in water. The sodium benzoate and optional flavor and color are diluted with some of the water and added with stirring. Sufficient water is then added to produce the required volume.

Example 5: Formulation of Intravenous Solution

An intravenous formulation may be prepared as follows:

| Ingredient | Amount |
|---|---|
| Hallucinogenic agent | 100 mg |
| Entactogenic agent | 500 mg |
| Isotonic saline | 1000 mL |

Active agents are dissolved in appropriate solvent as will be understood by those of ordinary skill; isotonic saline is used in this Example, but it will be appreciated that other solvents may be used, and additional active or inactive ingredients such as preservatives may be added, as otherwise described above, and within the general knowledge of the art. It will be understood that the amount of each agent can be adjusted to reach the desired mg/mL.

Example 6: Formulations of Injectable Solution

Injectable formulations may be prepared as follows:

| Ingredient | Amount |
|---|---|
| Hallucinogenic agent | 25 mg |
| Entactogenic agent | 125 mg |
| Isotonic saline | 5 mL |

Active agents are dissolved in appropriate solvent as will be understood by those of ordinary skill; isotonic saline is used in this Example, but it will be appreciated that other solvents may be used, and additional active or inactive ingredients such as preservatives may be added, as otherwise described above, and within the general knowledge of the art.

Example 7: Formulation of Topical for Transdermal Administration

A topical formulation may be prepared as follows:

| Ingredient | Amount (g) |
|---|---|
| Hallucinogenic agent | 0.5 |
| Entactogenic agent | 1.0 |
| Emulsifying Wax | 30.0 |
| Liquid Paraffin | 20.0 |
| White Soft Paraffin | To 100 |

The white soft paraffin is heated until molten. The liquid paraffin and emulsifying wax are incorporated and stirred until dissolved. The active ingredient is added and stirring is continued until dispersed. The mixture is then cooled until solid.

Example 8: Formulation of Cut Matrix Sublingual or Buccal Tablets

Sublingual or buccal tablets are made as a single matrix and then cut to size:

| Ingredient | Amount (mg/tablet) |
|---|---|
| Ketamine | 25.0 |
| 9:1 R:S-MDMA | 250.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Example 9: Formulation of Individually Formed Sublingual or Buccal Lozenges

Sublingual or buccal lozenges are made from individual forms or molds:

| Ingredient | Amount (mg/each lozenge) |
|---|---|
| Ketamine | 100.0 |
| 9:1 R:S-MDMA | 175.0 |
| Silica gel powder | 350.0 |
| Citric acid powder | 400.0 |
| Acacia powder | 600.0 |
| Flavor (optional) | 100.0 |
| Polyethylene glycol | 1,000 |

The inactive ingredients are admixed by continuous stirring and maintaining the temperature at about 90° C. When the PEG has melted and the other ingredients have gone into solution, the solution is cooled to about 50-55° C. and the active agents are slowly admixed. The homogenous mixture is poured into separate molds and allowed to cool. Reference may also be made to U.S. Pat. No. 10,034,832 and the Examples therein, the entirety of which is incorporated herein.

It should be readily appreciated that the above formulation examples are illustrative only. Any "active agent" or "active ingredient" in the above examples will be understood to include any hallucinogenic agent or entactogenic agent that comprises the formulation, a dissociative agent if one is included in addition or instead or the hallucinogenic agent, and any additional active compound(s), if included.

Any of the compounds may be substituted with the same compound in a different dosage amount, including but not limited to the exemplary dosage amounts below.

Reference to particular compound(s) is merely illustrative, and both active and inactive compounds in any Example may be substituted by any other disclosed compounds. For example, as will be readily appreciated from the disclosure and evident from the Examples, a hallucinogenic agent of the invention may in some embodiments include or be replaced by another compound, for example, in some aspects, a dissociative agent such as ketamine, or, e.g., an enantiomer (e.g., R- or S-), metabolite, derivative, or analog thereof.

In some embodiments, a formulation will only comprise a single active compound of the invention, e.g., a hallucinogen but not a dissociative or entactogen, a dissociative but not a hallucinogen or entactogen, an entactogen but not a hallucinogen or dissociative, or an additional active compound formulated alone. It will be readily appreciated that any single active compound may be formulated according to the teachings herein, such as above, for example when a hallucinogen and an entactogen are administered separately, including when they are administered as different formulations and/or by different routes of administration, including at different times. When two compounds such as a hallucinogen and an entactogen are administered in physically separate dosage forms, they may be administered simultaneously, or temporally separate, e.g., sequentially in time.

Moreover, for any of the compounds of the invention, substitution of the compound by its ion, free base, salt form, polymorph, hydrate or solvate form, co-crystal, or an isomer or enantiomerically enriched mixture, shall be understood to provide merely an alternative embodiment still within the scope of the invention (with modifications to the formulation and dosage amounts made according to the teachings herein and ordinary skill, if necessary or desired). Further, compositions within the scope of the invention should be understood to be open-ended and may include additional active or inactive compounds and ingredients. For example, a composition for oral or mucosal administration comprising DMT, 5-MeO-DMT, or another compound that is poorly bioactive when so administered, may comprise, for example, one or more β-carboline alkaloids, e.g., harmine, harmaline, and tetrahydroharmine.

The type of formulation employed for the administration of the compounds employed in the methods of the present invention generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

b. Dosage

Administration of pharmaceutical compositions in a "therapeutically effective amount," or an "effective amount" to a subject means administration of an amount of composition sufficient to achieve the desired effect. When an "effective amount" means an amount effective in treating the stated disorder or symptoms in a subject, "therapeutic effect" would be understood to mean the responses(s) in a mammal after treatment that are judged to be desirable and beneficial. Depending on the mental health disorder to be treated, or improvement in mental health or functioning sought, and depending on the particular constituent(s) in the compositions of the invention under consideration, those responses shall differ, but would be readily understood by those of skill, through an understanding of this disclosure and the general knowledge of the art (e.g., by reference to the symptoms listed in the Diagnostic and Statistical Manual of Mental Disorders [DSM-5] for the stated disorder).

In embodiments, the pharmaceutical compositions disclosed herein comprise therapeutic amounts of a hallucinogenic agent and an entactogenic agent and in some embodiments other active or inactive ingredients. Dosage amounts will be understood by reference to all of the teachings herein as well as the general knowledge in the art, but certain exemplary dosage amounts, known to be useful in the practice of the invention, are listed below for ease of reference.

In some embodiments, a disclosed therapeutic combination or composition thereof comprises a hallucinogenic agent in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, a disclosed therapeutic combination or composition thereof comprises a hallucinogenic agent in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, at least 250 mg, at least 275 mg, or at least 300 mg, as well as amounts within these ranges.

In some embodiments, a disclosed therapeutic combination or composition thereof comprises a hallucinogenic agent, such as psilocybin or psilocin, or a derivative or analog thereof, in an amount so that a single dose is (whether or not such dose is present in a unit dosage form, and irrespective of method of administration) 0.1 mg or less, at least 0.1 mg, at least 0.5 mg, at least 0.75 mg, at least 1 mg, at least 5 mg, at least 10 mg, at least 15 mg, at least 20 mg, at least 25 mg, at least 30 mg at least 35 mg, at least 40 mg, at least 45 mg, at least 50 mg, at least 55 mg, at least 60 mg, or at least 65 mg.

In some embodiments, a disclosed therapeutic combination or composition thereof comprises a hallucinogenic agent, such as LSD or a derivative or analog thereof, e.g., PRO-LAD, ETH-LAD, AL-LAD, 1P-LSD, in an amount so that a single dose is (whether or not such dose is present in a unit dosage form, and irrespective of method of administration), e.g., 5 μg or less, at least 5 μg, at least 10 μg, at least 15 μg, at least 20 μg, at least 25 μg, at least 30 μg, at least 35 μg, at least 40 μg, at least 45 μg, at least 50 μg, at least 55 μg, at least 60 μg, at least 65 μg, at least 70 μg, at least 75 μg, at least 80 μg, at least 85 μg, at least 90 μg, at least 95 μg, at least 100 μg, at least 125 μg, at least 150 μg, at least 175 μg, at least 200 μg, at least 250 μg, at least 300 μg, at least 400 μg, at least 500 μg, at least 750 μg, or at least 1,000 μg.

In some embodiments, a disclosed therapeutic combination or composition thereof comprises a hallucinogenic agent, such as a 2C-X compound, e.g., 2C-B, or a derivative or analog thereof, in an amount so that a single dose is (whether or not such dose is present in a unit dosage form, and irrespective of method of administration) 0.1 mg or less, at least 0.1 mg, at least 0.5 mg, at least 0.75 mg, at least 1 mg, at least 5 mg, at least 10 mg, at least 15 mg, at least 20 mg, at least 25 mg, at least 30 mg at least 35 mg, at least 40 mg, at least 45 mg, at least 50 mg, at least 55 mg, at least 60 mg, or at least 65 mg.

In some embodiments, a disclosed therapeutic combination or composition thereof includes ketamine, it may be present in an amount so that a single dose is (in a milligram dosage amount calculated based on the kilogram weight of the patient), e.g., 0.1 mg/kg or less, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1.0 mg/kg, at least 1.1 mg/kg, at least 1.2 mg/kg, at least 1.3 mg/kg, or at least 1.4 mg/kg, as well as amounts within these ranges.

In some embodiments, a disclosed therapeutic combination or composition thereof includes ketamine or another agent in an oral dosage form, it may be present in an amount so that a single dose is (whether or not such dose is present in a unit dosage form), e.g., 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 175 mg, or at least 200 mg.

In some embodiments, a disclosed therapeutic combination or composition thereof includes ketamine or another agent in an intranasal dosage form for insufflation, it may be present in an amount so that a single dose is (whether or not such dose is present in a unit dosage form), e.g., 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 175 mg, or at least 200 mg.

In some embodiments, a disclosed therapeutic combination or composition thereof includes ketamine or another agent in a liquid dosage form, for intramuscular (IM) or subcutaneous administration, it may be present in an amount so that a single dose is (whether or not such dose is present in a unit dosage form), e.g., 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 175 mg, or at least 200 mg.

In some embodiments, a disclosed therapeutic combination or composition thereof includes ketamine or another agent in a liquid dosage form, for intravenous administration, it may be present in an amount so that a single dose is (whether or not such dose is present in a unit dosage form), e.g., 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 125 mg, at least 150 mg, at least 175 mg, or at least 200 mg.

In some embodiments, a disclosed therapeutic combination or composition thereof includes ketamine or another agent in a liquid solution, a dosage amount may be determined based on the concentration of ketamine or the agent in the solution; for example, where a solution of 500 mg ketamine in 5 mL liquid is used for injection, a volume of liquid for intramuscular injection may be, e.g., 0.1 mL or less, at least 0.1 mL, at least 0.2 mL, at least 0.3 mL, at least 0.4 mL, at least 0.5 mL, at least 0.6 mL, at least 0.7 mL, at least 0.8 mL, at least 0.9 mL, or at least 1.0 mL, as well as amounts within these ranges.

In some embodiments, a disclosed therapeutic combination or composition thereof includes ketamine or another agent in a liquid solution, and a solution of, e.g., 500 mg ketamine in 10 mL liquid is used for injection, a volume of liquid for IM injection may be, e.g., 0.2 mL or less, at least 0.2 mL, at least 0.4 mL, at least 0.6 mL, at least 0.8 mL, at least 1.0 mL, at least 1.2 mL, at least 1.4 mL, at least 1.6 mL, at least 1.8 mL, or at least 2.0 mL, as well as amounts within these ranges.

In some embodiments, a disclosed therapeutic combination or composition thereof comprises an entactogenic agent in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, a disclosed therapeutic combination or composition comprises an entactogenic agent in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, at least 250 mg, at least 275 mg, or at least 300 mg, as well as amounts within these ranges.

In some embodiments, a disclosed therapeutic combination or composition comprises a non-racemic entactogenic agent, such as MDMA, wherein R-MDMA is present in enantiomeric excess, in an amount of 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 205 mg, at least 210 mg, at least 215 mg, at least 220 mg, at least 225 mg, at least 230 mg, at least 235 mg, at least 240 mg, at least 245 mg, at least 250 mg, at least 255 mg, at least 260 mg, at least 265 mg, at least 270 mg, at least 275 mg, at least 280 mg, at least 285 mg, at least 290 mg, at least 295 mg, at least 300 mg, at least 305 mg, at least 310 mg, at least 315 mg, at least 320 mg, or at least 325 mg.

In some embodiments, a disclosed combination comprises non-racemic MDMA having an enantiomeric excess of R-MDMA of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a disclosed combination comprises non-racemic MDMA having an enantiomeric excess R-MDMA of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, a disclosed combination comprises non-racemic MDMA having an enantiomeric excess of R-MDMA of about 10%, 15%, 20%, 25%, 30%, 35%, 40%, 45%, 50%, 55%, 60%, 65%, 70%, 75%, 80%, 85%, 90%, or 95%. In some embodiments, a disclosed combination comprises non-racemic MDMA having an enantiomeric excess of R-MDMA of about 75%, 76%, 77%, 78%, 79%, 80%, 81%, 82%, 83%, 84%, or 85%. In some embodiments, a disclosed combination comprises non-racemic MDMA having an enantiomeric excess of R-MDMA of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a disclosed combination comprises non-racemic MDMA having an enantiomeric excess of R-MDMA of about 79.5%, 79.6%, 79.7%, 79.8%, 79.9%, 80%, 80.1%, 80.2%, 80.3%, 80.4%, or 80.5%. In some embodiments, a disclosed combination comprises non-racemic MDMA, wherein R-MDMA and S-MDMA are present in a ratio of about 6:1 to 12:1, 7:1 to 11:1, or 8:1 to 10:1. In some embodiments, a disclosed combination comprises non-racemic MDMA, wherein R-MDMA and S-MDMA are present in a ratio of about 6:1, 7:1, 8:1, 9:1, 10:1, 11:1, or 12:1. In some embodiments, a disclosed combination comprises non-racemic MDMA, wherein R-MDMA and S-MDMA are present in a ratio of 9:1. In some embodiments, a disclosed combination comprises non-racemic MDMA having an enantiomeric excess of R-MDMA within 0.05% of 90%, or within 0.1% of 90%. For reference, comparative dosing of exemplary non-racemic MDMA in a ratio of 9:1 R-MDMA to S-MDMA is shown in Table 2 below.

TABLE 2

No Adverse Effect Level (NOAEL) Doses of MDMA, Enantiomers, and an Exemplary Non-Racemic Mixture Thereof

| Compound | No adverse effect level (NOAEL) | Human Equivalent Dose (HED) | Maximum Recommended Starting Dose (MRSD) |
|---|---|---|---|
| SR(±)MDMA | NOAEL: 100 mg/kg (p.o.) in rat with single housing$_1$<br>NOAEL: 15 mg/kg in dog (p.o.)$_1$<br>Neurotoxicology: in rat:<br>(♀) NOAEL: 25 mg/kg/week p.o$_1$<br>(♂) NOAEL: 20 mg/kg/week p.o$_1$.<br>in dog:<br>(♀, ♂) NOAEL: 4 mg/kg/week p.o | NOAEL (human): 34 mg/kg → 2080 mg*<br>Neurotoxicology: NOAEL (human): 6 mg/kg → 342.9 mg* | 80 mg-120 mg initial dose MDMA HCl<br>40 mg-60 mg supplemental dose MDMA HCl<br>Maximum proposed dose: 125 mg<br>Maximum tested single dose: 150 mg |
| R(−)MDMA | NOAEL: >200 mg/kg (p.o) in rat$_3$<br>Neurotoxicology: NOAEL: in rat: 50 mg/kg i.v$_2$ | NOAEL (human): >68 mg/kg → >4100 mg<br>Neurotoxicology: NOAEL (human): 7.4 mg/kg → 450 mg* | Expected MSRD: >300 mg:<br>62.5 mg tested in humans |
| S(+)MDMA | Expected: <100 mg/kg (p.o) in rat$_3$<br>Neurotoxicology: NOAEL: in rat: 20 mg/kg i.v$_{2,3}$ | NOAEL (human): → <34 mg/kg → <2080 mg*<br>Neurotoxicology: NOAEL (human): 6 mg/kg → 342.9 mg* | Expected MSRD: 150 mg<br>62.5 mg tested in humans |

TABLE 2-continued

No Adverse Effect Level (NOAEL) Doses of MDMA, Enantiomers, and an Exemplary Non-Racemic Mixture Thereof

| Compound | No adverse effect level (NOAEL) | Human Equivalent Dose (HED) | Maximum Recommended Starting Dose (MRSD) |
|---|---|---|---|
| Exemplary Compound 9:1 R:S MDMA | Expected >100 mg/kg (p.o) in rat (p.o) Neurotoxicology: Expected NOAEL: in rat: >40 mg/kg (i.v) | Expected NOAEL (human): >64 mg/kg → >3800 mg* (p.o) Neurotoxicology: NOAEL (human): >7.2 mg/kg → >440 mg* (i.v) | Expected MSRD: >280 mg Safest validated MPSD dose (Phase I): 62 mg Proposed clinical dosing range: 141 mg-285 mg single dose 9:1 R:S MDMA |

*Assuming a 60 kg human.

1(MAPS, 2884-005, 2021),

2(Curry et al., Neuropharmacology, 2018; 128: 196-206),

3(Fantegrossi et al., Psychopharmacology (Berl)., 2003; 166(3): 202-11)

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

It will be understood that, in some embodiments, the dose actually administered will be determined by a physician, in light of the relevant circumstances, including the disorder to be treated, the chosen route of administration, the actual composition or formulation administered, the age, weight, and response of the individual patient, and the severity of the patient's symptoms, and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In these embodiments, the disclosed pharmaceutical compositions will be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions and formulations, but shall be able to be determined with ordinary skill.

It should be appreciated that in other embodiments, e.g., when the compositions of the invention are taken without the direct intervention or guidance of a medical professional, appropriate dosages to achieve a therapeutic effect, including the upper and lower bounds of any dose ranges, can be determined by an individual by reference to available public information and knowledge, and reference to subjective considerations regarding desired outcomes and effects.

Determination of appropriate dosing shall include not only the determination of single dosage amounts, but also the determination of the number and timing of doses, e.g., administration of a particular dosage amount once per day, twice per day, or more than twice per day, and the time(s) of day or time(s) during a psychotherapeutic session preferable for their administration.

In some embodiments, such as where a formulation is prepared in a single unit dosage form, such as a capsule, tablet, or lozenge, suggested dosage amounts may be known by reference to the format of the preparation itself. In other embodiments, where a formulation is prepared in multiple dosage form, for instance liquid suspensions and topical preparations, suggested dosage amounts may be known by reference to the means of administration or by reference to the packaging and labeling, package insert(s), marketing materials, training materials, or other information and knowledge available to those of skill or the public.

c. Kits

In another aspect are provided pharmaceutical kits containing a disclosed combination or composition, suggested administration guidelines or prescribing information therefor, and a suitable container. In some embodiments a kit comprises a hallucinogenic agent and an entactogenic agent. In some embodiments, a kit comprises a hallucinogenic agent, an entactogenic agent, and a dissociative agent. In some embodiments, a kit comprises a dissociative agent and an entactogenic agent. A suitable container may provide protection from light, for example where a compound is affected by ultraviolet or visible light energy.

Individual unit dosage forms can be included in multidose kits or containers. pharmaceutical formulations also can be packaged in single or multiple unit dosage forms for uniformity of dosage and ease of administration. In an exemplary pharmaceutical kit, capsules, tablets, caplets, or other unit dosage forms are packaged in blister packs. "Blister pack" refers to any of several types of pre-formed container, especially plastic packaging, that contains separate receptacles (e.g., cavities or pockets) for single unit doses, where such separate receptacles are individually sealed and can be opened individually.

Blister packs include such pharmaceutical blister packs known to those of skill, e.g., Aclar® Rx160, Rx20e, SupRx, and UltRx 2000, 3000, 4000, and 6000 (Honeywell). Within the definition of multi-dose containers, and also often referred to as blister packs, are blister trays, blister cards, strip packs, push-through packs, and the like.

In some embodiments, information pertaining to dosing and proper administration (if needed) will be printed onto a multi-dose kit directly (e.g., on a blister pack or other interior packaging holding the compositions or formulations of the invention). Kits also can contain package inserts and other printed instructions (e.g., on exterior packaging) for administering the disclosed combinations or compositions and for their appropriate therapeutic use.

In some embodiments, a patient will have the option of using online software such as a website, or downloadable software such as a mobile application, to assist with compliance or to provide data relating to treatment. Such software can be used to, e.g., keep track of last dose taken and total doses taken, provide reminders and alerts for upcoming doses, provide feedback to discourage taking doses outside of set schedules, and allow for recording of specific subjective effects, or provide means for unstructured journaling. Such data collection can assist with individual patient compliance, can be used to improve or tailor individual patient care plans, and can be anonymized, aggregated, and analyzed (including by AI or natural language processing means) to allow research into the effects of methods of use.

C. Methods of Use

In some aspects, provided herein are methods of using the disclosed therapeutic combinations comprising a hallucinogen and an entactogen, including compositions thereof. In some embodiments, disclosed combinations and compositions thereof are used to modulate neurotransmission. In some embodiments, disclosed combinations and compositions thereof are used to treat a condition, such as a disorder or a disease. In some embodiments, disclosed combinations and compositions thereof are used to improve reward learning, such as social reward learning, and social cognition.

In some embodiments, a disclosed therapeutic combination or composition thereof, e.g., comprising a hallucinogenic agent and non-racemic MDMA are administered to a subject in need thereof. In some embodiments, a therapeutic combination or composition thereof comprising the hallucinogenic agent and non-racemic MDMA comprising 90% or less of R-MDMA and 10% or more of S-MDMA, or a pharmaceutically acceptable salt thereof, is administered to a subject in need thereof. In some embodiments, the therapeutic combination or composition thereof for administration to a subject comprises the hallucinogenic agent and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the therapeutic combination or composition thereof for administration to a subject comprises the hallucinogenic agent and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the therapeutic combination or composition thereof for administration to a subject comprises the hallucinogenic agent and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the therapeutic combination or composition thereof for administration to a subject comprises the hallucinogenic agent and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the therapeutic combination or composition thereof for administration to a subject comprises the hallucinogenic agent and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the therapeutic combination or composition thereof for administration to a subject comprises the hallucinogenic agent and non-racemic MDMA, wherein R-MDMA and S-MDMA, or pharmaceutically acceptable salt(s) thereof, are present in a ratio of 9:1.

In some embodiments, a therapeutic combination or composition thereof for administration to a subject comprises a hallucinogenic agent and a non-racemic entactogen. In some embodiments, the therapeutic combination or composition thereof for administration to a subject comprises any of psilocybin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, psilocin and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-MeO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, mescaline and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, salvinorin A and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, THC and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4-Aco-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Br-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-Cl-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 5-F-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-MDO-DMT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 4,5-

MDO-DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, PRO-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, ETH-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, AL-LAD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, 1P-LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, LSD and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1, and DiPT and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1.

In some embodiments, a therapeutic combination or composition thereof for administration to a subject comprises a 2C-X compound and non-racemic MDMA. In some embodiments, the therapeutic combination or composition thereof for administration to a subject comprises the 2C-X compound and non-racemic MDMA comprising 90% or less of R-MDMA and 10% or more of S-MDMA, or pharmaceutically acceptable salt(s) thereof. In some embodiments, the therapeutic combination or composition thereof for administration to a subject comprises the 2C-X compound and a non-racemic MDMA, wherein R-MDMA, or a pharmaceutically acceptable salt thereof, is present in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the therapeutic combination or composition thereof for administration to a subject comprises the 2C-X compound and non-racemic MDMA, wherein R-MDMA, or a pharmaceutically acceptable salt thereof, is present in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the therapeutic combination or composition thereof for administration to a subject comprises the 2C-X compound and non-racemic MDMA, wherein R-MDMA, or a pharmaceutically acceptable salt thereof, is present in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the therapeutic combination or composition thereof for administration to a subject comprises the 2C-X compound and non-racemic MDMA, wherein R-MDMA and S-MDMA, or pharmaceutically acceptable salt(s) thereof, are present in a ratio of about 6:1 to 12:1, 7:1 to 11:1, or 8:1 to 10:1. In some embodiments, the therapeutic combination or composition thereof for administration to a subject comprises the 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the therapeutic combination or composition thereof for administration to a subject comprises the 2C-X compound and non-racemic MDMA, wherein R-MDMA and S-MDMA, or pharmaceutically acceptable salt(s) thereof, are present in a ratio of 9:1.

In some embodiments, a disclosed therapeutic combination or composition thereof for administration to a subject comprises a 2C-X compound and non-racemic MDMA, wherein R-MDMA and S-MDMA, or pharmaceutically acceptable salt(s) thereof, are present in a ratio of about 6:1, 7:1, 8:1, 9:1, 10:1, 11:1, or 12:1. In some embodiments, the therapeutic combination or composition thereof for administration to a subject comprises any of 2C-B and about 6:1, 7:1, 8:1, 9:1, 10:1, 11:1, or 12:1 R:S-MDMA, 2C-B-AN and about 6:1, 7:1, 8:1, 9:1, 10:1, 11:1, or 12:1 R: S-MDMA, 2C-B-FLY and about 6:1, 7:1, 8:1, 9:1, 10:1, 11:1, or 12:1 R:S-MDMA, 2C-B-Butterfly and about 6:1, 7:1, 8:1, 9:1, 10:1, 11:1, or 12:1 R:S-MDMA, 2C-B-Fly-NBOMe and about 6:1, 7:1, 8:1, 9:1, 10:1, 11:1, or 12:1 R:S-MDMA, 2C-B-Fly-NB2EtO5Cl and about 6:1, 7:1, 8:1, 9:1, 10:1, 11:1, or 12:1 R:S-MDMA, 2C-Bn and about 6:1, 7:1, 8:1, 9:1, 10:1, 11:1, or 12:1 R:S-MDMA, 2C-Bu and about 6:1, 7:1, 8:1, 9:1, 10:1, 11:1, or 12:1 R: S-MDMA, 2C-B-5-Hemifly and about 6:1, 7:1, 8:1, 9:1, 10:1, 11:1, or 12:1 R: S-MDMA, 2C-C and about 6:1, 7:1, 8:1, 9:1, 10:1, 11:1, or 12:1 R: S-MDMA, 2C-C-3 and about 6:1, 7:1, 8:1, 9:1, 10:1, 11:1, or 12:1 R:S-MDMA, 2C-CN and about 6:1, 7:1, 8:1, 9:1, 10:1, 11:1, or 12:1 R:S-MDMA, 2C-CP and about 6:1, 7:1, 8:1, 9:1, 10:1, 11:1, or 12:1 R: S-MDMA, 2C-D and about 6:1, 7:1, 8:1, 9:1, 10:1, 11:1, or 12:1 R:S-MDMA, 2C-E and about 6:1, 7:1, 8:1, 9:1, 10:1, 11:1, or 12:1 R:S-MDMA, 2C-EF and about 6:1, 7:1, 8:1, 9:1, 10:1, 11:1, or 12:1 R:S-MDMA, 2C-F and about 6:1, 7:1, 8:1, 9:1, 10:1, 11:1, or 12:1 R:S-MDMA, 2C-G and about 6:1, 7:1, 8:1, 9:1, 10:1, 11:1, or 12:1 R: S-MDMA, 2C-G-1 and about 6:1, 7:1, 8:1, 9:1, 10:1, 11:1, or 12:1 R:S-MDMA, 2C-G-2 and about 6:1, 7:1, 8:1, 9:1, 10:1, 11:1, or 12:1 R:S-MDMA, 2C-G-3 and about 6:1, 7:1, 8:1, 9:1, 10:1, 11:1, or 12:1 R:S-MDMA, 2C-G-4 and about 6:1, 7:1, 8:1, 9:1, 10:1, 11:1, or 12:1 R:S-MDMA, 2C-G-5 and about 6:1, 7:1, 8:1, 9:1, 10:1, 11:1, or 12:1 R: S-MDMA, 2C-G-6 and about 6:1, 7:1, 8:1, 9:1, 10:1, 11:1, or 12:1 R:S-MDMA, 2C-G-N and about 6:1, 7:1, 8:1, 9:1, 10:1, 11:1, or 12:1 R: S-MDMA, 2C-H and about 6:1, 7:1, 8:1, 9:1, 10:1, 11:1, or 12:1 R:S-MDMA, 2C-I and about 6:1, 7:1, 8:1, 9:1, 10:1, 11:1, or 12:1 R: S-MDMA, 2CB-Ind and about 6:1, 7:1, 8:1, 9:1, 10:1, 11:1, or 12:1 R: S-MDMA, 2C-iP and about 6:1, 7:1, 8:1, 9:1, 10:1, 11:1, or 12:1 R:S-MDMA, 2C-N and about 6:1, 7:1, 8:1, 9:1, 10:1, 11:1, or 12:1 R:S-MDMA, 2C-NH2 and about 6:1, 7:1, 8:1, 9:1, 10:1, 11:1, or 12:1 R: S-MDMA, 2C-PYR and about 6:1, 7:1, 8:1, 9:1, 10:1, 11:1, or 12:1 R:S-MDMA, 2C-PIP and about 6:1, 7:1, 8:1, 9:1, 10:1, 11:1, or 12:1 R:S-MDMA, 2C-O and about 6:1, 7:1, 8:1, 9:1, 10:1, 11:1, or 12:1 R: S-MDMA, 2C-O-4 and about 6:1, 7:1, 8:1, 9:1, 10:1, 11:1, or 12:1 R: S-MDMA, 2C-MOM and about 6:1, 7:1, 8:1, 9:1, 10:1, 11:1, or 12:1 R:S-MDMA, 2C-P and about 6:1, 7:1, 8:1, 9:1, 10:1, 11:1, or 12:1 R:S-MDMA, 2C-Ph and about 6:1, 7:1, 8:1, 9:1, 10:1, 11:1, or 12:1 R:S-MDMA, 2C-Se and about 6:1, 7:1, 8:1, 9:1, 10:1, 11:1, or 12:1 R:S-MDMA, 2C-T and about 6:1, 7:1, 8:1, 9:1, 10:1, 11:1, or 12:1 R:S-MDMA, 2C-T-2 and about 6:1, 7:1, 8:1, 9:1, 10:1, 11:1, or 12:1 R:S-MDMA, 2C-T-3 and about 6:1, 7:1, 8:1, 9:1, 10:1, 11:1, or 12:1 R:S-MDMA, 2C-T-4 and about 6:1, 7:1, 8:1, 9:1, 10:1, 11:1, or 12:1 R:S-MDMA, 2C-T-5 and about 6:1, 7:1, 8:1, 9:1, 10:1, 11:1, or 12:1 R:S-MDMA, 2C-T-6 and about 6:1, 7:1, 8:1, 9:1, 10:1, 11:1, or 12:1 R:S-MDMA, 2C-T-7 and about 6:1, 7:1, 8:1, 9:1, 10:1, 11:1, or 12:1 R:S-MDMA, 2C-T-8 and about 6:1, 7:1, 8:1, 9:1, 10:1, 11:1, or 12:1 R: S-MDMA, 2C-T-9 and about 6:1, 7:1, 8:1, 9:1, 10:1, 11:1, or 12:1 R:S-MDMA, 2C-T-10 and about 6:1, 7:1, 8:1, 9:1, 10:1, 11:1, or 12:1 R:S-MDMA, 2C-T-11 and about 6:1, 7:1, 8:1, 9:1, 10:1, 11:1, or 12:1 R:S-MDMA, 2C-T-12 and about 6:1, 7:1, 8:1, 9:1, 10:1, 11:1, or 12:1 R:S-MDMA, 2C-T-13 and about 6:1, 7:1, 8:1, 9:1, 10:1, 11:1, or 12:1 R:S-MDMA, 2C-T-14 and about 6:1, 7:1, 8:1, 9:1, 10:1, 11:1, or 12:1 R:S-MDMA, 2C-T-15 and about 6:1, 7:1, 8:1, 9:1, 10:1, 11:1, or 12:1 R:S-MDMA, 2C-T-16 and about 6:1, 7:1, 8:1, 9:1, 10:1, 11:1, or 12:1 R:S-MDMA, 2C-T-17 and about 6:1, 7:1, 8:1, 9:1, 10:1, 11:1, or 12:1 R:S-MDMA, 2C-T-18 and about 6:1, 7:1, 8:1, 9:1, 10:1, 11:1, or 12:1 R:S-MDMA, 2C-T-19 and about 6:1, 7:1, 8:1, 9:1, 10:1, 11:1, or 12:1 R:S-MDMA, 2C-T-21 and about 6:1, 7:1, 8:1, 9:1, 10:1, 11:1, or 12:1 R:S-MDMA, 2C-T-21.5 and about 6:1, 7:1, 8:1, 9:1, 10:1, 11:1, or 12:1 R:S-MDMA, 2C-T-22 and about 6:1, 7:1, 8:1, 9:1, 10:1, 11:1, or 12:1 R:S-MDMA, 2C-T-23 and about 6:1, 7:1, 8:1, 9:1, 10:1, 11:1, or 12:1 R:S-MDMA, 2C-T-24 and about 6:1, 7:1, 8:1, 9:1, 10:1, 11:1, or 12:1 R:S-MDMA, 2C-T-25 and about 6:1, 7:1, 8:1, 9:1, 10:1, 11:1, or 12:1 R: S-MDMA, 2C-T-27 and about 6:1, 7:1, 8:1, 9:1, 10:1, 11:1, or 12:1 R:S-MDMA, 2C-T-28 and about 6:1, 7:1, 8:1, 9:1, 10:1, 11:1, or 12:1 R:S-MDMA, 2C-T-30 and about 6:1, 7:1, 8:1, 9:1, 10:1, 11:1, or 12:1 R:S-MDMA, 2C-T-31 and about 6:1, 7:1, 8:1, 9:1, 10:1, 11:1, or 12:1 R:S-MDMA, 2C-T-32 and about 6:1, 7:1, 8:1, 9:1, 10:1, 11:1, or 12:1 R: S-MDMA, 2C-T-33 and about 6:1, 7:1, 8:1, 9:1, 10:1, 11:1, or 12:1 R:S-MDMA, 2C-DFM and about 6:1, 7:1, 8:1, 9:1, 10:1, 11:1, or 12:1 R:S-MDMA, 2C-TFM and about 6:1, 7:1, 8:1, 9:1, 10:1, 11:1, or 12:1 R: S-MDMA, 2C-TFE and about 6:1, 7:1, 8:1, 9:1, 10:1, 11:1, or 12:1 R:S-MDMA, 2C-YN and about 6:1, 7:1, 8:1, 9:1, 10:1, 11:1, or 12:1 R:S-MDMA, 2C-V and about 6:1, 7:1, 8:1, 9:1, 10:1, 11:1, or 12:1 R: S-MDMA, and 2C-AL and about 6:1, 7:1, 8:1, 9:1, 10:1, 11:1, or 12:1 R:S-MDMA.

a. Methods of Modulating Neurotransmission

In some embodiments, the disclosed combinations and compositions thereof modulate neurotransmission. In some embodiments, modulating neurotransmission comprises regulating levels of monoamines in, for example, the CNS and peripheral tissues. In some embodiments, modulating neurotransmission comprises increasing levels of monoamines in, for example, the CNS and peripheral tissues of a subject to whom a therapeutic combination or composition has been administered. In some embodiments, modulating neurotransmission comprises decreasing levels of monoamines in, for example, the CNS and peripheral tissues of a subject to whom a therapeutic combination or composition has been administered. In some embodiments, modulating neurotransmission by administering a disclosed combination or composition to a subject treats a disease or disorder in the subject.

In some embodiments, the therapeutic combination or composition thereof for modulating neurotransmission comprises a hallucinogen and an entactogen. In some embodiments, the therapeutic combination or composition thereof for modulating neurotransmission comprises a hallucinogen and a non-racemic entactogen, e.g., non-racemic MDMA, wherein R-MDMA is present in enantiomeric excess.

In some embodiments, a therapeutic combination or composition thereof comprising a hallucinogen and non-racemic MDMA, wherein R-MDMA is present in enantiomeric excess of 10%-95%, 20%-95%, 30%-95%, 40%-95%, 50%-95%, 55%-95%, 60%-90%, 65%-90%, or 75%-85%, is used to modulate neurotransmission. In some embodiments, a therapeutic combination or composition thereof comprising a hallucinogen and non-racemic MDMA, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95%, is used to modulate neurotransmission. In some embodiments, a therapeutic combination or composition thereof comprising a hallucinogen and non-racemic MDMA, wherein R:S MDMA is present in a ratio of about 6:1, 7:1, 8:1, 9:1, 10:1, 11:1, or 12:1, is used to modulate neurotransmission.

Detecting a change in monoamine levels in a subject, such as an increase or a decrease, can be achieved according to methods known to one of skill, for example, brain microdialysis (Chefer et al., Curr Protoc Neurosci. 2009; Ch.: Unit 7.1; Darvesh et al., Expert Opin Drug Discov. 2011; 6(2): 109-127) and brain imaging, for example, positron emission tomography (PET) and single photon emission computed tomography (SPECT) (see e.g., Wong & Gjedde, Encycl. Neurosci., 2009; 939-52; Takano, Front Psychiatry., 2018; 9:228).

In some embodiments, a disclosed therapeutic combination comprising a hallucinogen and non-racemic MDMA, wherein R-MDMA is present in enantiomeric excess, has reduced affinity for NET relative to a comparator combination comprising the same hallucinogen and racemic MDMA. In some embodiments, a disclosed therapeutic combination comprising a hallucinogen and non-racemic MDMA, wherein R-MDMA is present in enantiomeric excess, has reduced potency for releasing norepinephrine (NE) relative to a comparator combination comprising the same hallucinogen and racemic MDMA.

In some embodiments, a disclosed therapeutic combination comprising a hallucinogen and non-racemic MDMA, wherein R-MDMA is present in enantiomeric excess, has reduced affinity for DAT relative to a comparator combination comprising the same hallucinogen and racemic MDMA. In some embodiments, a disclosed therapeutic combination comprising a hallucinogen and non-racemic MDMA, wherein R-MDMA is present in enantiomeric excess, has reduced potency for releasing dopamine relative to a comparator combination comprising the same hallucinogen and racemic MDMA.

In some embodiments, a disclosed therapeutic combination comprising a hallucinogen and non-racemic MDMA, wherein R-MDMA is present in enantiomeric excess, has comparable affinity for SERT relative to a comparator combination comprising the same hallucinogen and racemic MDMA. In some embodiments, a disclosed therapeutic combination comprising a hallucinogen and non-racemic MDMA, wherein R-MDMA is present in enantiomeric excess, has comparable affinity for 5-$HT_{2A}$ relative to a comparator combination comprising the same hallucinogen and racemic MDMA.

In some embodiments, modulating neurotransmission comprises modulating activity at the $\alpha4\beta2$ receptor nicotinic acetylcholine receptor. In some embodiments, a disclosed therapeutic combination, e.g., comprising a hallucinogen and non-racemic MDMA having R-MDMA in enantiomeric excess, has comparable affinity for the $\alpha4\beta2$ receptor nicotinic acetylcholine receptor relative to a comparator combination comprising the same hallucinogen and racemic MDMA. In some embodiments, a disclosed therapeutic combination, e.g., comprising a hallucinogen and non-racemic MDMA having R-MDMA in enantiomeric excess, has increased affinity for the $\alpha4\beta2$ receptor nicotinic acetylcholine receptor relative to a comparator combination comprising the same hallucinogen and R-MDMA. In some embodiments, and in addition to in addition to reduced affinity for DAT and NET, a disclosed therapeutic combination, e.g., comprising a hallucinogen and non-racemic MDMA having R-MDMA in enantiomeric excess, has comparable affinity for the $\alpha4\beta2$ receptor nicotinic acetylcholine receptor relative to a comparator combination comprising the same hallucinogen and racemic MDMA. In some embodiments, a disclosed therapeutic combination, e.g., comprising a hallucinogen and non-racemic MDMA having R-MDMA in enantiomeric excess, has comparable activity at the $\alpha4\beta2$ receptor nicotinic acetylcholine receptor, such as agonism, relative to a comparator combination comprising the same hallucinogen and racemic MDMA.

The $\alpha4\beta2$ nicotinic acetylcholine receptor is implicated in learning, analgesia, reinforcement, development and aging in the brain (Cordero-Erausquin et al., Trends Pharmacol Sci., 2000 June; 21(6):211-7). In comparison to a combination comprising a hallucinogen and racemic MDMA, a disclosed therapeutic combination, such as comprising a hallucinogen and non-racemic MDMA having R-MDMA in enantiomeric excess, shows comparable affinity and/or activity at $\alpha4\beta2$ nicotinic acetylcholine receptor without further modulating dopaminergic and/or noradrenergic neurotransmission, such as by having relatively reduced affinity for DAT and NET. Methods for determining affinity for and activity at $\alpha4\beta2$ nicotinic acetylcholine receptor is available to one of skill in the art, including, e.g., the methods described in Llabres et al., European Journal of Medicinal Chemistry, 2014; 81:35e46. For methods of assessing this and other targets, see also Roth's NINM Psychoactive Drug Screening Program (PDSP) Assay Protocol Book Ver. III, 2018.

b. Methods of Treatment

In some aspects, provided herein are methods for treating a subject by administering the therapeutic combinations and pharmaceutical compositions thereof. In some embodiments, a therapeutically effective amount of a disclosed combination or composition thereof is administered to a subject in need thereof to treat a condition in said subject. In some embodiments, the condition is a disorder or a disease, such as a mental health disorder or a neurodegenerative disease.

In some embodiments, compositions comprising compounds of a disclosed therapeutic combination, such as two or more of a hallucinogenic agent, an entactogenic agent, and a dissociative agent, are suitable for any of oral, sublingual, buccal, mucosal, ocular, rectal, intravaginal, parenteral, subcutaneous, intravenous, intramuscular, intranasal, inhaled, and transdermal administration to a subject, and can be prepared for such administration by known methods in the art. In some embodiments, a disclosed combination is administered to a subject in the same dosage form by the same route of administration. In some embodiments, a disclosed combination is administered to a subject in different dosage forms by the same route of administration. In some embodiments, a disclosed combination is administered to a subject in different dosage forms by distinct routes of administration.

As used herein, the terms "subject," "user," "patient," and "individual" are used interchangeably, and refer to any mammal although preferably a human. Such terms will be understood to include one who has an indication for which a formulation described herein may be efficacious, or who otherwise may benefit by the combinations, compositions, and methods of the invention. As used herein, a "subject having" a condition, disease, or disorder will be understood as the subject suffering from or experiencing one or more symptoms of said condition, disease, or disorder, whether or not a formal diagnosis has been made. In general, all of the formulations and methods of the invention will be appreciated to work for all individuals, although individual variation is to be expected, and will be understood. The disclosed methods of treatment also can be modified to treat multiple patients at once, including couples, families, or groups. Hence, these terms will be understood to also mean two or more individuals. In some embodiments, the disclosed combinations and compositions are used with patients in long-term or institutional care.

As used herein, "an effective amount," "a pharmacologically effective amount," or "therapeutically effective amount" refers to an amount of a compound that is non-toxic and sufficient to provide the desired therapeutic effect with performance at a reasonable benefit/risk ratio attending any medical treatment. The effective amount will vary depending upon the subject and the disease condition being treated or health benefit sought, the weight and age of the subject, the severity of the disease condition or degree of health benefit sought, the manner of administration, and the like, all of which can readily be determined by one of ordinary skill in the art.

As used herein, "therapeutic effect" or "therapeutic efficacy" means the responses(s) in a mammal, and preferably a human, after treatment that are judged to be desirable and beneficial. Hence, depending on the disorder to be treated, or improvement in physiological or psychological functioning sought, and depending on the particular constituent(s) in the disclosed combinations and compositions under consideration, those responses shall differ, but would be readily understood by those of ordinary skill.

Measures of therapeutic effect include any outcome measure, endpoint, effect measure, or measure of effect within clinical or medical practice or research which is used to assess the effect, including both positive and/or negative, of an intervention or treatment, whether patient-reported (e.g., questionnaires), based on other patient data (e.g., patient monitoring), gathered through laboratory tests such as blood work, urine samples, etc., through medical examination by a doctor or other medical professional, or by digital tools or means, e.g., electronic tools such as online tools, smartphones, wireless devices, biosensors, or health apps, including by, e.g., digital phenotyping.

In embodiments, the invention provides methods of treating and/or preventing a condition in a mammal, the method comprising administering to the mammal a therapeutically effective and/or prophylactically effective amount of a combination or composition. As used herein, "treating" or "treatment" covers any treatment of a disorder in a mammal, and preferably in a human, and includes causing a desired biological or pharmacological effect as above, as well as any one or more of: (a) preventing a disorder from occurring in a subject who may be predisposed to the disorder but has not yet been diagnosed with it; (b) inhibiting a disorder, i.e. arresting its development; (c) relieving a disorder, i.e., causing regression thereof; (d) protection from or relief of a symptom or pathology caused by or related to a disorder; (e) reduction, decrease, inhibition, amelioration, or prevention of onset, severity, duration, progression, frequency or probability of one or more symptoms or pathologies associated with a disorder; and (f) prevention or inhibition of a worsening or progression of symptoms or pathologies associated with a disorder or comorbid with a disorder. Other such measurements, benefits, and surrogate or clinical endpoints, alone or in combination, will be understood to one of ordinary skill based on the teachings herein and the knowledge in the art.

In general, all of the disclosed combinations, compositions, and methods will be appreciated to work for all individuals, although individual variation is to be expected, and will be understood. Where there is variation between individuals, modification to the combinations, compositions, and methods will be understood based on the disclosure together with the general knowledge of the art. In some instances, certain personalized approaches ("personalized" or "precision" medicine) may be utilized, based on individual characteristics, including drug metabolism (e.g., CYP2D6 or CYP3A4) or individual genetic variation.

The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations. In one embodiment, the genetic variation is a genetic variation in metabotropic glutamate receptor type 5 (mGluR5), which has been implicated in mood and anxiety symptoms in humans. In another embodiment, the genetic variation is one or more single nucleotide polymorphisms (SNPs) in the FKBP5 gene that are associated with elevated levels of FKBP51 protein relative to persons lacking such SNPs. The FKBP5 gene has been implicated in responses to stress and trauma, and such SNPs are correlated with susceptibility to certain depression, PTSD, and anxiety disorders.

As used herein, the terms "drug," "pharmaceutical agent," "pharmacologically active agent," "active agent," or any other similar term means a chemical or biological material or compound suitable for administration by the methods previously known in the art and/or by the methods taught in the present invention, such as when prepared as a pharmaceutical formulation of the invention, and that induces a desired biological or pharmacological effect, which can include but is not limited to: (1) having a prophylactic effect on the organism and preventing an undesired biological effect; (2) alleviating the effect of a condition; (3) alleviating, reducing, or eliminating a disease, disorder, or particular biological state; and/or (4) providing a curative, or other beneficial effect. In some preferred embodiments, and as further discussed below, the compositions of the invention include a combination of an hallucinogenic agent and an entactogenic agent that when administered to a patient produce in the patient at least one improved physiological or psychological effect compared to those agents given alone.

i. Mental Health Disorders

In some embodiments, the disclosed therapeutic combinations or compositions thereof are used to treat mental health disorders. In some embodiments, treating a mental health disorder comprises administering a therapeutic combination or composition thereof in a therapeutically effective amount to a subject having and/or diagnosed with said disorder. In some embodiments, administering a therapeutic combination or composition thereof in a therapeutically effective amount to a subject reduces the incidence and/or the severity of at least one symptom of a mental health disorder in a subject having and/or diagnosed with said disorder. In some embodiments, the disclosed therapeutic combinations or compositions thereof for treating a mental health disorder comprise a hallucinogen and an entactogen. In some embodiments, the disclosed therapeutic combinations or compositions thereof for treating a mental health disorder comprise a hallucinogen and a non-racemic entactogen, e.g., non-racemic MDMA, wherein R-MDMA is present in enantiomeric excess.

In some embodiments, a provided therapeutic combination or composition thereof comprising a hallucinogen and a non-racemic mixture of R-MDMA and S-MDMA is used to treat a mental health disorder. In some embodiments, a therapeutic combination or composition thereof comprising a hallucinogen and a non-racemic mixture of R-MDMA and S-MDMA, wherein R-MDMA is present in enantiomeric excess, is used to treat a mental health disorder. In some embodiments, a therapeutic combination or composition thereof comprising a hallucinogen and a non-racemic mixture of R-MDMA and S-MDMA, wherein R-MDMA is present in an enantiomeric excess of 10%-95%, 20%-95%, 30%-95%, 40%-95%, 50%-95%, 55%-95%, 60%-90%, 65%-90%, or 75%-85% is used to treat a mental health disorder. In some embodiments, a therapeutic combination or composition thereof comprising a hallucinogen and a non-racemic mixture of R-MDMA and S-MDMA, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95%, is used to treat a mental health disorder. In some embodiments, a therapeutic combination or composition thereof comprising a hallucinogen and a non-racemic mixture of R-MDMA and S-MDMA, wherein R-MDMA and S-MDMA are present in a ratio of about 6:1, 7:1, 8:1, 9:1, 10:1, 11:1, or 12:1, is used to treat a mental health disorder. In some embodiments, a therapeutic combination or composition thereof comprising any of the disclosed MDMA enantiomers or mixtures thereof in a therapeutically effective amount is used to treat a mental health disorder.

"Mental health disorder" or "psychiatric disorder" refers to a disease condition in a mammal, and preferably in a human, that generally involves negative changes in emotion, mood, thinking, and/or behavior. Mental health disorders may also be understood to include "CNS disorders." For example, mental health disorders include those characterized by the DSM-5, the ICD-11, the Merck Manual, e.g., anxiety and depressive disorders, earlier or later versions thereof, or other such diagnostic resources known to those of skill.

In some methods herein, the disclosed combinations and compositions, when administered in a pharmacologically effective amount, provide beneficial therapeutic effects for the treatment of mental health disorders. Non-limiting examples of such disorders, which may be treated using a disclosed therapeutic combination or composition thereof, include anxiety and stressor related disorders, dissociative disorders, eating disorders, mood disorders, e.g., depressive disorders, depression, major depressive disorder, treatment resistant depression, dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive and related disorders, paranoid, schizoid and schizotypal personality disorders), schizophrenia and related disorders, attachment disorders, autism, and dissociative disorders, sexuality, gender dysphoria, and paraphilias, somatic symptom and related disorders, suicidal behavior and self-injury, and substance-related disorders, which includes substance-induced and substance use disorders. Substance abuse disorders include, for example, alcoholism, tobacco abuse, drug abuse or dependence disorders (See Merck Manual of Diagnosis and Therapy, 20th Ed., 2018).

In some embodiments, the therapeutic combinations and pharmaceutical compositions of the invention are used to manage emotional regulation, for example in a patient with a stress disorder, acute stress disorder, brief psychotic disorder with marked stressor(s), delirium, mild cognitive impairment (MCI), dementia, psychosis, and psychotic major depression, as those terms are generally understood, for example by reference to the DSM-5. “Psychological distress” related to life-threatening illness or death includes depression, anxiety, and existential distress.

While the neurophysiology underlying mental health disorders may be distinct, an aspect in common of many is the presence of a deleterious, repetitive, and often “rigid” thought process that negatively impacts an individual's ability to function. For someone with PTSD, for instance, symptoms involve re-experiencing trauma and the feelings associated with it; for depression it can take the form of a recurrent internal editor that attaches negative connotations to normal life events; and for addiction it is the preoccupation with acquiring and using the substance of choice. Thus, in many embodiments, the method of treating a mental health disorder involves the treatment of a disorder related to rigid modes of thinking. In different embodiments, the disorder related to rigid modes of thinking can be anxiety, depression, addiction, an eating disorder, obsessive compulsive disorder, or PTSD.

In some embodiments, the therapeutic combinations and pharmaceutical compositions of the invention are used to reduce the symptoms of a mental health disorder. The symptoms of the mental health disorder to be treated shall be able to be determined by one of skill in the art, by reference to the general understanding of the art regarding that disorder.

A variety of methods are available for screening or assessing a subject for a mental health disorder, and/or to determine a reduction in symptom severity. In some embodiments, a diagnosis of a mental health disorder is facilitated with use of the Diagnostic and Statistical Manual of Mental Disorders, such as the DSM-5. In some embodiments, diagnosis of a mental health disorder is facilitated with use of self-reported or observer-reported surveys or questionnaires. Non-limiting examples of such questionnaires include the Clinician-Administered PTSD Scale for DSM-5 (CAPS-5), Montgomery-Asberg Depression Rating Scale (MADRS), Patient Health Questionnaire 9 (PHQ-9), the Generalized Anxiety Disorder 7 (GAD-7), PTSD Checklist for DSM-5 (PCL-5), The Alcohol Use Disorders Identification Test (AUDIT), Binge Eating Scale (BES), Obsessive-Compulsive Inventory (OCI), the Personality Disorders Questionnaire (PDQ-IV), Dissociative Experiences Scale (DES), Drug Use Questionnaire (DAST-20), The Mood Disorder Questionnaire (MDQ), and other similar questionnaires. In some embodiments, alternative questionnaires, such as the Clinical Global Impression—Improvement scale (CGI-I), may be used to assess improvement of a subject's mental health state, such as by comparing baseline responses to responses after a treatment intervention. In some embodiments, any of the diagnostic manuals and assessments described, and other similar tools, may be used to confirm a reduction in symptoms, a reduction in symptom severity, or elimination of symptoms and/or a previous diagnosis.

In some embodiments, mental health disorders of the invention are specifically the “trauma- and stressor-related disorders,” which include acute stress disorder, adjustment disorders, and post-traumatic stress disorder (Merck Manual, 20th Ed.), as well as reactive attachment disorder, disinhibited social engagement disorder, and others (DSM-5), including such stressor-related disorders as brief psychotic disorder with marked stressor(s), and other disorders associated with psychological trauma. In certain embodiments, the mental health disorder of the invention is specifically PTSD, e.g., moderate to severe PTSD.

In some embodiments, a therapeutic combination or composition thereof comprising a hallucinogen and a non-racemic mixture of R-MDMA HCl and S-MDMA HCl in a ratio of 8:1, 9:1, 10:1, 11:1, or 12:1 is used to treat PTSD. In some embodiments, a therapeutic combination or composition thereof comprising a hallucinogen and a mixture of R-MDMA HCl and S-MDMA HCl in a ratio of about 8:1, 9:1, or 10:1 is used to treat moderate to severe PTSD in conjunction with psychotherapy. In some embodiments, psychotherapy is conducted in an outpatient setting. The severity of PTSD can be determined according to assessments available to one of skill in the art, e.g., the Clinician-Administered PTSD Scale for DSM-5 (CAPS-5). Additional implications and symptoms of PTSD, and comorbidities associated with the same, which may benefit from the provided therapeutic compounds, are described in, e.g., Davis et al., J Clin Psychiatry, 2022; 83(3):21m14116; Steenkamp et al., JAMA, 2020; 323(7):656-657.

Symptoms of PTSD, for example, include transient waking dissociative states in which events are relived as if happening (“flashbacks”), nightmares, distressing and intense memories, other intrusive negative memories, distress or physical reactions after being exposed to triggers, blaming self or others for the trauma, decreased interest in things that were once enjoyable and other feelings of emotional numbness, negative feelings about one's self and the world, inability to remember the trauma clearly, difficulty feeling positive, feelings of isolation, negative affect, difficulty feeling positive, other negative alterations in cognition and mood, avoidance, aggression or irritability, hypervigilance and hyper-awareness, difficulty concentrating, difficulty sleeping, heightened startle response, engaging in self-destructive, or risky behavior, difficulty sleeping or staying asleep, and suicidal ideation. Accordingly, methods of the invention that reduce the symptoms of PTSD would be understood to reduce any such symptoms.

ii. Neurodegenerative Disorders

In some embodiments, the disclosed therapeutic combinations or compositions thereof are used to treat neurodegenerative conditions. In some embodiments, administering a therapeutic combination or composition thereof in a therapeutically effective amount to a subject treats a neurodegenerative condition in a subject having and/or diagnosed with said condition. In some embodiments, administering a therapeutic combination or composition thereof in a therapeutically effective amount to a subject reduces the incidence and/or the severity of at least one symptom of a neurodegenerative condition in a subject having and/or diagnosed with said condition. In some embodiments, administering a therapeutic combination or composition thereof in a therapeutically effective amount to a subject prevents or reduces neurodegeneration in a subject having and/or diagnosed with said condition. In some embodiments, the disclosed therapeutic combinations or compositions thereof for treating a neurodegenerative condition comprise a hallucinogen and an entactogen. In some embodiments, the disclosed therapeutic combinations or compositions thereof for treating a neurodegenerative condition comprise a hallucinogen and a non-racemic entactogen, e.g., non-racemic MDMA, wherein R-MDMA is present in enantiomeric excess.

In some embodiments, a provided therapeutic combination or composition thereof comprising a hallucinogen and a non-racemic mixture of R-MDMA and S-MDMA is used to treat a neurodegenerative condition. In some embodiments, a therapeutic combination or composition thereof comprising a hallucinogen and a non-racemic mixture of R-MDMA and S-MDMA, wherein R-MDMA is present in enantiomeric excess, is used to treat a neurodegenerative condition. In some embodiments, a therapeutic combination or composition thereof comprising a hallucinogen and a non-racemic mixture of R-MDMA and S-MDMA, wherein R-MDMA is present in an enantiomeric excess of 10%-95%, 20%-95%, 30%-95%, 40%-95%, 50%-95%, 55%-95%, 60%-90%, 65%-90%, or 75%-85%, is used to treat a neurodegenerative condition. In some embodiments, a therapeutic combination or composition thereof comprising a hallucinogen and a non-racemic mixture of R-MDMA and S-MDMA, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95%, is used to treat a neurodegenerative condition. In some embodiments, a therapeutic combination or composition thereof comprising a hallucinogen and a non-racemic mixture of R-MDMA and S-MDMA, wherein R-MDMA and S-MDMA are present in a ratio of about 6:1, 7:1, 8:1, 9:1, 10:1, 11:1, or 12:1, is used to treat a neurodegenerative condition. In some embodiments, treating a neurodegenerative condition comprises reducing and/or preventing neurodegeneration.

Neurodegenerative conditions, such as diseases or disorders include, e.g., dementia, Alzheimer's disease, Huntington's disease, multiple sclerosis, and Parkinson's disease. A feature of neurodegenerative conditions is neuronal cell death, which, among other aspects, has been implicated in the promotion of inflammation. See, e.g., Chan et al., Annu Rev Immunol. 2015; 33: 79-106 and Chi et al., Int J Mol Sci. 2018; 19(10):3082. Neurodegenerative diseases can be classified according to primary clinical features, e.g., dementia, parkinsonism, or motor neuron disease, anatomic distribution of neurodegeneration, e.g., frontotemporal degenerations, extrapyramidal disorders, or spinocerebellar degenerations, or principal molecular abnormality (Dugger & Dickson, Cold Spring Harb Perspect Biol. 2017; 9(7): a028035.

Neurodegeneration may be assessed, e.g., by measuring markers of neuronal loss, such as cerebrospinal fluid markers, e.g., visinin-like protein 1 (VILIP-1), tau, and p-tau181 (Tarawneh et al., Neurol. 2015; 72(6): 656-665). Cognitive decline may also be used as a measure of neurodegeneration. Methods for assessing cognitive decline, e.g., comprehensive neuropsychological testing, are known to one of skill in the art. Exemplary cognitive evaluations include Mini-Mental State Examination (MMSE) and Montreal Cognitive Assessment (MoCA). See, e.g., Toh et al., Transl Neurodegener. 2014; 3:15. Cognitive decline and the progression of disease state may also be assessed using a condition-specific measure, e.g., the Unified Huntington's Disease Rating Scale (UHDRS).

c. Reward Learning and Social Cognition

In some embodiments, the disclosed therapeutic combinations or compositions thereof are used to enhance reward learning and/or social cognition. In some embodiments, administering a therapeutic combination or composition thereof in a therapeutically effective amount to a subject improves reward learning and/or social cognition in said subject. In some embodiments, the disclosed therapeutic combinations or compositions thereof are used to treat disorders mediated by impaired reward learning and/or social cognition. Applications of improvements in reward learning and social cognition include, e.g., treatment of social anxiety, such as social anxiety disorder, and autism, such as an autism spectrum disorder.

In some embodiments, disclosed therapeutic combinations agonize 5-$HT_{1A}$ and 5-$HT_{2A}$. Such combined agonism is critical for production of oxytocin and extinction of fear conditioning responses. In some embodiments, features of the combination allow for a reduced effective dose of a hallucinogen, when combined with a 5-$HT_{2A}$ modulating entactogen. In some aspects, the disclosed therapeutic combinations facilitate changes to functional connectivity in the brain. In some embodiments, changes in functional connectivity include a reduction in amygdala activation in response to negative stimuli and promotion of resting-state functional connectivity of the default mode network (DMN). In other aspects, features of a disclosed therapeutic combination or composition thereof improve social reward learning over use of either a hallucinogen or an entactogen alone. In some embodiments, the disclosed combinations facilitate enhanced oxytocin (OTC) secretion, which is critical for reward learning. Improving integration of insight and learning results in more favorable therapeutic outcomes. The safer psychological experience of adding a prosocial and/or high empathy phase to classic psychedelics, e.g., LSD, psilocin, and psilocybin, leads to improved therapeutic outcomes. See, e.g., Roseman et al., Front Pharmacol. 2018; 8:974.

Reward learning is a type of reinforcement learning ("Reward Learning," NIMH, accessed Jul. 3, 2022). Rewards are desired, appetitive, and positive outcomes of motivated behavior that can increase and maintain the frequency and strength of the behavior they are contingent on (Matyjek et al., Front Psychiatry. 2020; 11: 818). They often serve as reinforcers, i.e. positive, or in other cases negative, stimuli or events that change the probability of that behavior's occurrence or its strength in the future (Tobler & Kobayashi, Handbook of Reward and Decision Making, Academic Press, 2009, pages 29-50).

Social reward learning is a process by which organisms acquire information about stimuli, actions, and contexts that predict positive outcomes. Acquiring such information may result in modified behavior, e.g., when a novel reward occurs, or outcomes are better than expected. Because humans do not live in isolation, many rewarding experiences stem from social interaction and relationships. Social rewards are a broad set of stimuli, which instigate positive experiences involving other people, including a vast repertoire of verbal and non-verbal behaviors, gestures, and feelings (Bhanji & Delgado, Wiley Interdiscip Rev Cogn Sci. 2014; 5(1):61-73) such as a smile (Spreckelmeyer et al., Social Cognitive and Affective Neuroscience, 2009; 4(2): 158-165), praise (Deci et al., Journal of Personality and Social Psychology, 1971; 18(1):105-115.), a thumbs-up (Oumeziane et al., Neuropsychologia. 2017; 107:48-59), and acquisition of a good reputation (Izuma et al., Neuron. 2008 24; 58(2):284-94), among others. For instance, the Social Motivation Hypothesis proposes that individuals with autism spectrum disorder (ASD) experience social interactions as less rewarding than their neurotypical peers, which may lead to reduced social initiation (Baker et al., Front Psychiatry. 2021; 12:742280).

Social reward outcomes are typically measured through a combination of Electroencephalographic (EEG) and functional magnetic resonance imaging (fMRI). EEG is relatively inexpensive, non-invasive, and well-tolerated across the psychiatric spectrum (Baker 2021, op cit.). In one example, event-related potentials (ERP) can be used to measure reward response. The slow cortical potential stimulus-preceding negativity can be used to measure brain activity prior to stimulus presentation and may serve as a measure of anticipation. Additionally, the reward-related positivity ERP measures response to rewards and reflects the evaluation of rewards, e.g., determining whether a reward is "liked" or "disliked" by comparing losses to gains, such as monetary losses and gains (Holroyd et al., Psychophysiology. (2008) 45:688-97; Proudfit, Psychophysiology. (2015) 52:449-59).

i. Social Anxiety

In some embodiments, the disclosed therapeutic combinations and compositions thereof are used to alleviate social anxiety or enhance social cognition. In some embodiments, alleviating social anxiety or enhancing social cognition comprises administering a therapeutically effective amount of a disclosed combination to a subject in need thereof. In some embodiments, the disclosed therapeutic combinations and compositions thereof are used to treat social anxiety disorder. In some embodiments, the effects of such combinations lead to a reduction in social awkwardness. In some embodiments, a disclosed therapeutic combination for alleviating social anxiety comprises a hallucinogen and an entactogen. In some embodiments, a disclosed therapeutic combination for alleviating social anxiety comprises a hallucinogen and a non-racemic entactogen.

In some embodiments, the disclosed therapeutic combinations and compositions thereof are used to treat social anxiety in autistic adults. In some embodiments, the social anxiety is graded as moderate to extremely severe social anxiety. In some embodiments, administering a disclosed therapeutic combination to a subject in need thereof improves Liebowitz Social Anxiety Scale (LSAS) scores from baseline levels. See, e.g., Danforth et al., Psychopharmacol (Berl)., 2018; 235(11):3137-3148 and Chaliha et al., Curr Neuropharmacol., 2021; 19(7):1101-1154. In some embodiments, administering a disclosed therapeutic combination to a subject having social anxiety disorder reduces the symptoms thereof relative to baseline levels, as determined using the DSM-5.

Social anxiety can be assessed with use of tools available to one of skill in the art, including, e.g., the Liebowitz Social Anxiety Scale (LSAS), the Social Anxiety Questionnaire for Adults (SAQ-A30), the Social Anxiety Scale for Adolescents (SAS-A), and the Social Interaction Anxiety Scale (SIAS). See, e.g., Ranta et al., Child Psychiatry Hum Dev., 2012; 43(4):574-91. Additionally, social anxiety disorder, which may also be referred to as social phobia, can be diagnosed or evaluated according to criteria provided by the DSM-5.

ii. Autism

In some embodiments, the disclosed therapeutic combinations and compositions thereof are used to treat autism, such as an autism spectrum disorder (ASD). In some embodiments, treating autism comprises administering a therapeutically effective amount of a disclosed combination to a subject in need thereof. In some embodiments, a disclosed therapeutic combination or composition thereof for treating autism comprises a hallucinogen and an entactogen. In some embodiments, a disclosed therapeutic combination or composition thereof for treating autism comprises a hallucinogen and a non-racemic entactogen, e.g., non-racemic MDMA, wherein R-MDMA is present in enantiomeric excess, such as 9:1 R:S-MDMA.

ASDs are characterized by impairments in social interaction, communication and behavioral functioning that can affect the health-related quality-of-life outcomes of the affected child and the family (Payakachat et al., Expert Rev Pharmacoecon Outcomes Res. 2012; 12(4): 485-503). Both the Autism Diagnostic Observation Schedule-Second Edition (ADOS-2) and Autism Diagnostic Interview-Revised (ADI-R) are standardized assessment tools which help providers diagnose ASD in children and adults in a clinical and nonclinical setting (Reaven et al., Clin Child Psychol Psychiatry. 2008; 13(1): 81-94). The ADOS Severity Score is an overall measure of autism severity that can be constructed from scores on the ADOS (Gotham et al., J Autism Dev Disord. 2009; 39(5):693-705). The ADOS Calibrated Severity Score provides a metric to quantify ASD severity with relative independence from the child's age and IQ. The raw ADOS totals can be mapped onto a 10-point severity metric. The ADOS Severity Score ranges from 1 to 10 with scores of 1-3 indicating a non-spectrum classification on the ADOS and scores of 4 and above indicating greater severity of autism on the ADOS (Payakachat et al., Expert Rev Pharmacoecon Outcomes Res. 2012; 12(4): 485-503. The Vineland-II Adaptive Behavior Scales (VABS) is a useful tool to capture adaptive functioning and may thus be particularly useful to assess the effects of various treatments or clinical interventions on levels of adaptive functioning (Carter et al., J Autism Dev Disord. 1998; 28(4):287-302). Currently, there exist several types of treatment and intervention for ASD, including behavioral, developmental, educational, socio-relational, psychological, and complementary approaches, which may be incorporated with administering a disclosed therapeutic combination (Autism Spectrum Disorder (ASD): Treatment, CDC.gov, Accessed Jun. 29, 2022).

d. Substance Use Disorders

In some aspects, provided herein are methods of using the disclosed therapeutic combinations to treat substance use disorders. In some embodiments, treating a substance use disorder comprises administering a therapeutically effective amount of the combination to a subject in need thereof. In some embodiments, disclosed combinations, or compositions comprising the same, are administered to a subject having a substance use disorder to treat or reduce the severity of said substance use disorder. In some embodiments, a disclosed therapeutic combination or composition thereof for treating a substance use disorder comprises a hallucinogen and an entactogen. In some embodiments, a disclosed therapeutic combination or composition thereof for treating a substance use disorder comprises a hallucinogen and a non-racemic entactogen, e.g., non-racemic MDMA, wherein R-MDMA is present in enantiomeric excess.

In some embodiments, a therapeutic combination comprising a hallucinogen and non-racemic MDMA, wherein R-MDMA is present in an enantiomeric excess of 10%-95%, 20%-95%, 30%-95%, 40%-95%, 50%-95%, 55%-95%, 60%-90%, 65%-90%, or 75%-85% of R-MDMA is administered to a subject in need thereof to treat a substance use disorder. In some embodiments, a therapeutic combination comprising a hallucinogen and non-racemic MDMA, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95% is administered to a subject in need thereof to treat a substance use disorder. In some embodiments, a therapeutic combination comprising a hallucinogen and about 6:1, 7:1, 8:1, 9:1, 10:1, 11:1, or 12:1 R:S MDMA is administered to a subject in need thereof to treat a substance use disorder.

Broadly, but without being bound by theory, substance use disorders are mediated by the dopamine system (Diana, Front Psychiatry, 2011; 2:64). Additionally, the noradrenergic system has been found to contribute to addiction, including reward and drug seeking behavior (Foster & Weinshenker, Neural Mechanisms of Addiction, 2019; 221-236). In some embodiments, therapeutic combinations or pharmaceutical compositions thereof are used to treat substance use disorders. In some examples, substance use disorders are characterized by excessive use of nicotine, alcohol, and narcotics including prescription drugs and drugs of abuse. Such use may lead to one or more of social, academic, and occupational impairment. Commonly abused substances include, e.g., alcohol, tobacco (nicotine), cannabis, sedatives, hypnotics, anxiolytics, inhalants, opiates, opioids, and stimulants (Jahan & Burgess, "Substance Use Disorder," Treasure Island (FL): StatPearls Publishing; 2022).

i. Alcohol Use Disorder

In some embodiments, the disclosed therapeutic combinations and compositions thereof are used to treat or reduce the severity of alcohol use disorder (AUD). AUD may refer to the disorder as defined in the Diagnostic and Statistical Manual of Mental Disorders, for example, the DSM-5. The severity of AUD, mild, moderate, or severe, is based on the number of criteria met. In some embodiments, a disclosed therapeutic combination or composition thereof for treating alcohol use disorder comprises a hallucinogen and an entactogen. In some embodiments, a disclosed therapeutic combination or composition thereof for treating alcohol use disorder comprises a hallucinogen and a non-racemic entactogen, e.g., non-racemic MDMA, wherein R-MDMA is present in enantiomeric excess, such as 9:1 R:S-MDMA.

In some embodiments, the disclosed therapeutic combinations and compositions thereof are used to treat alcohol abuse, alcohol dependence, or alcohol use in a subject who has not yet had a formal clinical diagnosis. See, e.g., "Alcohol Dependence Syndrome," see Edwards, Brit. J. Addiction, 81:171-183. In some embodiments, administration of the provided combinations and compositions thereof to a subject, results in a reduction of subject's alcohol use. Reducing alcohol use, or reduction of alcohol use, refers to reducing the amount or frequency of alcohol use, for example as assessed by urinalysis e.g., by measuring metabolites of alcohol in urine, such as Ethyl Glucuronide (EtG) or as assessed by using self reported alcohol use with standardized tools like the Timeline Follow Back self report. See, e.g., Robinson et al., Psychol Addict Behav., 2014; 28(1):154-62; Sobell et al., Drug Alcohol Depend., 1996; 42(1):49-5.

ii. Opiate Use Disorder

In some embodiments, the disclosed therapeutic combinations and compositions thereof are used to treat opioid use disorder (OUD). Herein, "opioid use disorder" may refer to "opiate use disorder," and the two are used interchangeably. In some embodiments, a disclosed therapeutic combination or composition thereof for treating OUD comprises a hallucinogen and an entactogen. In some embodiments, a disclosed therapeutic combination or composition thereof for treating OUD comprises a hallucinogen and a non-racemic entactogen, e.g., non-racemic MDMA, wherein R-MDMA is present in enantiomeric excess, such as 9:1 R:S-MDMA.

Receptors of the opioid system, mu, kappa, delta, and opioid receptor like-1 (ORL1) are G-protein coupled receptors that activate inhibitory G-proteins (Al-Hasani & Bruchas, Anesthesiology, 2011; 115(6):1363-1381). Opioids activate the mesolimbic reward system, which promotes signaling in the ventral tegmental area and results in dopamine release (Kosted & George, Sci Pract Perspect., 2002; 1(1):13-20). Representative examples of opioids include codeine, heroin, hydrocodone, hydromorphone, methadone, meperidine, morphine, and oxycodone. It will be appreciated that "opiates" may be included among "opioids" for purposes of the inventions herein.

Opioid use disorder (OUD) is characterized by an overwhelming desire to use opioids, the development of tolerance to opioids, and withdrawal syndrome once opioids are discontinued. Criteria for opioid use disorder are available to one of skill. In one example, the DSM-5 describes criteria, for example: Opioids are often taken in larger amounts or over a longer period of time than intended; Tolerance, as defined by either of the following: (a) a need for markedly increased amounts of opioids to achieve intoxication or desired effect or (b) markedly diminished effect with continued use of the same amount of an opioid; Withdrawal, as manifested by either of the following: (a) the characteristic opioid withdrawal syndrome or (b) the same (or a closely related) substance is taken to relieve or avoid withdrawal symptoms. In some embodiments, therapeutic compounds alleviate or reduce the signs or symptoms of opioid use disorder. In some embodiments, a therapeutic compound may be used as an adjunct to clinical opioid therapy.

Treatments for OUD include opioid receptor agonists, for example, methadone and buprenorphine, and opioid receptor antagonists, for example, naltrexone (Kampman et al., J. Addict. Med., 2015; 9(5):358-367). However, such treatments are associated with limited success in preventing relapse and, in some cases, carry abuse liability themselves. The dopamine system has been implicated in opioid reward (Fields & Margolis, Trends Neurosci., 2015; 38(4):217-225; Steidl et al., Neurosci. Biobehav. Rev., 2017; 83:72-82). D3 antagonists may be useful to treat opioid addiction and to potentiate the effects of prescribed opiates (Galaj et al., Neurosci. Biobehav. Rev., 2020; 114: 38-52). The effects of the provided enantiomeric mixtures on opioid-seeking behavior may be evaluated according to methods available to one of skill, including self-administration models, e.g., the IV self-administration reinstatement rodent model described by Fattore et al., Methods Mol Biol. 2021; 2201: 231-245.

iii. Nicotine Dependence and Tobacco Use Disorder

In some embodiments, the disclosed therapeutic combinations and compositions thereof are used to treat nicotine dependence or tobacco use disorder. In some embodiments, a disclosed therapeutic combination or composition thereof for treating nicotine dependence or tobacco use disorder comprises a hallucinogen and an entactogen. In some embodiments, a disclosed therapeutic combination or composition thereof for treating nicotine dependence or tobacco use disorder comprises a hallucinogen and a non-racemic entactogen, e.g., non-racemic MDMA, wherein R-MDMA is present in enantiomeric excess, such as 9:1 R:S-MDMA.

Nicotine addiction is mediated by activation of neuronal nicotinic acetylcholine receptors in the dopamine pathway, and nicotine exposure results in release of dopamine and an increase in extracellular dopamine levels (Laviolette & van der Kooy, Nat. Rev. Neurosci., 2004; 5(1):55-65; Nisell et al., Synapse, 1994; 16(1):36-44; Pierce & Kumaseran, Neurosci. Biobehav. Rev., 2006; 30(2):215-38). Tobacco is a common vehicle for nicotine and so nicotine dependence may be referred to as tobacco use disorder.

Criteria for nicotine dependence or tobacco use disorder are available to one of skill. See, e.g., Baker et al., Addiction, 2012; 107(2):263-275. In one example, the DSM-5 describes tobacco use disorder and criteria for the same, for example: Unsuccessful efforts to quit or reduce intake of tobacco; Inordinate amount of time acquiring or using tobacco products; Cravings for tobacco. In embodiments, therapeutic compounds alleviate or reduce the signs or symptoms of nicotine dependence or tobacco use disorder. A combinations effects on nicotine seeking behavior may be evaluated according to methods available to one of skill, including self-administration, place conditioning, and intracranial self-stimulation paradigms in rodents (O'Dell & Khroyan, Pharmacol Biochem Behav., 2009; 91(4): 481-488).

iv. Sedative, Hypnotic, and Anxiolytic Use Disorder

In some embodiments, the disclosed therapeutic combinations and compositions thereof are used to treat sedative, hypnotic, and anxiolytic use disorder. In some embodiments, a disclosed therapeutic combination or composition thereof for treating sedative, hypnotic, and anxiolytic use disorder comprises a hallucinogen and an entactogen. In some embodiments, a disclosed therapeutic combination or composition thereof for treating sedative, hypnotic, and anxiolytic use disorder comprises a hallucinogen and a non-racemic entactogen, e.g., non-racemic MDMA, wherein R-MDMA is present in enantiomeric excess, such as 9:1 R:S-MDMA.

Sedatives, hypnotics, and anxiolytics can cause CNS depression, which may be fatal. Exemplary CNS depressants include benzodiazepines, such as alprazolam, clonazepam, lorazepam, diazepam, chlordiazepoxide, and barbiturates, such as phenobarbital, pentobarbital, butabarbital. Other classes of drugs have properties that share a similar mechanism of action with benzodiazepine and barbiturates, including alcohol. These agents mediate gamma-aminobutyric acid (GABA) effects, producing inhibitory effects within the central nervous system.

Criteria for sedative, hypnotic, and anxiolytic use disorder are available to one of skill. In one example, the DSM-5 describes sedative, hypnotic, and anxiolytic use disorder and criteria for the same, for example: Sedatives, hypnotics, or anxiolytics are often taken in larger amounts or over a longer period than was intended; There is a persistent desire or unsuccessful efforts to cut down or control sedative, hypnotic, or anxiolytic use; A great deal of time is spent in activities necessary to obtain the sedative, hypnotic, or anxiolytic; use the sedative, hypnotic, or anxiolytic; or recover from its effects. In some embodiments, therapeutic combinations and compositions thereof alleviate or reduce the signs or symptoms of sedative, hypnotic, and anxiolytic use disorder.

v. Stimulant Use Disorder

In some embodiments, the disclosed therapeutic combinations and compositions thereof are used to treat stimulant use disorder. In some embodiments, a disclosed therapeutic combination or composition thereof for treating stimulant use disorder comprises a hallucinogen and an entactogen. In some embodiments, a disclosed therapeutic combination or composition thereof for treating stimulant use disorder comprises a hallucinogen and a non-racemic entactogen, e.g., non-racemic MDMA, wherein R-MDMA is present in enantiomeric excess, such as 9:1 R:S-MDMA.

Stimulants increase synaptic levels of the monoamines dopamine, serotonin, and norepinephrine. Both the dopaminergic and the noradrenergic systems play critical roles in the effects of stimulants, including reward (Sofuoglu & Sewell, Addict Biol., 2009; 14(2): 119-129; Wise, Brain Res., 1978; 152(2):215-47). Non-limiting examples of stimulants include amphetamines, methamphetamine, and cocaine. Nicotine/tobacco may also be considered a stimulant. In some embodiments, the provided combinations and compositions thereof are used to treat cocaine use disorder. In some embodiments, the provided combinations and compositions thereof are used to treat methamphetamine use disorder.

Criteria for stimulant use disorder are available to one of skill. For example, exemplary DSM-5 criteria include: The stimulant is often taken in larger amounts or over a longer period than was intended; There is a persistent desire or unsuccessful efforts to cut down or control stimulant use; A great deal of time is spent in activities necessary to obtain the stimulant, use the stimulant, or recover from its effects. In some embodiments, therapeutic combinations and compositions thereof alleviate or reduce the signs or symptoms of stimulant use disorder.

Treatment options for stimulant use disorder include contingency management, CBT, acupuncture, antidepressants, dopamine agonists, antipsychotics, anticonvulsants, disulfiram, opioid agonists, N-Acetylcysteine, and psychostimulants (Ronsley et al., PLoS One, 2020; 15(6): e0234809). Psychostimulants, for example, bupropion and dexamphetamine, appear to be promising treatment options. In contrast, dopamine modulators, including agonists and antagonists appear to lack efficacy in stimulant use disorders, such as cocaine use disorder (Cochrane Database Syst Rev. 2015 May; 2015(5): CD003352; Id. Rev. 2016 March; 2016(3): CD006306). The effects of a therapeutic combination or a composition thereof on stimulant addiction may be assessed using methods available to one of skill, including self-administration models, e.g., the hold down procedures described by Zimmer & Roberts, Psychiatric Disorders, 2011; 279-290.

e. Co-Administration with an Oxytocin Agent

In some embodiments, the therapeutic combinations are co-administered with an oxytocin agent. In some embodiments, the oxytocin agent is an oxytocin agonist and/or an oxytocin releasing agent (ORA). In some embodiments, an ORA is co-administered with a hallucinogen and an entactogen to a subject. In some embodiments, an ORA is co-administered with a hallucinogen and a non-racemic entactogen to a subject.

In some embodiments, the oxytocin agonist is an oxytocin-releasing agent (ORA), such as a melanocortin (MC) receptor agonist, a melanocyte stimulating hormone (MSH), α-melanocortin, α-melanotropin, melanotan II (MT-11), bremelanotide, a 5-$HT_{1A}$ agonist, a 5-$HT_{2A}$ agonist, a 5-$HT_{2C}$ agonist, 6-(2-Aminopropyl)-2,3-dihydrobenzofuran (6-APDB), 6-(2-aminopropyl)benzofuran (6-APB), (4-fluoro-N-(2-{4-[(2S)-2-(hydroxymethyl)-2,3-dihydro-1,4-benzodioxin-5-yl]piperazin-1-yl}ethyl)benzamide (flesinoxan), 5-(3-[((2S)-1,4-benzodioxan-2-ylmethyl)amino]propoxy)-1,3-benzodioxole, (osemozotan), buspirone, gepirone, befiradol, eptapirone, 8-OH-DPAT, tandospirone, serotonin, ergine, ergotamine, lysergic acid, lysergic acid diethylamide (LSD), psilocybin, 4-hydroxy-dimethyltryptamine (psilocin), N,N-dimethyltryptamine (DMT), 5-methoxy-dimethyltryptamine (5-MeO-DMT), mescaline, an entactogen, 4-bromo-2,5-dimethoxyphenethylamine (2C-B), 3,4-methylenedioxyamphetamine (MDA), methylenedioxyethylamphetamine (MDEA), 3-methoxy-4,5-methylenedioxyamphetamine (MMDA), racemic 3,4-methylenedioxymethamphetamine (MDMA), tenamfetamine, or lorcaserin, and including their analogs, derivatives, and enantiomers, where applicable, and the prodrugs and salts thereof.

f. Administration in Conjunction with Psychotherapy

In some embodiments, the therapeutic combinations are administered in conjunction with psychotherapy. In some embodiments, the therapeutic combinations are for use in psychedelic-assisted psychotherapy. In some embodiments, a hallucinogen and an entactogen are administered in conjunction with psychotherapy to a subject in need thereof. In some embodiments, a hallucinogen and a non-racemic entactogen, e.g., non-racemic MDMA, wherein R-MDMA is present in enantiomeric excess, such as 9:1 R:S-MDMA, are administered in conjunction with psychotherapy to a subject in need thereof.

"Psychedelic-assisted psychotherapy" will be readily understood in the art, and appreciated to refer, broadly, to a range of related approaches that involve at least one session where the subject ingests a composition (in the prior art, a psychedelic; in the methods of the invention, a composition of the invention comprising a hallucinogenic agent and an entactogenic agent, as disclosed and claimed herein) and is monitored, supported, and/or otherwise engaged by one or more trained mental health professionals while under the effects of the composition. See, e.g., Schenberg, Front. Pharmacol., 2018; 9:733; Johnson, J. Psychopharmacol., 2008; 22, 603-620; Mithoefer et al., MAPS Treatment Manual, 2015.

In some embodiments, administration of a provided therapeutic combination or composition thereof, e.g., comprising a hallucinogen and an entactogen, is preceded by one or more preparatory sessions. In some embodiments, administration of a provided therapeutic combination or composition thereof, e.g., comprising a hallucinogen and an entactogen, is followed by one or more integration sessions. In some embodiments, the entactogen is a non-racemic mixture of R-MDMA and S-MDMA, wherein R-MDMA is present in enantiomeric excess, such as 9:1 R:S-MDMA.

Preparatory sessions may focus on any of educating a subject on what to expect following administration of the disclosed combinations, building rapport with a therapist, setting an intention for the experience, and familiarizing with set and setting. In some examples, integration sessions focus on translating gained insights into meaningful and lasting change. See, e.g., Pilecki et al., Harm Reduct J. 2021; 18: 40; Bogenschutz & Forcehimes, J Humanist Psychol. 2017; 57:389-414.

D. Improved Physiological and Psychological Effects

In some embodiments, administering disclosed combinations and compositions thereof to a subject produces at least one improved physiological or psychological effect compared to either the agents of the combination alone or compared to those agents when given in a comparator composition. In some embodiments, administering a disclosed combination comprising a hallucinogen and an entactogen, and compositions thereof, to a subject produces at least one improved physiological or psychological effect compared to either the hallucinogen or the entactogen alone or a comparator comprising the hallucinogen and the entactogen. In some embodiments, administering a combination of a hallucinogen and non-racemic MDMA to a subject produces at least one improved physiological or psychological effect relative to administration of any one of i) the hallucinogen alone, ii) non-racemic MDMA alone, or iii) the hallucinogen and racemic MDMA.

Improvements in "physiological or psychological effect" include any one or more of, and alone or in combination: (1) a reduction in nausea and vomiting; (2) an improved pharmacokinetic profile; (3) a reduction in subjective body load during the therapeutic window; (4) an improvement in the subjective valence of the experience; (5) an improvement in feelings of positive affect; (6) an increase in the therapeutic window; (7) an improvement in behavioral integration; (8) a reduction of anxiety; (9) a reduction in addictive liability or abuse potential; (10) a reduction in neurotoxicity; (11) a reduction in hyperthermia or hypothermia; (12) and a reduction in stimulation.

In some embodiments, the hallucinogen and non-racemic MDMA are administered simultaneously. In some embodiments, the hallucinogen and non-racemic MDMA are administered sequentially. In some embodiments, the hallucinogen is administered prior to administering non-racemic MDMA. In some embodiments, the hallucinogen is administered after administering non-racemic MDMA. In some embodiments, the dose of the hallucinogen and the dose of non-racemic MDMA are separated by about 0.25 to 6 hours, 0.5 to 5.5 hours, 1 to 5 hours, 1.5 to 4.5 hours, 2 to 4 hours, or 2.5 to 3.5 hours.

In some embodiments, administering the hallucinogen and non-racemic MDMA simultaneously to a subject produces at least one improved physiological or psychological effect relative to administration of any one of i) the hallucinogen alone, ii) non-racemic MDMA alone, or iii) the hallucinogen and racemic MDMA. In some embodiments, administering the hallucinogen and non-racemic MDMA sequentially to a subject produces at least one improved physiological or psychological effect relative to administration of any one of i) the hallucinogen alone, ii) non-racemic MDMA alone, or iii) the hallucinogen and racemic MDMA. In some embodiments, administering the hallucinogen to a subject prior to administering non-racemic MDMA produces at least one improved physiological or psychological effect relative to administration of any one of i) the hallucinogen alone, ii) non-racemic MDMA alone, or iii) the hallucinogen and racemic MDMA. In some embodiments, administering the hallucinogen to a subject after administering non-racemic MDMA produces at least one improved physiological or psychological effect relative to administration of any one of i) the hallucinogen alone, ii) non-racemic MDMA alone, or iii) the hallucinogen and racemic MDMA. In some embodiments, the dose of the hallucinogen and the dose of non-racemic MDMA are separated by about 0.25 to 6 hours, 0.5 to 5.5 hours, 1 to 5 hours, 1.5 to 4.5 hours, 2 to 4 hours, or 2.5 to 3.5 hours.

Co-administration of an entactogen, such as MDMA, and either a hallucinogen or a dissociative is colloquially referred to as "flipping." Non-limiting examples of "flips" include "kitty flipping," which refers to co-administration of ketamine and MDMA, "*nexus* flipping," which refers to co-administration of MDMA and the hallucinogenic agent 2C-B, "candy flipping," which refers to co-administration of LSD and MDMA, "hippie flipping," which refers to co-administration of psilocybin mushrooms with MDMA, and "jedi flipping," which refers to co-administration of LSD, psilocybin mushrooms, and MDMA.

Although recommendations on dosing vary, the general consensus is that the hallucinogen, such as LSD and psilocybin, should be dosed prior to MDMA. The rationale for this dosing order is rooted in the unpleasant effects that many experience as MDMA wears off (the "comedown"). Such effects, which include, e.g., headaches, nausea, jaw clenching, and anxiety, may be potentiated by the overlapping hallucinogen experience, thereby emphasizing negative aspects of the drug combination. In some cases, negative effects carry over to the next day (the "hangover"). See, e.g., Janiakin, "'Candy Flip' Explainer: What Happens When You Mix Acid and Molly?," Double Blind, Updated Jul. 22, 2021, Accessed Jul. 3, 2022; Elyse, "Hippie Flipping: What to Know About Mixing MDMA and Mushrooms," Double Blind, Updated Oct. 27, 2021, Accessed Jul. 3, 2022. One advantage of a disclosed combination, which comprises a hallucinogenic agent and non-racemic MDMA, wherein R-MDMA is present in enantiomeric excess, such as 9:1 R:S-MDMA, is avoidance of such negative effects regardless of the dosing regimen, due to its reduced activity at DAT and NET, which lessen the potential for neurotoxicity and abuse relative to racemic MDMA.

Co-administration of LSD and racemic MDMA has neurotoxic implications (Schechter, Eur J Pharmacol. 1998; 341(2-3):131-4). Alone, IDMA has been shown to manifest selective serotonergic neurotoxicity (Monks T J, et al. Serotonergic neurotoxicity of methylenedioxyamphetamine and methylenedioxymethamphetamine. Adv Exp Med Biol. 2001; 500:397-406). In a primate study, MDMA treatment resulted in profound reductions in all three serotonergic presynaptic markers, leading to permanent serotonergic deficits in almost all brain regions examined (Ricaurte, et al., J Pharnacol Exp Ther. 1992 May; 261(2):616-22). Both LSD and MDMA stimulate central serotonin, so a synergistic effect of co-administration is likely (Mohamed et al., Pharmacol Biochem Behav. 2011; 99(4):759-74). When LSD was administered concurrently with MDMA, a dramatic dose release increase in neurotoxicity was observed, as confirmed by a decrease in serotonin transporters (SERT) in the hippocaampus. This result corroborates results from a previous study showing that LSD potentiates the neurotoxicity of MDMA (Armstrong, et al., Neuroscience Research Communications, 2004; 35: 83-95).

In some embodiments, administering a hallucinogen and non-racemic MDMA, wherein R-MDMA is present in enantiomeric excess, such as 9:1 R:S-MDMA, to a subject produces improved "physiological or psychological effect(s)," including any one or more of, and alone or in combination: (1) a reduction in nausea and vomiting; (2) an improved pharmacokinetic profile; (3) a reduction in subjective body load during the therapeutic window; (4) an improvement in the subjective valence of the experience; (5) an improvement in feelings of positive affect; (6) an increase in the therapeutic window; (7) an improvement in behavioral integration; (8) a reduction of anxiety; (9) a reduction in addictive liability or abuse potential; (10) a reduction in neurotoxicity; (11) a reduction in hyperthermia or hypothermia; (12) and a reduction in stimulation.

A "reduction" (here and elsewhere, e.g., for other effects described herein) will be understood to mean a decrease in "incidence" which refers to a decrease in a specified quantity of events or a decrease in a risk measure associated with a condition occurring within a specified period of time (e.g., #/hour), or a decrease in "incidence rate" which refers to the total number of incidence events divided by the duration of the observation interval in which the incidence events occurred, expressed as a rate (e.g., %/hour).

An "increase" (here and elsewhere, e.g., for other effects described herein) may be understood to mean an increase in "incidence," as defined herein. Increase may also be understood to mean an increase in magnitude. In one example, increases may be understood to mean higher scores, as it relates to a subject-reported questionnaire relating to subjective experiences, e.g., the Hallucinogen Rating Scale (HRS) or the 5D-ASC and subscales thereof.

An "improvement" may encompass increases in some features, such as desirable features, and/or decreases in others, such as undesirable, negative features. In one example, an improvement in subject valence experience may be characterized by decreased anxiety and increased positive affect.

In some embodiments, administering a hallucinogen and non-racemic MDMA comprising R-MDMA in enantiomeric excess of 90% or less to a subject produces one or more improved physiological or psychological effect(s). In some embodiments, administering a hallucinogen and non-racemic MDMA comprising R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% to a subject produces one or more improved physiological or psychological effect(s). In some embodiments, administering a hallucinogen and non-racemic MDMA comprising R-MDMA in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive, to a subject produces one or more improved physiological or psychological effect(s). In some embodiments, administering a hallucinogen and non-racemic MDMA comprising R-MDMA in enantiomeric excess of about 10%, 15%, 20%, 25%, 30%, 35%, 40%, 45%, 50%, 55%, 60%, 65%, 70%, 75%, 80%, 85%, 90%, or 95% to a subject produces one or more improved physiological or psychological effect(s). In some embodiments, administering a hallucinogen and non-racemic MDMA comprising R-MDMA in enantiomeric excess of about 75%, 76%, 77%, 78%, 79%, 80%, 81%, 82%, 83%, 84%, or 85% to a subject produces one or more improved physiological or psychological effect(s). In some embodiments, administering a hallucinogen and non-racemic MDMA comprising R-MDMA in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1% to a subject produces one or more improved physiological or psychological effect(s). In some embodiments, administering a hallucinogen and non-racemic MDMA comprising R-MDMA in enantiomeric excess of about 79.5%, 79.6%, 79.7%, 79.8%, 79.9%, 80%, 80.1%, 80.2%, 80.3%, 80.4%, or 80.5% to a subject produces one or more improved physiological or psychological effect(s). In some embodiments, administering a hallucinogen and non-racemic MDMA comprising R-MDMA and S-MDMA in a ratio of about 6:1 to 12:1, 7:1 to 11:1, or 8:1 to 10:1 to a subject produces one or more improved physiological or psychological effect(s). In some embodiments, administering a hallucinogen and non-racemic MDMA comprising R-MDMA and S-MDMA in a ratio of about 6:1, 7:1, 8:1, 9:1, 10:1, 11:1, or 12:1 to a subject produces one or more improved physiological or psychological effect(s). In some embodiments, administering a hallucinogen and non-racemic MDMA comprising R-MDMA and S-MDMA in a ratio of about 9:1 to a subject produces one or more improved physiological or psychological effect(s).

a. Pharmacokinetics and Pharmacodynamics

In some embodiments, a therapeutic combination provides an improved pharmacokinetic profile. In some embodiments, administering a disclosed therapeutic combination or composition thereof to a subject results in an improved pharmacokinetic profile relative to administration of a hallucinogen or an entactogen alone. In some embodiments, administering a disclosed therapeutic combination or composition thereof to a subject results in an improved or enhanced subject experience relative to administration of a hallucinogen or an entactogen alone. In some embodiments, administering a disclosed therapeutic combination or composition thereof to a subject results in improved safety relative to a hallucinogen or an entactogen alone. In some embodiments, administering a disclosed therapeutic combination or composition thereof to a subject results in improved efficacy relative to a hallucinogen or an entactogen alone. In another example, disclosed combinations and compositions comprising a hallucinogen and non-racemic MDMA, wherein R-MDMA is present in enantiomeric excess, will improve treatment efficacy compared to combinations and compositions comprising racemic MDMA. In some embodiments, administering a disclosed therapeutic combination or composition thereof produces at least a 5% improvement, at least a 10% improvement, at least a 15% improvement, at least a 25% improvement, at least a 30% improvement, at least a 50% improvement, at least a 75% improvement, at least a 90% improvement, at least a 95% improvement, or at least a 99% improvement in at least one measure of treatment efficacy relative to a comparator as described herein.

Signs of therapeutic efficacy that correspond to improvements in a treated condition, disease, or disorder are known to one of skill in the art. In some embodiments, therapeutic efficacy is assessed by determining a reduction, i.e., a percent improvement, in symptom severity. In some embodiments, an improvement in therapeutic efficacy is assessed by determining the number of diagnostic criteria that are met for a condition, disease, or disorder. In some embodiments, an improvement in therapeutic efficacy is assessed by determining one or more reductions in symptom severity by evaluating diagnostic criteria for a condition, disease, or disorder. Diagnostic criteria for mental health disorders, social anxiety disorders, neurodegenerative conditions, substance use disorders, and conditions mediated by impaired social reward learning and social cognition are available to one of skill in the art, including, e.g., reference to relevant disclosure in the DSM-5 and applicable observer and/or subject-reported questionnaires. Improvements in therapeutic efficacy may also be shown by assessing reductions in relapse rates of substance use for applicable conditions, such as substance use disorders.

Improved pharmacokinetic profile refers to the profile of receptor affinity and binding, bioavailability, potency, excretion and metabolism, metabolite profile, and other parameters related to the activity of the drug and changes to the aforementioned profile which result in an improved patient experience, improved safety, and improved efficacy. In some embodiments, an improved pharmacokinetic profile is a result of "tuning" the pharmacology of the composite therapy of the invention (i.e., the hallucinogenic agent and entactogenic agent administered in combination). In some embodiments, administering a disclosed therapeutic combination or composition thereof to a subject results in an improved PK profile relative to a hallucinogen or an entactogen alone. In another example, disclosed combinations and compositions comprising a hallucinogen and non-racemic MDMA, wherein R-MDMA is present in enantiomeric excess, will show an improved pharmacokinetic profile compared to combinations and compositions comprising racemic MDMA. In some embodiments, administering a disclosed therapeutic combination or composition thereof produces at least a 5% improvement, at least a 10% improvement, at least a 15% improvement, at least a 25% improvement, at least a 30% improvement, at least a 50% improvement, at least a 75% improvement, at least a 90% improvement, at least a 95% improvement, or at least a 99% improvement in at least one pharmacokinetic parameter relative to a comparator as described herein.

In some embodiments, disclosed combinations comprising non-racemic MDMA, wherein R-MDMA is present in enantiomeric excess, display improved pharmacokinetics. Herein, improved pharmacokinetics include, e.g., a reduced duration of action and faster clearance. In some embodiments, disclosed combinations comprising non-racemic MDMA, wherein R-MDMA is present in enantiomeric excess, display reduced duration of action relative to racemic MDMA and/or R-MDMA. In some embodiments, disclosed combinations comprising non-racemic MDMA, wherein R-MDMA is present in enantiomeric excess, display faster clearance relative to a comparator combination comprising racemic MDMA and/or R-MDMA. In embodiments, clearance is increased by at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, or at least 200% relative to racemic MDMA and/or R-MDMA. In some embodiments, clearance is determined in vitro, for example by a liver microsomes study. See, e.g., Knights et al., Curr Protoc Pharmacol., 2016; 74:7.8.1-7.8.24; Obach, Curr Opin Drug Discov Devel., 2001; 4(1):36-44; Gollamundi et al., Neurotoxicol, 1989; 10(3):455-66. In some embodiments, clearance is determined in vivo, for example, by a pharmacokinetic study. See, e.g., R de la Torre et al., Br J Clin Pharmacol., 2000; 49(2): 104-109.

In comparison to S-MDMA, the R-enantiomer has been found to display an increased AUC and a longer half-life (Fallon et al., Clin Chem., 1999; 45(7):1058-69; Fitzgerald et al., Chirality, 1990; 2(4):241-8). Regarding racemic MDMA, doses ranging from 100-125 mg reached peak plasma concentration in humans after 2-3 hours. In patients with PTSD administered this dosing regime, onset of action occurred 45-75 minutes after the initial dose and peak drug effects were reported at 2-5 hours (Mithoefer et al., J Psychopharmacol, 2013; 27(1): 28-39). For those receiving one dose, the effects lasted 4-5 hours, which was extended with the booster dose to 5-6 hours. In a prior study, subjective effects were reported after approximately 45 mins, peaking around 1.5-2 hours, and decreasing to baseline values 5-6 hours later (Harris et al., Psychopharmacology, 2002; 162, 396-405). The elimination half-life of MDMA is between 7-9 hours, with similar results for doses ranging from 50-125 mg (Mas et al., J Pharmacol Exp. Ther., 1999; 290(1):136-45). In brain imaging studies, peak subjective effects have been reported at 100 mins and have lasted approximately 4.5 hours after 100 mg MDMA in healthy volunteers (Carhart-Harris & Nutt, Journal of Psychoactive Drugs, 2013; 45(4): 322-328).

In some embodiments, disclosed combinations comprising non-racemic MDMA, wherein R-MDMA is present in enantiomeric excess, have reduced affinity for a cytochrome P450 isoform, as compared to a comparator combination comprising racemic MDMA or S-MDMA as the entactogenic agent. In some embodiments, disclosed combinations comprising non-racemic MDMA, wherein R-MDMA is present in enantiomeric excess of 10%-95%, 20%-95%, 30%-95%, 40%-95%, 50%-95%, 55%-95%, 60%-90%, 65%-90%, or 75%-85%, have reduced affinity for a cytochrome P450 isoform. In some embodiments, disclosed combinations comprising non-racemic MDMA, wherein R-MDMA is present in enantiomeric excess of 10%, 15%, 20%, 25%, 30%, 35%, 40%, 45%, 50%, 55%, 60%, 65%, 70%, 75%, 80%, 85%, 90%, or 95%, have reduced affinity for a cytochrome P450 isoform. In some embodiments, a disclosed combination comprising R-MDMA and S-MDMA in an amount of about 6:1, 7:1, 8:1, 9:1, 10:1, 11:1, or 12:1 has reduced affinity for a cytochrome P450 isoform. In some embodiments, the cytochrome P450 isoform is selected from the group consisting of CYP2C8, CYP2C9, CYP2C19, and CYP2D6.

In some embodiments, administering a disclosed combination comprising non-racemic MDMA, wherein R-MDMA is present in enantiomeric excess, to a subject results in decreased metabolism by at least one polymorphically-expressed cytochrome P450 isoform in the subject, as compared to administration of a comparator combination comprising racemic MDMA or S-MDMA as the entactogenic agent. In some embodiments, the cytochrome P450 isoform is selected from the group consisting of CYP2C8, CYP2C9, CYP2C19, and CYP2D6. Methods for measuring metabolism are known in the art, including, e.g., liver microsomal stability assays and in vitro metabolism with human cytochrome P450 enzymes. See, e.g., U.S. application Ser. No. 11/890,255.

In some embodiments, administering a disclosed combination comprising non-racemic MDMA, wherein R-MDMA is present in enantiomeric excess, to a subject results in decreased average plasma levels of at least one metabolite of MDMA per dosage unit thereof, as compared to racemic MDMA. In some embodiments, administering a disclosed combination comprising non-racemic MDMA, wherein R-MDMA is present in enantiomeric excess in an amount of about 6:1, 7:1, 8:1, 9:1, 10:1, 11:1, or 12:1 to a subject in need thereof results in decreased average plasma levels of at least one metabolite of MDMA per dosage unit thereof, as compared to administration of a comparator combination comprising racemic MDMA. In some embodiments, the metabolite is MDA. In some embodiments, the metabolite is HHMA. In some embodiments, the metabolite is HMMA.

Enantiospecific analyses have determined that the disposition of MDMA, such as the absorption, distribution, metabolism, and excretion, in humans is stereoselective. Regarding metabolism, the different pharmacokinetic properties of the MDMA enantiomers may be caused by enantioselective metabolism by CYP2C19 and CYP2D6. The S-enantiomer has a higher affinity for CYP2D6, a major CYP450 isoenzyme in the metabolism of MDMA, and CYP2C19 preferentially metabolizes S-MDMA (Pizarro et al., J Anal Toxicol., 2002; 26(3):157-65; Maurer, Ther Drug Monit., 1996; 18(4):465-70; Meyer et al., Drug Metab Dispos., 2008; 36(11):2345-54; Tucker et al., Biochem Pharmacol., 1994; 47(7):1151-6).

MDMA and its metabolites can pose safety risks associated with toxicity, such as neurotoxicity. Side effects range in severity and include but are not limited to elevation in heart rate and blood pressure, hyperthermia, and hepatic toxicity (Kalant, C M A J, 2001; 165(7), 917-928). Major metabolites of MDMA include 3,4-methylenedioxyamphetamine (MDA), 4-hydroxy-3-methoxy-methamphetamine (HMMA) and 4-hydroxy-3-methoxy-amphetamine (HMA). In some embodiments, a toxic metabolite of MDMA is MDA. MDMA is mainly metabolized in the liver, where several different enzymes play a role in its metabolism, including CYP2D6 (Tucker et al., Biochemical Pharmacol, 1994; 47(7): 1151-1156; de la Torre et al., Frontiers In Genetics, 2012; 3:235).

High interpatient variability is also implicated with MDMA use, as such enzymes may be saturated at relatively low levels of the drug. Non-linearity in MDMA pharmacokinetics has been identified, and a small increase in dose of the drug has been shown to translate into a disproportionately high increase in plasma concentration (de la Torre et al., British Journal of Clinical Pharmacology, 2000; 49(2), 104-109). Additionally, some MDMA metabolites, such as MDA, retain pharmacological activity and extend the duration of action, which can increase the likelihood of toxicity.

The catechol moieties of MDMA and certain metabolites thereof, such as MDA, are postulated to be inherently reactive. Downstream effects of such reactivity include generation of reactive oxygen species, reactive nitrogen species, and other toxic byproducts (Carvalho et al., Curr Pharm Biotechnol. 2010; 11(5):476-95). In one example, catechol metabolites induced significant toxicity in rat cardiomyocytes. The toxic effects were characterized by a loss of normal cell morphology, which was preceded by a loss of GSH homeostasis due to conjugation of GSH with N-Me-α-MeDA and α-MeDA, sustained increase of intracellular Ca2+ levels, ATP depletion, and decreases in the antioxidant enzyme activities (Carvalho et al., Chem Res Toxicol. 2004; 17(5):623-32). The results obtained in these studies provide evidence that metabolism of MDMA is required for the expression of MDMA-induced cardiotoxicity in vitro. Accordingly, the prevention or reduction of MDMA metabolism may decrease interpatient variability, decrease drug-drug interactions, decrease the necessary $C_{max}$, and increase $T_{1/2}$. Analysis of MDMA metabolites is additionally described in, e.g., Helmlin et al., J Anal Toxicol., 1996; 20(6):432-40.

Tuning the pharmacology of a composite therapy may also refer to limiting binding at receptors or sites in the brain associated with unfavorable physical or psychological effects, such as the dopamine and/or norepinephrine receptors or transporters. Tests to determine improved pharmacokinetic profile may include rodent tests to determine extent of a drug's effect on prosocial behavior (stimulation vs. adjacent lying or investigation, see Stove et al., Current Pharmaceutical Biotechnology, 2010; 11(5), 421-433) or anxiolysis (Lezak et al., Dialogues in Clinical Neuroscience, 2017; 19(2):181-191). They may also include tests to determine whether the compound(s) when administered result in activation of receptors linked in prior art to singular or combinational reductions in anxiety or improvement of mood (Brambilla et al., Mol. Psychiatry, 2003; 8, 721-737).

In one example, tuning the pharmacology of the composite therapy to improve the valence subjective state could include pairing a common hallucinogenic substance with a serotonin or oxytocin agonist, thereby increasing overall well-being of state (and therefore, also causing an improvement in the subjective valence of the experience; accordingly, one will readily appreciate that improvements in certain physiological or psychological effects may also cause or be correlated with improvements in one or more others).

i. Nausea and Vomiting

In some embodiments, a therapeutic combination provides a reduction in nausea and vomiting. In some embodiments, a therapeutic combination comprises a hallucinogenic agent and an entactogenic agent. In some embodiments, a therapeutic combination comprises a hallucinogenic agent and a non-racemic entactogenic agent, e.g., non-racemic MDMA, wherein R-MDMA is present in enantiomeric excess. In some embodiments, administering a disclosed therapeutic combination or composition thereof to a subject results in reduced nausea and vomiting relative to administration of the hallucinogen or the entactogen alone. In another example, disclosed combinations and compositions comprising a hallucinogen and non-racemic MDMA, wherein R-MDMA is present in enantiomeric excess, will reduce the severity and/or incidence of nausea or vomiting compared to combinations and compositions comprising racemic MDMA. In some embodiments, administering a disclosed therapeutic combination or composition thereof produces at least a 5% reduction, at least a 10% reduction, at least a 15% reduction, at least a 25% reduction, at least a 30% reduction, at least a 50% reduction, at least a 75% reduction, at least a 90% reduction, at least a 95% reduction, or at least a 99% reduction in at least one measure of nausea and/or vomiting relative to a comparator as described herein.

Nausea and vomiting will be understood by those of skill, by reference to the general knowledge in the art, such as described in "How to study postoperative nausea and vomiting," Acta Anaesthesiol. Scand. 2002:46:921-928. For example, "nausea" refers to a subjective sensation of an urge to vomit, in the absence of expulsive muscular movements; when severe, it is associated with increased salivary secretion, vasomotor disturbances, and sweating. "Vomiting" refers to the forcible expulsion through the mouth of the gastric contents, and results from coordinated activity of the abdominal, intercostals, laryngeal, and pharyngeal muscles. In some embodiments, a reduction in nausea and vomiting will also refer to a reduction in "retching" which refers to an unproductive effort to vomit (i.e., vomiting without the expulsion of gastric contents), or the rhythmic action of respiratory muscles preceding vomiting. In a model rodent system, a possible way of evaluating decreases in nausea and vomiting would be monitoring changes in facial expression or using predictive behavioral patterns associated with emesis (Yamamoto et al., Front. Pharmacol., 2017; 7, 534).

ii. Subjective Body Load

In some embodiments, a therapeutic combination provides a reduction in subjective body load. In some embodiments, administering a disclosed therapeutic combination or composition thereof to a subject results in reduced subjective body load relative to administration of hallucinogen or an entactogen alone. In another example, disclosed combinations and compositions comprising a hallucinogen and non-racemic MDMA, wherein R-MDMA is present in enantiomeric excess, will show a reduction in subjective body load compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in at least one measure of subjective body load relative to a comparator as described herein.

Reduction in subjective body load refers to the decrease in the subject's sensation of being placed under exceptional stress, which is a state of preliminary shock. Common symptoms include stomach ache, nausea, dizziness, feelings of being over-stimulated or "wired," shivering, feelings of excessive tension in the torso, or, in more severe cases, shortness of breath or a feeling of being suffocated. In animal models of body load, the constituent parts of body load including respiration depression, stimulation, and temperature regulation will be measured and evaluated to determine the emergent effect. Affect may be measured using any assessment known to those in the art, for example with the Visual Analog Scale (VAS). VAS is a self-report device that is used extensively to measure such complaints as pain, nausea, fatigue, and dyspnea. The VAS is a line, usually 100 mm in length, and occasionally 150 or 160 mm long with anchors at each end to indicate the extremes of the sensation under study (Gift, Nursing Research. 1989; 38(5): 286-288).

iii. Subjective Valence Experience

In some embodiments, a therapeutic combination provides an improved subjective valence experience. In some embodiments, administering a disclosed therapeutic combination or composition thereof to a subject results in improved subjective valence experience relative to administration of a hallucinogen or an entactogen alone. In another example, combinations and compositions comprising a hallucinogen and non-racemic MDMA, wherein R-MDMA is present in enantiomeric excess, will show an improvement in subjective valence experience compared to combinations and compositions comprising racemic MDMA. In some embodiments, administering a disclosed therapeutic combination or composition thereof produces at least a 5% increase, at least a 10% increase, at least a 15% increase, at least a 25% increase, at least a 30% increase, at least a 50% increase, at least a 75% increase, at least a 90% increase, at least a 95% increase, or at least a 99% increase in at least one measure of subjective valence experience relative to a comparator as described herein.

Improvement of the subjective valence of the experience refers to the increase in perceptual and physiological changes induced by a hallucinogenic or entactogenic substance which the patient or subject refers to as "positive" or "good." These include parameters such as bliss, one-ness, physical euphoria, anxiolysis, empathy, or insightfulness.

iv. Positive Affect

In some embodiments, a therapeutic combination provides an improvement in feelings of positive affect. In some embodiments, administering a disclosed therapeutic combination or composition thereof to a subject results in improved feelings of positive affect relative to administration of a hallucinogen or an entactogen alone. In another example, disclosed combinations and compositions comprising a hallucinogen and non-racemic MDMA, wherein R-MDMA is present in enantiomeric excess, will show an improvement in positive affect compared to combinations and compositions comprising racemic MDMA. In some embodiments, administering a disclosed therapeutic combination or composition thereof produces at least a 5% increase, at least a 10% increase, at least a 15% increase, at least a 25% increase, at least a 30% increase, at least a 50% increase, at least a 75% increase, at least a 90% increase, at least a 95% increase, or at least a 99% increase in positive affect relative to a comparator as described herein.

Positive affect will be understood to refer to mental feelings underlying all emotional experience generally associated with optimism, extraversion, agreeableness, and openness to experience (Isik & Üzbe, Kuram ve Uygulamada Egitim Bilimleri/Educational Sciences: Theory & Practice, 2015; 15(3):587-595). Individuals experiencing positive affect express more flexible, creative, and integrative thought patterns, and show an increased preference for broad behavioral options (Fredrickson, The American Psychologist, 2001; 56(3):218-226). Affect may be measured using any assessment known to those in the art, for example with the Positive and Negative Affect Schedule (PANAS). The PANAS consists of a series of 20 emotions, and individuals are asked to rate the extent that they have experienced them on a Likert Scale.

v. Therapeutic Window

In some embodiments, a therapeutic combination provides an extended therapeutic window. In some embodiments, administering a disclosed therapeutic combination or composition thereof to a subject results in an increased or extended therapeutic window relative to administration of a hallucinogen or an entactogen alone. In another example, disclosed combinations and compositions comprising a hallucinogen and non-racemic MDMA, wherein R-MDMA is present in enantiomeric excess, will have an extended therapeutic window compared to combinations and compositions comprising racemic MDMA. In some embodiments, administering a disclosed therapeutic combination or composition thereof produces at least a 5% increase, at least a 10% increase, at least a 15% increase, at least a 25% increase, at least a 30% increase, at least a 50% increase, at least a 75% increase, at least a 90% increase, at least a 95% increase, or at least a 99% increase in therapeutic window relative to a comparator as described herein.

Curry et al. demonstrated differences in fear conditioning elicited by enantiomeric MDMA. Specifically, R(−)-MDMA did not reduce fear behavior during the fear extinction session, but significantly reduced conditioned fear when retention of extinction was assessed the following day. In contrast, S(+)-MDMA reduced conditioned fear behavior during extinction training, but a reduction thereof was not observed the following day (Curry et al., Neuropharmacology. 2018; 128:196-206). In some embodiments, extinction of fear conditioning is used as a proxy to determine the length of the therapeutic window.

Additionally, evidence shows that developmental regulation of oxytocin-mediated synaptic plasticity (long-term depression) in the nucleus accumbens establishes a critical period for social reward learning. A critical period is a phase during which the nervous system is especially sensitive to certain environmental stimuli. A single dose of MDMA has been shown to reopen the critical period for social reward learning, leading to a metaplastic upregulation of oxytocin-dependent long-term depression. The length of the therapeutic window can be exploited by engaging in therapeutic activity during this time (Nardou, R., et al., Nature. 2019; 3(4): 116-120).

In connection with this, and emphasizing the significance of extending the therapeutic window, Dr. Gul Dolen noted that the second most important thing the study found was that "after MDMA, the critical period starts to open about six hours after the acute dose. And then it kind of peaks out at 40 hours and stays up for at least two weeks, and then by a month it comes back down. So just to kind of put that into perspective, two weeks in a mouse is probably more like two months in a human . . . . What we really ought to be saying here is that the therapeutic window here is actually for weeks, if not months after the acute psychedelic effects have worn off. We need to treat that period of time as precious and really make there be a lot of intensive focus and therapeutic activity happening during that window rather than just kind of setting them off and letting them be on their own" (Mind Foundation, Beyond the Therapeutic Alliance How MDMA and Classic Psychedelics Modify Social Learning—An Interview With Gul Dolen, Accessed Jul. 6, 2022).

In some embodiments, the therapeutic window is the amount of time during which 1) a subject experiences noticeable changes in perception and/or 2) levels of exposure are maintained at an effective dose without incurring adverse effects. An increase in the therapeutic window refers to the increase in the span of time in which the therapeutic combination is one or more of 1) pharmacokinetically active, such as detectable in a sample obtained from a subject administered said combination; 2) producing noticeable changes in perception; and 3) avoiding the occurrence of an adverse effect.

Pharmacological assays such as receptor binding studies and pharmacokinetic rate-of-excretion studies validate the improvement in half-life as well as the effective open therapeutic window. Additionally, clearance may be determined in vitro, e.g., using liver microsomes. See, e.g., Knights et al., Curr Protoc Pharmacol., 2016; 74:7.8.1-7.8.24; Obach, Curr Opin Drug Discov Devel., 2001; 4(1): 36-44; Gollamundi et al., Neurotoxicol, 1989; 10(3):455-66. In some embodiments, clearance is determined in vivo, for example, by conducting a pharmacokinetic study to determine parameters such as Cmax, Tmaax, half-life, and clearance. See, e.g., methods described in R de la Torre et al., Br J Clin Pharmacol., 2000; 49(2): 104-109.

vi. Behavioral Integration

In some embodiments, a therapeutic combination provides an improvement in behavioral integration. In some embodiments, administering a disclosed therapeutic combination or composition thereof to a subject results in improved behavioral integration relative to administration of a hallucinogen or an entactogen alone. In another example, disclosed combinations and compositions comprising a hallucinogen and non-racemic MDMA, wherein R-MDMA is present in enantiomeric excess, will show an improvement in behavioral integration compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in at least one measure of behavioral integration relative to a comparator as described herein.

In some embodiments, measures of behavioral integration, and improvements thereof, comprise one or more of increased fear extinction, reduced functional impairment, and increased prosocial behavior. Improvement in behavioral integration refers to a developmental epoch during which the nervous system is expressly sensitive to specific environmental stimuli that are required for proper circuit organization and learning. In disease states, closure of critical periods limits the ability of the brain to adapt even when optimal conditions are restored. Thus, identification of methods and strategies that reopen critical periods has been a priority for translational neuroscience. Serotonin releasing agents, such as those described herein as "entactogens" result in metaplastic upregulation of oxytocin-dependent long-term depression and have been shown to result in reopening of critical reward learning (see, e.g., Nardou et al., Nature, 2019; 569:116-120; Kirkpatrick et al., Psychoneuroendocrinology, 2014; 46:23-31).

Furthermore, the use of enriched serotoninergic transporting agents with a limited level of dopamine activity, such as R-MDMA can further improve on longer term reward learning and conditioning (Curry et al., Neuropharmacol., 2018; 128:196-206). The behavioral reinforcing effects of primarily serotonergic transporting substances can improve on the reward learning integration process in humans. Improvements in behavioral integration include overall improvements in trip valence as well as such improvements as involve the following animal model behavioral assays: fear extinction conditioning, functional impairment batteries (Verbitsky et al., Transl. Psychiatry, 2020; 10:132), or prosocial batteries such as incidence of adjacent lying or investigation (id.).

vii. Anxiety

In some embodiments, a therapeutic combination provides a reduction in anxiety. In some embodiments, administering a disclosed therapeutic combination or composition thereof to a subject results in reduced anxiety relative to administration of a hallucinogen or an entactogen alone. In another example, disclosed combinations and compositions comprising a hallucinogen and non-racemic MDMA, wherein R-MDMA is present in enantiomeric excess, will show a reduction in anxiety compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in at least one measure of anxiety relative to a comparator as described herein.

Reduction in anxiety refers to the decrease in sensations or symptoms associated with anxiety or an anxiety disorder, which will be appreciated to include: Feeling nervous, restless or tense; Feelings of panic; Having a sense of impending danger, panic or doom; Having an increased heart rate; Breathing rapidly (hyperventilation); Sweating; Tremor or trembling; Feeling weak or tired; Trouble concentrating or thinking about anything other than the present worry; Having trouble sleeping; Experiencing gastrointestinal (GI) problems; Having difficulty controlling worry; Having the urge to avoid things that trigger anxiety. Affect and anxiety may be measured using any assessment known to those in the art, for example with the General Anxiety Disorder-7 (GAD-7), the Hamilton Anxiety Scale (HAM-A) or the Anxiety Symptoms Questionnaire (ASQ) (Baker A, Simon N, Keshaviah A, et al., Gen Psychiatr. 2019; 32:e100144).

viii. Abuse Potential

In some embodiments, a therapeutic combination provides a reduction in addictive liability or abuse potential. In some embodiments, administering a disclosed therapeutic combination or composition thereof to a subject results in reduced addictive liability or abuse potential relative to administration of a hallucinogen or entactogen alone. In another example, disclosed combinations and compositions comprising a hallucinogen and non-racemic MDMA, wherein R-MDMA is present in enantiomeric excess, will show reduced addictive liability compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in at least one measurement of relative to a comparator as described herein.

"Abuse potential" will be understood to include the likelihood of any use of a composition by an individual in non-medical or non-therapeutic contexts, whether repeatedly or even sporadically, for one or more "positive" psychoactive effects. Broadly speaking, and without being bound by theory, compositions that are characterized by or that produce such psychoactive effects and are sought out by an individual, for instance because they are found to be pleasurable or desirable (such as euphoria, stimulation, sedation, mood changes, and the like) are more prone to abuse, and therefore have greater abuse potential. "Addictive liability" will be understood to include the potential of any composition for psychological or physical dependence which promotes drug-seeking behavior, and especially dependence which is characterized by compulsive engagement in the drug-seeking behavior despite one or more adverse consequences. Drug-seeking behavior and "abuse potential" may be measured using any assessment known to those in the art, for example with the Drug Liking Visual Analogue Scale (VAS) (Seifritz et al., Int J Neuropsychopharmacol. 2021; 24(30):171-180) and/or the Addiction Research Center Inventory (ARCI) (Johnson et al., Neuropharmacology. 2018; 142:143-166).

ix. Neurotoxicity

In some embodiments, a therapeutic combination, e.g., comprising a hallucinogen and non-racemic MDMA, provides no neurotoxic effects or reduced neurotoxic effects relative to a comparator. In some embodiments, administering a disclosed therapeutic combination or composition thereof to a subject results in reduced neurotoxicity relative to administration of a hallucinogen, an entactogen alone, or a comparator combination comprising the same hallucinogen and racemic MDMA. Herein, "neurotoxicity" and "neurotoxic effects" are used interchangeably and refer to adverse effects on the structure or function of the central and/or peripheral nervous system.

Reductions in neurotoxicity will be understood to include those compositions and formulations that when administered according to the methods of the invention, and whether acutely or chronically, are without measurable neurotoxic effect, or without substantial or significant neurotoxic effect, or without neurotoxic effect relative to the hallucinogen or the entactogen alone. In another example, disclosed combinations and compositions comprising a hallucinogen and non-racemic MDMA, wherein R-MDMA is present in enantiomeric excess, will show a reduction in at least one measurement of neurotoxicity compared to combinations and compositions comprising racemic MDMA.

In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in at least one measurement of neurotoxicity relative to a comparator as described herein. In some embodiments, a provided combination or composition thereof, such as comprising a hallucinogen and non-racemic MDMA, results in reduced neurotoxicity relative to a hallucinogen and racemic MDMA. In some embodiments, the reduced neurotoxicity is observed in comparison to an equal or greater dose of a hallucinogen in combination with a reduced, equal, or greater dose of MDMA. In some embodiments, reduced neurotoxicity of a disclosed combination or composition thereof is evident even when comparing a dose of a non-racemic MDMA, such as comprising R-MDMA in enantiomeric excess, that is at least 10%, at least 25%, at least 50%, at least 75%, at least 100%, at least 150%, or at least 200% greater than that of racemic MDMA, either alone or as part of a disclosed combination.

Exemplary tests and procedures for measuring neurotoxicity include in silico methods (e.g., by computer analysis or simulation and including by using AI, machine learning, or deep learning models), in vitro methods (e.g., biochemical assays, tissue culture, etc.), and in vivo methods (e.g., behavioral assessment; functional observational batteries; tests of motor activity, schedule-controlled operant behavior, neurological function, neurophysiological function, nerve-conduction, evoked-potential; neurochemical, neuroendocrine, or neuropathological measures; EEG; imaging; etc.). See, e.g., Baumann et al., Psychopharmacology. 2007; 189: 407-424; Costa et al., Front Pharmacol. 2021; 12:713486, Costa & Golembiowska, Experimental Neurology 2022; 347:113894; Kasteel & Westerink, Expert Opin Drug Metab Toxicol. 2021; 17(8):1007-1017; Pitts et al., Psychopharmacology, 2017; 235(2), 377-392; Rudin et al., Exp Neurol., 2021; 343:113778; Steinkellner et al., Biol Chem. 2011; 392(0):103-115; Taghizadeh et al., Free Radic. Biol. Med. 2016; 99: 11-19; White et al., Neurotoxicology, 2011; 32(6): 975-80.

In some embodiments, the neurotoxic effect is determined by measuring one or more of: a) at least one toxic metabolite of MDMA; b) oxidative stress and dopamine-based quinones; c) mitochondrial dysfunction; and d) activation of glial cells.

In some embodiments, neurotoxicity or a reduction thereof is determined by measuring the generation of toxic MDMA metabolites, e.g., MDA, such as from evaluating levels in blood, brain, or cerebrospinal fluid (CSF) samples. In some embodiments, neurotoxicity or a reduction thereof is determined by evaluating oxidative stress and dopamine-based quinones. In some embodiments, neurotoxicity or a reduction thereof is determined by evaluating activity and gene expression of antioxidant enzymes and/or pathways. In some embodiments, neurotoxicity or a reduction thereof is determined by measuring reactive oxygen species (ROS) production. See, e.g., Costa et al.'s assessment of superoxide dismutase and ubiquitin-proteasome system expression and activity in mouse neurons (Costa et al., Front Pharmacol. 2021; 12:713486). In humans, oxidative stress associated with administration of MDMA has been shown using blood samples. Specifically, Zhou et al., determined higher levels of erythrocyte lipoperoxide, superoxide dismutase, and catalase, and lower levels of plasma vitamin C, vitamin E, and carotene, in MDMA abusers (Zhou et al., Free Radic Res. 2003; 37(5):491-7).

In some embodiments, neurotoxicity or a reduction thereof is determined by evaluating mitochondrial dysfunction. Mitochondrial dysfunction may be evaluated by measuring one or more of mitochondrial membrane potential (MMP), mitochondrial swelling, mitochondrial outer membrane damage, the mitochondrial cytochrome c release, and ADP/ATP ratio. See, e.g., Taghizadeh et al.'s assessment of MDMA toxicity in mice, which showed markers of mitochondrial dysfunction following administration of MDMA, including significant increase in ROS formation, collapse of MMP, mitochondrial swelling, outer membrane damage, cytochrome c release from the mitochondria, and increased ADP/ATP ratio (Taghizadeh et al., Free Radic. Biol. Med. 2016; 99: 11-19).

In some embodiments, neurotoxicity or a reduction thereof is determined by assessing the activation of glial cells. Activation of quiescent glial cells by MDMA, MDA, and thioether metabolites of MDA derived from α-methyldopamine has been described, e.g., by Herndon et al., Toxicological Sciences, 2014; 138(1):130-138. Reactive astrogliosis can be measured with glial fibrillary acidic protein (GFAP) staining, and microglia reactivity can be visualized by immunostaining complement type 3 receptor (CD11b). See, e.g., Frau et al., J Neurochem. 2013; 124(1): 69-78 and Frau et al., Neurotoxicology. 2016; 56:127-138. In embodiments, neurotoxicity or a reduction thereof is determined in vitro. In embodiments, neurotoxicity or a reduction thereof is determined in vivo.

x. Disturbance of Thermoregulation

In some embodiments, a therapeutic combination provides a reduction in body temperature disturbance, such as hyperthermia or hypothermia. In some embodiments, administering a disclosed therapeutic combination or composition thereof to a subject results in reduced hyperthermia relative to administration of a hallucinogen or entactogen alone. In some embodiments, administering a disclosed therapeutic combination or composition thereof to a subject results in reduced hypothermia relative to administration of a hallucinogen or an entactogen alone. In another example, disclosed combinations and compositions comprising a hallucinogen and non-racemic MDMA, wherein R-MDMA is present in enantiomeric excess, will reduce the severity and/or incidence of temperature disturbances, such as hyperthermia and hypothermia, compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in temperature disturbance relative to a comparator as described herein. Temperature disturbance can refer to temperature fluctuations observed in hypothermia and hyperthermia, as well as the incidence of body temperature reaching a threshold for hypothermia or hyperthermia, as described herein.

Hypothermia and hyperthermia are conditions created by thermal disturbances wherein a subject's body temperature is either lower or higher than the average or "normal" body temperature for that species (e.g., about 98.6° F. for a human, or within the range of 36.5-37.5° C. (97.7-99.5° F.)) by a clinically significant amount. In humans, for example, hyperthermia is generally defined as a temperature greater than 37.5-38.3° C. (99.5-100.9° F.); hypothermia is generally defined as temperatures below 35.0° C. (95.0° F.). Body temperature may be recorded at one or more time points after administration of the compound, as will be understood by those in the art.

xi. Stimulation

In some embodiments, a therapeutic combination provides a reduction in stimulation. In some embodiments, administering a disclosed therapeutic combination or composition thereof to a subject results in reduced stimulation relative to a hallucinogen or an entactogen alone. In another example, disclosed combinations and compositions comprising a hallucinogen and non-racemic MDMA, wherein R-MDMA is present in enantiomeric excess, will reduce stimulation compared to combinations and compositions comprising racemic MDMA. In some embodiments, administering a disclosed therapeutic combination or composition thereof produces at least a 5% reduction, at least a 10% reduction, at least a 15% reduction, at least a 25% reduction at least a 30% reduction, at least a 50% reduction, at least a 75% reduction, at least a 90% reduction, at least a 95% reduction, or at least a 99% reduction in stimulation relative to a comparator as described herein.

Reduction in stimulation will be generally understood to refer to any diminishment in central nervous system (CNS) excitation upon administration of a composition of the invention, relative to a comparator (such as R-MDMA or an enantiomerically enriched MDMA (e.g., 10:1 R:S-MDMA or 9:1 R:S-MDMA) versus racemic MDMA, or a compound of the invention against a similarly comparable comparator compound). Traditional stimulants, for example, as well as some entactogens including many known in the prior art upon which this invention improves (such as racemic MDMA), indiscriminately increase activation across dopaminergic, noradrenergic, and serotonergic pathways in the brain, which can induce a multitude of undesirable effects such as anxiety, insomnia, headaches, pupil dilation, jaw clenching, dry mouth, hyperthermia, hypertension, rapid heartbeat, chest pain, palpitations, anorexia, nausea, vomiting, and abdominal pain (Luethi & Liechti, Arch. Toxicol., 2020; 94:1085-1133; Hysek et al., Clinical Pharmacology & Therapeutics, 2011; 90:246-255). Modifications to chemical structure can alter biochemical side effects, thereby ameliorating some or all of these symptoms (Oeri, J. Psychopharmacology, 2021; 35(5):512-536).

b. Subjective Effects and Therapeutic Efficacy

In some embodiments, administering a disclosed therapeutic combination or composition thereof to a subject produces an enhanced subjective experience relative to a comparator. In some embodiments, administering a disclosed therapeutic combination comprising a hallucinogen and an entactogen to a subject produces an enhanced subjective experience relative to a comparator. In some embodiments, administering a disclosed therapeutic combination comprising a hallucinogen and a non-racemic entactogen to a subject produces an enhanced subjective experience relative to a comparator. In some embodiments, administering a disclosed therapeutic combination comprising a hallucinogen and a non-racemic MDMA to a subject produces an enhanced subjective experience relative to a comparator. In some embodiments, the comparator is the hallucinogen alone, the entactogen or non-racemic entactogen alone. In some embodiments, where the combination comprises a non-racemic entactogen, such as non-racemic MDMA, the comparator can be a combination comprising the same hallucinogen and the racemic form of the entactogen, e.g., racemic MDMA. In some embodiments, the provided therapeutic combinations, compositions, and methods, which produce an enhanced subjective experience, improve therapeutic efficacy. In some embodiments, a disclosed therapeutic combination or composition thereof comprises a reduced dose of a hallucinogen. In some embodiments, a disclosed therapeutic combination or composition thereof comprises a reduced dose of a hallucinogen, such as a non-racemic entactogen.

In some embodiments, the provided therapeutic combinations, compositions, and methods synergistically enhance subjective effects and/or therapeutic efficacy. In some embodiments, a disclosed combination comprising a reduced dose of a hallucinogen produces an enhanced subjective experience relative to the subjective experience reported following administration of a greater dose of the hallucinogen alone. In some embodiments, administering a disclosed combination or composition thereof comprising an entactogen and a reduced dose of a hallucinogen produces an enhanced subjective experience relative to the subjective experience reported following administration of a greater dose of the hallucinogen alone in a comparator combination having a greater total dose of said hallucinogen and entactogen. In some embodiments, administering a disclosed combination or composition thereof comprising a non-racemic entactogen and a reduced dose of a hallucinogen produces an enhanced subjective experience relative to the subjective experience reported following administration of a greater dose of the hallucinogen alone. In some embodiments, the reduced dose of the hallucinogen is at least 5% less, at least 10% less, at least 15% less, at least 25% less, at least 30% less, at least 50% less, at least 75% less, at least 90% less, at least 95% less, or at least 99% less than the dose of the hallucinogen alone.

In some embodiments, a disclosed combination comprising a reduced dose of an entactogen produces an enhanced subjective experience relative to a comparator. In some embodiments, a disclosed combination comprising a reduced dose of a non-racemic entactogen produces an enhanced subjective experience relative to a comparator. In some embodiments, administering a disclosed combination or composition thereof comprising a hallucinogen and a reduced dose of an entactogen produces an enhanced subjective experience relative to the subjective experience reported following administration of a greater dose of the entactogen alone. In some embodiments, administering a disclosed combination or composition thereof comprising a hallucinogen and a reduced dose of a non-racemic entactogen produces an enhanced subjective experience relative to the subjective experience reported following administration of a greater dose of the non-racemic entactogen alone. In some embodiments, the reduced dose of the entactogen or the non-racemic entactogen is at least 5% less, at least 10% less, at least 15% less, at least 25% less, at least 30% less, at least 50% less, at least 75% less, at least 90% less, at least 95% less, or at least 99% less than the dose of the entactogen or non-racemic entactogen alone.

In some embodiments, a disclosed combination comprising a reduced dose of a non-racemic entactogen produces an enhanced subjective experience relative to a comparator combination comprising the racemic entactogen. In some embodiments, a disclosed combination comprising a reduced dose of a hallucinogen and a reduced dose of a non-racemic entactogen produces an enhanced subjective experience relative to a comparator combination comprising the hallucinogen and the racemic entactogen. In some embodiments, the reduced dose of the non-racemic entactogen is at least 5% less, at least 10% less, at least 15% less, at least 25% less, at least 30% less, at least 50% less, at least 75% less, at least 90% less, at least 95% less, or at least 99% less than the dose of the racemic entactogen in the comparator combination. In some embodiments, the reduced dose of the hallucinogen is at least 5% less, at least 10% less, at least 15% less, at least 25% less, at least 30% less, at least 50% less, at least 75% less, at least 90% less, at least 95% less, or at least 99% less than the dose of a hallucinogen in the comparator combination.

In some embodiments, administering a reduced dose of a hallucinogen prior to administering an entactogen produces enhanced subjective effects compared to administration of a relatively greater dose of the hallucinogen. In some embodiments, administering a reduced dose of a hallucinogen after administering an entactogen produces enhanced subjective effects compared to administration of a relatively greater dose of the hallucinogen. In some embodiments, the provided therapeutic combinations, compositions, and methods, which produce an enhanced subjective experience at a reduced dose, improve therapeutic efficacy.

In some embodiments, administering a reduced dose of an entactogen, such as non-racemic MDMA, prior to administering a hallucinogen produces enhanced subjective effects compared to administration of a relatively greater dose of the entactogen. In some embodiments, administering a reduced dose of an entactogen, such as non-racemic MDMA, after administering a hallucinogen produces enhanced subjective effects compared to administration of a relatively greater dose of the entactogen. In some embodiments, administering non-racemic MDMA, such as 9:1

R:S-MDMA, produces enhanced subjective effects and/or therapeutic efficacy relative to a higher dose of racemic MDMA.

Enhanced subjective effects may be determined according to various methods known to one of skill in the art. Such methods include, e.g., observer-report and subject reported questionnaires and brain imaging, such as fMRI and EEG. See, e.g., the task-free functional MRI (fMRI) protocol described by Carhart-Harris et al., Proc Natl Acad Sci USA. 2012; 109(6): 2138-2143. In some embodiments, a subject's subjective experience is measured using the altered states of consciousness (ASC) questionnaire, such as the 5 Dimensions of Altered States of Consciousness (5D-ASC). See, e.g., Dittrich, Pharmacopsychiatry, 1998; 31: 80-84 and Studerus et al., PLoS One. 2010; 5(8): e12412. Oceanic Boundlessness (OBN) and Dread of Ego Dissolution (DED) are dimensions of the ASC.

In some embodiments, a subject's subjective experience, such as an enhanced subjective experience, is determined using the Hallucinogen Rating Scale (HRS). The HRS is used to evaluate the subjective effects elicited by psychoactive drugs with hallucinogenic properties. Dimensions of the HRS include somaesthesia, affect, perception, cognition, volition, and intensity. Higher scores indicate experiences of greater magnitude or intensity. See, e.g, Riba et al., Drug Alcohol Depend. 2001; 62(3):215-23 and Mwesiga, (2020), "Hallucinogen rating scale", Mendeley.

In some embodiments, a subject's subjective experience, such as an enhanced subjective experience, is determined using the Oceanic Boundlessness scale. The OBN scale comprises items measuring positively experienced depersonalization and derealization, deeply-felt positive mood, and experiences of unity. High scores on the OBN scale therefore indicate an experience of greater magnitude, a state similar to mystical experiences as described in the scientific literature on the psychology of religion (Studerus et al., PLoS One. 2010; 5(8): e12412).

In some embodiments, a subject's subjective experience, such as an enhanced subjective experience, is determined using the Mystical Experience Questionnaire (MEQ), e.g., the MEQ30 and the MEQ43. Iterations of the MEQ have been used to evaluate the occurrence and character of individual, discrete mystical experiences. Such experiences are characterized by an experience of profound unity with all that exists, a felt sense of sacredness, a sense of the experience of truth and reality at a fundamental level (noetic quality), deeply felt positive mood, transcendence of time and space, and difficulty explaining the experience in words (ineffability). See, e.g., Stace. Mysticism and Philosophy. New York: MacMillan Press; 1960 and Barrett et al., J Psychopharmacol. 2015; 29(11): 1182-1190. The four factors of the MEQ30 are mystical, which includes items from the internal unity, external unity, noetic quality, and sacredness scales of the MEQ43, positive mood, transcendence of time and space, and ineffability. MEQ scores are summed to determine the magnitude of a mystical experience, and a score ≥60% of the maximum possible score on each of the four subscales of the MEQ30 may be considered a "complete mystical experience" (Barrett et al., J Psychopharmacol. 2015; 29(11): 1182-1190).

In some embodiments, a subject's subjective experience, such as an enhanced subjective experience, is determined using the Dread of Ego Dissolution (DED) scale, which may also be referred to as the Anxious Ego Dissolution (AED) scale. The AED includes items measuring negatively experienced derealization and depersonalization, cognitive disturbances, catatonic symptoms, paranoia, and loss of thought and body control. High scores on the AED scale therefore indicate a very unpleasant state similar to so-called "bad trips" described by drug-users.

In some embodiments, the methods may be conducted before or after drug administration. In one example, the ASC may be provided to a subject at one or more points following drug administration for retrospective input. Methods for determining whether a subjective experience is enhanced in comparison to another will be known to one of skill in the art. For example, a feature of an enhanced experience can include a score of greater magnitude on a questionnaire designed to probe unity, spiritual experience, blissful state, insightfulness, and disembodiment, such as the OBN, and/or a score of lesser magnitude on a questionnaire designed to probe effects like impaired control or cognition, and anxiety, such as the AED scale.

In some embodiments, therapeutic efficacy, and improvements or enhancements thereof may be compared to baseline levels at 1 month, 2 months, 3 months, 4 months, 5 months, 6 months, 7 months, 8 months, 9 months, 10 months, 11 months, 12 months, or greater than 12 months post-administration of a disclosed therapeutic combination or composition. In some embodiments, therapeutic efficacy, and improvements or enhancements thereof may be compared to baseline levels at 1-week, 2-weeks, 3-weeks, 4-weeks, 5-weeks, 6-weeks, 7-weeks, 8-weeks, 9-weeks, 10-weeks, 11-weeks, 12-weeks, 13-weeks, 14-weeks, or 15-weeks post-administration of a disclosed therapeutic combination or composition.

In some embodiments, a subject having a mental health disorder experiences enhanced therapeutic efficacy following administration of a disclosed combination or composition thereof. In some embodiments, a subject having a neurodegenerative condition experiences enhanced therapeutic efficacy following administration of a disclosed combination or composition thereof. In some embodiments, a subject having a mental health disorder experiences enhanced therapeutic efficacy following administration of a disclosed combination or composition thereof. In some embodiments, a subject having social anxiety experiences enhanced therapeutic efficacy following administration of a disclosed combination or composition thereof. In some embodiments, a subject having autism experiences enhanced therapeutic efficacy following administration of a disclosed combination or composition thereof. In some embodiments, a subject having a substance use disorder experiences enhanced therapeutic efficacy following administration of a disclosed combination or composition thereof.

Signs of therapeutic efficacy that correspond to the conditions, diseases, and disorders are known to one of skill in the art. Non-limiting examples of such measures of therapeutic efficacy follow. Regarding mental health disorders, such as depression, a reduction in depressive symptoms, as determined using the Quick Inventory of Depressive Symptoms (QIDS SR) may be used to assess the therapeutic efficacy of administering a disclosed combination or composition thereof to a subject to treat depression. In another mental health example, a reduction in anxiety, as determined using the Generalized Anxiety Disorder scale, e.g., the GAD-7, may be used to assess the therapeutic efficacy of administering a disclosed combination or composition thereof to a subject to treat anxiety. With respect to PTSD, a reduction in symptoms thereof, as determined using Clinician-Administered PTSD Scale for DSM-5 (CAPS-5), may be used to assess therapeutic efficacy of administering a disclosed combination or composition thereof to a subject to treat depression. Regarding social anxiety, reductions in symptoms thereof, as determined using the Liebowitz Social Anxiety Scale (LSAS), may be used to assess therapeutic efficacy of administering a disclosed combination or composition thereof to a subject to treat social anxiety. In the case of autism, reductions of symptoms thereof, as determined using the Autism Diagnostic Interview-Revised (ADI-R), may be used to assess therapeutic efficacy of administering a disclosed combination or composition thereof to a subject to treat autism. In the example of substance abuse disorders, reductions in cravings and substance use, as determined using applicable measures and criteria, such as the Alcohol Dependence Scale (ADS) for alcoholism and the DSM-5 OUD for opiate use disorder. In any case, increases in quality of life, including any of social, environmental, economic, and health satisfaction, health-related quality of life, as determined using the World Health Organization Quality of Life assessment (WHOQOL), may be used to assess therapeutic efficacy of administering a disclosed combination or composition thereof to a subject in need thereof. It will be understood that the measures described herein are exemplary and other like measures, e.g., those that are relevant, current, and validated, may be used instead.

The quality of the psychedelic experience has been shown to impact therapeutic efficacy. For example, Roseman et al. showed that greater mystical experiences, as determined using the OBN, and reduced experiences of anxiety and impaired control/cognition, as determined using DED, in response to psilocybin were predictive of long-term positive outcomes in subjects having treatment-resistant depression (Roseman et al., Front Pharmacol. 2018; 8:974). Less DED combined with high OBN predicted 54% of the variance of clinical change at 5 weeks, whereas greater DED was predictive of less positive clinical outcomes. In the study, a ≥50% reduction in depressive symptoms, as determined using the Quick Inventory of Depressive Symptoms (QIDS SR), was observed at 5-weeks post-treatment.

E. Definitions

The terminology used herein is for describing embodiments and is not intended to be limiting. As such, the definitions below will be appreciated to provide examples of definitions that may be considered to assist in understanding and practicing the invention, but the full scope of any term (and especially the ultimate definition of any term used in the claims) will be found only in light of the entirety of the application and in view of any plain meaning known in the art.

When introducing elements of the present invention or the preferred embodiments thereof, the articles "a," "an," "the," and "said" are intended to mean that there are one or more of the elements. The terms "comprising," "including," and "having" are intended to be inclusive and not exclusive (i.e., there may be other elements in addition to the recited elements). Thus, the terms "including," "may include," and "include," each mean and are used interchangeably with the phrase "including but not limited to." The term "or" is used herein to mean, and is used interchangeably with, the term "and/or," unless context clearly indicates otherwise.

Unless otherwise stated, all measurements, values, ratings, positions, magnitudes, sizes, locations, orientations, configurations, and other specifications that are set forth (either expressly or impliedly) in this specification, including in the figures and in the claims that follow, are approximate, and not exact. They are intended to have a reasonable range that is consistent with the functions to which they relate and with what is customary in the art to which they pertain. Where a range of values is provided, it will be understood that the upper and lower limit, and each intervening value between the upper and lower limit of the range, is encompassed within the embodiments. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used herein, "experience," such as a "subject's experience," relates to subjective drug effects following administration of a disclosed therapeutic combination, e.g., a combination comprising a hallucinogen and non-racemic MDMA, to a subject. Herein "subjective effects," "subjective drug effects," "subjective experience," and "experience" may be used interchangeably. Enhancing or otherwise improving a subjective experience, e.g., "producing an enhanced subjective experience," refers to increased feelings of unity, blissful state, and insightfulness, e.g., as determined using the 5 Dimensions of Altered States of Consciousness (5D-ASC) questionnaire's Oceanic Boundlessness (OBN) scale or the MEQ, and/or reductions in feelings of anxiety, impared control or cognition, and disembodiment, e.g., as determined using the 5D-ASC questionnaire's Anxious Ego Dissolution (AED) scale. Such effects are determined relative to administration of a comparator combination comprising the same hallucinogen and racemic MDMA. In one example, an enhanced subjective experience comprises a score of greater magnitude on the OBN and/or the MEQ following administration of a disclosed therapeutic combination comprising a hallucinogen and non-racemic MDMA, where R-MDMA is present in enantiomeric excess, to a subject, as compared to a score reported following administration of a comparator combination comprising the same hallucinogen and racemic MDMA. In another example, an enhanced subjective experience comprises a score of lesser magnitude on the AED scale following administration of a disclosed therapeutic combination comprising a hallucinogen and non-racemic MDMA, where R-MDMA is present in enantiomeric excess, to a subject, as compared to a score reported following administration of a comparator combination comprising the same hallucinogen and racemic MDMA. In some embodiments, an enhanced subjective experience comprises an increased OBN score and/or an increased MEQ score and decreased AED scores following administration of a disclosed therapeutic combination comprising a hallucinogen and non-racemic MDMA, where R-MDMA is present in enantiomeric excess, to a subject, as compared to the scores reported following administration of a comparator combination comprising the same hallucinogen and racemic MDMA.

Unless defined otherwise, all technical and scientific terms herein have the meaning as commonly understood by one of ordinary skill in the art to which this invention belongs. In the event there is a plurality of definitions for a term herein, those in this section prevail unless stated otherwise. Further definitions that may assist the reader to understand the disclosed embodiments are as follows, and such definitions may be used to interpret the defined terms, when those terms are used herein. However, the examples given in the definitions are generally non-exhaustive and must not be construed as limiting the invention. It also will be understood that a substituent should comply with chemical bonding rules and steric compatibility constraints in relation to the particular molecule to which it is attached.

This disclosure is not limited to particular embodiments described as such may vary. The terminology used herein is for the purpose of describing particular embodiments only and is not intended to be limiting. Although any materials and methods similar or equivalent to those described herein can be used in the practice or testing of the present invention, certain preferred materials and methods described herein.

F. Examples

Example 10: Synthesis of 9:1 R:S MDMA

Purpose:

To synthesize an enantiomeric mixture of R-MDMA and S-MDMA in a ratio of 9:1.

Methods—Chiral Resolution of Sulfinamides:

Scheme 4 shows synthesis started from commercially available 3,4-di-benzyloxybenzaldehyde, which was transformed into the methyl ketone (3) by condensation with nitroethane followed by reduction with Fe/HCl. The corresponding imine, formed by treatment of ketone (3) with (R)-( þ )-tert-butylsulfinamide and Ti(OEt)4 was reduced in situ with NaBH4 at room temperature to afford the two diastereomeric sulfinamides in excellent yield but with moderate (3:1) diastereomeric ratio. The diastereoselectivity rose to 14:1 by lowering the temperature to 20 C in the reduction step. The major isomer was easily purified by crystallization from hexane affording diastereomerically pure (R,RS)-4a as a white solid.

-continued

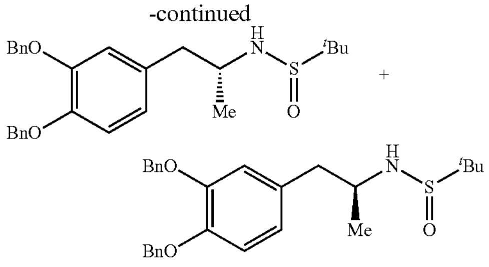

Scheme 4 shows chiral resolution of sulfinamides.

Enantioselective Synthesis of R-MDMA and S-MDMA:

Methylation of sulfonamide (R,RS)-4a was carried out with NaH and MeI in DMF at room temperature to give (R,RS)-5a in 900% yield. However, cleavage of the benzyloxy groups by catalytic hydrogenation (Pd/C) even at high hydrogen pressures (50 bar) and/or temperatures (50 C) was not achieved. It was hypothesized that sulphur byproducts derived from sulfinimides hampered the reaction poisoning of the catalyst.

Alternatively, derivatization of (R,RS)-4a as ethyl carbamate was unsuccessful since this sulfonamide is a very weak nucleophile. Thus, we envisaged the hydrolysis of (R,RS)-4a to the primary amine. Reductive cleavage of NeS bond was easily performed with 4 M MeOH/HCl in dioxane affording amine (R)-6a in 9400 yield. Formation of the carbamate of the primary amine (R)-7a was carried out with ClCO2Et, Et3N in DMF. This compound was highly crystalline and allowed to confirm its high optical purity (9900 ee by chiral HPLC). Cleavage of the dibenzyloxy group in (R)-7a could be performed by hydrogenolysis and the resulting diphenol was cyclized with bromochloromethane and cesium carbonate as described by Pizarro et al. Finally, reduction with lithium aluminium hydride in THF yielded the desired compound (R)-10a (MDMA) in 85% yield, which was isolated as a sulfate. The enantiomeric purity of the final product was checked by chiral HPLC of the corresponding N-Boc derivative, being 9900 ee as expected. Since both enantiomers of tert-butylsulfinamide are commercially available, the same sequence as shown in Scheme 5, starting from (S)-(−)-tert-butylsulfinamide, afforded the (S)-MDMA enantiomer also in 9900 ee.

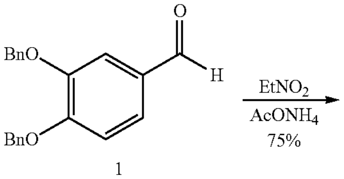

1

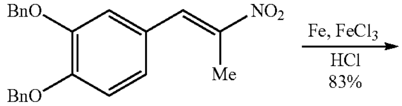

2

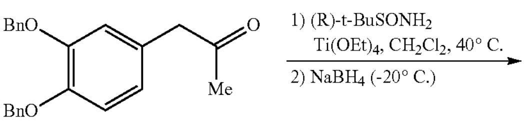

3

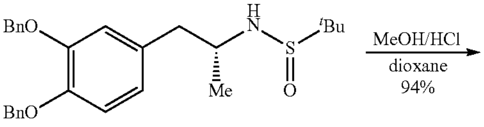

(R, Rs)-4a

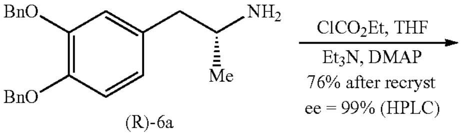

(R)-6a

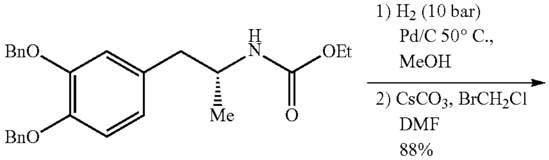

(R)-7a

-continued

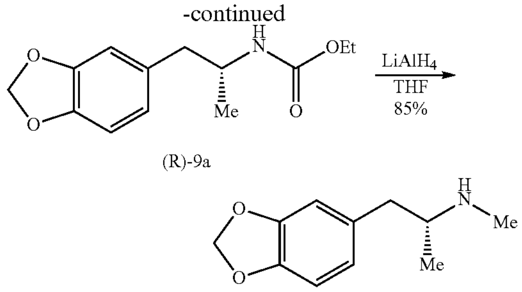

(R)-9a (R)-10a, (R)-MDMA
ee = 99% (HPLC)

Scheme 5 shows an exemplary synthesis of R-MDMA from the R-enantiomer of a sulfinamide precursor.

Reconstitution In a 9:1 Ratio:

Sulfate salts of R- and S-MDMA were recrystallized at a ratio of 9:1 and passed through a chiral column to ensure the correct enantiomeric ratio.

Example 11: Subjective Report of R-MDMA and Non-Racemic MDMA Comprising R-MDMA and S-MDMA in a Ratio of 9:1

L. R-MDMA

Purpose:

To determine the physiological and subjective effects of the hydrochloride salt of R-MDMA (oral administration, 250 (±) 10 mg), supplemented with acetyl-L-carnitine (ALCAR), alpha lipoic acid (ALA), ascorbate to reduce or prevent neurotoxicity.

Methods—Synthesis and Chiral Separation from Racemic MDMA:

2.2 g of racemic MDMA was obtained and dissolved in methanol at a stock concentration of 10 mg/mL. A ChiralPak Ad-H column (150×4.6 mm, 5 μm particle size) was flushed with mobile phase solution on an Agilent 1260 machine with a variable UV-Vis detector and 10 uL of the final concentrated solution (1:100) was injected on a 35 min run cycle. Due to the preliminary nature of the testing, no further characterization was done. The laevo-rich form was the first eluted. It was collected and roto-evaporated into solid form and then dried over magnesium pellets. The product, when dried and washed thoroughly, was sent out for anonymized 1H-NMR testing to determine identity.

Results—Physiological Effects:

Vitals were taken hourly, and were taken four times between hours two and three. Heart rate rose for a short period to 115-125 from 85 resting. Blood pressure increased for a short period, however it was later determined that the monitor was of low precision and the result is therefore inconclusive. No noticeable hyperthermia or hypothermia was recorded. No incidence of jaw clenching was recorded.

Results—Subjective Effects of Subject A:

"I slept well the previous night and came into the experience in a good mood. The initial dose was taken orally with 500 mg ALCAR and 300 mg ALA with the assumption that these two potentially neuroprotective agents would not significantly interfere with the subjective effects of R-MDMA. Blood pressure, heart rate, and temperature were taken and shown to be in normal range, though blood pressure was noticeably slightly elevated. For the first 30-40 minutes, I felt only slight lightheadedness. Noticeable effects off-baseline started somewhere around 40 minutes in, at which point the colors in the kitchen began to become slightly brighter and left slight ray traces when the visual frame moved. The empathogenic come-up was fast. Around the one hour mark, I was suddenly whacked in the head with an overwhelming, all-encompassing sense of compassion and love. Waves of euphoria rolled over the body, as if being cradled by the warm center of physical reality itself, the most perfect and sublime space. In many ways, it felt like coming back home, something that my life was leading me to, a kind of ultimate conclusion. My mind kept repeating to me: 'Oh my god, this is it, this is it!' Noticeably, unlike racemic MDMA, the R-MDMA experience was almost entirely absent of any high energy 'amphetamine'-like stimulant effects. This is probably not a substance that will make you dance. Instead, the waves of euphoria and troughs of gratitude were much more subdued and 'meditative.' It felt more like a spiritual type of grace. At the peak of the experience, somewhere around two hours after ingestion, my mind began to pan to various people in my life and focus in on the intense gratitude I felt for their existence and my knowing them and my desire for them to have a good and meaningful life. I talked consistently throughout the session, while also spending blocks of time exploring the entactogenic space. Every inch of my body was tingling with the waves of love and cradling that was coming from every direction. Notably the peak of R-MDMA was quite long and lasted several hours. When my eye mask was off, I looked around the room and noticed everything was more perfect and beautiful. Come-down started at approximately hour 4 and the whole experience lasted for approximately 7 hours, though glimmers of this total beauty and perfection lasted much much longer, well into the night. Definitely a (+++)."

II. 9:1 R:S-MDMA

Methods:

In contrast to the previous report on R-MDMA, no supplements taken prior to oral administration of 230-240 mg 9:1 R:S MDMA. MDMA enantiomers were recombined in a 9:1 ratio through crystallization and washing.

Results—Subjective Effects of Subject A:

"Maybe it was the large size of the crystals which were ingested, but it took a long time to take effect, at least an hour and 10 minutes. The effect was very MDMA-like, maybe a tad less stimulating on the whole. Visuals were more noticeable after the first hour and a half. Heart rate seemed to be pretty steady the few times that we took vitals, somewhere in the 95 range. Not a lot of hot-and-cold feelings the whole time. Body euphoria was intense for the first three hours, then the comedown was pretty rapid. No jaw clenching either, but I usually don't get that anyway with the racemic form. Overall, a (+++). Relative to R enantiomer alone, the effects of the 9:1 R:S enantiomeric mixture, which were comparable to the entactogenic experience of R-MDMA alone, dissipated more rapidly."

Overall, positive affect, body euphoria, and insightfulness were main features of enantiomeric R-MDMA and exemplary non-racemic MDMA comprising R-MDMA and S-MDMA in a ratio of 9:1. One exemplary advantage of R-MDMA and non-racemic MDMA comprising R-MDMA in enantiomeric excess was the noted reduction in stimulation relative to racemic MDMA. One distinction is the reduced duration of action, e.g., noticeable subjective drug effects, of 9:1 R:S-MDMA. Such abbreviated drug action provides several advantages, which, in one example, may facilitate broader adoption in a patient care setting.

Example 12: Modeling the Pharmacology of a Therapeutic Combination Comprising a Hallucinogen and Exemplary Non-Racemic Entactogen 9:1 R:S-MDMA Purpose:

To assess the effects of an exemplary disclosed combination comprising the hallucinogenic agent psilocin and the non-racemic entactogenic agent 9:1 R:S-MDMA in silico.

Methods:

Modeling of drug activity was performed by analyzing benchmark data sets from ToxCast and a hand-curated psychoactive library ligand binding dataset on a proprietary computational platform. A recurrent neural network (RNN) model similar in structure to DeepAffinity was used, and SMILES were used to represent structural small molecule information.

Affinity data was used to generate an expected binding curve at the 5-$HT_{2A}$ receptor for a combination of 9:1 R:S-MDMA and a variety of molecules such as psilocin, as compared to the molecules alone. Approximated binding and potency data generated from crystal structures were used to determine approximate contributions to effective dose levels. For this experiment, effective dose levels were those that facilitated hallucinogenic effects, e.g., approximated on an exemplary hallucinogen rating scale. Receptor affinity and activation was used to determine whether, in combination with 9:1 R:S-MDMA, the dose of the hallucinogen could be reduced and affect comparable potency, i.e., using hallucinogen rating scale scores as a benchmark.

Additionally, hallucinogenic rating scale (HRS) radar plots were generated by training the proprietary computational model on a database of labeled molecules corresponding to average human experience measurements on the HRS. Using the average potency of each molecule, a probabilistic profile of the molecule was constructed. The features of the psilocin and 9:1 R:S-MDMA experience were also assessed using the Altered States of Consciousness—11 (ASC-11) dimensions.

Figure 6:
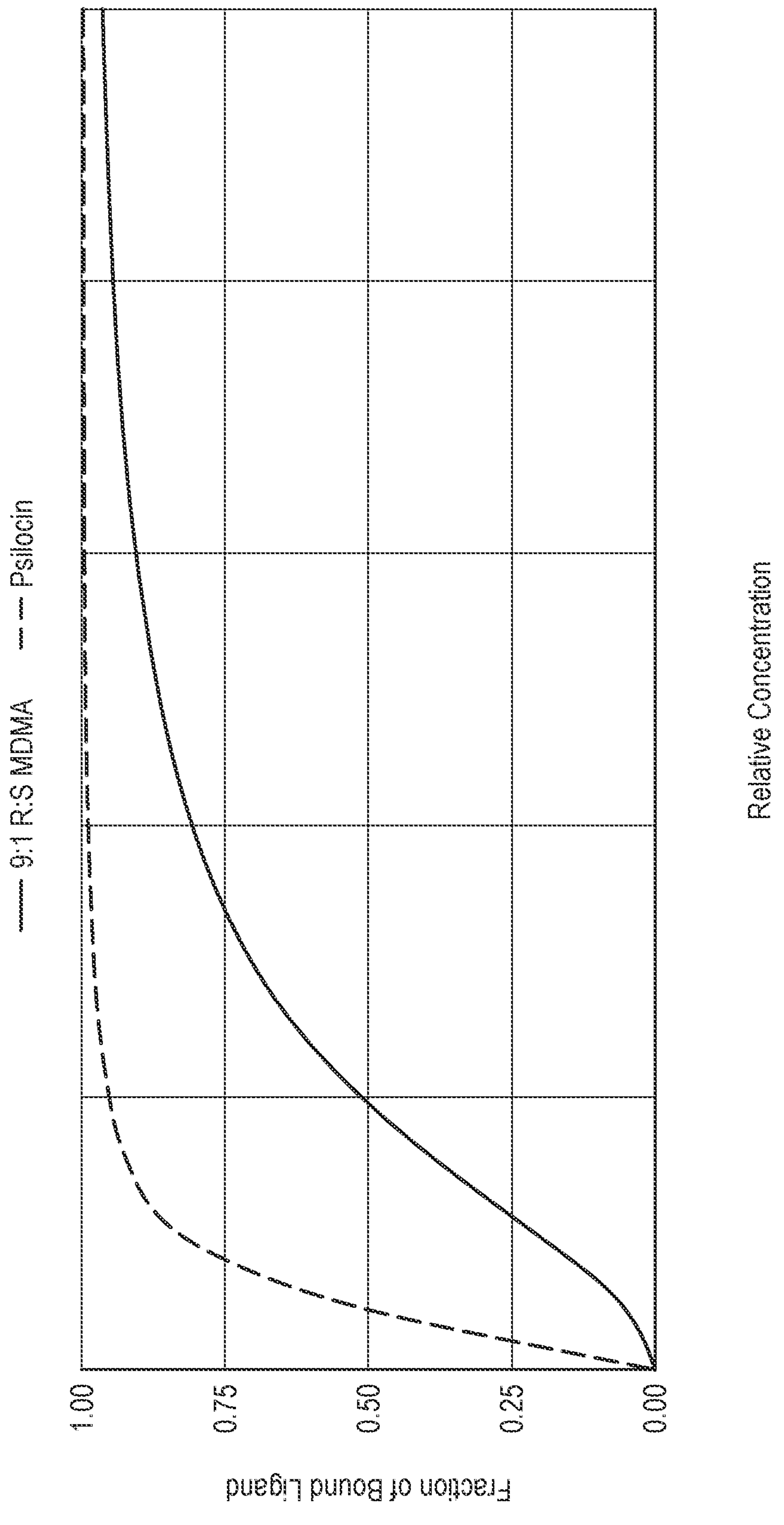
FIG. 6: dose response curve for psilocin and 9:1 R:S-MDMA at the 5-$HT_{2A}$ receptor.
Figure 7:
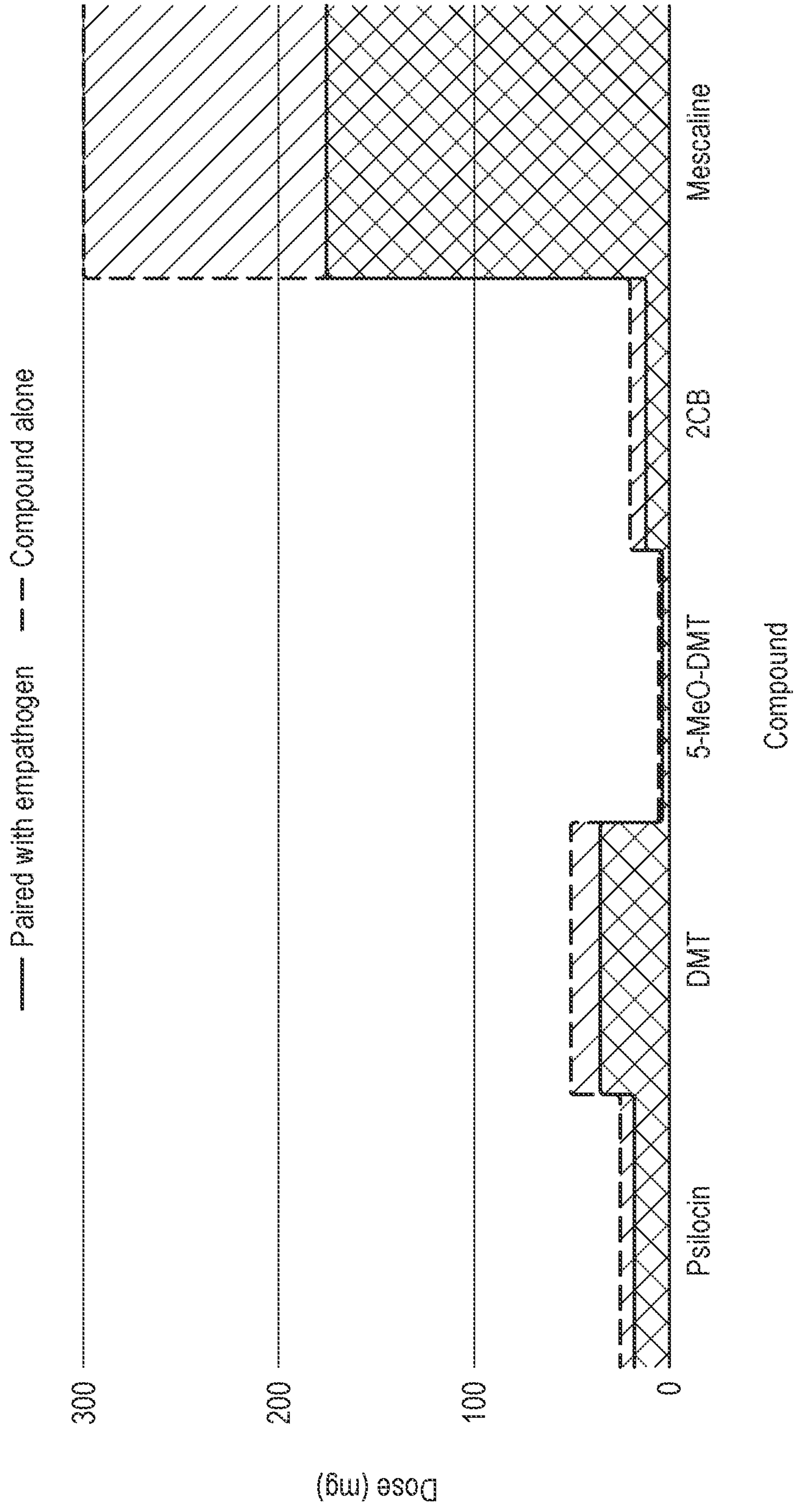
FIG. 7: dose reduction of hallucinogens in combination with the exemplary non-racemic entactogen 9:1 R:S-MDMA to achieve a hallucinogenic effect of comparable strength, as measured by an exemplary hallucinogen rating scale.
Figure 8A:
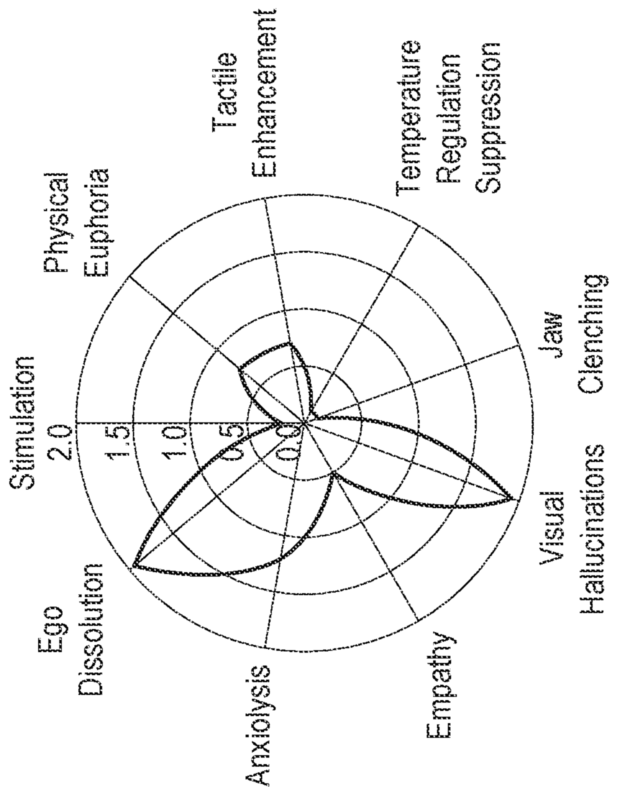
FIG. 8: predicted principal components of the subjective effects of the exemplary hallucinogen psilocin (FIG. 8A) and the subjective effects of psilocin combined with exemplary non-racemic entactogen 9:1 R:S-MDMA (FIG. 8B) in a subject.
Figure 8B:
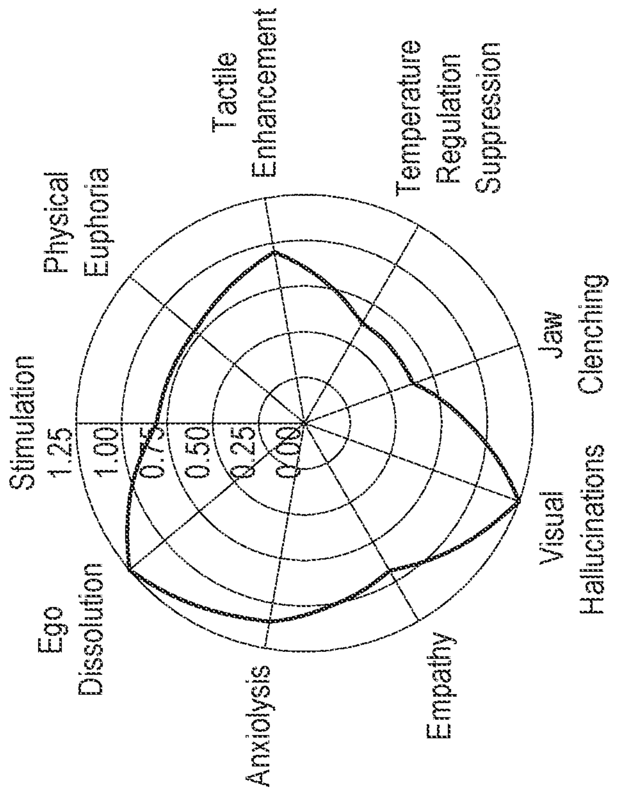
Figure 9:
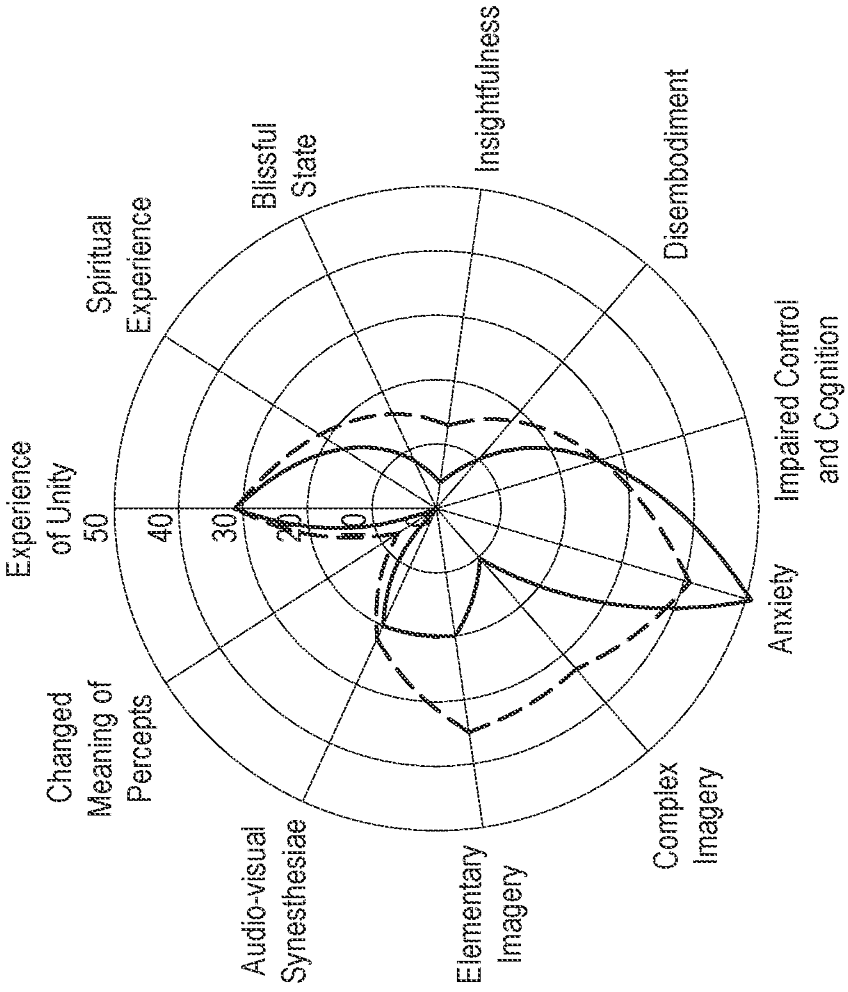
FIG. 9: predicted principal components of the subjective effects elicited by the exemplary hallucinogen psilocin (solid line) and exemplary non-racemic entactogen 9:1 R:S-MDMA (dashed line) in a subject.

Results: FIG. 6 shows a dose response curve for psilocin and 9:1 R:S-MDMA at the 5-$HT_{2A}$ receptor. FIG. 7 shows estimated effective doses (mg) of various hallucinogens and reductions thereof when paired with exemplary non-racemic entactogen 9:1 R:S-MDMA. Table 3 additionally shows percent dose reductions that facilitated comparable effects when the hallucinogen was paired with 9:1 R:S-MDMA. FIG. 8A and FIG. 8B show the magnitude of effects of psilocin alone and in combination with 9:1 R:S-MDMA, respectively. Stimulation, physical euphoria, tactile enhancement, temperature regulation suppression, jaw clenching, visual hallucinations, empathy, anxiolysis, and ego dissolution are among the assessed effects. FIG. 9 also shows effects of psilocin and 9:1 R:S-MDMA, but the ASC-11 dimensions are assessed. The ASC-11 dimensions include experience of unity, spiritual experience, blissful state, insightfulness, disembodiment, impaired control and cognition, anxiety, complex imagery, elemental imagery, audio-visual synesthesiae, and changed meaning of precepts.

TABLE 3

Estimated Effective Doses of Hallucinogens Alone and Combined with Exemplary Non-Racemic Entactogen 9:1 R:S-MDMA

| Molecule | Dose (mg) of Hallucinogen Alone | Estimated Hallucinogen Dose (mg) In Combination with 235 mg 9:1 R:S-MDMA | Dose Reduction (% Change) |
|---|---|---|---|
| Psilocin | 25 | 18 | −28% |
| DMT | 50 | 35 | −30% |
| 5-MeO-DMT | 5 | 4 | −20% |
| 2CB | 20 | 12 | −40% |
| Mescaline | 300 | 175 | −42% |

The results show certain advantages of combining a hallucinogen with non-racemic entactogen 9:1 R:S-MDMA. In one exemplary advantage, combining a reduced dose of a hallucinogen with 9:1 R: S-MDMA results in comparable subjective experiences that are achieved with elevated doses of the hallucinogen alone. In the example of 2C-B, the effects of a 20 mg dose of 2C-B alone were approximated by a 40% lower dose of 2C-B (12 mg) in combination with 235 mg 9:1 R:S-MDMA.

Regarding the computed subjective experience plots, combining psilocin with 9:1 R-S-MDMA dramatically altered the features of the computed subjective experience. Relative to psilocin alone, the combination of psilocin and 9:1 R:S-MDMA enhanced the exemplary dimensions of empathy, anxiolysis, and physical euphoria. When assessed using the ASC-11 dimensions, 9:1 R:S-MDMA displayed a profile that further indicates the potential to enhance empathogenic, prosocial, and insightful qualities of the psilocin experience, as well as mitigate negative aspects of the hallucinogen experience, such as anxiety. An experience characterized by enhanced empathogen effects and reduced anxiety has been shown to predict positive treatment outcomes. See, e.g., Roseman et al., Front Pharmacol. 2018; 8:974.

Example 13: Determining Improved Physiological and Psychological Features Following Administration of a Disclosed Combination Purpose:

To compare the effects of administering a disclosed combination, e.g., comprising a hallucinogen and exemplary non-racemic entactogen 9:1 R:S-MDMA, and comparable combination comprising the same hallucinogen and racemic MDMA.

Methods:

Human subjects are divided into two age- and condition- or symptom-matched groups. Group A is administered a treatment regimen (e.g., psychedelic-assisted psychotherapy) comprising racemic MDMA+psilocybin. Group B is administered a like treatment regimen using a combination of the present invention, such as 9:1 R:S-MDMA+psilocybin. The assessments described herein are non-limiting, and additional improvements, and methods of evaluating such advantages, will be appreciated by those of skill in the art.

Determining a Reduction in Nausea and Vomiting:

The subjects of both groups are subjected to standard assessments to measure the severity of each subject's nausea and vomiting. Comparison of the results demonstrates a reduction in nausea and vomiting in Group B versus Group A, such as a greater incidence of nausea and vomiting in Group A.

Determining an Improved Pharmacokinetic Profile:

The subjects of both groups are subjected to standard assessments to measure, e.g., the level of at least one toxic metabolite of MDMA, e.g., MDA, and an absence or a reduction in drug interaction, e.g., at a CYP450 isoform. Comparison of the results demonstrates a reduction in the level of at least one toxic metabolite in Group B versus Group A, such as a relatively higher level of MDA in Group A.

Determining a Reduction in Subjective Body Load:

The subjects of both groups are subjected to standard assessments to measure the severity of each subject's subjective body load. Comparison of the results demonstrates a reduction in subjective body load in Group B versus Group A.

Determining an Improvement in Subjective Valence:

The subjects of both groups are subjected to standard assessments to measure each subject's subjective valence of the experience. Comparison of the results demonstrates an improvement in subjective valence in Group B versus Group A.

Determining an Improvement in Subject Affect:

The subjects of both groups are subjected to standard assessments to measure each subject's positive affect, e.g., using PANAS. Comparison of the results demonstrates an improvement in positive affect in Group B versus Group A.

Determining an Increase in Therapeutic Window:

The subjects of both groups are subjected to standard assessments, e.g., to assess any one of extinction of fear conditioning, conditioned place preference, the span of time in which the composition is pharmacokinetically active, the duration of subjective and/or reporter-observed changes in perception, and the critical reward learning period of behavioral integration thereafter. Comparison of the results demonstrates an increase in therapeutic window in Group B versus Group A.

Determining a Reduction in Anxiety:

The subjects of both groups are subjected to standard assessments to measure levels of anxiety during the period of drug administration and, in some embodiments, for a period thereafter. Comparison of the results demonstrates a reduction in anxiety in Group B versus Group A.

Determining a Decrease in Abuse Potential:

The subjects of both groups are subjected to standard assessments to measure levels of drug-seeking behavior and quantify any self-administration of the drug outside of the therapeutic context. Comparison of the results shows a reduction in addictive liability and abuse potential in Group B versus Group A.

Determining a Reduction in Neurotoxicity:

The subjects of both groups are subjected to standard assessments to measure neurotoxic effects, including determining any one or more of: a) the level of at least one toxic metabolite of MDMA; b) oxidative stress and dopamine-based quinones; c) mitochondrial dysfunction; and d) activation of glial cells. Comparison of the results demonstrates a reduction in neurotoxic effects in Group B versus Group A, in any amount as above.

Determining an Absence or Reduced Severity of Hypothermia and Hyperthermia:

The subjects of both groups are subjected to standard assessments to measure body temperature. Comparison of the results demonstrates a reduction in both hyperthermia and hypothermia in Group B versus Group A.

Determining a Reduction in Stimulation:

The subjects of both groups are subjected to standard assessments to measure stimulation or one or more undesirable effects relating thereto, such as listed above and the like. Comparison of the results demonstrates a reduction in stimulation and/or its undesirable effects in Group B versus Group A.

Example 14: In Vivo Determination of Hallucinogenic Agents Using a Head-Twitch Response (HTR) Assay Purpose: The mouse head-twitch response (HTR) is a behavioral test that reflects 5-$HT_{2A}$ receptor activation and can be predictive of hallucinogenic effects in humans (Halberstadt et al., J Psychopharmacol. 2011; 25(11): 1548-1561). The HTR is widely used as a behavioral surrogate for human psychedelic effects for its ability to reliably distinguish psychedelic from non-psychedelic 5-$HT_{2A}$ receptor agonists (Halberstadt & Geyer, Psychopharmacol (Berl). 2013; 227(4):727-3). The HTR is used to distinguish a hallucinogenic agent for use in a disclosed therapeutic combination or composition thereof.

Methods:

An HTR assay will be performed in accordance with the methods described in Klein et al., Neuropharmacol, 2018; 142:231-239 to assess whether a compound may be used as a hallucinogenic agent for inclusion in the disclosed therapeutic combinations. Male C57BL/6 J mice (6-8 weeks old) are obtained and housed in a vivarium that meets all requirements for care and treatment of laboratory animals. Mice are housed up to four per cage in a climate-controlled room on a reverse-light cycle (lights on at 1900 h, off at 0700 h) and are provided with ad libitum access to food and water, except during behavioral testing. Testing is conducted between 1000 and 1800 h. All animal experiments are conducted in accordance with applicable guidelines and are approved by an appropriate animal care committee.

A head-mounted magnet and a magnetometer detection coil will be used to assess HTR, as previously described (Halberstadt & Geyer, Psychopharmacol (Berl). 2013; 227 (4):727-3, Halberstadt & Geyer, Neuropharmacol, 2014; 77:200-7; Nichols et al., ACS Chem Neurosci. 2015; 6(7): 1165-1175). Briefly, mice are anesthetized and a small neodymium magnet is attached to the dorsal surface of the cranium using dental cement. Following a two-week recovery period, HTR experiments are carried out in a well-lit room with at least 7 days between sessions to avoid carry-over effects.

Test compounds are dissolved in a suitable solvent, e.g., water containing 5% Tween 80, and administered IP at a volume of 5 or 10 mL/kg body weight immediately prior to testing. Different doses are tested to produce a dose-response curve. Mice are injected with drug or vehicle, and HTR activity is recorded in a glass cylinder surrounded by a magnetometer coil for 30 min. Coil voltage is low-pass filtered (2e10 kHz cutoff frequency), amplified, and digitized (20 kHz sampling rate) using a Powerlab/8SP with LabChart v 7.3.2 (ADInstruments, Colorado Springs, CO, USA), then filtered off-line (40e200 Hz band-pass).

Head twitches are identified manually based on the following criteria: 1) sinusoidal wavelets; 2) evidence of at least two sequential head movements (usually exhibited as bipolar peaks) with frequency 40 Hz; 3) amplitude exceeding the level of background noise; 4) duration <0.15 s; and 5) stable coil voltage immediately preceding and succeeding each response.

Head twitch counts will be analyzed using one-way analyses of variance (ANOVA). Post hoc pairwise comparisons between selected groups are performed using Tukey's studentized range method. The entire recordings are examined for head twitches. In some cases a shorter block of time is analyzed to accommodate compounds with a brief duration-of-action, as potency calculations can be confounded by extended periods of inactivity. $ED_{50}$ values and 95% confidence limits are calculated using nonlinear regression. Relationships between HTR potency and binding affinities are assessed using linear regression and ordinary least-squares regression. For all analyses, significance is demonstrated by surpassing an a-level of 0.05.

Results:

The results will show whether a compound is likely to produce psychedelic effects in humans. Accordingly, it will be determined whether a compound is suitable for use as a hallucinogenic agent in a disclosed combination or composition comprising, e.g., a hallucinogenic agent and an entactogenic agent, as disclosed herein. Results can be represented as $ED_{50}$ (mg/kg). The magnitude of such effects is also evaluated and compared amongst test compounds.

Example 15: Assessments for Reward Learning and Subjective Effects

I. Social Reward Learning

Purpose:

To assess improvements in social reward learning elicited by administering a disclosed combination comprising a hallucinogen and an entactogen, as compared to a hallucinogen alone.

Methods:

A randomized, placebo-controlled study is conducted wherein participants are administered a single dose of:

i) A placebo capsule for oral administration
ii) A 30 mg dose of psilocin as an oral capsule
iii) A 235 mg dose of 9:1 R:S-MDMA as an oral capsule; or
iv) A 30 mg dose of psilocin and a 235 mg dose of 9:1 R:S-MDMA, subjects ingest the non-racemic MDMA 2 hours after administration of psilocin.

Participants will play three multi-round trust games during functional magnetic resonance imaging scanning, with no information, positive information, and negative information about the counterpart's trustworthiness, while all counterparts are programmed to behave trustworthy. The main outcome variable is the height of the shared amount in the trust game, i.e. investment, representing an indication of trust. See, e.g., methods for a modified trust game described in Hanssen et al., Australian & New Zealand Journal of Psychiatry, 2022; 56(1): 59-70.

Results:

Subjects who are administered a disclosed combination comprising a hallucinogen and a non-racemic entactogen are expected to experience enhanced social reward learning relative to subjects who ingest placebo, the hallucinogen, or non-racemic MDMA alone. Increased sensitivity to social context and social reward learning is exemplified by greater investments from subjects who are administered psilocin and 9:1 R:S-MDMA.

II. Subjective Effects

Purpose:

To assess anxiety or negative subjective effects of a disclosed combination comprising a hallucinogen and an entactogen relative to effects of a hallucinogen alone.

Methods:

A randomized, placebo-controlled study is conducted wherein participants are administered a single dose of:

i) A placebo capsule
ii) A 100 μg dose of LSD on blotter paper for sublingual administration
iii) A 235 mg oral dose of 9:1 R:S-MDMA administered as a capsule;
iv) A 50 μg dose of LSD on blotter paper for sublingual administration and a 235 mg oral dose of 9:1 R:S-MDMA administered as a capsule; subjects ingest the non-racemic MDMA 2 hours prior to administration of LSD Participants report the empathogenic effects of the combination using metrics such as the hallucinogenic rating scale (HRS) or the Altered States of Consciousness Rating Scale.

Results:

Participants who are administered a reduced dose of a hallucinogen and non-racemic MDMA are expected to report scores of greater magnitude on measures of mystical experience, such as the Oceanic Boundlessness scale, and scores of lesser magnitude on measures of anxiety and negative subjective effects, such as the Dread of Ego Dissolution scale, as compared to participants who ingest a greater dose of the hallucinogen alone.

III. Therapeutic Window

Purpose:

To assess the effects of a reduced effective dose of a hallucinogen and an exemplary non-racemic entactogen on total therapeutic window.

Methods:

A randomized, placebo-controlled study is conducted wherein participants are administered:

i) A placebo capsule
ii) A 25 mg dose of 2C-B as a tablet for oral administration
iii) A 235 mg dose of 9:1 R:S-MDMA as a capsule for oral administration
iv) A 20 mg dose of 2C-B as a tablet for oral administration and a 175 mg dose of 9:1 R:S-MDMA as an oral capsule; subjects ingest the 2C-B 2 hours prior to administration of non-racemic MDMA
v) A 20 mg dose of 2C-B as a tablet for oral administration and a 175 mg dose of racemic MDMA as an oral capsule; subjects ingest the 2C-B 2 hours prior to administration of racemic MDMA Participants are asked to measure the empathogenic effects of the combination using possible metrics such as the hallucinogenic rating scale (HRS) or the Altered States of Consciousness Rating Scale, such as the 5D-ASC, to compare average effect size in key categories of the hallucinogenic effect. Tests are administered hourly after the dose of MDMA is ingested to determine the duration of drug effects and subjective peak effects. Samples may also be collected from subjects to evaluate pharmacokinetic properties, including half life, clearance, and Cmax, e.g., to determine the duration the drug combination is "pharmacokinetically active."

Results:

The combination comprising a reduced dose of a hallucinogen and a reduced dose of exemplary non-racemic entactogen 9:1 R:S-MDMA is expected to produce subjective effects that are comparable or enhanced relative to a higher dose of the hallucinogen alone, a higher dose of the entactogen alone, or a comparator combination comprising 2C-B and racemic MDMA. Enhanced subjective effects include higher ratings on the Hallucinogen Rating Scale, higher ratings related to positive affect, insightfulness, e.g., as assessed using the 5D-ASC's Oceanic Boundlessness scale, and lower ratings related to anxiety and impaired cognition or control, e.g., as assessed using the 5D-ASC's Anxious Ego Dissolution scale.

Example 16: Neurotoxicity Assessments

Purpose:

To determine whether disclosed therapeutic combinations cause neurotoxic effects. Neurotoxic effects are exemplified by, e.g., activation of glial cells, structural and functional dysfunction of mitochondria, and oxidative stress, Additionally, the effects of a disclosed therapeutic combination can be compared to a comparator to determine differences in neurotoxic effects. In the subsequent experiments, exemplary therapeutic combinations, such as comprising a hallucinogen and non-racemic entactogen 9:1 R:S-MDMA are compared to a comparator combination comprising the same hallucinogen and racemic MDMA. A control group is also included. The hallucinogen and the entactogen may be administered to a subject simultaneously or sequentially. An appropriate comparator has the same dosing regimen, e.g. the same dosing order and the same doses, and is administered to, e.g., a separate, matched subject. A substituted phenethylamine compound, such as 2C-B, may be co-administered with 9:1 R:S-MDMA as part of a disclosed therapeutic combination. Measurements may be taken post-administration of the disclosed and comparator combinations, and in some cases compared baseline levels, to determine the absence of or comparative reductions in neurotoxic effects, as is known to one of skill in the art.

I. Assessing Activation of Glial Cells

Methods:

Neurotoxic effects, as determined by evaluating glial cell activation, will be measured according to the methods described by Frau et al., J Neurochem. 2013; 124(1):69-78 and Frau et al., Neurotoxicology. 2016; 56:127-138, with modifications. Briefly, following drug administration, Relevant portions of mice will be coronally cut on a vibratome and immunoreacted with CD11b and glial fibrillary acidic protein (GFAP) antibodies 1:1000 and monoclonal mouse anti-GFAP, 1:400 and proper secondary antibodies, e.g., goat anti-rat IgG for CD11b and goat anti-mouse IgG for GFAP. Sections to be cut may include the nucleus accumbens, shell and core, M1 and M2 areas of motor cortex, striatum, and substantia nigra, both pars *compacta* and pars *reticulata.*

For visualization, the avidin-peroxidase protocol will be applied, using 3,3'-diaminobenzidine as chromogen. Sections will be mounted on gelatine-coated slides, dehydrated and cover slipped for subsequent analysis. Images of the sections cut on the vibratome will be digitized and magnified [at 20×]. PixeLink software, for example, can be used to carry out analysis, which is performed by counting the total number of GFAP-positive cells in the selected areas.

Results:

Disclosed therapeutic combinations comprising, e.g., a hallucinogen and exemplary non-racemic entactogen 9:1 R:S-MDMA are expected to show reduced glial cell activation, as evidenced by a lower total number of GFAP-positive cells, relative to a combination comprising the same hallucinogen and racemic MDMA.

II. Determining Mitochondrial Dysfunction

Methods:

Evaluating structural and functional dysfunction of mitochondria is conducted according to the methods described by Taghizadeh et al., Free Radic. Biol. Med. 2016; 99: 11-19, with modifications. Briefly, brain mitochondria are isolated and subjected to various analyses that relate to structure and function.

Measuring Brain Mitochondrial ROS Levels:

ROS levels will be measured over 5 time points (5, 15, 30, 45, and 60 minutes) by fluorescence spectrophotometry using a Shimadzu RF5000 at an excitation and emission wavelength of 500 and 520 nm for example. Isolated brain mitochondria will be prepared for spectrophotometry with an incubation in respiration buffer before having 2', 7'-dichlorofluorescein diacetate (DCFH-DA) added to the mitochondria followed by incubation for 10 minutes. After entry to the brain mitochondria DCFH-DA is hydrolyzed to non-fluorescent dichloro fluorescin (DCFH) which reacts with the ROS and forms highly fluorescent dichlorofluorescin (DCF). The ROS labels are proportional to DCF fluorescence. The ROS levels will be quantified by a spectrophotometer.

Measuring Brain Mitochondrial Membrane Potential:

In order to estimate the brain mitochondrial membrane potential (MMP) over 5 time points (5, 15, 30, 45, and 60 minutes) a cationic fluorescent dye, such as Rh 123, will be added to brain mitochondrial fractions in a MMP assay buffer. The fluorescence can then be measured by a spectrophotometer at an excitation wavelength of 490 nm and emission wavelength of 535 nm.

Measuring Brain Mitochondrial Swelling:

Mitochondrial swelling is determined by changes in light scattering measured spectrophotometrically at 540 nm. This can be determined using an ELISA reader.

Measuring Brain Mitochondrial Outer Membrane Damage:

Outer membrane damage is determined using a cytochrome c oxidase assay kit (Sigma, Taufkirchen, Germany) for example and can be completed according to the manufacturer's protocol. In one example, determining cytochrome c release is conducted using a cytochrome c ELISA kit. Briefly, a monoclonal antibody of appropriate origin targeting cytochrome c will be precoated onto the microplate. Seventy-five microliter of conjugate and 50 μl of standard and positive control will be added to each well of the microplate. One microgram of protein from each supernatant fraction would be added to the sample wells. All of the standards, controls, and samples will be added to two wells of the microplate. After 2 h of incubation, the substrate solution (100 μl) will be added to each well and incubated for 30 min. After 100 μl of the stop solution was added to each well; the optical density of each well was determined by the aforementioned microplate spectrophotometer set to 450 nm.

Determining Brain ADP/ATP Ratio:

Samples are removed from ice and homogenized in 1 ml of an ice cold TCA (6%) before being centrifuged at 12,000 g's for 10 minutes at 4° C. the supernatant will then be removed and neutralized with potassium hydroxide. High-performance liquid chromatography (HPLC) will be performed. Levels of ATP and ADP are to be determined by the standard curve and then the ratio will be calculated.

Results:

In ROS evaluations, administering a disclosed combination comprising a hallucinogen and 9:1 R:S-MDMA is expected to result in lower measured ROS levels than administration of the same hallucinogen and racemic MDMA. Regarding brain MMP, controls will show low fluorescence and higher fluorescence is indicative of mitochondrial damage. Accordingly, administering a disclosed combination comprising 9:1 R:S-MDMA is expected to cause less fluorescence than administration of the same hallucinogen and racemic MDMA. In other measures of structure and function, administering a therapeutic combination comprising 9:1 R:S-MDMA is expected to show reduced mitochondrial swelling and reduced outer membrane damage, e.g., as evidenced by reduced release of cytochrome c, as compared to a combination comprising racemic MDMA. Elevated ADP/ATP ratios may be used as an indicator of MDMA-induced neurotoxicity and so the ADP/ATP ratio of a disclosed therapeutic combination comprising 9:1 R:S-MDMA is expected to be reduced relative to a combination comprising racemic MDMA.

III. Evaluating Oxidative Stress

Methods:

Indicators of oxidative stress are determined from blood broadly in accordance with the methods described by Zhou et al., Free Radic Res. 2003; 37(5):491-7. Briefly, spectrophotometric methods are used to evaluate levels of lipoperoxide (LPO), superoxide dismutase (SOD), catalase (CAT), glutathione peroxidase (GPX) and acetylcholinesterase (AChE), as potential indicators of neurotoxic effects.

Blood samples will be collected and then processed into plasma and erythrocytes, which are stored at 50° C. The spectrophotometry of thiobarbituric acid reactive substances will be used to determine plasma LPO concentration and erythrocytic LPO concentration, while the spectrophotometry of inhibiting pyrogallol auto-oxidation will be used to determine erythrocytic SOD activity. The spectrophotometry of coloration of hydrogen peroxide and acetic acid-potassium dichromate will be used to determine erythrocytic CAT activity. Improved Hafeman's spectrophotometry will be used to determine erythrocytic GPX activity expressed as U/mg Hb, and the spectrophotometry of coloration of acetylcholine chloride-alkalescent hydroxylamine-ferric chloride will be used to determine erythrocytic AChE activity.

Results:

Increased levels of the oxidative constituent LPO and reduced levels of antioxidative constituents SOD, CAT, GPX, and AChE are associated with a greater potential for causing neurotoxicity. It is anticipated that administering a therapeutic combination comprising 9:1 R:S-MDMA will result in reduced LPO levels and increased SOD, CAT, GPX, and AChE levels relative to a comparator composition comprising racemic MDMA.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise forms disclosed; obviously, many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A therapeutic combination comprising:

a) a non-racemic mixture comprising R(−)-3,4-methylenedioxymethamphetamine (R-MDMA) or a pharmaceutically acceptable salt thereof, and S(+)-3,4-methylenedioxymethamphetamine (S-MDMA) or a pharmaceutically acceptable salt thereof; and b) a hallucinogenic agent or a pharmaceutically acceptable salt thereof.

2. The therapeutic combination of claim 1, wherein the non-racemic mixture comprises R-MDMA and S-MDMA in a molar ratio of between about 4:1 and about 12:1.

3. The therapeutic combination of claim 1, wherein the non-racemic mixture comprises R-MDMA and S-MDMA in a molar ratio of between about 6:1 and about 12:1, between about 7:1 and about 11:1, or between about 8:1 and about 10:1.

4. The therapeutic combination of claim 1, wherein the non-racemic mixture comprises R-MDMA and S-MDMA in a molar ratio of about 4:1, about 5:1, about 6:1, about 7:1, about 8:1, about 9:1, about 10:1, about 11:1, or about 12:1.

5. The therapeutic combination of claim 1, wherein the non-racemic mixture comprises R-MDMA and S-MDMA in a molar ratio of about 9:1.

6. The therapeutic combination of claim 1, wherein the non-racemic mixture comprises, on a molar basis:

a) 90%±5% R-MDMA and 10%±5% S-MDMA;

b) 90%±2.5% R-MDMA and 10%±2.5% S-MDMA;

c) 90%±2% R-MDMA and 10%±2% S-MDMA;

d) 90%±1% R-MDMA and 10%±1% S-MDMA;

e) 90%±0.1% R-MDMA and 10%±0.1% S-MDMA; or f) 90%±0.05% R-MDMA and 10%±0.05% S-MDMA.

7. The therapeutic combination of claim 1, wherein the hallucinogenic agent comprises any of a phenethylamine, a tryptamine, and a lysergamide.

8. The therapeutic combination of claim 1, wherein the hallucinogenic agent comprises any of a 2C-x compound, psilocybin, psilocin, DMT, 5-MeO-DMT, 4-Aco-DMT, 5-Br-DMT, 5-Cl-DMT, 5-F-DMT, 4,5-MDO-DMT, DiPT, 4,5-MDO-DiPT, LSD, 1P-LSD, PRO-LAD, ETH-LAD, AL-LAD, mescaline, salvinorin A, and THC.

9. The therapeutic combination of claim 8, wherein the 2C-x compound is any of 2C-B, 2C-B-AN, 2C-B-FLY, 2C-B-BUTTERFLY, 2C-B-FLY-NBOMe, 2C-B-FLY-NB2EtO5Cl, 2C-Bn, 2C-Bu, 2C-B-5-HEMIFLY, 2C-C, 2C-C-3, 2C-CN, 2C-CP, 2C-D, 2C-E, 2C-EF, 2C-F, 2C-G, 2C-G-1, 2C-G-2, 2C-G-3, 2C-G-4, 2C-G-5, 2C-G-6, 2C-G-N, 2C-H, 2C-I, 2CB-Ind, 2C-iP, 2C-N, 2C-NH2, 2C-PYR, 2C-PIP, 2C-O, 2C-O-4, 2C-MOM, 2C-P, 2C-Ph, 2C-Se, 2C-T, 2C-T-2, 2C-T-3, 2C-T-4, 2C-T-5, 2C-T-6, 2C-T-7, 2C-T-8, 2C-T-9, 2C-T-10, 2C-T-11, 2C-T-12, 2C-T-13, 2C-T-14, 2C-T-15, 2C-T-16, 2C-T-17, 2C-T-18, 2C-T-19, 2C-T-21, 2C-T-21.5, 2C-T-22, 2C-T-23, 2C-T-24, 2C-T-25, 2C-T-27, 2C-T-28, 2C-T-30, 2C-T-31, 2C-T-32, 2C-T-33, 2C-DFM, 2C-TFM, 2C-TFE, 2C-YN, 2C-V, and 2C-AL.

10. The therapeutic combination of claim 9, wherein the 2C-x compound is 2C-B.

11. The therapeutic combination of claim 1, wherein the hallucinogenic agent is any of psilocybin, psilocin, DMT, and 5-MeO-DMT.

12. A pharmaceutical composition comprising the therapeutic combination of claim 1, and a pharmaceutically acceptable carrier, diluent, or excipient.

13. The pharmaceutical composition of claim 12, in unit dosage form.

* * * * *